(12) United States Patent
Ribble et al.

(10) Patent No.: US 10,660,807 B2
(45) Date of Patent: May 26, 2020

(54) SYSTEMS, METHODS, AND DEVICES FOR THE TREATMENT OF SLEEP DISORDERS

(71) Applicant: Hill-Rom Services, Inc., Batesville, IN (US)

(72) Inventors: David Ribble, Indianapolis, IN (US); Charles A. Howell, Batesville, IN (US); Neal Wiggermann, Batesville, IN (US); Michael Scott Hood, Batesville, IN (US); Travis Pelo, Batesville, IN (US); Kirsten M. Emmons, Batesville, IN (US); Eric D. Agdeppa, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 25 days.

(21) Appl. No.: 14/454,961

(22) Filed: Aug. 8, 2014

(65) Prior Publication Data
US 2014/0345060 A1 Nov. 27, 2014

Related U.S. Application Data

(63) Continuation-in-part of application No. PCT/US2013/042313, filed on May 22, 2013, and a
(Continued)

(51) Int. Cl.
*A47C 27/08* (2006.01)
*A61G 7/015* (2006.01)
(Continued)

(52) U.S. Cl.
CPC .............. *A61G 7/015* (2013.01); *A61B 5/002* (2013.01); *A61B 5/1126* (2013.01);
(Continued)

(58) Field of Classification Search
CPC ........ A61G 7/015; A61G 7/001; A61G 7/018; A61G 7/05776; A61G 7/012;
(Continued)

(56) References Cited

U.S. PATENT DOCUMENTS

| 3,775,785 A | 12/1973 | Mittendorf |
| 4,754,510 A | 7/1988 | King |

(Continued)

FOREIGN PATENT DOCUMENTS

| DE | 4137631 A1 | 5/1992 |
| EP | 262771 | 4/1991 |

(Continued)

OTHER PUBLICATIONS

PCT Search Report and Written Opinion for PCT/US2014/18033, completed Aug. 18, 2014.
(Continued)

*Primary Examiner* — Nicholas F Polito
*Assistant Examiner* — Morgan J McClure
(74) *Attorney, Agent, or Firm* — Barnes & Thornburg LLP

(57) ABSTRACT

A sleep apparatus, such as a mattress for example, is provided in one embodiment. The apparatus comprises a head support surface sized to support a person's head, and a torso support surface sized to support a person's torso. The head support surface is generally laterally sloped moving from the first side toward the second side, and the torso support surface is generally laterally sloped moving from the first side toward the second side. In some embodiments, the lateral slope of the head support surface is at least about 15°, the lateral slope of the head support surface is greater than the lateral slope of the torso support surface, and/or, the sleep apparatus slopes in the longitudinal direction as well.

34 Claims, 89 Drawing Sheets

Related U.S. Application Data continuation-in-part of application No. PCT/US2014/018033, filed on Feb. 24, 2014.

(60) Provisional application No. 61/650,022, filed on May 22, 2012, provisional application No. 61/729,868, filed on Nov. 26, 2012, provisional application No. 61/792,911, filed on Mar. 15, 2013, provisional application No. 61/896,358, filed on Oct. 28, 2013.

(51) Int. Cl.

| | |
|---|---|
| *A61G 7/057* | (2006.01) |
| *A61B 5/00* | (2006.01) |
| *A61G 7/00* | (2006.01) |
| *A61G 7/018* | (2006.01) |
| *A61B 5/11* | (2006.01) |
| *A61G 7/05* | (2006.01) |
| *A61B 5/024* | (2006.01) |
| *A61G 7/012* | (2006.01) |
| *A61B 5/08* | (2006.01) |
| *A47C 20/04* | (2006.01) |

(52) U.S. Cl.
CPC .......... *A61B 5/4818* (2013.01); *A61B 5/6891* (2013.01); *A61B 5/6892* (2013.01); *A61B 5/747* (2013.01); *A61G 7/001* (2013.01); *A61G 7/018* (2013.01); *A61G 7/0509* (2016.11); *A61G 7/05776* (2013.01); *A47C 20/04* (2013.01); *A47C 20/041* (2013.01); *A47C 20/048* (2013.01); *A61B 5/024* (2013.01); *A61B 5/0816* (2013.01); *A61B 5/1113* (2013.01); *A61B 5/1116* (2013.01); *A61B 5/4812* (2013.01); *A61B 5/6831* (2013.01); *A61B 5/7282* (2013.01); *A61B 2562/0247* (2013.01); *A61B 2562/0252* (2013.01); *A61B 2562/046* (2013.01); *A61G 7/012* (2013.01); *A61G 7/0525* (2013.01); *A61G 7/05707* (2013.01); *A61G 7/05715* (2013.01); *A61G 7/05723* (2013.01); *A61G 2203/32* (2013.01); *A61G 2203/34* (2013.01); *A61G 2203/40* (2013.01); *A61G 2203/42* (2013.01)

(58) Field of Classification Search
CPC .............. A61G 7/0525; A61G 7/05707; A61G 7/05715; A61G 7/05723; A61G 5/002; A61G 5/1126; A61G 5/4818; A61G 5/6891; A61G 5/6892; A61G 5/747; A61G 5/024; A61G 5/0816; A61G 5/1113; A61G 5/1116; A61G 5/4812; A61G 5/6831; A61G 5/7282; A61G 2007/0509; A61G 2203/32; A61G 2203/34; A61G 2203/40; A61G 2203/42; A61B 2562/0247; A61B 2562/0252; A61B 2562/046; A47C 20/041; A47C 20/04; A47C 20/048

See application file for complete search history.

(56) References Cited

U.S. PATENT DOCUMENTS

| | | | |
|---|---|---|---|
| 4,807,313 A | 2/1989 | Ryder et al. | |
| 5,092,007 A | 3/1992 | Hasty | |
| 5,097,551 A | 3/1992 | Smith | |
| 5,611,096 A * | 3/1997 | Bartlett .................. | A61G 7/001 5/424 |
| 5,640,729 A | 6/1997 | Mariño | |
| 5,745,937 A | 5/1998 | Weismiller et al. | |
| 5,754,998 A | 5/1998 | Selton | |
| 5,910,080 A | 6/1999 | Selton | |
| 5,966,762 A | 10/1999 | Wu | |
| 6,047,419 A | 4/2000 | Ferguson | |
| 6,081,950 A | 7/2000 | Selton | |
| 6,154,900 A | 12/2000 | Shaw | |
| 6,163,903 A | 12/2000 | Weismiller et al. | |
| D446,676 S | 8/2001 | Mayes | |
| 6,370,716 B1 | 4/2002 | Wilkinson | |
| 6,485,441 B2 | 11/2002 | Woodward | |
| 6,536,056 B1 | 3/2003 | Phillips et al. | |
| 6,578,219 B1 * | 6/2003 | Gabel .................. | A61G 7/05715 5/600 |
| 6,671,907 B1 | 1/2004 | Zuberi | |
| 6,681,424 B1 | 1/2004 | Bourgraf et al. | |
| 6,751,817 B1 | 6/2004 | Leach | |
| 6,904,631 B2 | 6/2005 | Vrzalik et al. | |
| 7,007,327 B2 | 3/2006 | Ogawa et al. | |
| 7,017,213 B2 | 3/2006 | Chisari | |
| 7,089,615 B1 | 8/2006 | Parimuha | |
| D527,937 S | 9/2006 | Aiken et al. | |
| 7,346,945 B2 | 3/2008 | Phillips et al. | |
| 7,418,751 B1 | 9/2008 | Bartlett et al. | |
| 7,464,422 B2 | 12/2008 | Townsend | |
| 7,513,003 B2 | 4/2009 | Mossbeck | |
| 7,654,974 B2 | 2/2010 | Bass | |
| 7,690,059 B2 | 4/2010 | Lemire et al. | |
| 7,805,784 B2 | 10/2010 | Lemire et al. | |
| 7,861,334 B2 | 1/2011 | Lemire et al. | |
| 7,886,379 B2 * | 2/2011 | Benzo .................... | A61G 7/008 5/608 |
| 7,962,981 B2 | 6/2011 | Lemire et al. | |
| 7,975,335 B2 | 7/2011 | O'Keefe et al. | |
| 8,006,332 B2 | 8/2011 | Lemire et al. | |
| 8,220,091 B2 | 7/2012 | Schultz | |
| 8,261,380 B2 | 9/2012 | Ferraresi et al. | |
| 8,356,602 B2 | 1/2013 | Crocetti | |
| 8,393,026 B2 | 3/2013 | Dionne et al. | |
| 8,413,271 B2 * | 4/2013 | Blanchard ................ | A61G 7/00 5/173 |
| 8,544,126 B2 | 10/2013 | Elliott et al. | |
| 8,661,586 B2 | 3/2014 | Melcher et al. | |
| 8,689,376 B2 | 4/2014 | Becker et al. | |
| 8,695,134 B2 | 4/2014 | Schultz | |
| 8,701,229 B2 | 4/2014 | Lemire et al. | |
| 8,720,447 B2 | 5/2014 | North | |
| 8,756,736 B1 | 6/2014 | Minson | |
| 8,789,222 B2 | 7/2014 | Blanchard et al. | |
| 8,832,887 B2 | 9/2014 | Mossbeck | |
| 8,844,076 B2 | 9/2014 | Becker et al. | |
| 8,870,764 B2 | 10/2014 | Rubin | |
| 9,038,217 B2 | 5/2015 | Elliot et al. | |
| 9,126,571 B2 | 9/2015 | Lemire et al. | |
| 2006/0173257 A1 * | 8/2006 | Nagai .................... | A61B 5/1116 600/323 |
| 2006/0179580 A1 | 8/2006 | Robertson et al. | |
| 2007/0163051 A1 * | 7/2007 | Straub .................. | A47D 15/008 5/655 |
| 2008/0109965 A1 | 5/2008 | Mossbeck | |
| 2008/0148487 A1 | 6/2008 | Lord et al. | |
| 2009/0250070 A1 | 10/2009 | Pfeifer | |
| 2011/0231996 A1 | 9/2011 | Lemire et al. | |
| 2012/0041343 A1 * | 2/2012 | Lyons .................... | A61B 5/002 600/587 |
| 2012/0138067 A1 * | 6/2012 | Rawls-Meehan .... | A47C 20/041 128/845 |
| 2012/0222214 A1 * | 9/2012 | Lachenbruch ......... | A61G 7/001 5/81.1 R |
| 2013/0198965 A1 | 8/2013 | Melcher et al. | |
| 2013/0245395 A1 | 9/2013 | Bidarian Moniri | |
| 2014/0059768 A1 | 3/2014 | Lemire et al. | |
| 2014/0088373 A1 | 3/2014 | Phillips et al. | |
| 2014/0173829 A1 | 6/2014 | Melcher et al. | |
| 2014/0180036 A1 | 6/2014 | Bukkapatnam et al. | |
| 2014/0245539 A1 * | 9/2014 | Ooba .................... | A47C 20/048 5/636 |
| 2014/0259417 A1 | 9/2014 | Nunn et al. | |
| 2014/0259418 A1 | 9/2014 | Nunn et al. | |

(56) References Cited

U.S. PATENT DOCUMENTS

| | | |
|---|---|---|
| 2014/0259419 A1 | 9/2014 | Stusynski et al. |
| 2014/0259433 A1 | 9/2014 | Nunn et al. |
| 2014/0259434 A1 | 9/2014 | Nunn et al. |
| 2014/0266733 A1 | 9/2014 | Hayes et al. |
| 2014/0277611 A1 | 9/2014 | Nunn et al. |
| 2014/0277822 A1 | 9/2014 | Nunn et al. |
| 2014/0283302 A1 | 9/2014 | Horstmann |
| 2014/0366274 A1 | 12/2014 | Melcher et al. |
| 2015/0000035 A1 | 1/2015 | Becker et al. |

FOREIGN PATENT DOCUMENTS

| | | | |
|---|---|---|---|
| EP | 2175822 B1 | 1/2012 | |
| EP | 2140847 B1 | 7/2012 | |
| EP | 2494946 | 9/2012 | |
| JP | 2011-143237 | 7/2011 | |
| JP | 2011143237 A * | 7/2011 | ............ A47C 20/04 |
| JP | WO2013031504 A1 | 7/2013 | |
| KR | 20110083167 | 7/2011 | |
| WO | WO 2010/048310 A1 | 4/2010 | |
| WO | WO2013/166003 | 4/2013 | |
| WO | WO2013031504 A1 | 7/2013 | |
| WO | 2013116676 A1 | 8/2013 | |
| WO | WO2013/177338 A2 | 11/2013 | |
| WO | WO 2014/069713 A1 | 5/2014 | |
| WO | WO 2014/151707 A1 | 9/2014 | |
| WO | WO 2014/152891 A1 | 9/2014 | |
| WO | WO2014/149392 A2 | 11/2014 | |

OTHER PUBLICATIONS

PCT Search Report for PCT/US2013/042313, completed Dec. 6, 2013.

Adesanya, Adebola O., et al., *Perioperative Management of Obstructive Sleep Apnea*, CHEST/138/6, Dec. 2010 (10 pages).

Ankichetty, Saravanan and Frances Chung, *Considerations for Patients with Obstructive Sleep Apnea Undergoing Ambulatory Surgery*, Current Opinion in Anesthesiology 2011, 24:605-611 (7 pages).

Arnold, Donald H., et al., *Estimation of Airway Obstruction Using Oximeter Plethysmograph Waveform Data*, Respiratory Research 2005, 6:65 (8 pages).

American Society of Anesthesiologists, Inc., *Practice Guidelines for the Perioperative Management of Patients with Obstructive Sleep Apnea*, Anesthesiology 2006, V. 104, 1081-93, No. 5, May 2006, (13 pages).

Benumof, Jonathan L., *Obstructive Sleep Apnea in the Adult Obese Patient: Implications for Airway Management*, Journal of Clinical Anesthesia 13:144-156, 2001 (13 pages).

Berend, Keith R., et al., *Prevalence and Management of Obstructive Sleep Apnea in Patients Undergoing Total Joint Arthroplasty*, The Journal of Arthroplasty vol. 25 No. 6 Suppl. 1 2010 (4 pages).

Berger, G., et al., *Progression of Snoring and Obstructive Sleep Apnoea: The Role of Increasing Weight and Time*, European Respiratory Journal, vol. 33, No. 2, 2009 (8 pages).

Bianchi, Matt T., *Screening for Obstructive Sleep Apnea: Bayes Weighs In*, The Open Sleep Hournal, 2009, 2, 56-59 (4 pages).

Bignold, James J., et al., *Accurate Position Monitoring and Improved Supine-Dependent Obstructive Sleep Apnea with a New Position Recording and Supine Avoidance Device*, Journal of Clinical Sleep Medicine, vol. 7, No. 4, 2001 (8 pages).

Bloom, Harrison G., et al., *Evidence-Based Recommendations for the Assessment and Management of Sleep Disorders in Older Persons*, J Am Geriatr Soc 57:761-789, 2009 (30 pages).

Bolden, Norman, et al., *Avoiding Adverse Outcomes in Patients with Obstructive Sleep Apnea (OSA): Development and Implementation of a Perioperative OSA Protocol*, Journal of Clinical Anesthesia (2009) 21, 286-293 (8 pages).

Bourne, Richard S., et al., *Clinical Review: Sleep Measurement in Critical Care Patients: Research and Clinical Implications*, Critical Care 2007, 11:226 (17 pages).

Brown, Carlos VR and George C. Velmahos, *The Consequences of Obesity on Trauma, Emergency Surgery, and Surgical Critical Care*, World Journal of Emergency Surgery 2006, 1:27 (5 pages).

Bush, Haydn, *Screening for Sleep Apnea*, American Hospital Association Health Forum, Hospital & Health Networks, hhn@omeda.com, 2013 (2 pages).

Camilo, Millene R., et al., *Supine Sleep and Positional Sleep Apnea After Acute Ischemic Stroke and Intracerebral Hemorrhage*, CLINICS 2012; 67(12); 1357-1360 (4 pages).

Carr, Gordon E., et al., *Acute Cardiopulmonary Failure From Sleep-Disordered Breathing*, CHEST 2012; 141(3); 798-808 (11 pages).

Casey, Kenneth R. and Michael J. Lefor, *Management of the Hospitalized Patient with Sleep Disordered Breathing*, Current Opinion in Pulmonary Medicine 2002, 8:511-515 (5 pages).

Chia, P., et al., *The Association of Pre-Operative STOP-BANG Scores with Postoperative Critical Care Admission*, Anaesthesia 2013, 68, 950-952 (3 pages).

Choi, Jae-Kap, et al., *Effect of Jaw and Head Position on Airway Resistance in Obstructive Sleep Apnea*, Sleep and Breathing, vol. 4, No. 4, 163-168, 2000 (8 pages).

Choi, Ji Ho, et al., *Efficacy Study of a Vest-Type Device for Positional Therapy in Position Dependent Snorers*, Sleep and Biological Rhythms 2009; 7; 181-187 (7 pages).

Chung, Sharon A., et al., *A Systemic Review of Obstructive Sleep Apnea and Its Implications for Anesthesiologists*, Ambulatory Anesthesiology, vol. 107, No. 5, Nov. 2008, 1543-1563 (21 pages).

Chung, F., et al., *High STOP-Band Score Indicates a High Probability of Obstructive Sleep Apnoea*, British Journal of Anaesthesia 108 (5): 768-75 (2012), (8 pages).

Chung, Frances and Babak Mokhlesi, *Postoperative Complications Associates with Obstructive Sleep Apnea: Time to Wake Up!*, Anesthesia & Analgesia, Feb. 2014, vol. 118, No. 2, 251-253 (3 pages).

Chung, Frances et al., *Preoperative Identification of Sleep Apnea Risk in Elective Surgical Patient6s, Using the Berlin Questionnaire*, Journal of Clinical Anesthesia (2007) 19, 130-134 (5 pages).

Chung, Frances and Hisham Elsaid, *Screening for Obstructive Sleep Apnea Before Surgery: Why is it Important?*, Current Opinion in Anaesthesiology 2009, 22:405-411 (7 pages).

Chung, Frances, et al., *Validation of the Berlin Questionnaire and American Society of Anesthesiologists Checklist as Screening Tools for Obstructive Sleep Apnea in Surgical Patients*, Anesthesiology, vol. 108, No. 5, May 2008, 822-830 (9 pages).

Curry, J. Paul and Lawrence A. Lynn, *Threshold Monitoring, Alarm Fatigue, and the Patterns of Unexpected Hospital Death*, The Official Journal of the Anesthesia Patient Safety Foundation, Fall 2011 (8 pages).

D'Apuzzo, Michele R. and James A. Browne, *Obstructive Sleep Apnea as a Risk Factor for Postoperative Complications After Revision Joint Arthroplasty*, The Journal of Arthroplasty, vol. 27, No. 8, Suppl. 1 (2012), 95-98 (4 pages).

Der Herder, Cindy, et al., *Risks of General Anaesthesia in People with Obstructive Sleep Apnoea*, British Medical Journal, vol. 329, Oct. 23, 2004, 955-959 (5 pages).

Dolezal, Donna, et al., *Implementing Preoperative Screening of Undiagnosed Obstructive Sleep Apnea*, Journal of PeriAnesthesia Nursing, vol. 26, No. 5 Oct. 2011, 338-342 (5 pages).

Ead, Heather, *Meeting the Challenge of Obstructive Sleep Apnea: Developing a Protocol that Guides Perianesthesia Patient Care*, Journal of PeriAnesthesia Nursing, vol. 24, No. 2 Apr. 2009, 103-113 (11 pages).

Farney, Robert J., et al., *The STOP-Bang Equivalent Model and Prediction of Severity of Obstructive Sleep Apnea: Relation to Polysomnographic Measurements of the Apnea/Hypopnea Index*, Journal of Clinical Sleep Medicine, vol. 7, No. 5, 2011, 459-467 (9 pages).

Finkel, Kevin J., et al., *Prevalence of Undiagnosed Obstructive Sleep Apnea Among Adult Surgical Patients in an Academic Medical Center*, Sleep Medicine 10 (2009) 753-758 (6 pages).

Finucane, Thomas E., *Evidence-Based Recommendations for the Assessment and Management of Sleep Disorders in Older Persons*, JAGS, Nov. 2009, vol. 57, No. 11, 2173-2174 (3 pages).

(56) References Cited

OTHER PUBLICATIONS

Fletcher, Eugene C., *"Near Miss" Death in Obstructive Sleep Apnea: A Critical Care Syndrome*, Critical Care Medicine, vol. 19, No. 9, Sep. 1991, 1158-1164 (7 pages).
Galhotra, Sanjay, *Mature Rapid Response System and Potentially Avoidable Cardiopulmonary Arrests in Hospital*, Qual. Saf. Health Care 2007, 16:260-265 (6 pages).
Gammon, Brian T. and Karen F. Ricker, *An Evidence-Based Checklist for the Postoperative Management of Obstructive Sleep Apnea*, Journal of PeriAnesthesia Nursing, vol. 27, No. 5 Oct. 2012, 316-322 (7 pages).
Gay, Peter C., *Sleep and Sleep-Disordered Breathing in the Hospitalized Patient*, Respiratory Care, Sep. 2010, vol. 55, No. 9, 1240-1254 (15 pages).
Gay, Peter C., *The Value of Assessing Risk of Obstructive Sleep Apnea in Surgical Patients: It Only Takes One*, Journal of Clinical Sleep Medicine, vol. 6, No. 5, 2010, 473-474 (2 pages).
Global Industry Analysts, Inc., *GIA Market Report: Sleep Apnea Diagnostic and Therapeutic Devices, A Global Strategic Business Report, MCP-3307*, Oct. 2010, www.StrategyR.com, (321 pages).
Gibson, G. J., *Obstructive Sleep Apnoea Syndrome: Underestimated and Undertreated*, British Medical Bulletin 2004; 72: 49-64 (16 pages).
Gupta, Rakesh M., et al., *Postoperative Complications in Patients With Obstructive Sleep Apnea Syndrome Undergoing Hip or Knee Replacement: A Case-Control Study*, May Clin Proc. 2001; 76:897-905 (9 pages).
Guralnick, Amy S., et al., *CPAP Adherence in Patients with Newly Diagnosed Obstructive Sleep Apnea Prior to Elective Surgery*, Journal of Clinical Sleep Medicine, vol. 8, No. 5, 2012, 501-506 (6 pages).
Heinzer, Raphael C., et al., *Positional Therapy for Obstructive Sleep Apnea: An Objective Measurement of Patients' Usage and Efficacy at Home*, Sleep Medicine 13 (2012) 425-428 (4 pages).
Hoque, Enamul, et al., *Monitoring Body Positions and Movements During Sleep Using WISPs*, Wireless Health '10, Oct. 5-7, 2010 (10 pages).
Isono, Shiroh, et al., *Lateral Position Decreases Collapsibility of the Passive Pharynx in Patients with Obstructive Sleep Apnea*, Anesthesiology, vol. 97, No. 4, Oct. 2002, 780-785 (6 pages).
Itasaka, Yoshiaki and Kazuo Ishikawa, *The Influence of Sleep Position and Obesity on Sleep Apnea*, Psychiatry and Clinical Neurosciences (2000), 54, 340-341 (3 pages).
Jensen, Candice, et al., *Postoperative CPAP and BiPAP Use Can be Safely Omitted after Laparoscopic Roux-en-Y Gastric Bypass*, Surgery for Obesity and Related Diseases 4 (2008) 512-514 (3 pages).
Joho, Shuji, et al., *Impact of Sleeping Position on Central Sleep Apnea/Cheyne-Stokes Respiration in Patients with Heart Failure*, Sleep Medicine 11 (2010) 143-148 (6 pages).
Jokie, Ruzica, et al., *Positional Treatment vs. Continuous Positive Airway Pressure in Patients with Positional Obstructive Sleep Apnea Syndrome*, CHEST/115/3/Mar. 1999, 771-781 (11 pages).
Joosten, S.A., et al., *Obstructive Sleep Apnea Phenotypic Trait Changes from Supine to Lateral Position*, Am J Respir Crit Care Med 189; 2014; A3909 (1 page).
Joshi, Girish P., et al., *Society for Ambulatory Anesthesia Consensus Statement on Preoperative Selection of Adult Patients with Obstructive Sleep Apnea Scheduled for Ambulatory Surgery*, Anesthesia & Analgesia, Nov. 2012, vol. 115, No. 5, 1060-1068 (9 pages).
Keenan, Sean P., et al., *Clinical Practice Guidelines for the Use of Noninvasive Positive-Pressure Ventilation and Noninvasive Continuous Positive Airway Pressure in the Acute Care Setting*, Canadian Medical Association Journal, Feb. 22, 2011, 183(3) (21 pages).
Khayat, Rami, et al., *In-Hospital Resting for Sleep-Disordered Breathing in Hospitalized Patients with Decompensated Heart Failure: Report of Prevalence and Patient Characteristics*, Journal of Cardiac Failure, vol. 15, No. 9 (2009) (739-746).
Kim, Eun Joong, *The Prevalence and Characteristics of Positional Sleep Apnea in Korea*, Korean J Otorhinolaryngol-Head Neck Surg. 2009:52:407-12 (6 pages).

Kulkarni, Gaurav V., et al., *Obstructive Sleep Apnea in General Surgery Patients: Is it More Common than we Think?*, The American Journal of Surgery (2014) 207, 436-440 (5 pages).
Lakdawala, Linda, *Creating a Safer Perioperative Environment With an Obstructive Sleep Apnea Screening Tool*, Journal of PeriAnesthesia Nursing, vol. 26, No. 1 Feb. 2001, 15-24 (10 pages).
Lee, Chul Hee, et al., *Changes in Site of Obstruction in Obstructive Sleep Apnea Patients According to Sleep Position: A DISE Study*, Laryngoscope 00: Month 2014 (7 pages).
Lee, Jung Bok, et al., *Determining Optimal Sleep Position in Patients with Positional Sleep-Disordered Breathing Using Response Surface Analysis*, J. Sleep Res. (2009) 18, 26-35 (10 pages).
Lockhart, Ellen M., et al. *Obstructive Sleep Apnea Screening and Postoperative Mortality in a Large Surgical Cohort*, Sleep Medicine 14 (2013) 407-415 (9 pages).
Lynn, Lawrence A. and J. Paul Curry, *Patterns of Unexpected In-Hospital Deaths: A Root Cause Analysis*, Patient Safety in Surgery 2011, 5:3 (25 pages).
Mador, M. Jeffrey, et al., *Are the Adverse Effects of Body Position in Patients with Obstructive Sleep Apnea Dependent on Sleep Stage?*, Sleep Breath (2010) 14:13-17 (7 pages).
Mador, M. Jeffrey, et al., *Prevalence of Positional Sleep Apnea in Patients Undergoing Polysomnography*, CHEST 2005; 128:2130-2137 (8 pages).
Marcus, Howard, *Obesity and Postoperative Surgical Risk*, The Doctors Company, Third Quarter 2010, 1-8 (8 pages).
Martin-Du Pan, Rémy, et al., *The Role of Body Position and Gravity in the Symptoms and Treatment of Various Medical Diseases*, Swiss Med. Wkly. 2004: 134:543-551 (10 pages).
Memtsoudis, Stavros G., et al., *A Rude Awakening—The Perioperative Sleep Apnea Epidemic*, N Engl. J. Med. 368:25, 2352-2353 (Jun. 20, 2013) (2 pages).
Menon, Akshay and Manoj Kumar, *Influence of Body Position on Severity of Obstructive Sleep Apnea: A Systematic Review*, Otolaryngology, vol. 2013, Article ID 670381 (2013) (8 pages).
Mininni, Nicolette C., et al., *Pulse Oximetry: An Essential Tool for the Busy Med-Surg Nurse*, American Nurse Today, Nov./Dec. 2009, 31-33 (3 pages).
Mokhlesi, Babak, *Empiric Postoperative Autotitrating Positive Airway Pressure Therapy/Generating Evidence in the Perioperative Care of Patients at Risk for Obstructive Sleep Apnea*, CHEST 144/1 (Jul. 2013) 5-7 (3 pages).
Mull, Yvonne and Marshall Bedder, *Obstructive Sleep Apnea Syndrome in Ambulatory Surgical Patients*, AORN Journal, vol. 76, No. 3, 458-462 (Sep. 2002) (5 pages).
Nader, Nizar Z., et al., *Newly Identified Obstructive Sleep Apnea in Hospitalized Patients: Analysis of an Evaluation and Treatment Strategy*, Journal of Sleep Medicine, vol. 2, No. 4, 2006, 431-437 (7 Pages).
Pevernagie, Dirk A., et al., *Effects of Body Position on the Upper Aiway of Patients with Obstructive Sleep Apnea*, Am J Respir Crit Care Med, vol. 152, 179-185, 1995 (7 pages).
Qureshi, Asher and Robert D. Ballard, *Obstructive Sleep Apnea*, J Allergy Clin Immunol, vol. 112, No. 4, 643-651 (2003) (9 pages).
Richard, Wietske, et al., *The Role of Sleep Position in Obstructive Sleep Apnea Syndrome*, Eur Arch Otorhinolaryngol (2006) 263:946-950 (5 pages).
Rocke, Daniel, et al., *Effectiveness of a Postoperative Disposition Protocol for Sleep Apnea Surgery*, American Journal of Otolaryngology—Head and Neck Medicine and Surgery 34 (2013) 273-277 (5 pages).
Gabbott, D.A., *The Effect of Single-Handed Cricoid Pressure on Neck Movement After Applying Manual In-Line Stabilisation*, Anaesthesia, 1997, 52, 586-602 (17 pages).
Ross, Jacqueline, *Obstructive Sleep Apnea: Knowledge to Improve Patient Outcomes*, Journal of PeriAnesthesia Nursing, vol. 23, No. 4 Aug. 2008, 273-275 (3 pages).
Setaro, Jill, *Obstructive Sleep Apnea: A Standard of Care That Works*, Journal of PeriAnesthesia Nursing, vol. 27, No. 5 Oct. 2012, 323-328 (6 pages).

(56) References Cited

OTHER PUBLICATIONS

Sheldon, Alison, et al., *Nursing Assessment of Obstructive Sleep Apnea in Hospitalised Adults: A Review of Risk Factors and Screening Tools*, Contemporary Nurse, vol. 34, Issue 1, Dec. 2009/Jan. 2010, 19-33 (16 pages).
Skinner, Margot A., et al., *Efficacy of the 'Tennis Ball Technique' Versus nCPAP in the Management of Position-Dependent Obstructive Sleep Apnoea Syndrome*, Respirology (2008) 13, 708-715 (8 pages).
Stearns, Joshua D. and Tracey L. Stierer, *Peri-Operative Identification of Patients at Risk for Obstructive Sleep Apnea*, Seminars in Anesthesia, Perioperative Medicine and Pain (2007) 26, 73-82 (10 pages).
Van Kesteren, Ellen R., et al., *Quantitative Effects of Trunk and Head Position on the Apnea Hypopnea Index in Obstructive Sleep Apnea*, SLEEP, vol. 34, No. 8 (2011), 1075-1081 (7 pages).
Veasey, Sigrid C., et al., *Medical Therapy for Obstructive Sleep Apnea: A Review by the Medical Therapy for Obstructive Sleep Apnea Task Force of the Standards of Practice Committee of the American Academy of Sleep Medicine*, SLEEP, vol. 29, No. 8 (2006), 1036-1044 (9 pages).
Wolfson, Alexander, et al., *Postoperative Analgesia for Patients with Obstructive Sleep Apnea Syndrome*, Seminars in Anesthesia, Perioperative Medicine and Pain (2007), 26, 103-109 (7 pages).
Yantis, Mary Ann, *Decreasing Surgical Risks for Patients with Obstructive Sleep Apnea*, AORN Journal, vol. 68, No. 1 (Jul. 1998), 50-55 (6 pages).
Ravesloot, M.J.L., and N. de Vries, *Reliable Calculation of the Efficacy of Non-Surgical Treatment of Obstructive Sleep Apnea Revisted*, SLEEP, vol. 34, No. 1 (2011), 105-110 (6 pages).
Moon, Il Joon, et al., *Sleep Magnetic Resonance Imagine as a New Diagnostic Method in Obstructive Sleep Apnea Syndrome*, Laryngoscope 120: Dec. 2010, 2546-2554 (9 pages).
Nepomnayshy, Dmitry, et al., *Sleep Apnea: Is Routine Preoperative Screening Necessary?*, OBES Surg (2013) 23:287-192 (5 pages).
Press Release: *World's Leading Health Media Promotes Disinformation on Best Sleeping Positions* (Sep. 22, 2010), Sleeping Positions Research Summary (24 Studies), http://www.normalbreathing.com/I-6-best-sleep-positions.php (14 pages).
Oksenberg, Arie, et al., *Association of Body Position with Severity of Apneic Events in Patients with Severe Nonpositional Obstructive Sleep Apnea*, CHEST 2000; 118; 1018-1024 (9 pages).
Oksenberg, Arie, *The Avoidance of the Supine Posture during Sleep for Patients with Supine-related Sleep Apnea*, BSM Protocols for Adherence and Treatment of Intrinsic Sleep Disorders, Chapter 23, 223-236 (14 pages).
Oksenberg, Arie and Donald Silverberg, *The Effect of Body Posture on Sleep-Related Breathing Disorders: Facts and Therapeutic Implications*, Sleep Medicine Reviews, vol. 2, No. 3, 139-162 (1998) (25 pages).
Oksenberg, Arie, et al., *Positional Therapy for Obstructive Sleep Apnea Patients: A 6-Month Follow-Up Study*, Laryngoscope 116, Nov. 2006, 1995-2000 (6 pages).
Oksenberg, Arie, et al., *REM-Related Obstructive Sleep Apnea: The Effect of Body Position*, Journal of Clinical Sleep Medicine, vol. 6, No. 4 (2010), 343-348 (6 pages).
Ozeke, Ozcan, et al., *Influence of the Right- Versus Left-Sided Sleeping Position on the Apnea-Hypopnea Index in Patients with Sleep Apnea*, Sleep Breath, published online Jun. 16, 2011 (5 pages).
Ozeke, Ozcan, et al., *Sleep Apnea, Heart Failure, and Sleep Position*, Sleep Breath, published online Nov. 9, 2011 (4 pages).
Permut, Irene, et al., *Comparison of Positional Therapy to CPAP in Patients with Positional Obstructive Sleep Apnea*, Journal of Clinical Sleep Medicine, vol. 6, No. 3 (2010), 238-243 (6 pages).
Author Unknown, *Positioning of Surgical Patients With Sleep Apnea*, ClinicalTrials.gov, http://clinicaltrials.gov/ct2/show/NCT02123238?term=apnea+and+position&rank=3 (2014) (5 pages).
Author Unknown, *Obstructive Sleep Apnea May Block the Path to a Positive Postoperative Outcome*, 2007 Pennsylvania Patient Safety Authority, reprinted from the PA-PSRS Patient Safety Advisory, vol. 4, No. 3 (Sep. 2007) (9 pages).
Proczko, Monika, et al., *STOP-Bang and the Effect on Patient Outcome and Length of Hospital Stay when Patients are not Using Continuous Positive Airway Pressure*, J Anesth, published online May 29, 2014 (7 pages).
Ramachandran, Satya Krishna, et al., *Derivation and Validation of a Simple Perioperative Sleep Apnea Prediction Score*, Society for Ambulatory Anesthesiology, vol. 110, No. 4 (Apr. 2010), 1007-1015 (9 pages).
Ravesloot, M.J.L. and N. de Vries, *Calculation of Surgical and Non-Surgical Efficacy for OSA / Reliable Calculation of the Efficacy of Non-Surgical and Surgical Treatment of Obstructive Sleep Apnea Revisted*, vol. 34, Issue 01 (2001) 105-110 (2 pages).
Ravesloot, M.J.L., et al., *The Undervalued Potential of Positional Therapy in Position-Dependent Snoring and Obstructive Sleep Apnea—A Review of the Literature*, Sleep Breath, published online Mar. 24, 2012 (11 pages).
Ravesloot, Madeline J.L., et al., *Treatment Adherence Should be Taken into Account when Reporting Treatment Outcomes in Obstructive Sleep Apnea*, Sleep Medicine, vol. 124, Issue 1 (Jan. 2014) 344-345 (3 pages).
Richardson, Annette and Anne Killen, *How Long do Patients Spend Weaning from CPAP in Critical Care?*, Intensive and Critical Care Nursing (2006) 22, 206-213 (8 pages).
Rosenberg, Russell and Paul Doghramji, *Optimal Treatment of Obstructive Sleep Apnea and Excessive Sleepiness*, Springer Healthcare Communication, published online Apr. 3, 2009, 295-312 (18 pages).
Rosenthal, Leon, *Got CPAP? Use it in the Hospital!*, Sleep Breath, published online Nov. 25, 2011 (4 pages).
Safiruddin, Faiza, et al., *Analysis of the Influence of Head Rotation During Drug-Induced Sleep Endoscopy in Obstructive Sleep Apnea*, Laryngoscope 124: Sep. 2014, 2195-2199 (5 pages).
Seet, Edwin and Frances Chung, *Obstructive Sleep Apnea: Preoperative Assessment*, Anesthesiology Clin 28 (2010) 199-215 (17 pages).
Seet, Edwin, et al., *Perioperative Clinical Pathways to Manage Sleep-Disordered Breathing*, Sleep Med Clin 8 (2013) 105-120 (16 pages).
Sforza, Emilia, et al., *A 3-Year Longitudinal Study of Sleep Disordered Breathing in the Elderly*, European Respiratory Journal, vol. 40, No. 3 (2012) 665-672 (8 pages).
Sforza, E., et al., *Natural Evolution of Sleep Apnoea Syndrome: A Five Year Longitudinal Study*, European Respiratory Journal, 1994, 7, 1765-1770 (6 pages).
Shafazand, Shirin, *Perioperative Management of Obstructive Sleep Apnea: Ready for Prime Time?*, Cleveland Clinic Journal of Medicine, vol. 76, Supp. 4, Nov. 2009 (6 pages).
Siddiqui, Fouzia, et al. *Half of Patients with Obstructive Sleep Apnea have a Higher NREM AHI than REM AHI*, Sleep Medicine 7 (2006) 281-285 (5 pages).
Singh, M., et al., *Proportion of Surgical Patients with Undiagnosed Obstructive Sleep Apnoea*, British Journal of Anaesthesia 110 (4); 629-636 (2013) (8 pages).
Skinner, Margot A., et al., *Elevated Posture for the Management of Obstructive Sleep Apnea*, Sleep and Breathing, vol. 8, No. 4 (2004) 193-200 (10 pages).
Author Unknown, *There's More than One Way to Improve Nightime Breathing*, European Sleep Works, http://www.sleepworks.com/resource/medical-needs/sleep-apnea (2014) (3 pages).
Park, Steven V., *Sleep Apnea CPAP Compliance Craziness*, Doctor Steven Y_Park, MD New York, NY Integrative Solutions for Obstructive Sleep Apnea, Upper Airway Resistance Syndrome, and Snoring (Nov. 10, 2009) (7 pages).
Monk, Timothy H., et al., *Measuring Sleep Habits Without Using a Diary: The Sleep Timing Questionnaire*, SLEEP, vol. 26, No. 2 (2003) 208-212 (5 pages).
Sorscher, Adam J. and Evan M. Caruso, *Frequency of Provision of CPAP in the Inpatient Setting: An Observational Study*, Sleep Breath, published online Nov. 23, 2011 (6 pages).

(56) References Cited

OTHER PUBLICATIONS

Spurr, Kathy F., et al., *Prevalence of Unspecified Sleep Apnea and the use of Continuous Positive Airway Pressure in Hospitalized Patients, 2004 National Hospital Discharge Survey*, Sleep Breath (2008) 12:229-234 (8 pages).
Srijithesh PR, et al., *Positional Therapy for Obstructive Sleep Apnoea (Protocol)*, The Cochrane Library 2014, Issue 2 (11 pages).
Sundar, Eswar, et al., *Perioperative Screening for the Management of Patients with Obstructive Sleep Apnea*, JCOM, vol. 18, No. 9, Sep. 2011, 399-411 (13 pages).
Szollosi, Irene, et al., *Lateral Sleeping Position Reduces Severity of Central Sleep Apnea/Cheyne-Stokes Respiration*, SLEEP, vol. 29, No. 8 (2006), 1045-1051 (7 pages).
Author Unknown, *A Promising Concept of Combination Therapy for Positional Obstructive Sleep Apnea*, Springer Link, http://link.springer.com/article/10.1007/s11325-014-1068-8, Oct. 2014 (4 pages).
Author Unknown, *Upper Airway Collapse During Drug Induced Sleep Endoscopy: Head Rotation in Supine Position Compared with Lateral Head and Truck Position*, Springer Link, http://link.springer.com/article/10.1007/s00405-014-3215-z, Aug. 2014 (4 pages).
Vasu, Tajender S., et al., *Obstructive Sleep Apnea Syndrome and Postoperative Complications*, Arch Otolaryngol Head Neck Surg, vol. 136, No. 10, Oct. 2010 (5 pages).
Matthews, Dan, *Mattresses—A Futile Weapon in the Fight Against Sleep Apnea*, http://www.danmatthewsdds.com/mattresses-%E2%80%93-futile-weapon-fight-sleep-apnea/ (2014) (1 page).
Marks, Steve, *Hospital Care of Patients with Sleep Apnea*, Areté Sleep Health, last modified on May 16, 2013 (63 pages).
Carlisle, Heather, *The Case for Capnography in Patients Receiving Opioids*, American Nurse Today, vol. 9, No. 9 (Sep. 2014) 22-27 (69 pages).
Gold, Jenny, *The Sleep Apnea Business Is Booming, and Insurers Aren't Happy*, NPR_ApnesvsInsurers.mht, (Jan. 16, 2012) (3 pages).
Author unknown, *Sleep right, Sleep tight, Natural sleep before medicines, Sleep Diary*, www.nps.org.au/sleep, last modified Jul. 7, 2010 (4 pages).
Quan, S. F., *Evolution of OSA*, Thorax 1998; 53:532 (4 pages).
Maurer, J. T., et al., *Treatment of Obstructive Sleep Apnea with a New Vest Preventing the Supine Position*, Thieme-Connect (2003) (1 page).
Schreuder, K.E., *The Effect of Cervical Positioning on Benign Snoring by Means of a Custom-Fitted Pillow*, Centre for Sleep and Wake Disorders Kempenhaeghe, 5591 Ve Heeze, the Netherlands, last modified Dec. 1, 2011 (4 pages).
Chung, Frances, *Semi-up Right Position Study*, Clinical Trials.gov, last updated May 28, 2014 (5 pages).
Author Unknown, *National Sleep Foundation Sleep Diary*, National Sleep Foundation, last modified Apr. 18, 2003 (2 pages).
Takaoka, Shanon, CPAP Adherence, Is it too much "pressure"?, Feb. 7, 2007 (41 pages).
Seren, Suaf, *The Effect of Pure Prone Positioning Therapy for the Patients With Mild to Moderate Obstructive Sleep Apnea*, ClinicalTrials.gov, last updated Jun. 7, 2011 (4 pages).
Jackman, Shawn M. and Bruce Hubbert, *Riding the Wireless Wave (without wiping out)*, HIMSS12 Annual Conference & Exhibition, last modified Feb. 20, 2012 (133 pages).
De Vries, Nico and Madeline Ravesloot, *Apnea Calculator*, http://apneacalculator.com (2014) (2 pages).
Oexman, Robert, *Can a Mattress Really Impact Your Sleep?*, Huffpost Healthy Living, Posted Oct. 14, 2012, 10:00 a.m. (8 pages).
Palmer, Laura and Suzanne R. Morrison, *Obesity and Obstructive Sleep Apnea / Is there a limit for ambulatory surgery?*, OR Nurse Journal, Sep. 2014 (9 pages).
Oksenberg, Arie, *Are We Missing a Simple Treatment for Most Adults Sleep Apnea Patients? The Avoidance of the Supine Sleep Position*, ResearchGate.net, Aug. 12, 2014 (2 pages).
Author Unknown, *Obstructive Sleep Apnea (OSA), Care of Adult Patients*, St. Anthony Central Hospital Clinical Standards, Jul. 8, 2009 (9 pages).
Gross, Jeffrey B., *Practice Guidelines for the Perioperative Management of Patients with Obstructive Sleep Apnea: An Updated Report by the American Society of Anesthesiologists Task Force on Perioperative Management of Patients with Obstructive Sleep Apnea*, U.S. Department of Health & Human Services, updated on May 9, 2014 (13 pages).
O'Connor, Anahad, *Treating Sleep Apnea Without the Mask*, NYTimes.com, Apr. 9, 2012 (7 pages).
Stradling, J. R. and R. J. O. Davies, *Sleep 1: Obstructive Sleep Apnea/Hypopnoea Syndrome: Definitions, Epidemiology, and Natural History*, Thorax 2004;59:73-78 (6 pages).
Pyke, Josh, et al, *Continuous Pulse Oximetry Monitoring in the Inpatient Population*, Patient Safety & Quality Healthcare, May/Jun. 2009 (5 pages).
EP Search Report for Application No. EP 13 79 3571, dated Sep. 8, 2015 (9 pages).
EP Search Report for Application No. 15180086.9-1651, dated Dec. 22, 2015, 7 pages.
Service Manual—"TotalCare® Bed System" from Hill-Rom, Product No. P1900, MAN112 Rev 7, by Hill-Rom Services, Inc. (2007) (1105 pages).
User Manual—"TotalCare® Bed System" from Hill-Rom, Product No. P1900, USR042 REV11, by Hill-Rom Services, Inc. (2009) (112 pages).
SleepEducation—Blog, "Positional therapy harness helps reduce sleep apnea for some," www.sleepeducation.com, posted Friday, Jun. 18, 2010 (7 pages).
SPANAmerica: PressureGuard® Turn Select®, www.archive.org/web/20090201172625/http://spanamerica.com/turn_select.php; Aug. 18, 2014 (2 pages).
Japanese Office Action for Japanese Patent Application No. 2017-073542 dated Feb. 7, 2018 and its English translation; 11 pages total.
Japanese Patent Application Publication No. JP 2011-143237A dated Jul. 28, 2011 and its machine-generated English translation; 34 pages total.
PCT Patent Application Publication No. WO 2013/031504 A1 published on Mar. 7, 2018 and the English translation of the Abstract only; 63 pages total.

\* cited by examiner

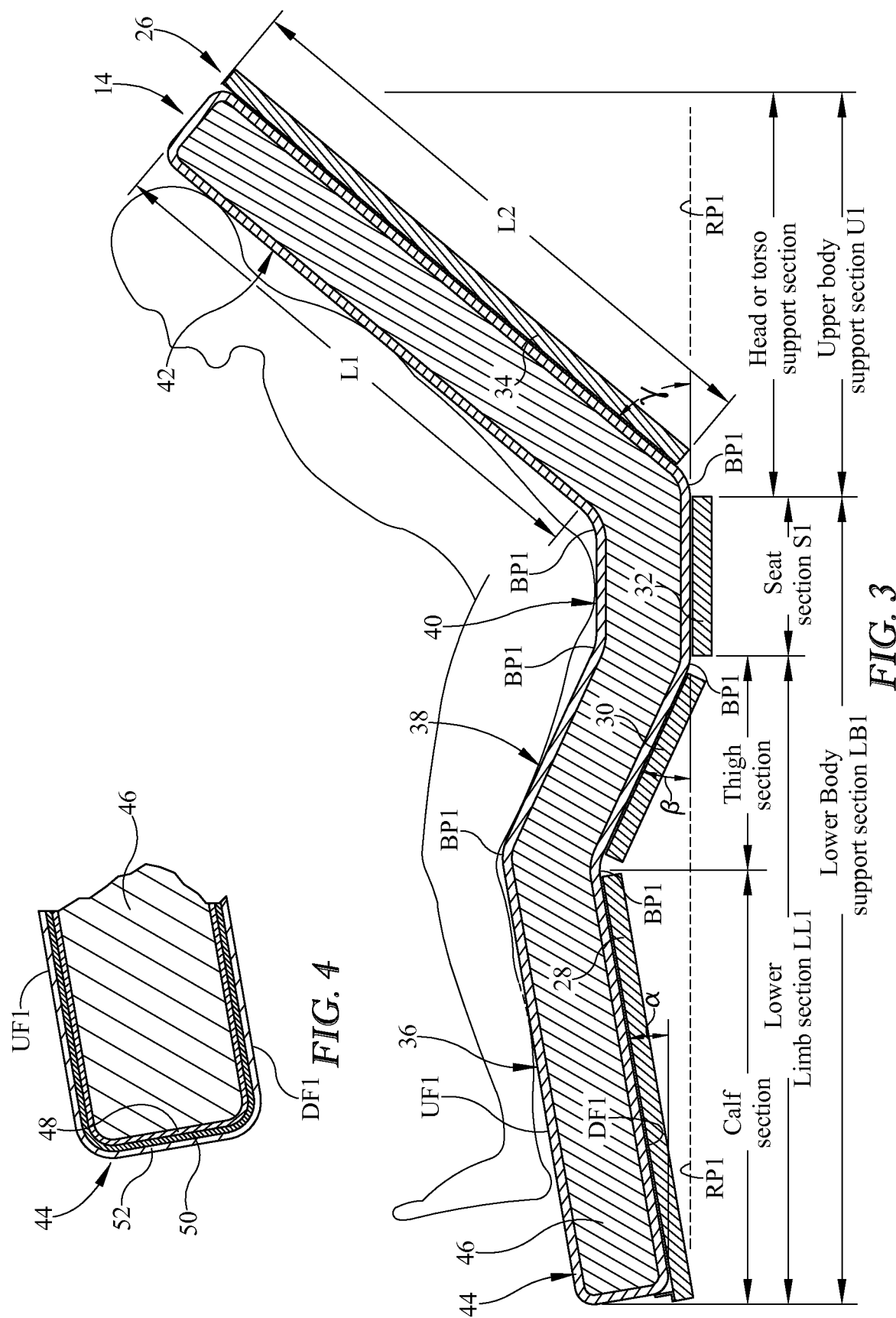

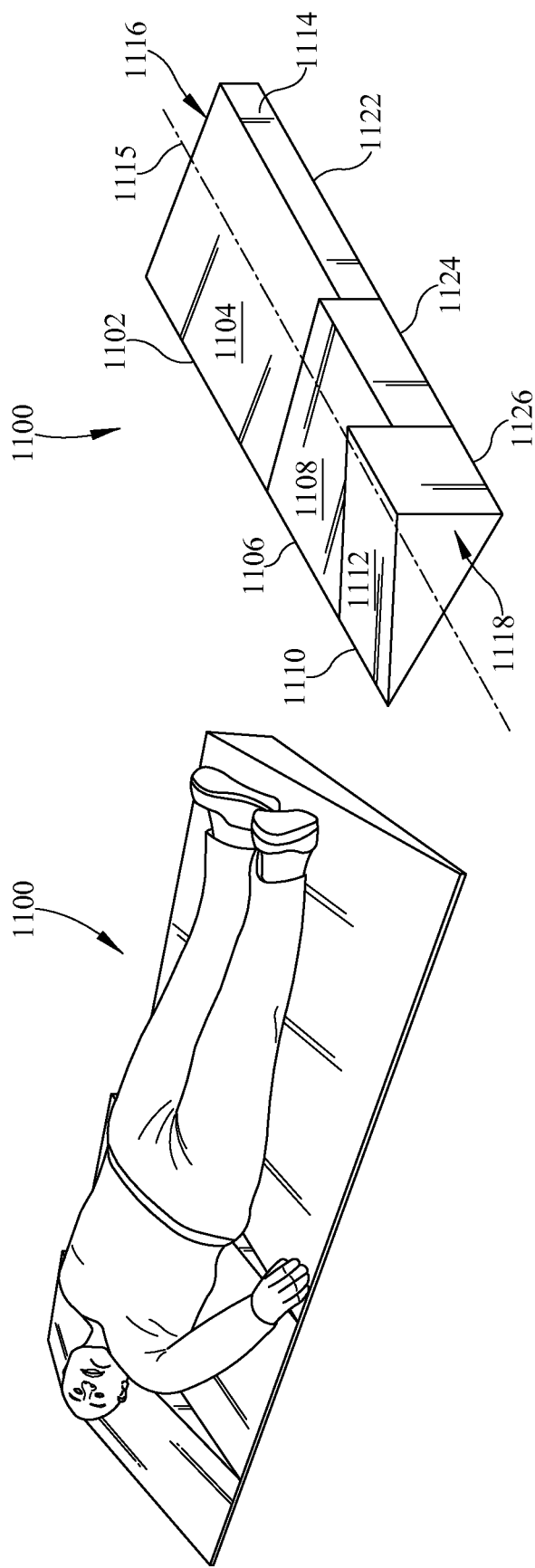
FIG. 11
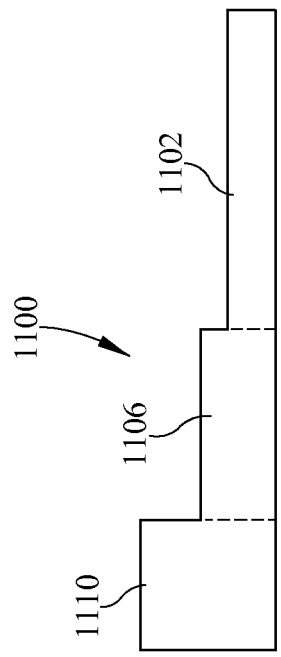
FIG. 12
FIG. 13
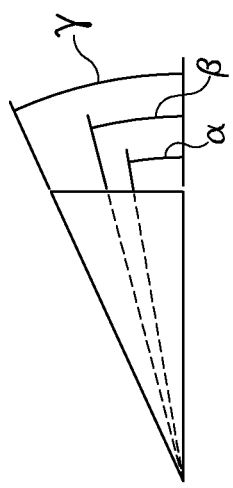
FIG. 14

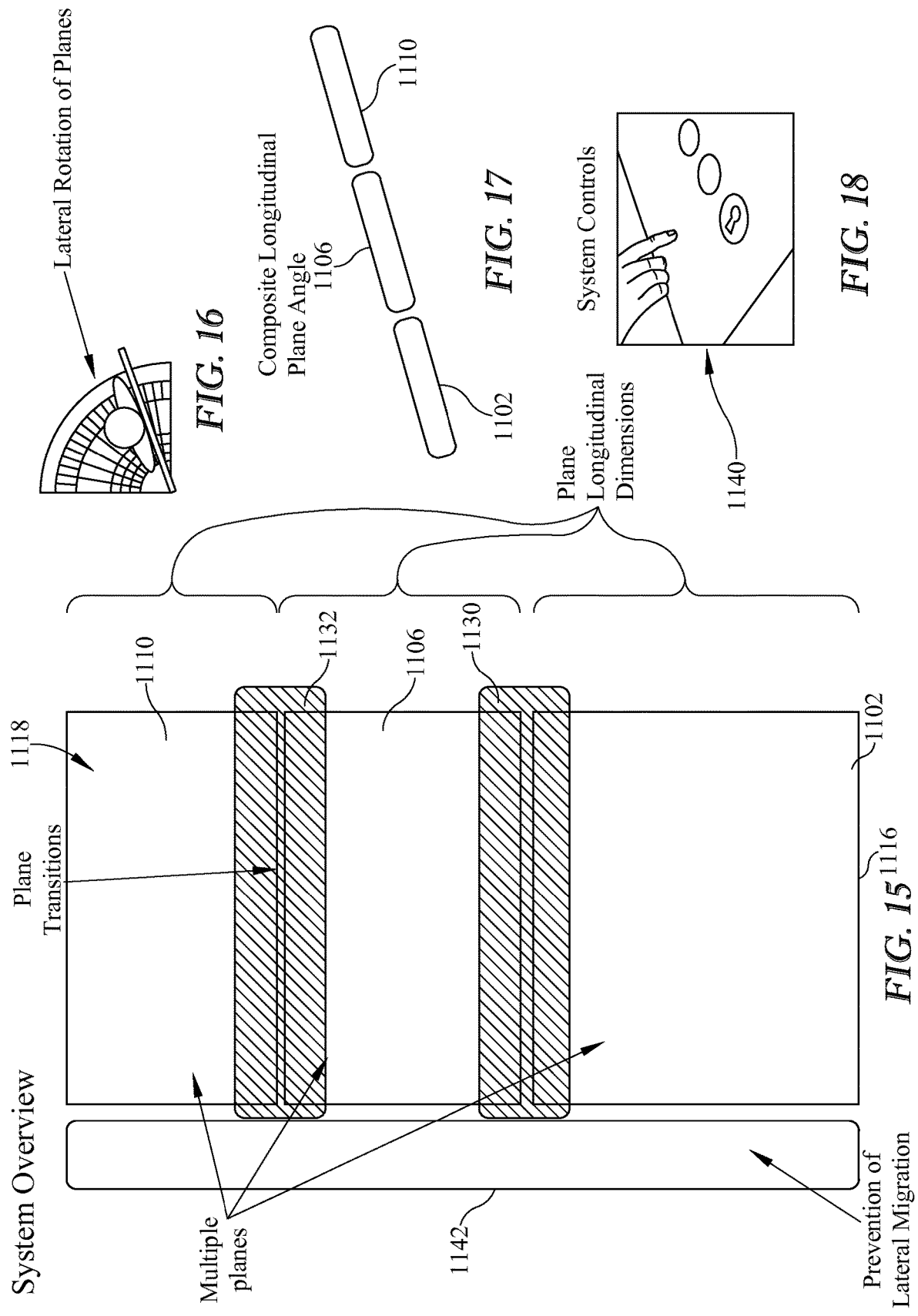

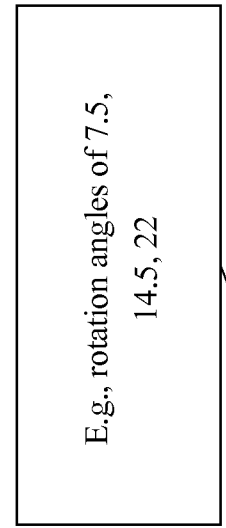
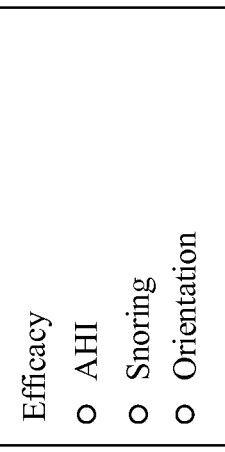
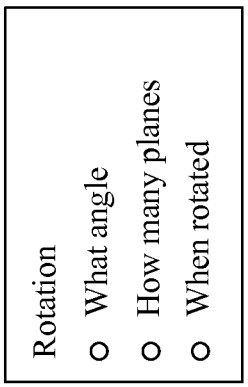
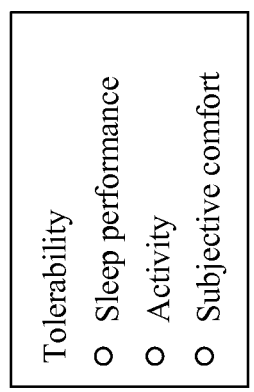
And evaluates connections between those elements...
FIG. 39

Modification of rotation function
- Constrained rotation at mid and upper section (e.g., by pressure modification, by physical constrain)
- Supplemented rotation via cushion Addition of apnea setting to device controls:
- Ability ot specify rotation (how many rotation planes, dimensions of each plane, angle of rotation for each plane)

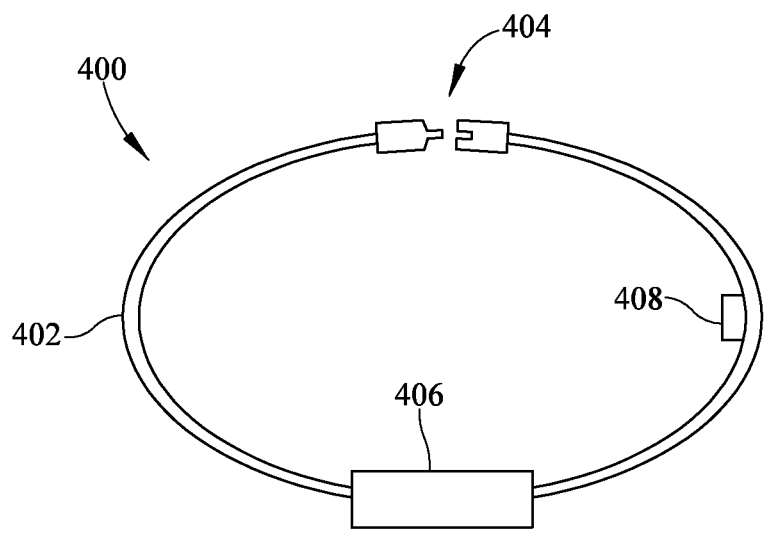
*FIG. 49*
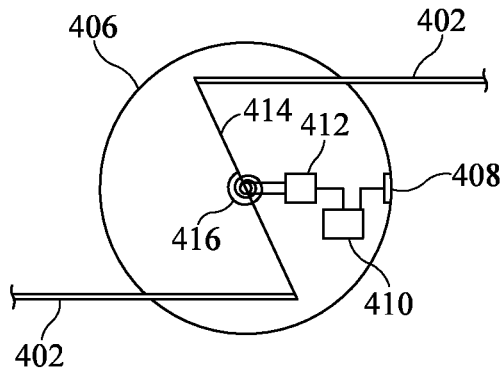
*FIG. 50*
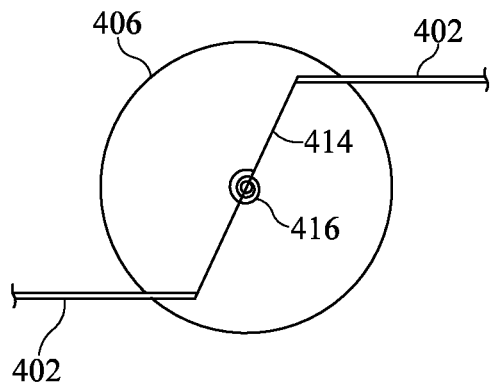 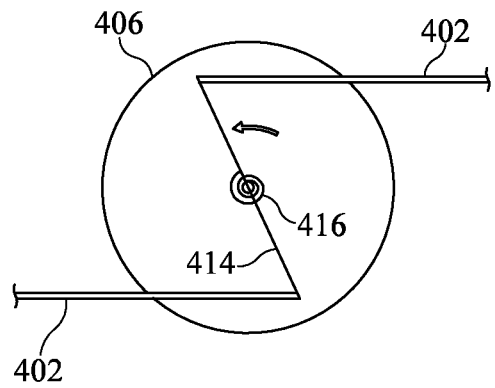
*FIG.51*    *FIG.52*

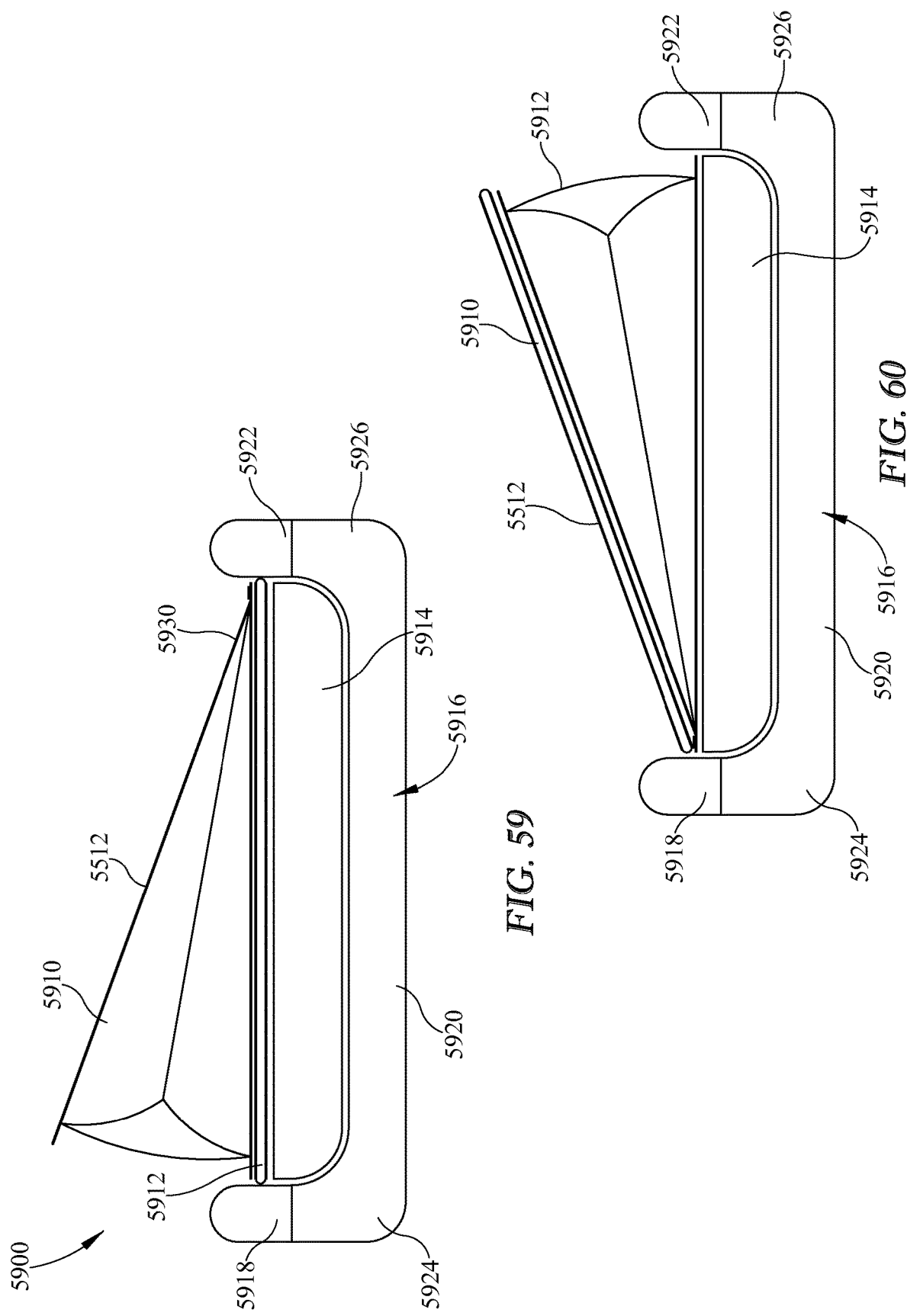

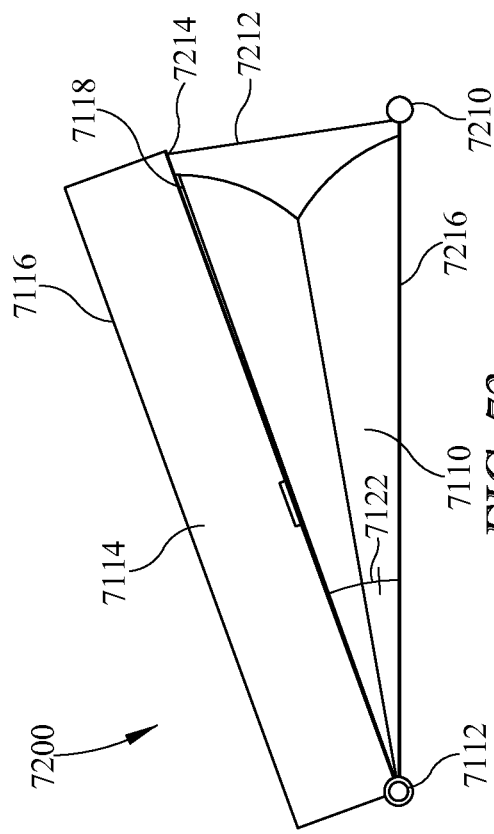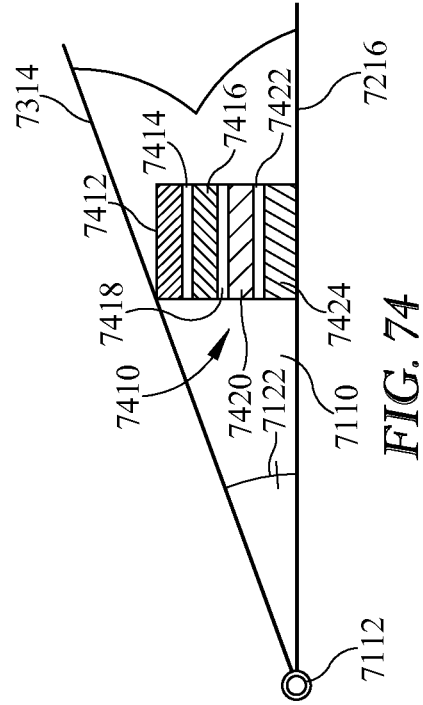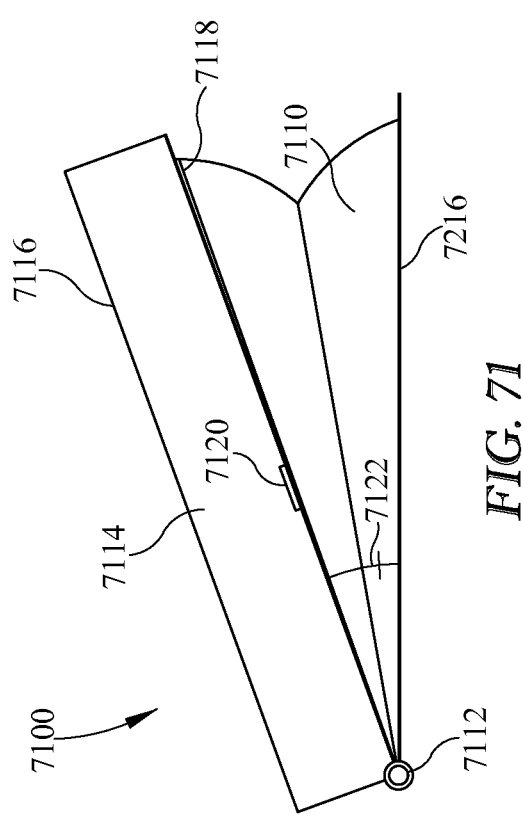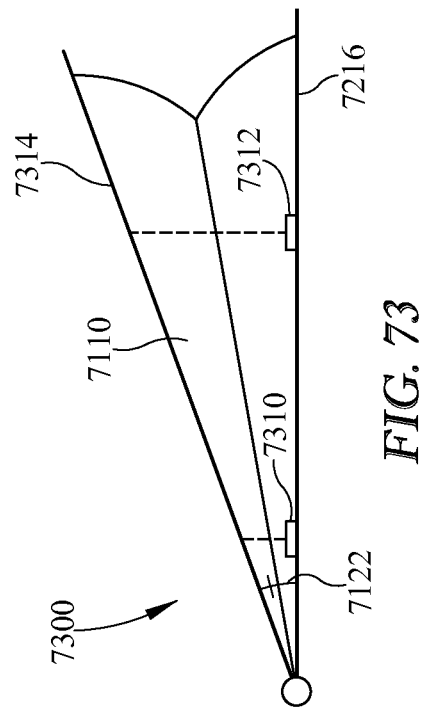
FIG. 71
FIG. 72
FIG. 73
FIG. 74

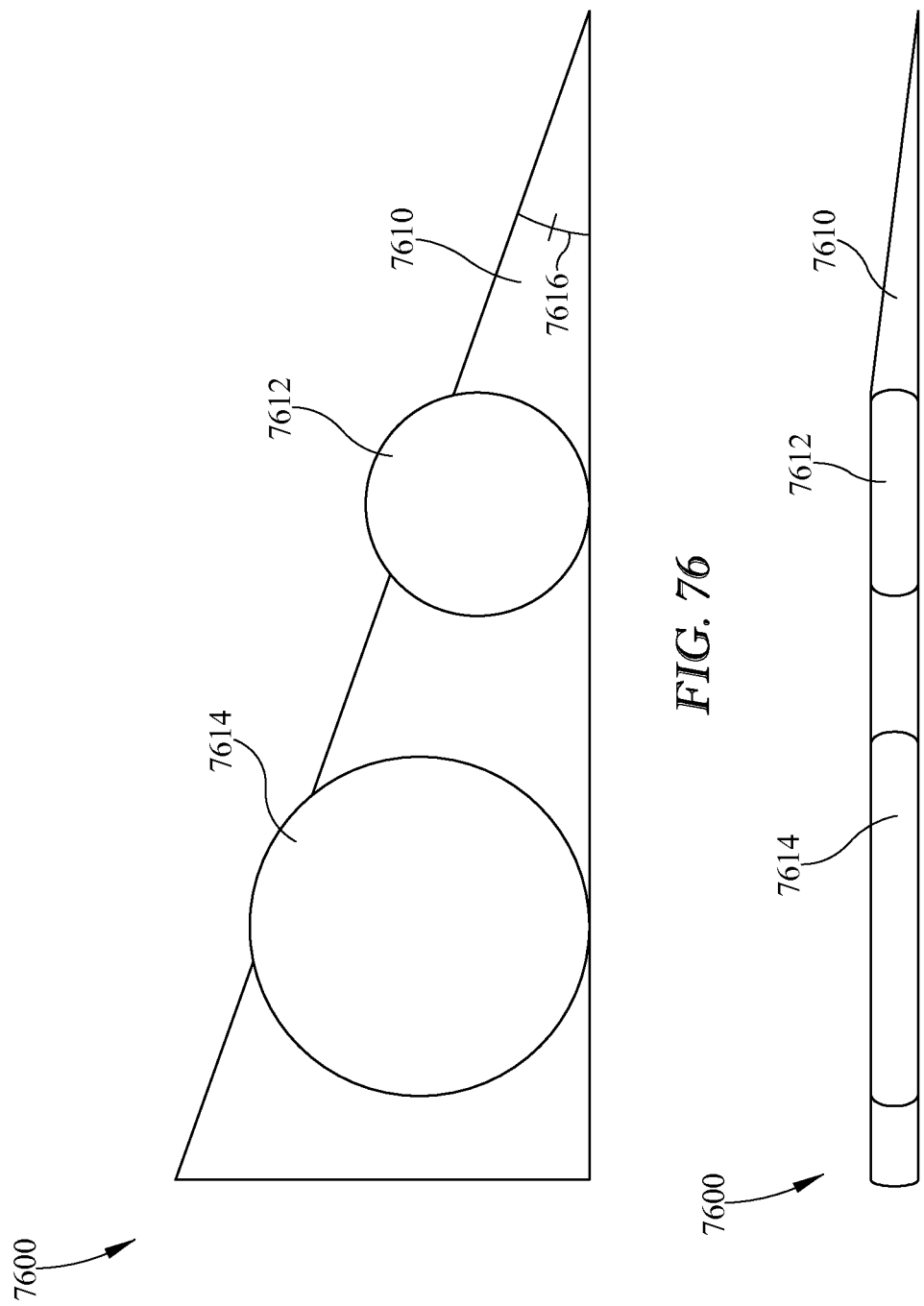

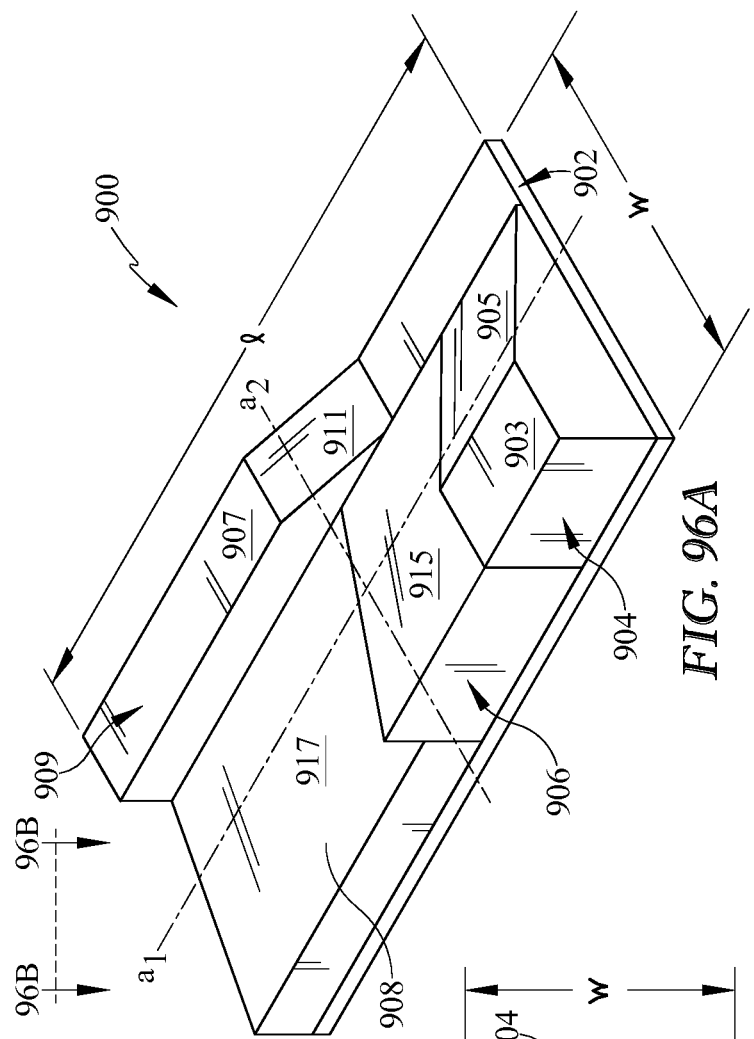
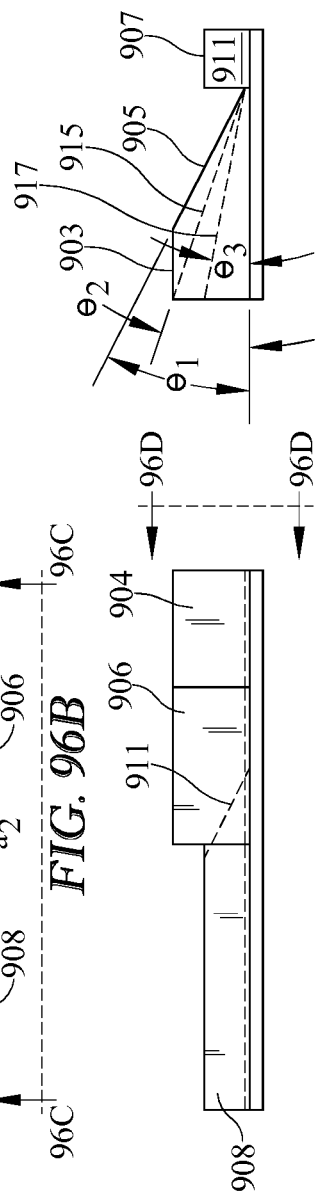
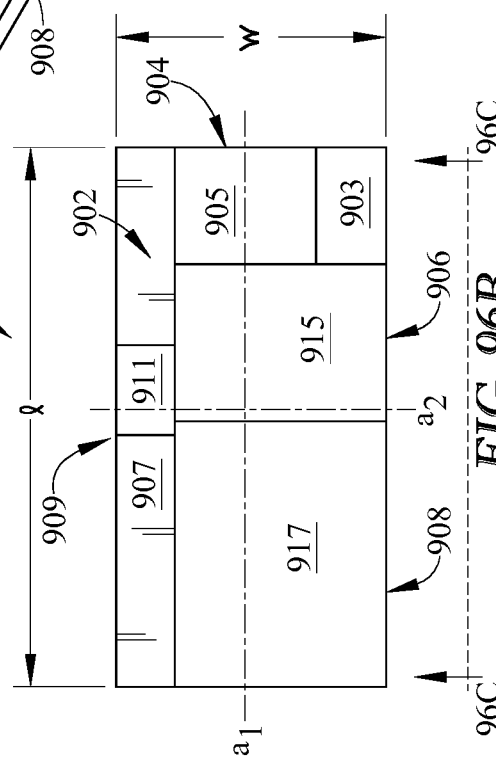
FIG. 96A
FIG. 96D
FIG. 96B
FIG. 96C

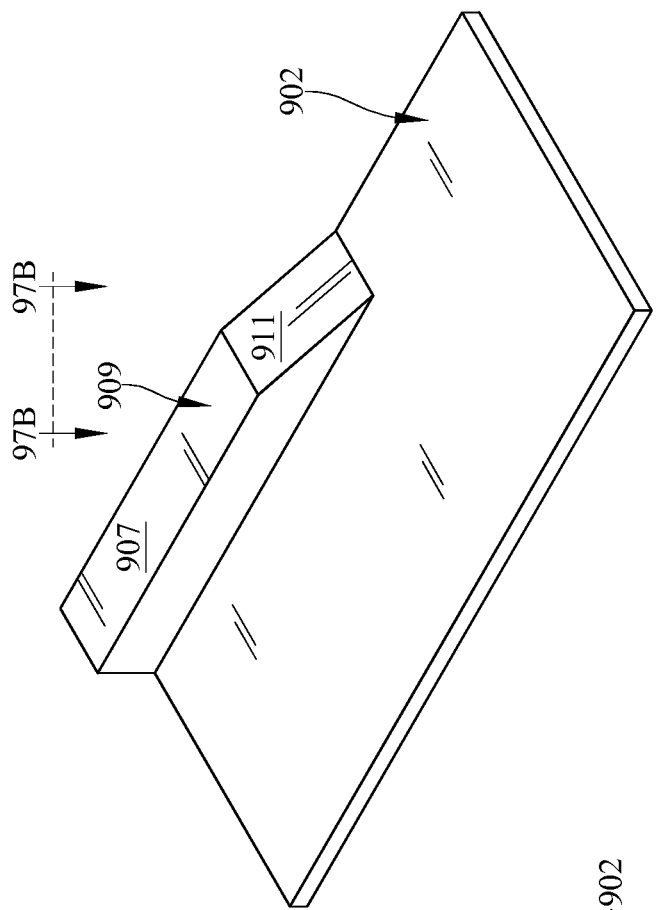
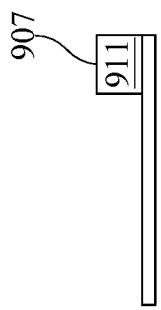
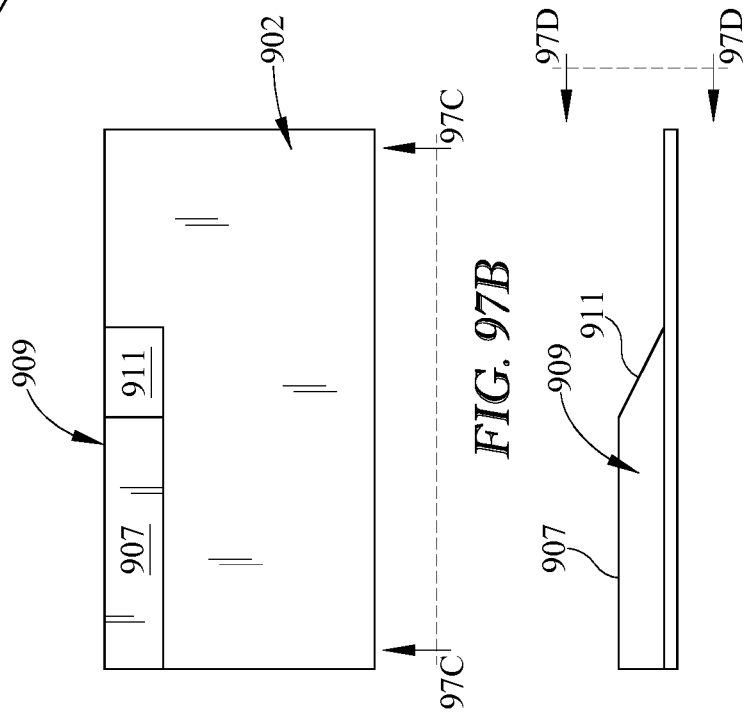
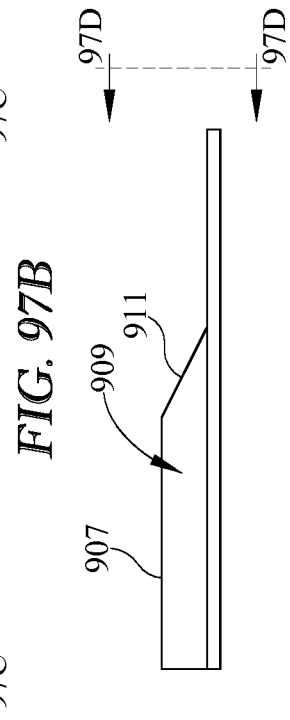
FIG. 97A
FIG. 97B
FIG. 97C
FIG. 97D

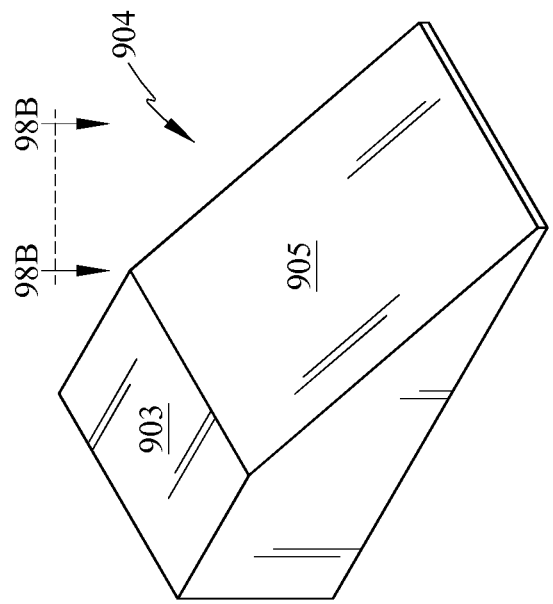
FIG. 98A
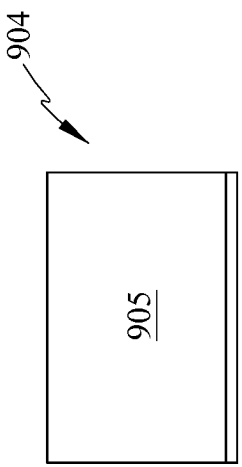
FIG. 98D
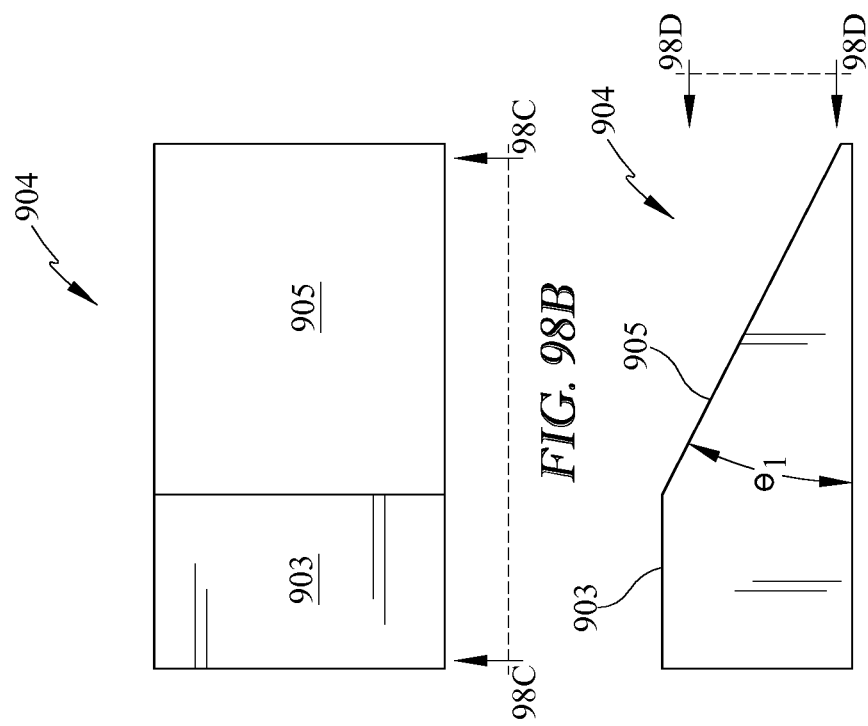
FIG. 98B
FIG. 98C

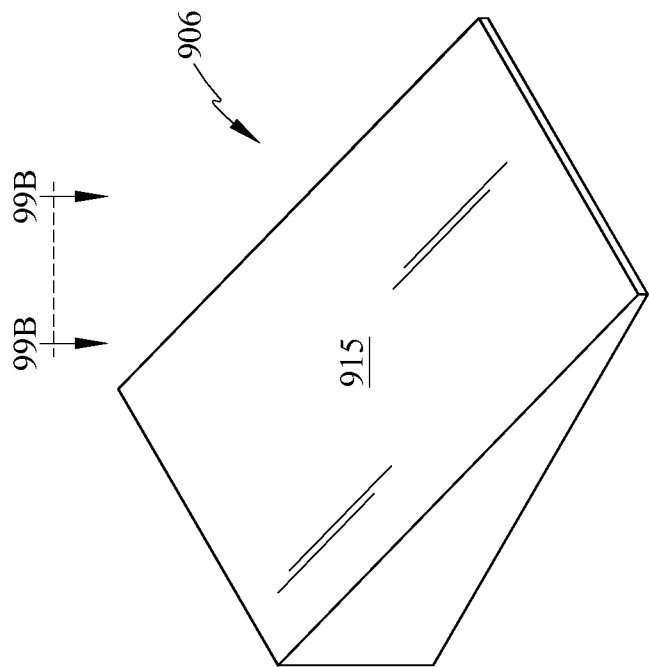
FIG. 99A
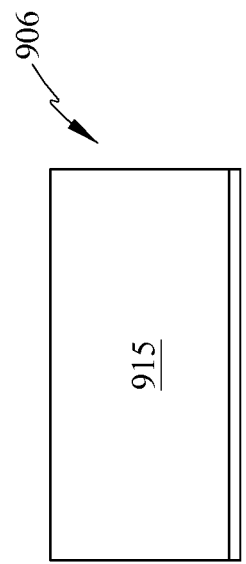
FIG. 99D
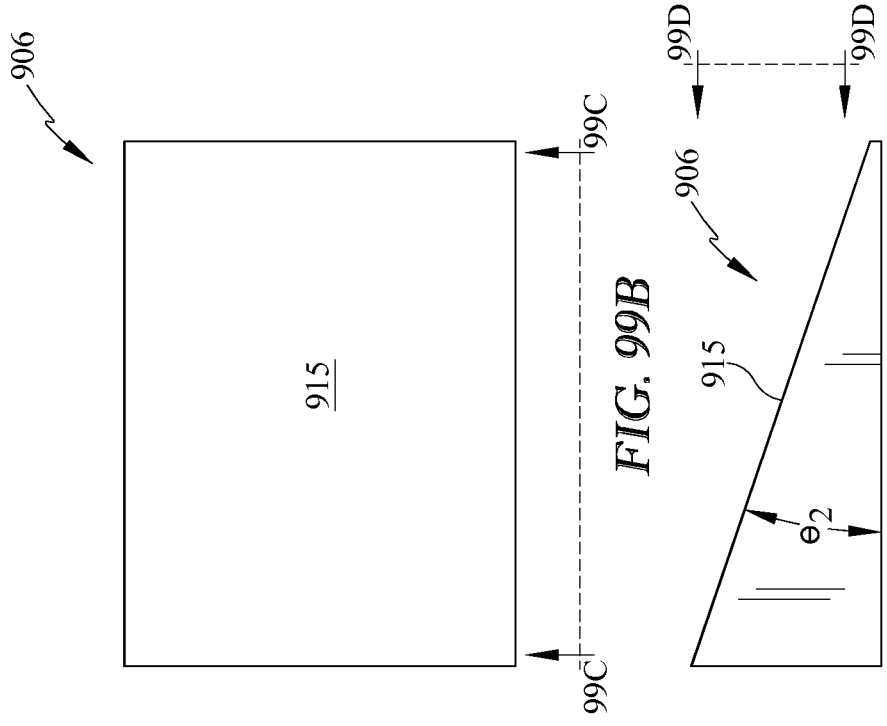
FIG. 99B
FIG. 99C

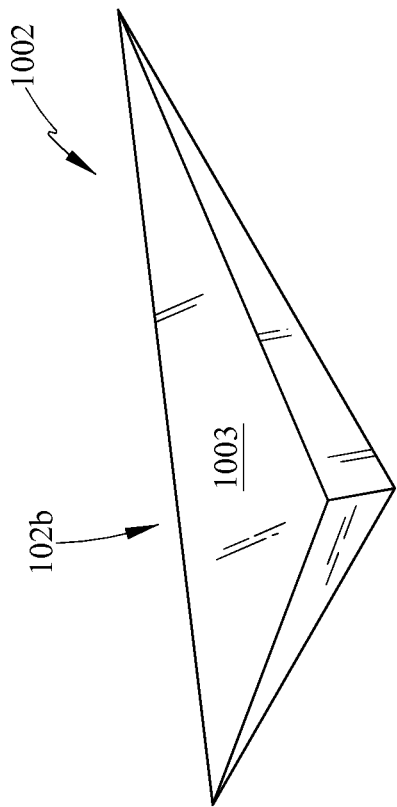
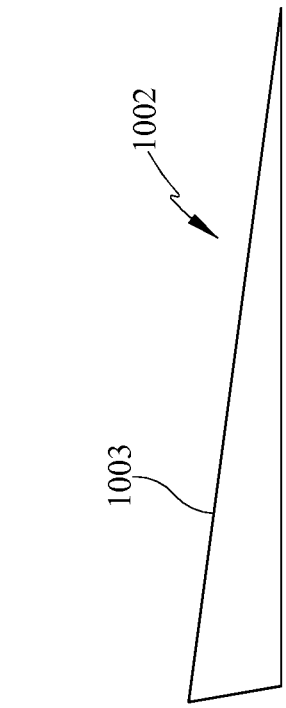
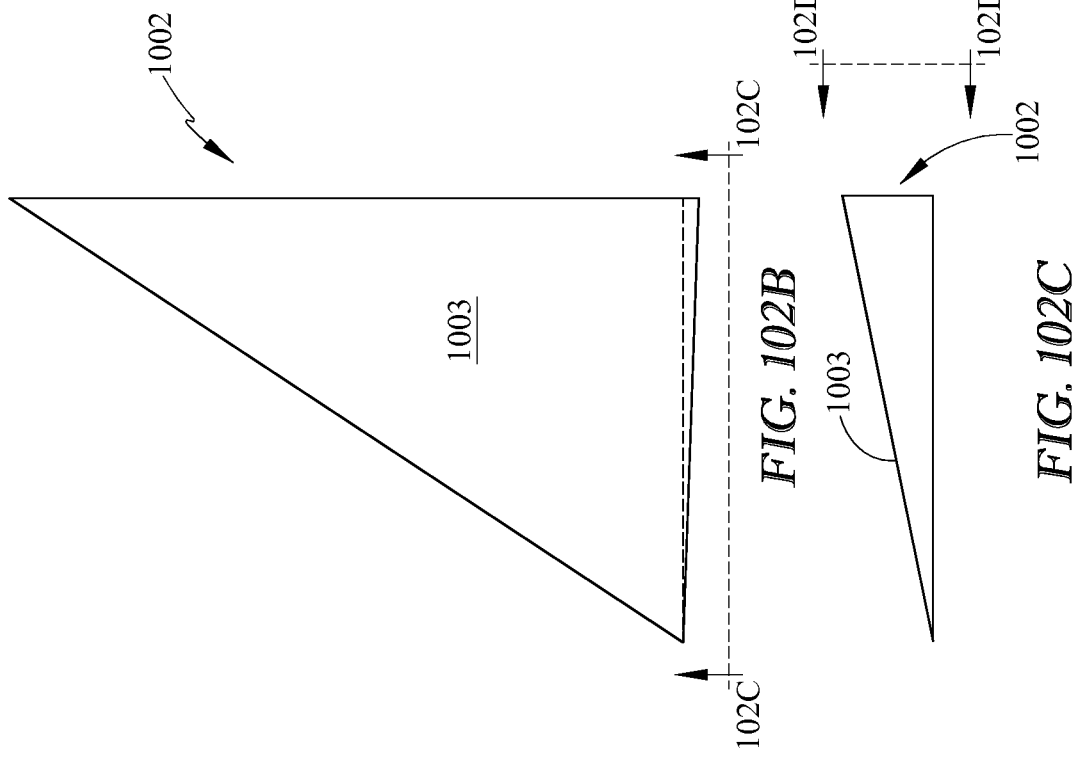

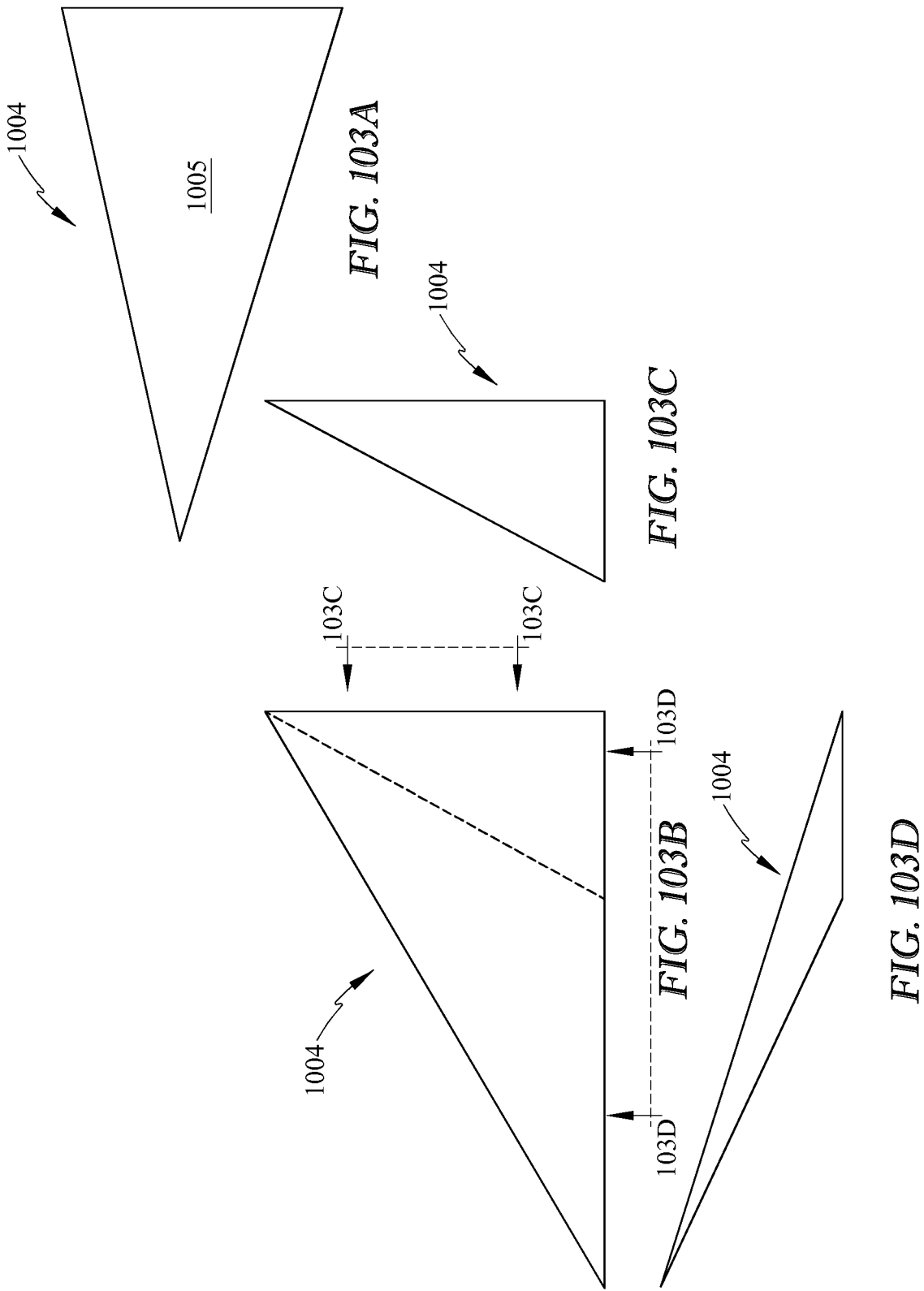

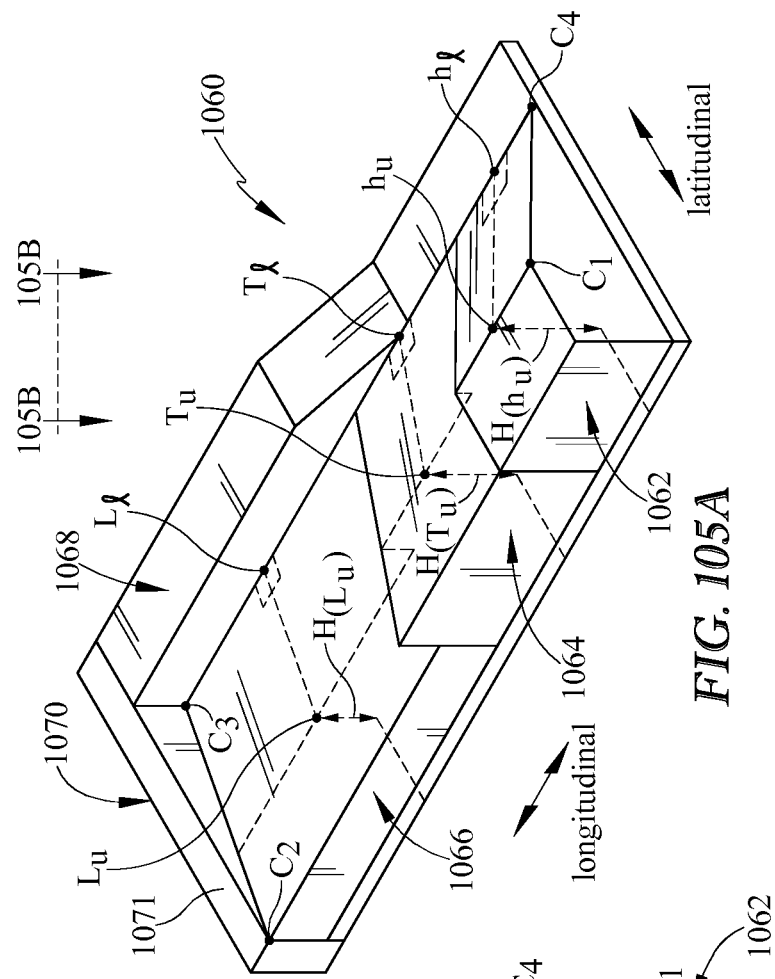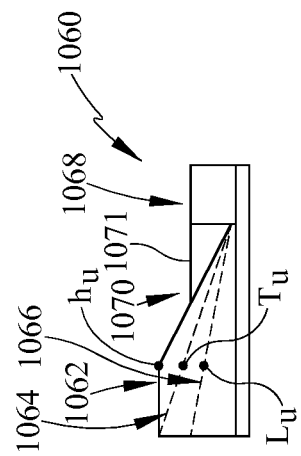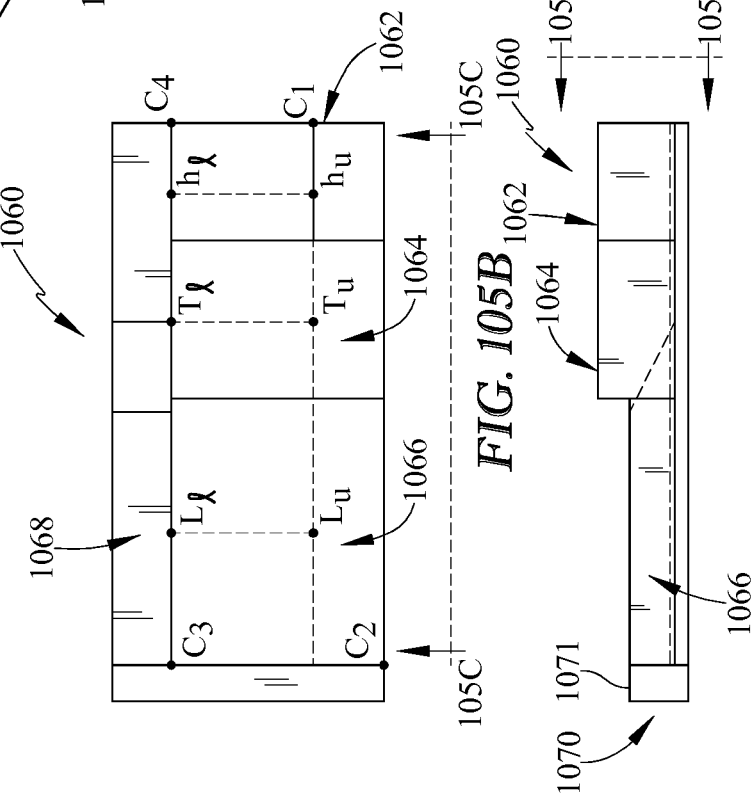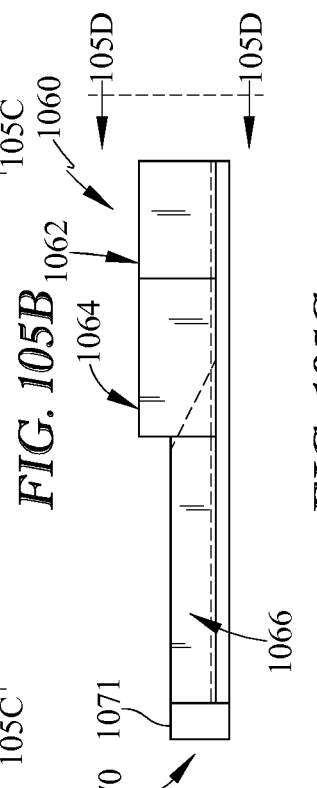
FIG. 105A
FIG. 105D
FIG. 105B
FIG. 105C

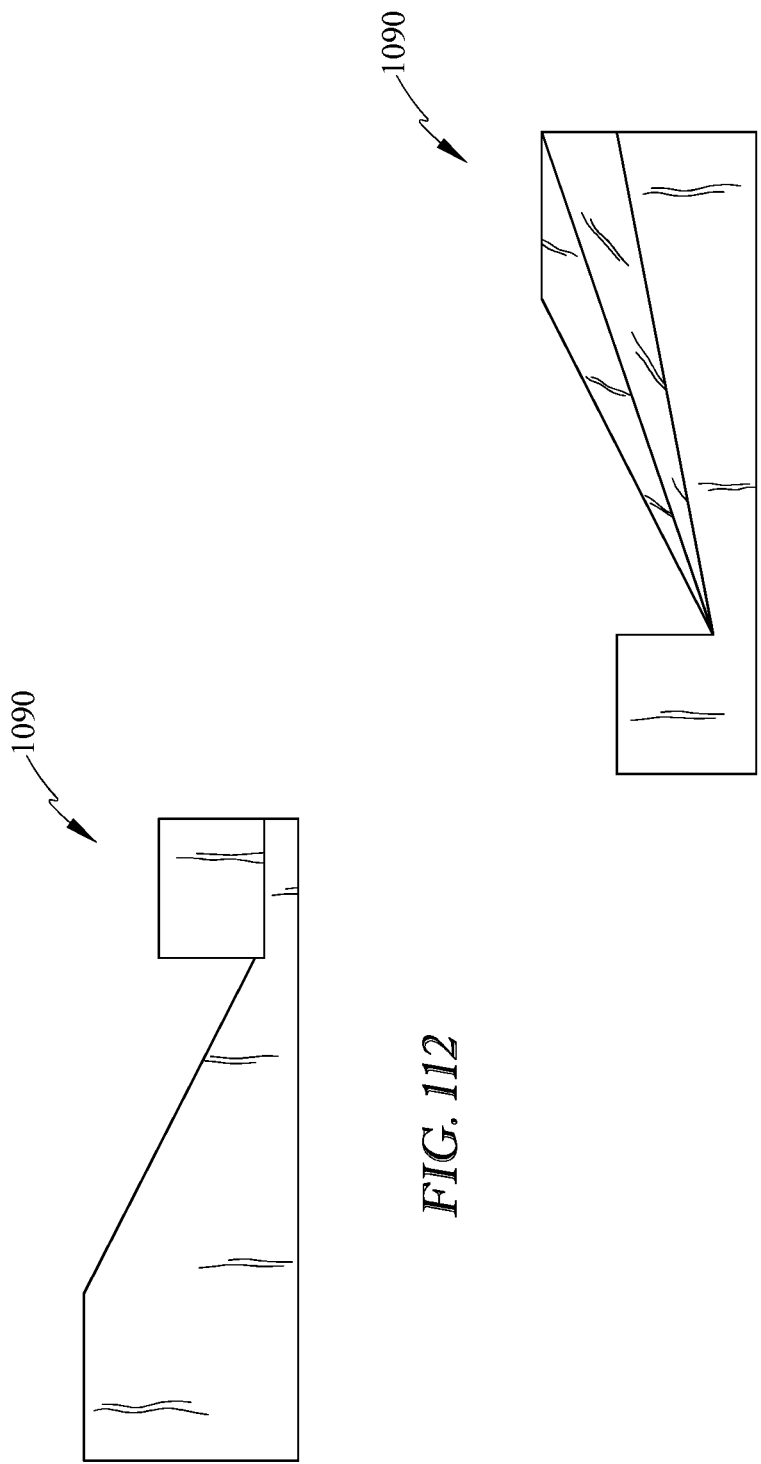

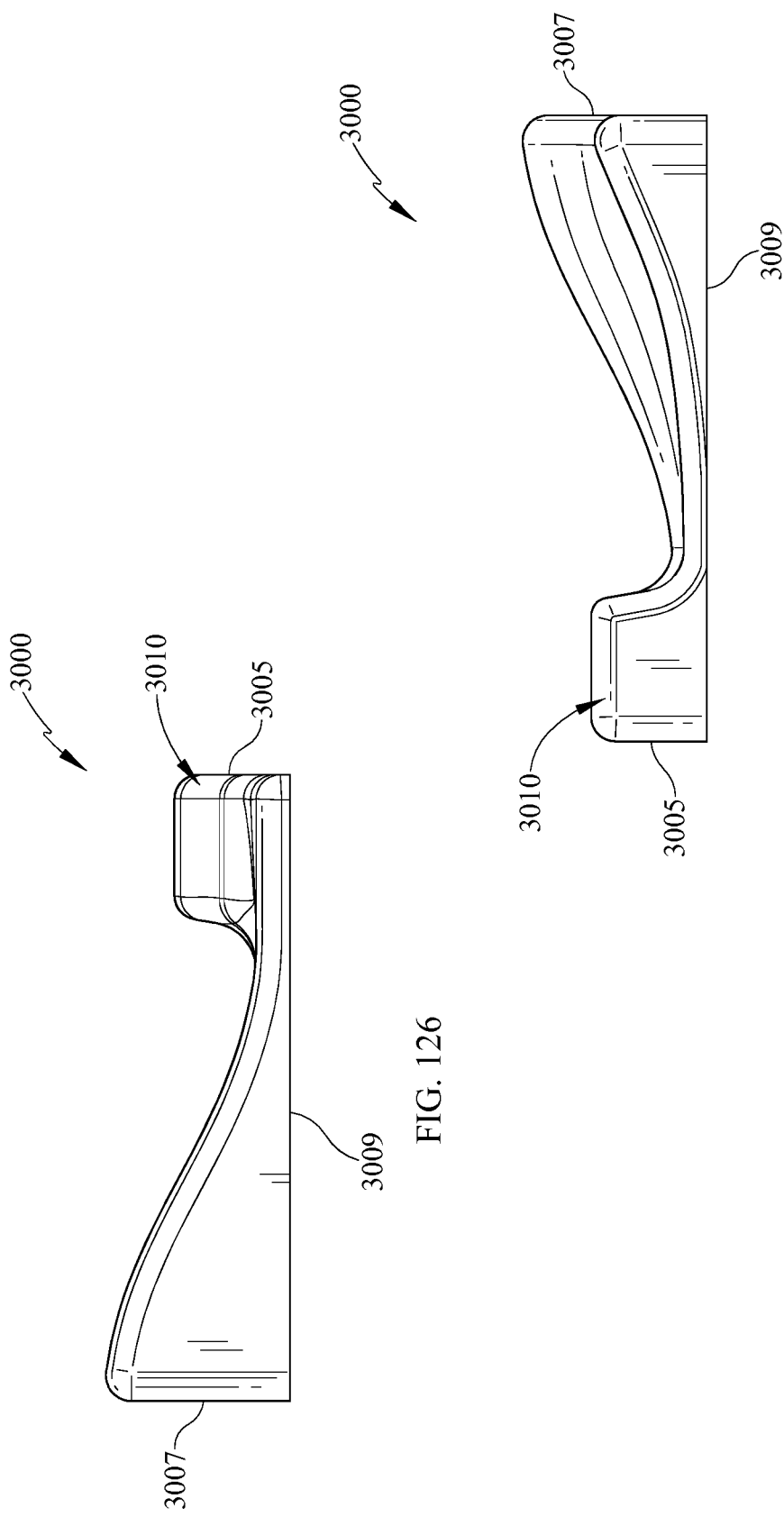

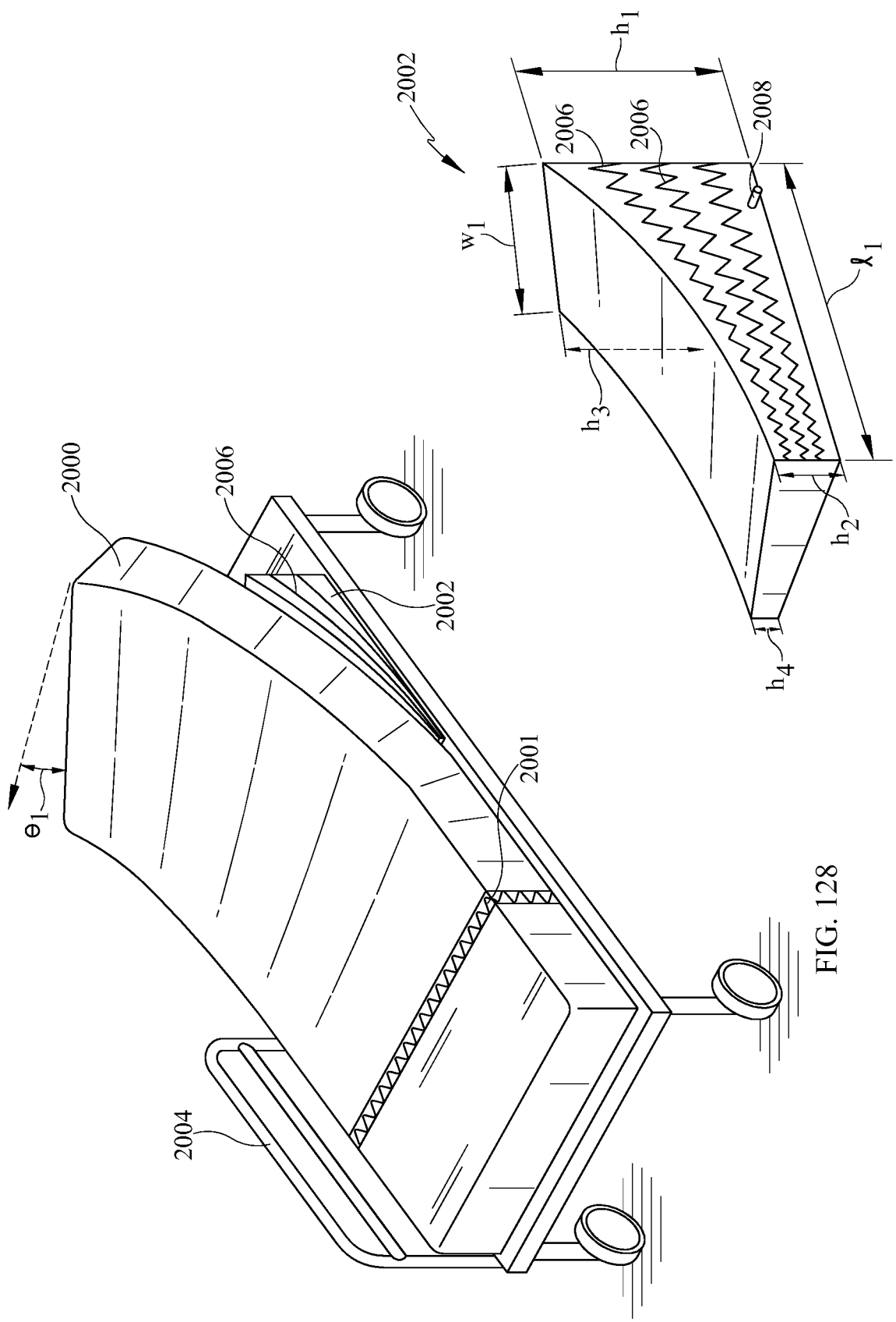

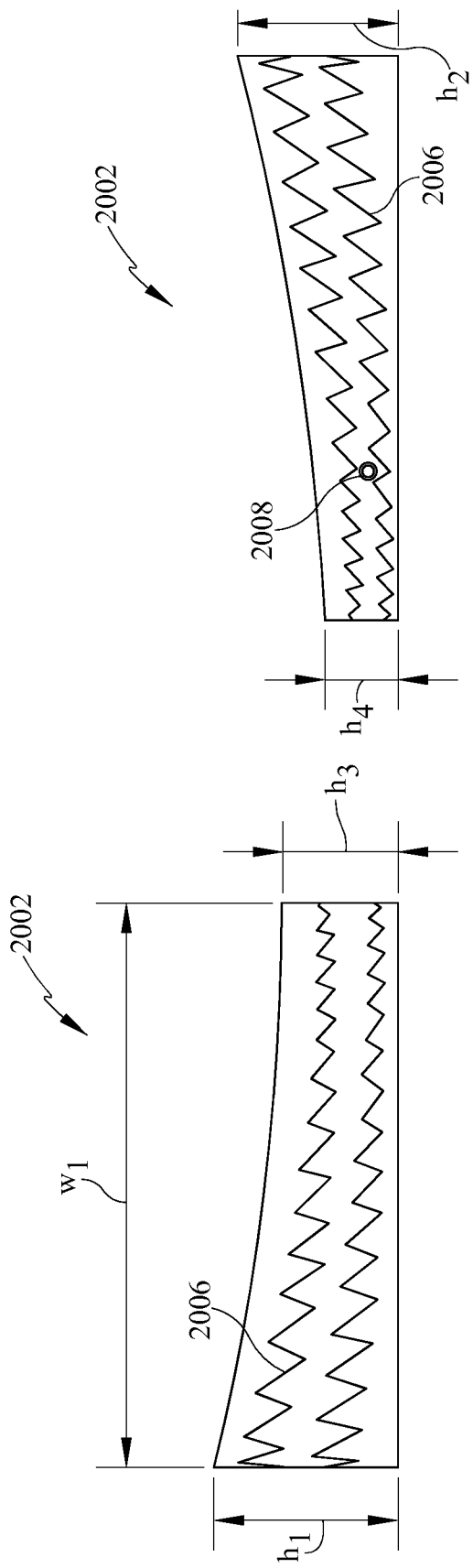
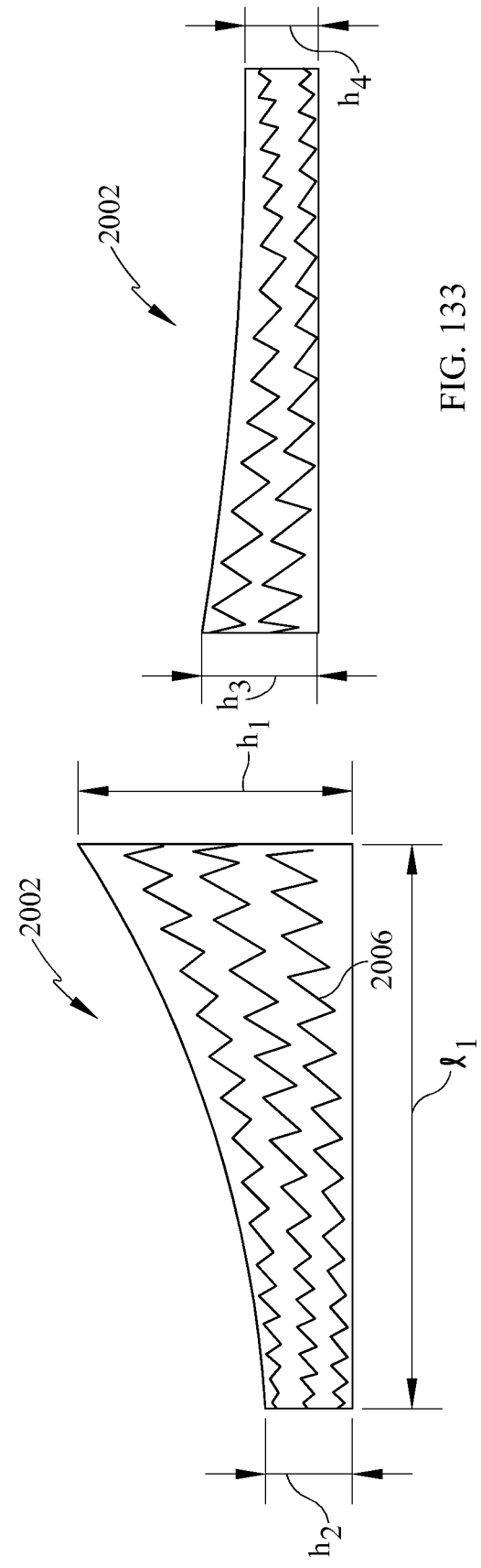
FIG. 130
FIG. 131
FIG. 132
FIG. 133

SYSTEMS, METHODS, AND DEVICES FOR THE TREATMENT OF SLEEP DISORDERS

CROSS REFERENCES TO RELATED APPLICATIONS

The present application is a continuation-in-part of, and claims the benefit of and priority to, PCT/US2013/042313, filed May 22, 2013, entitled Adverse Event Mitigation Systems, Methods, and Devices, and is a continuation-in-part of, and claims the benefit of and priority to, PCT/US2014/018033 filed Feb. 24, 2014, entitled Adverse Event Mitigation Systems, Methods, and Devices, the entire disclosures of which are hereby incorporated herein by reference. PCT/US2013/042313 claims priority to: U.S. Provisional Application Ser. No. 61/650,022, filed on May 22, 2012, entitled ADVERSE EVENT MITIGATION SYSTEMS, METHODS AND DEVICES; U.S. Provisional Application Ser. No. 61/729,868, filed on Nov. 26, 2012, entitled ADVERSE EVENT MITIGATION SYSTEMS, METHODS AND DEVICES; and U.S. Provisional Application Ser. No. 61/792,911, filed on Mar. 15, 2013, entitled DEVICES, SYSTEMS, AND METHODS FOR THE PREVENTION AND TREATMENT OF SLEEP APNEA; the entire disclosures of each are hereby incorporated herein by reference. PCT/US14/018,033 claims priority to U.S. Provisional Application Nos. 61/792,911 filed Mar. 15, 2013 and 61/896,358 filed Oct. 28, 2013, the entire disclosures of which are hereby incorporated by reference herein.

BACKGROUND OF THE DISCLOSURE

This disclosure relates generally to systems, methods, and devices for the treating persons. More particularly, but not exclusively, one illustrative embodiment relates to an apparatus for treating sleep disorders. While various systems have been developed, there is still room for improvement. Thus, a need persists for further contributions in this area of technology.

SUMMARY OF THE DISCLOSURE

According to one embodiment, a mattress is provided having a longitudinal length defined by a longitudinal axis of the mattress when the mattress is in its most horizontal position and a lateral width defined by a lateral axis of the mattress when the mattress is in its most horizontal position. The mattress comprises a head section having a head support surface to support at least a portion of a person's head. At least a portion of the head support surface is generally sloped in the lateral direction at a first angle relative the lateral axis. The first angle is from about 15 to about 30 degrees. The mattress further comprises a torso section having a torso support surface to support at least a portion of a person's torso. At least a portion of the torso support surface is generally sloped in the lateral direction at a second angle relative to the lateral axis. The second angle is from about 1 to about 25 degrees less than the first angle.

In accordance with another embodiment, a person support apparatus is provided having a longitudinal length from its head end to its foot end, and a lateral width from side to side. The person support apparatus comprises a head section having a head support surface to support at least a portion of a person's head. At least a portion of the head support surface is generally sloped downward in a lateral direction. The person support apparatus further comprises a torso section having a torso support surface to support a least a portion of the person's torso. At least a portion of the torso support surface is generally sloped downward in the lateral direction, and the slope of the torso support surface is different from the slope of the head support surface. The apparatus further comprises a bolster extending along a side of person support apparatus and extending above the side.

Furthermore, a sleeping apparatus is provided in one embodiment having a longitudinal centerline. The apparatus comprises at least one bottom surface that is generally horizontal when the person support apparatus is in a generally horizontal position for sleeping. The apparatus comprises a support section sized to support a person's head or torso. The support section has a top surface extending from a first side of the longitudinal centerline to a second side of the longitudinal centerline. The top surface slopes generally laterally downwardly relative to horizontal, at an angle of at least approximately 10 degrees, and slopes generally longitudinally downwardly relative to horizontal, when the person support apparatus is in a horizontal position.

In one embodiment, a sleep support apparatus is provided having a longitudinal axis when in a horizontal position. The sleep support apparatus comprises a body part support section. The body support section comprises at least one surface configured to support at least a portion of a person's body during sleep. The body support section permits the person's head to turn sideways substantially in at least one direction, but at the same time urges the longitudinal center plane of the person's face to rest at a first angle during sleep relative to a vertical plane extending upwardly against the direction of gravity and along the longitudinal axis of the sleep support apparatus. The first angle is equal to or greater than about +/−35 degrees from the upwardly extending vertical plane, and up to about +130 degrees, whether the patient is supported generally on the patient's back/rear, on the patient's side, or on the patient's front side and/or stomach.

In one embodiment, a sleep apparatus is provided having a longitudinal dimension moving from a head end to a foot end, and a lateral dimension moving from a first side to a second side when in a generally horizontal position for sleeping. The apparatus comprises a head support section sized to support a person's head. The head support section is generally laterally sloped moving from the first side toward the second side. The apparatus further comprises a torso support section sized to support a person's torso. The torso support section is generally laterally sloped moving from the first side toward the second side. The sleep apparatus is also generally longitudinally sloped moving from the head end to the foot end. In some embodiments, the slopes are achieved by linear surfaces, non-linear surfaces, or stepped surfaces. In some embodiments, the sleep apparatus further comprises a leg support section sized to support a person's legs, and the leg support section is generally laterally sloped moving from the first side toward the second side.

Additional features and embodiments, alone or in combination with any other features of any other embodiments, including those listed above and those listed in the claims, and those described in detail below, can comprise patentable subject matter. Other features and embodiments will become apparent to those skilled in the art upon consideration of the following detailed description of illustrative embodiments. Any feature or aspect disclosed herein, or any embodiment disclosed herein, can be combined with any other feature or aspect or embodiment disclosed herein. One or more features of any embodiment disclosed herein can be combined with one or more features of any other embodiment disclosed herein, and other features can be removed or added to create still further embodiments. Accordingly, many other features, aspects, and embodiments are possible without departing from the spirit, scope, and principles of this document.

BRIEF DESCRIPTION OF THE DRAWINGS

Referring now to the illustrative examples in the drawings, wherein like numerals represent the same or similar elements throughout:

FIG. 3 is a cross-sectional side view of the deck of the upper frame and the person support surface of FIG. 2;

FIG. 4 is a cross-sectional view of a portion of the person support surface of FIG. 2 showing the layers of the person support surface;

FIG. 11 is a perspective view of an exemplary support system supporting a user on a sleep surface defined by the support system;

FIG. 12 is a perspective side view of the support system shown in FIG. 11;

FIG. 13 is a side elevational view of the support system shown in FIG. 11;

FIG. 14 is a front elevational view of the support system shown in FIG. 11;

FIG. 15 is a schematic view of an exemplary support system;

FIG. 16 is a partial front view of the support system shown in FIG. 15 illustrating a lateral rotation of planes;

FIG. 17 is a partial side view of the support system shown in FIG. 15 illustrating a longitudinal rotation of planes;

FIG. 18 shows an exemplary control system operatively coupled to the support system shown in FIG. 15;

FIGS. 38-41 illustrate an exemplary heuristic control of an apnea therapy surface function;

FIG. 49 is a top view of an exemplary chest constriction device;

FIG. 50 is a top view of a constriction device of the chest constriction device shown in FIG. 49;

FIG. 51 is a top view of a portion of the constriction device shown in FIG. 50 with the lever in a relaxed position;

FIG. 52 is a top view of a portion of the constriction device shown in FIG. 50 with the lever in a constricted position;

FIGS. 59-60 are simplified end views of at least one embodiment of a support section for the person support apparatus of FIGS. 53-54, showing different lateral tilt angles of a support surface of the support section;

FIGS. 71-74 are simplified sectional views of various embodiments of a support section similar in some respects to the support section of FIG. 55, where the sectional views are similar to the view of FIG. 56;

FIGS. 76-77 are simplified side views of at least one embodiment of a support section for the person support apparatus of FIG. 53, showing a lateral tilt position and a substantially flat position, respectively;

FIG. 96a is a perspective view of a mattress according to another illustrative embodiment of the present disclosure;

FIG. 96b is a top view of the illustrative embodiment of FIG. 96a looking in the direction labeled 96b in FIG. 96a.

FIG. 96c is a longitudinal side view (viewed along the longer side) of the illustrative embodiment of FIG. 96a, looking in the direction labeled 96c in FIG. 96b;

FIG. 96d is a lateral side view (viewed along the shorter side, or end) of the illustrative embodiment of FIG. 96a, looking in the direction labeled 96d in FIG. 96c;

FIG. 97a is a perspective view of the base, having a side bolster on top of it, of the illustrative embodiment of FIG. 96;

FIG. 97b is a top view of the base and bolster of FIG. 97a, looking in the direction labeled 97b in FIG. 97a;

FIG. 97c is a left side view of the base and bolster of FIG. 97a, looking in the direction labeled 97c in FIG. 97b;

FIG. 97d is a head end view of the base and bolster of FIG. 97a, looking in the direction labeled 97d in FIG. 97c;

FIG. 98a is a perspective view of the head section of the illustrative embodiment of FIG. 96;

FIG. 98b is a top view of the head section of FIG. 98a, looking in the direction labeled 98b in FIG. 98a;

FIG. 98c is an end view of the head section of FIG. 98a, looking in the direction labeled 98c in FIG. 98b;

FIG. 98d is an end view of the head section of FIG. 97a, looking in the direction labeled 98d in FIG. 98c;

FIG. 99a is a perspective view of the torso section of the illustrative embodiment of FIG. 96;

FIG. 99b is a top view of the torso section of FIG. 99a, looking in the direction labeled 99b in FIG. 99a;

FIG. 99c is a side view of the torso section of FIG. 99a, looking in the direction labeled 99c in FIG. 99b;

FIG. 99d is a side view of the torso section of FIG. 99a, looking in the direction labeled 99d in FIG. 99c;

FIG. 100b is a top view of the leg section of FIG. 100a, looking in the direction labeled 100b in FIG. 100a;

FIG. 102a is a perspective view of the first transition section of the illustrative embodiment of FIG. 101;

FIG. 102b is a top view of the first transition section of FIG. 101, looking in the direction labeled 102b in FIG. 102a;

FIG. 102c is a side view of the first transition section of FIG. 101, looking in the direction labeled 102c in FIG. 102b;

FIG. 102d is a side view of the first transition section of FIG. 101, looking in the direction labeled 102d in FIG. 102c;

FIG. 103a is a perspective view of the second transition section of the illustrative embodiment of FIG. 101;

FIG. 103b is a top view of the second transition section of FIG. 101, looking in the direction labeled 103b in FIG. 103a;

FIG. 103c is a side view of the second transition section of FIG. 101, looking in the direction labeled 103c in FIG. 103b;

FIG. 103d is a side view of the second transition section of FIG. 101, looking in the direction labeled 103d in FIG. 103b;

FIG. 105a is a perspective view of a mattress according to another illustrative embodiment of the present disclosure;

FIG. 105b is a top view of the illustrative embodiment of FIG. 105a looking in the direction labeled 105b in FIG. 105a.

FIG. 105c is a longitudinal side view (viewed along the longer side) of the illustrative embodiment of FIG. 105a, looking in the direction labeled 105c in FIG. 105b;

FIG. 105d is a lateral side view (viewed along the shorter side, or end) of the illustrative embodiment of FIG. 105a, looking in the direction labeled 105d in FIG. 105c;

FIG. 106b is a top view of the illustrative embodiment of FIG. 106a looking in the direction labeled 106b in FIG. 106a.

FIG. 108 is a top plan view of the mattress of FIG. 107;

FIG. 109 is a back plan view of the mattress of FIG. 107;

FIG. 110 is a first side elevation view of the mattress of FIG. 107;

FIG. 111 is a second side elevation view of the mattress of FIG. 107;

FIG. 112 is a head end elevation view of the mattress of FIG. 107;

FIG. 113 is a foot end elevation view of the mattress of FIG. 107;

FIG. 114 is a top, foot end, perspective view of a mattress design according to another embodiment;

FIG. 115 is a top plan view of the mattress of FIG. 114;

FIG. 116 is a back plan view of the mattress of FIG. 114;

FIG. 117 is a first side elevation view of the mattress of FIG. 114;

FIG. 118 is a second side elevation view of the mattress of FIG. 114;

FIG. 119 is a head end elevation view of the mattress of FIG. 114;

Figure 114:
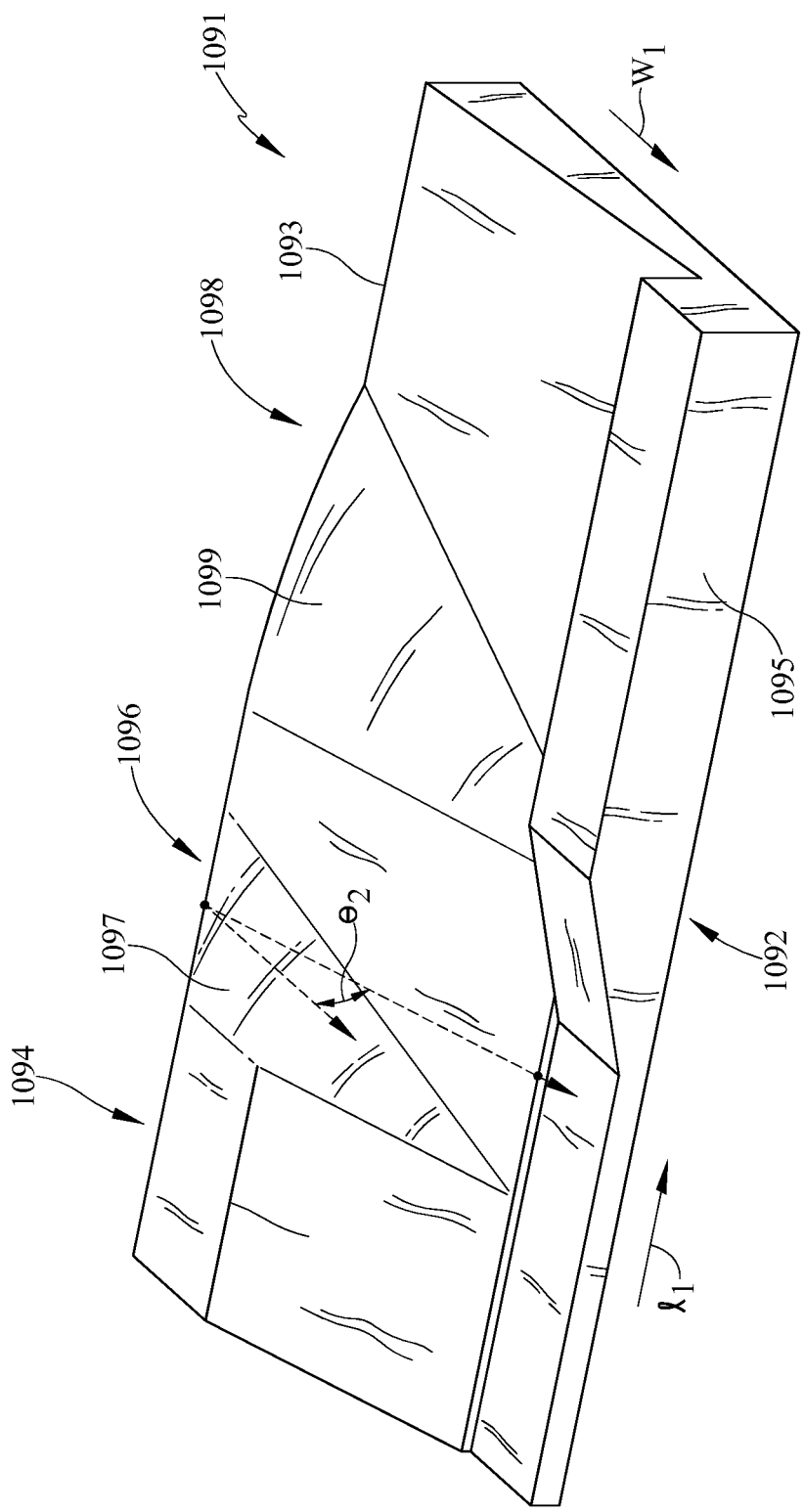
Figure 115:
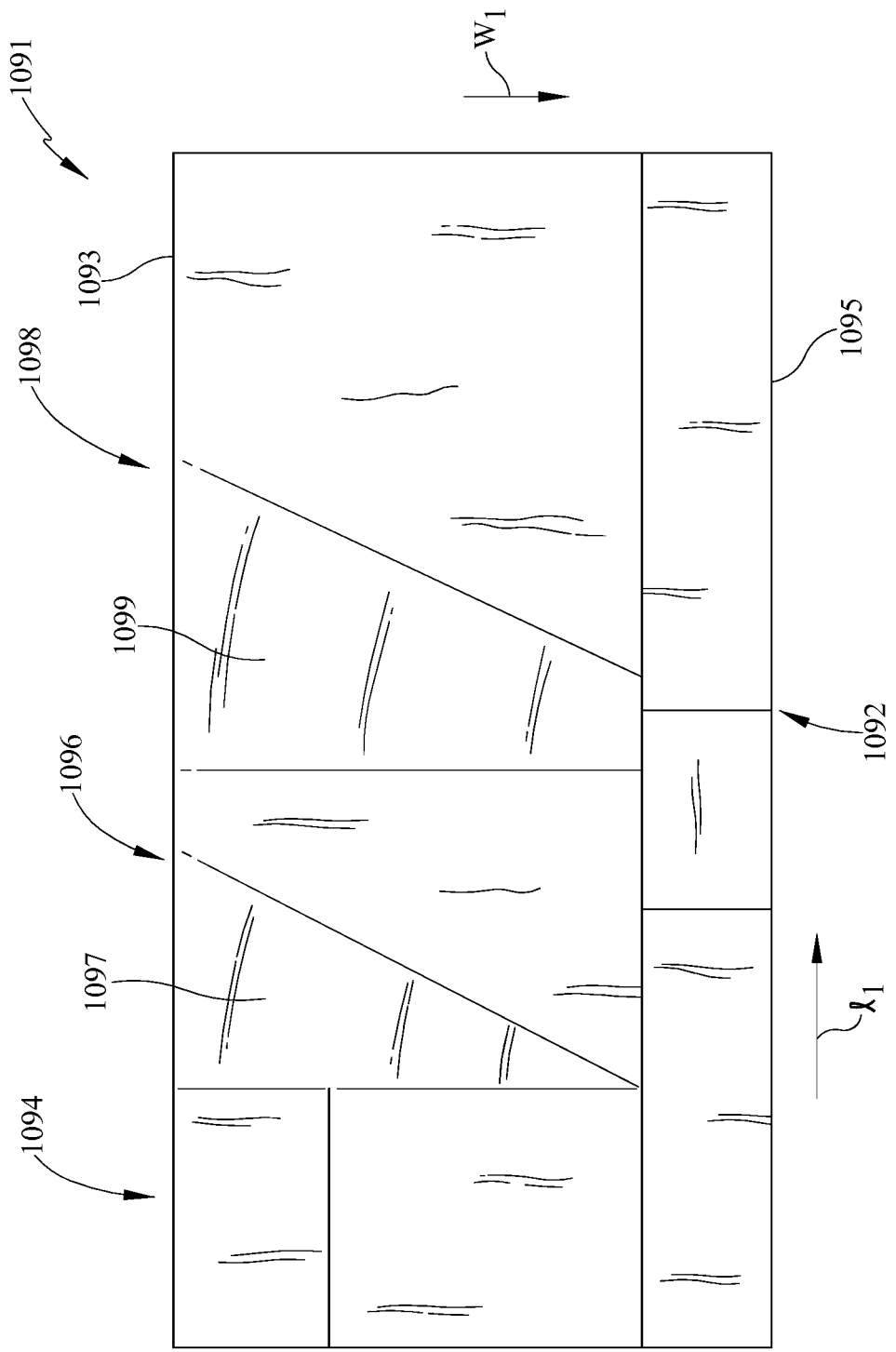
Figure 116:
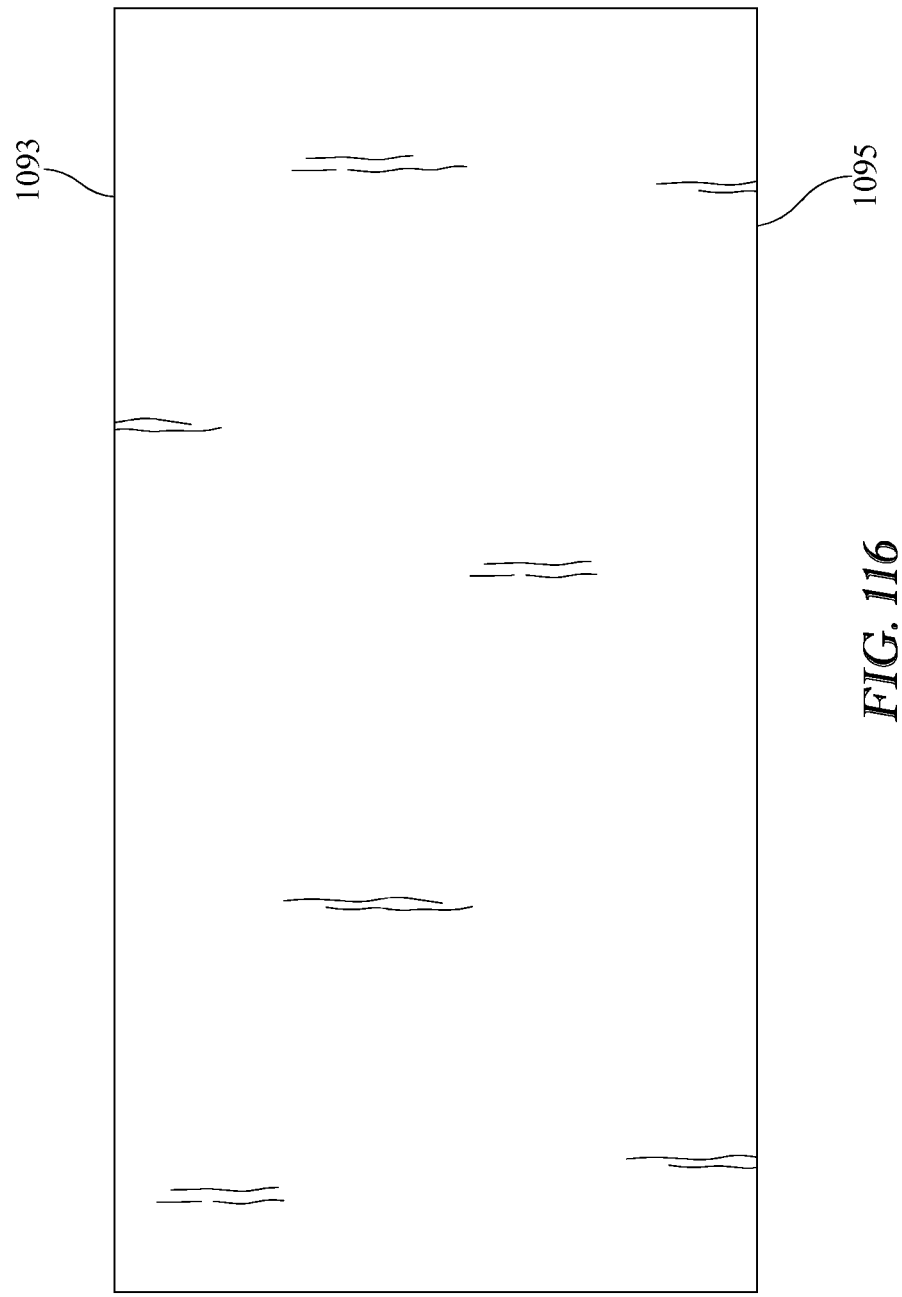
Figure 117:
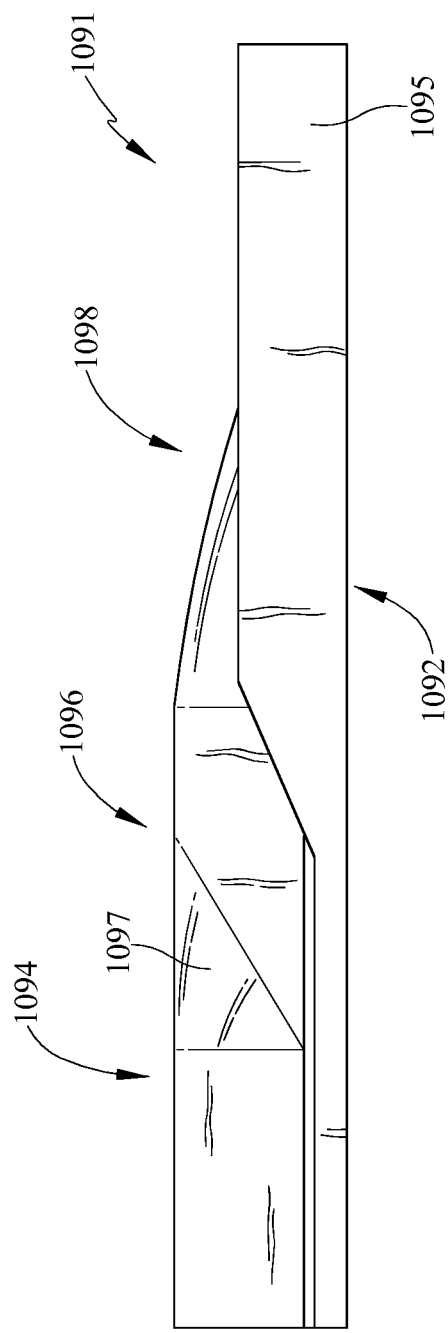
Figure 118:
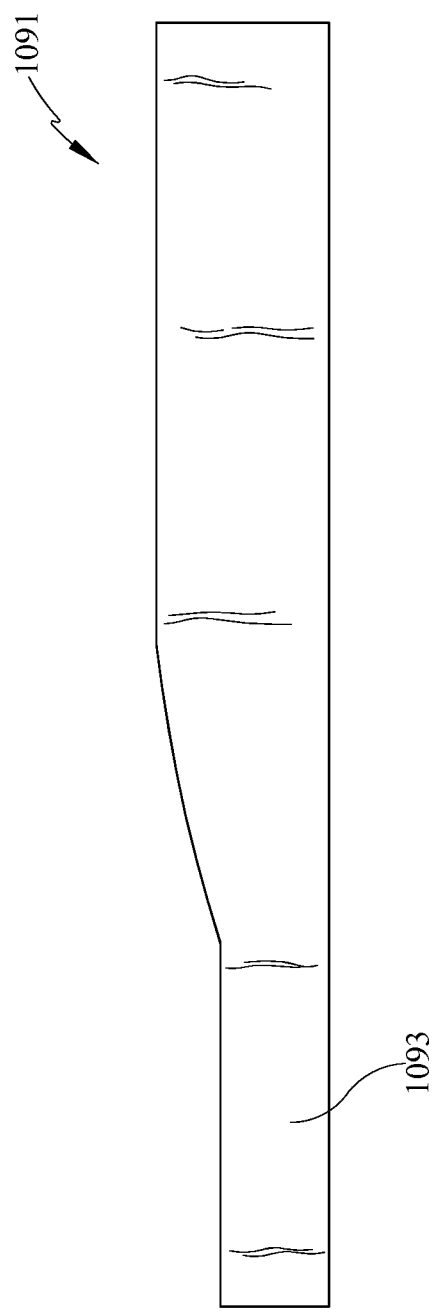
Figures 119, 120:
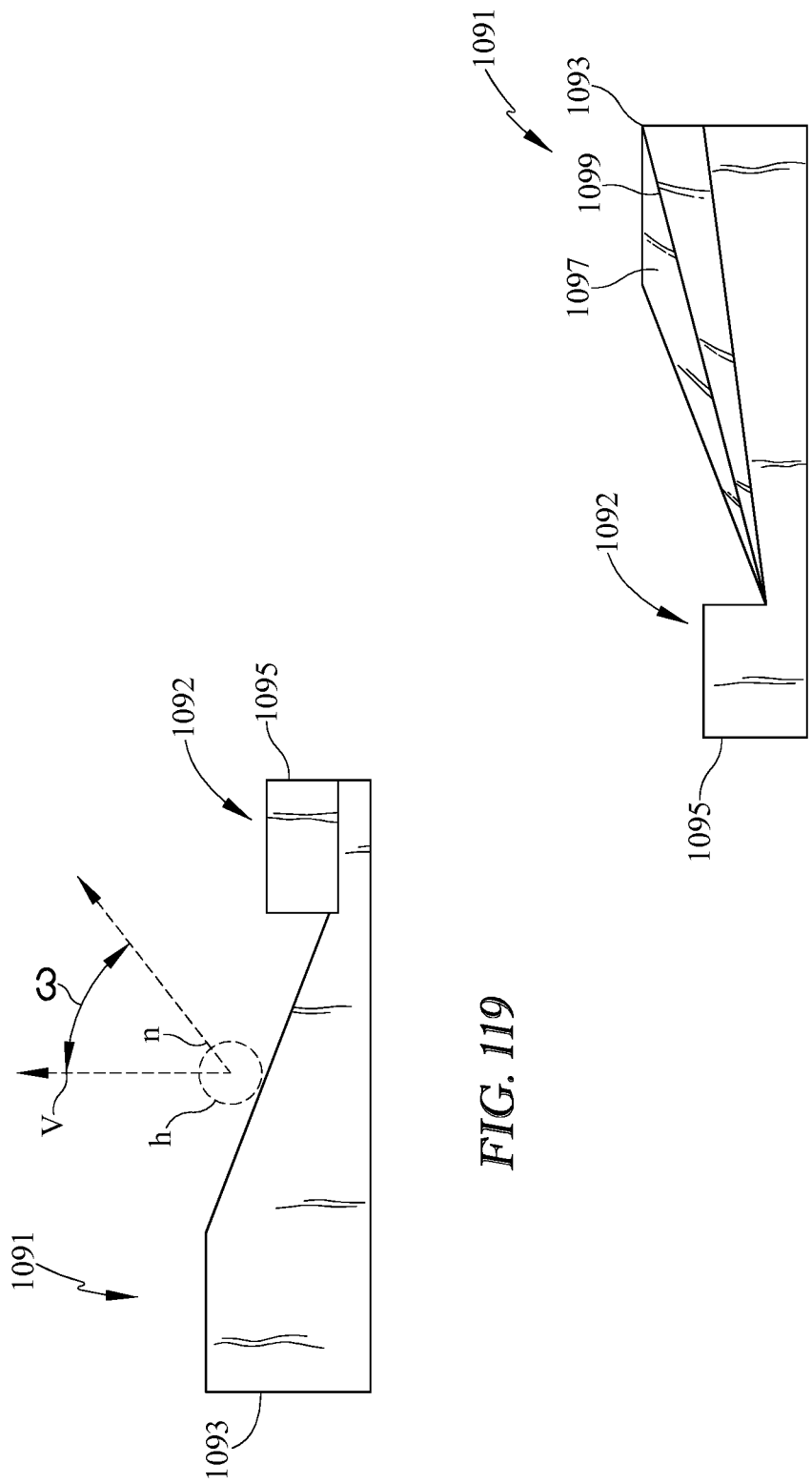
Figure 121:
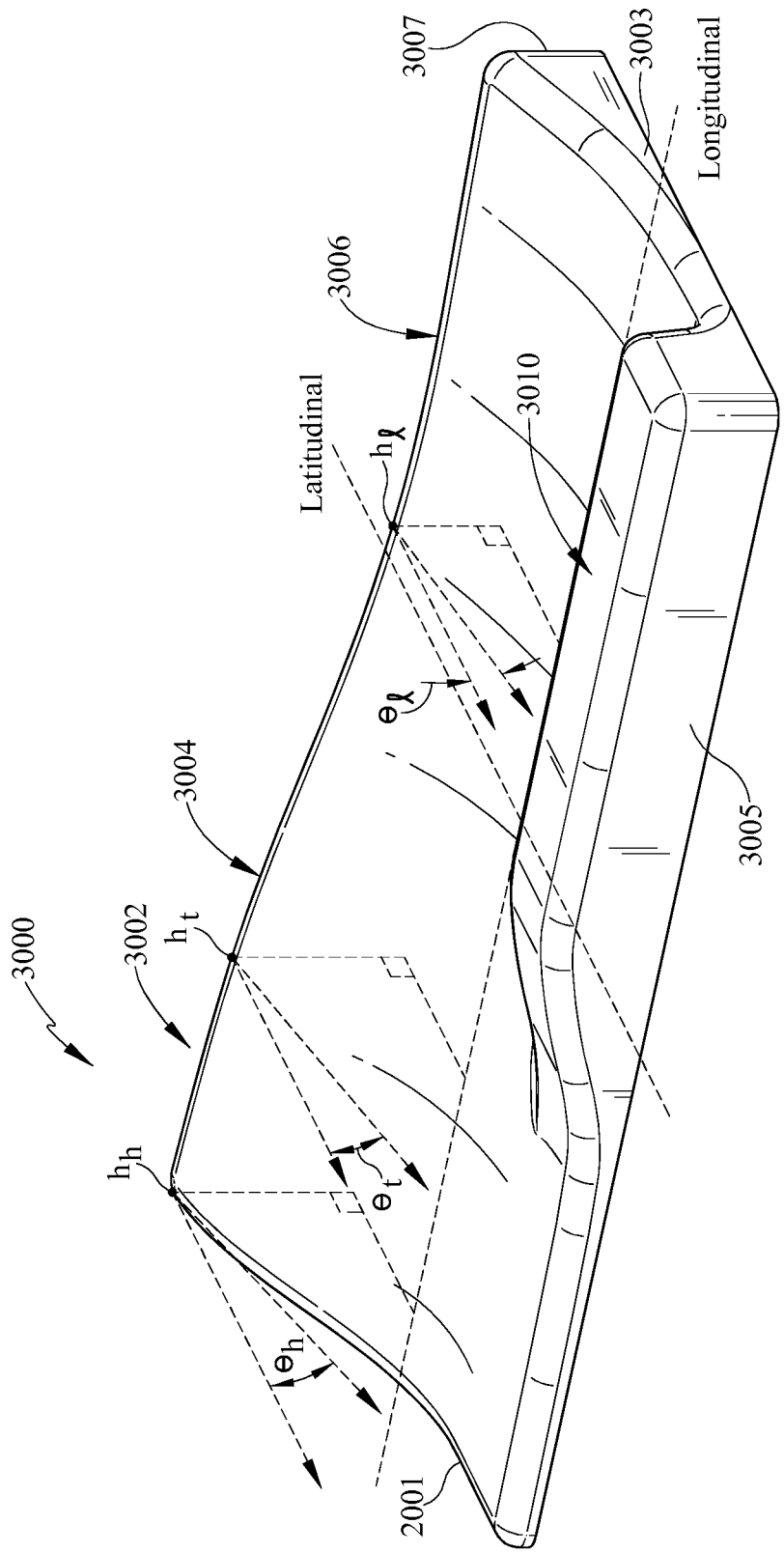
Figure 122:
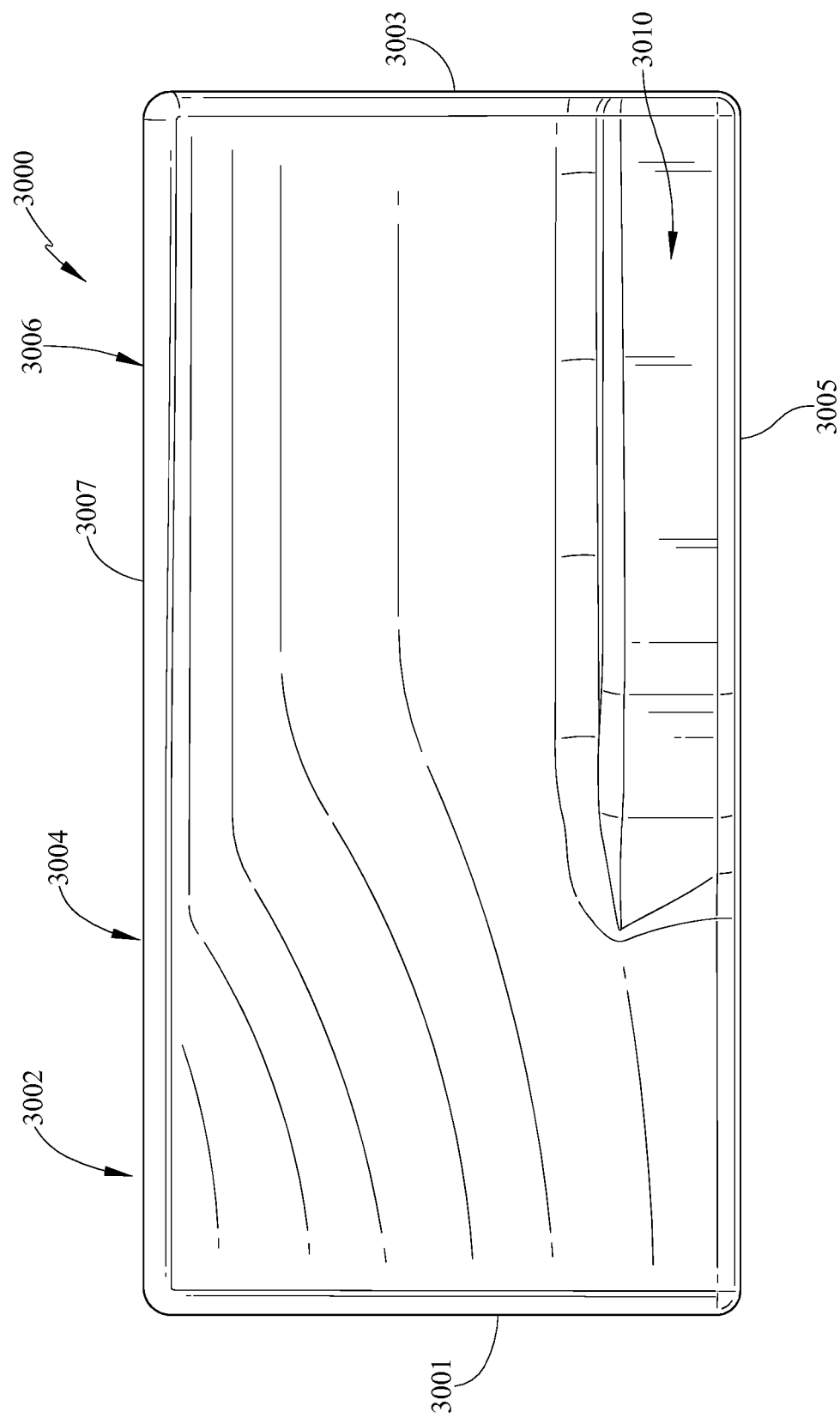
Figure 123:
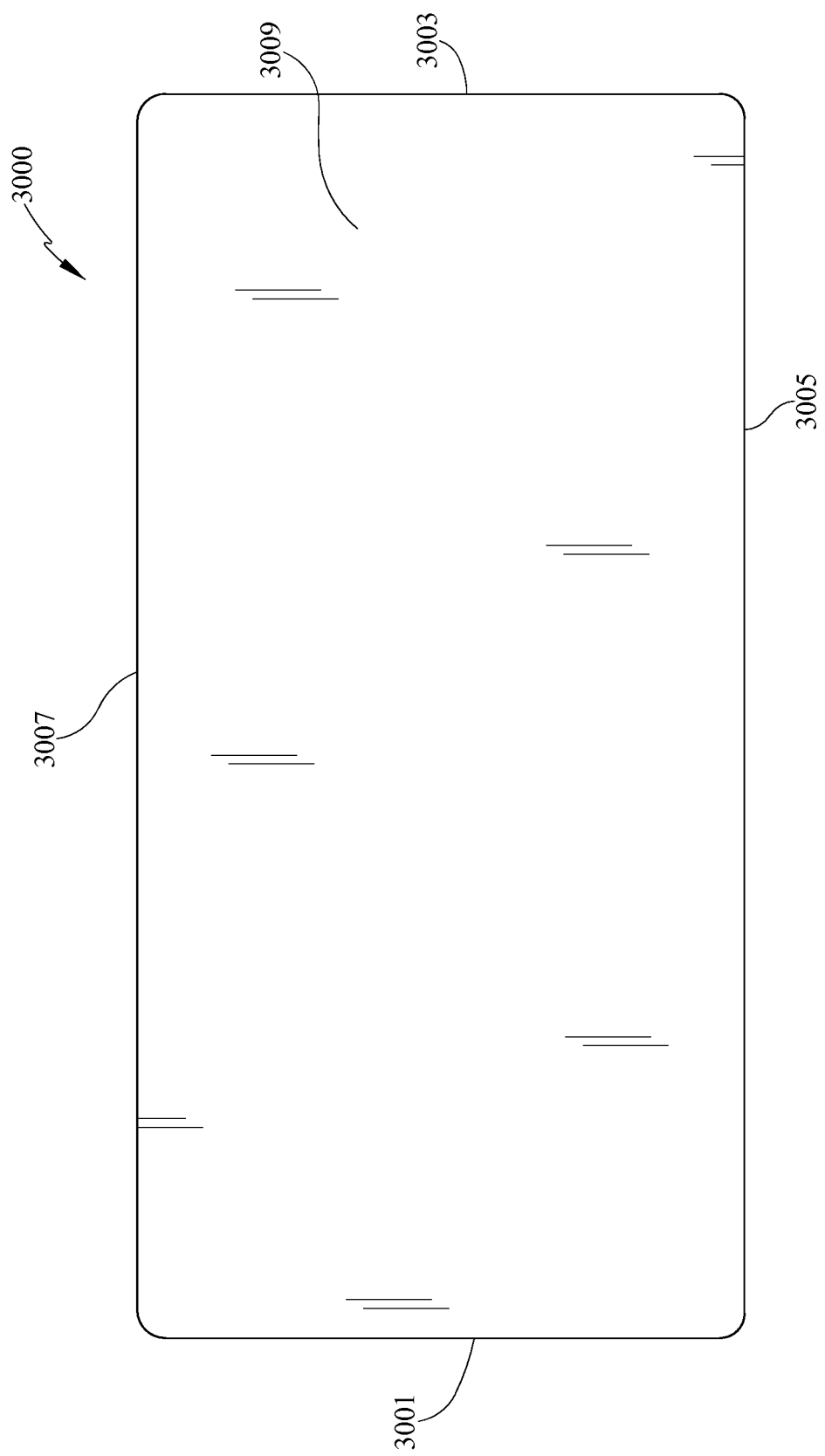
Figure 124:
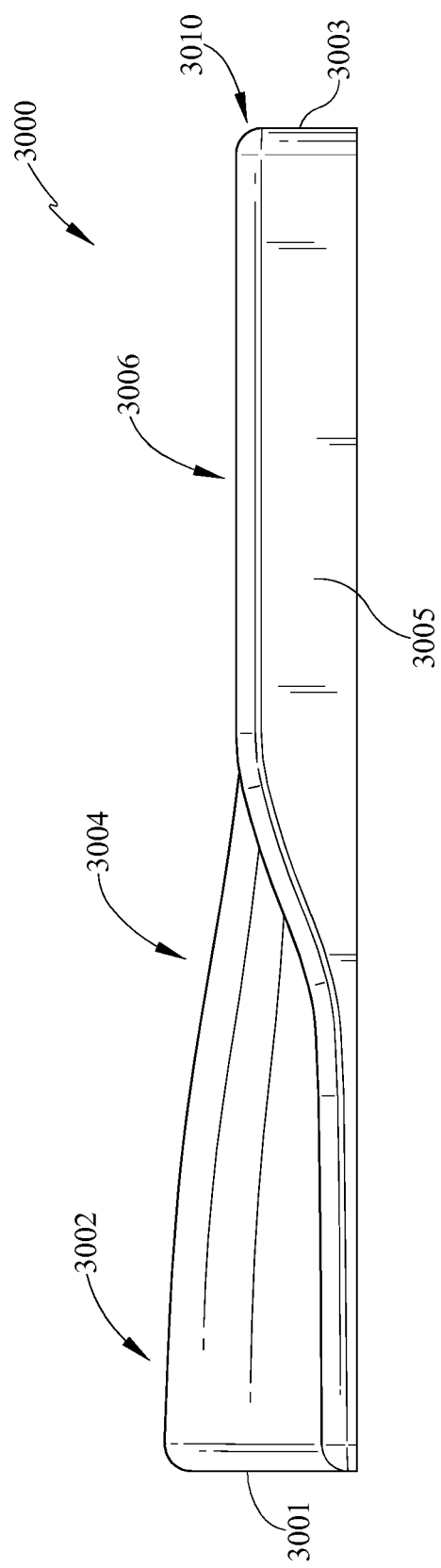
Figure 125:
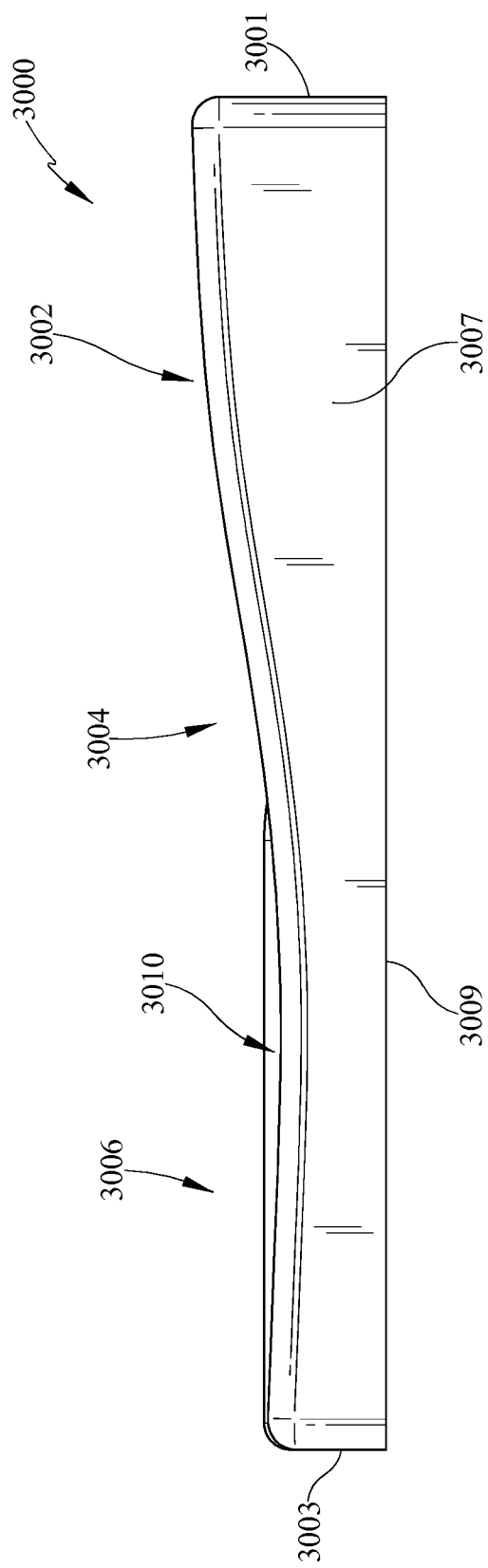

FIG. 120 is a foot end elevation view of the mattress of FIG. 114;

FIG. 121 is a top, foot end, perspective view of a mattress according to another embodiment of an illustrative design;

FIG. 122 is a top plan view of the mattress of FIG. 121;

FIG. 123 is a back plan view of the mattress of FIG. 121;

FIG. 124 is a first side elevation view of the mattress of FIG. 121;

FIG. 125 is a second side elevation view of the mattress of FIG. 121;

FIG. 126 is a head end elevation view of the mattress of FIG. 121;

FIG. 127 is a foot end elevation view of the mattress of FIG. 121;

FIG. 128 is a top, foot end perspective view of a sleep apparatus according to another embodiment;

FIG. 129 is a side, foot end perspective view of a tilting insert device used in the apparatus of FIG. 128;

FIG. 130 is a head end elevation view of the device of FIG. 129;

FIG. 131 is a foot end elevation view of the device of FIG. 129;

FIG. 132 is a left side elevation view of the device of FIG. 129; and

FIG. 133 is a right side elevation view of the device of FIG. 129

DETAILED DESCRIPTION OF THE ILLUSTRATED EMBODIMENTS

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

An adverse event mitigation system 10 according to one contemplated embodiment is shown in FIGS. 1-8. The adverse event mitigation system 10 is configured to help reduce the likelihood of an adverse event occurring and/or stop an adverse event in progress. In some contemplated embodiments, the adverse event mitigation system 10 may help reduce the likelihood of obstructive sleep apnea occurring and/or may help stop an obstructive apnea event in progress. In other contemplated embodiments, the adverse event mitigation system 10 may help reduce the likelihood of other adverse events occurring and/or stop other adverse events in progress.

Figure 1:
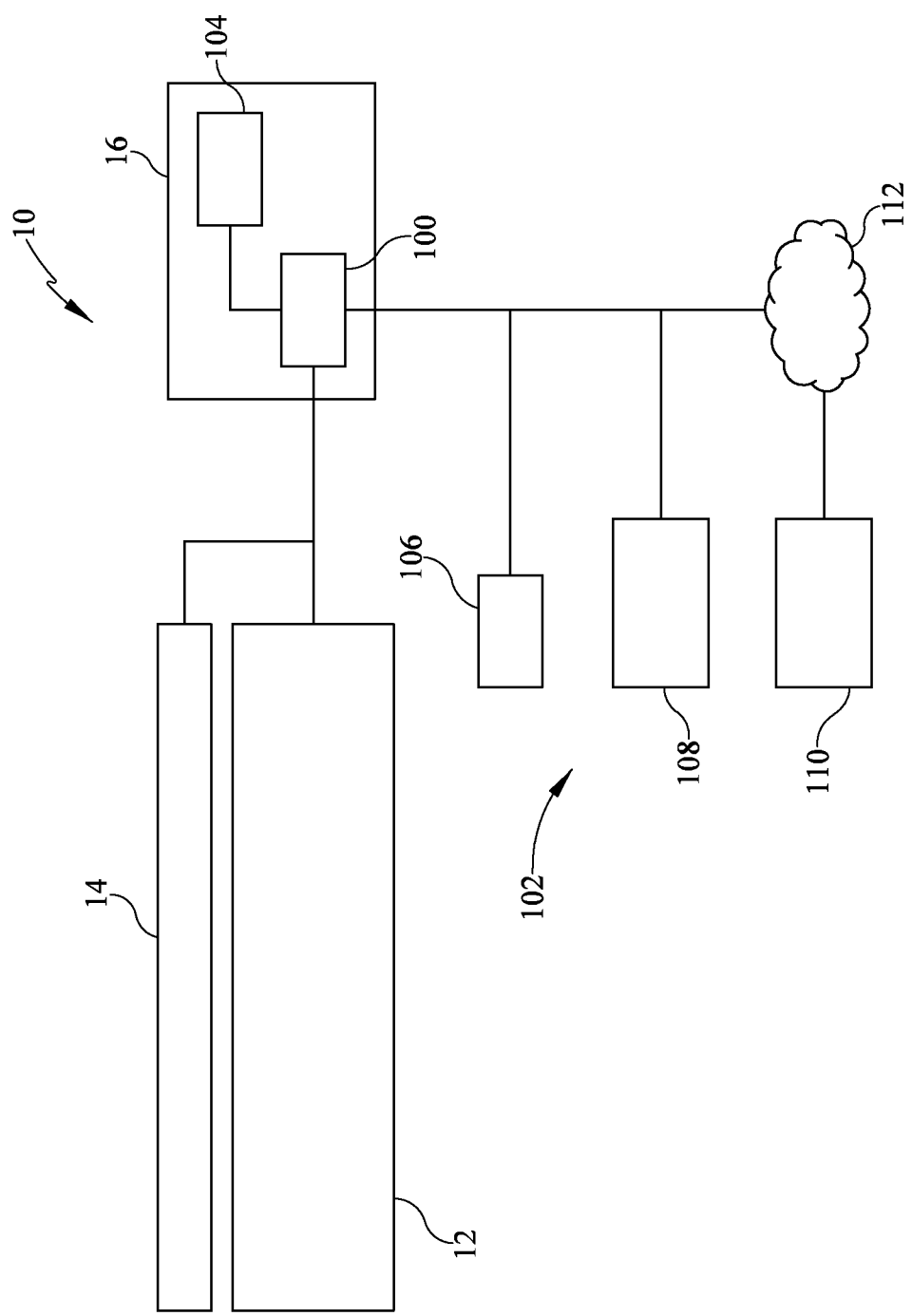
FIG. 1 is a partial diagrammatic view of an adverse event mitigation system according to one embodiment of the current disclosure.
Figure 2:
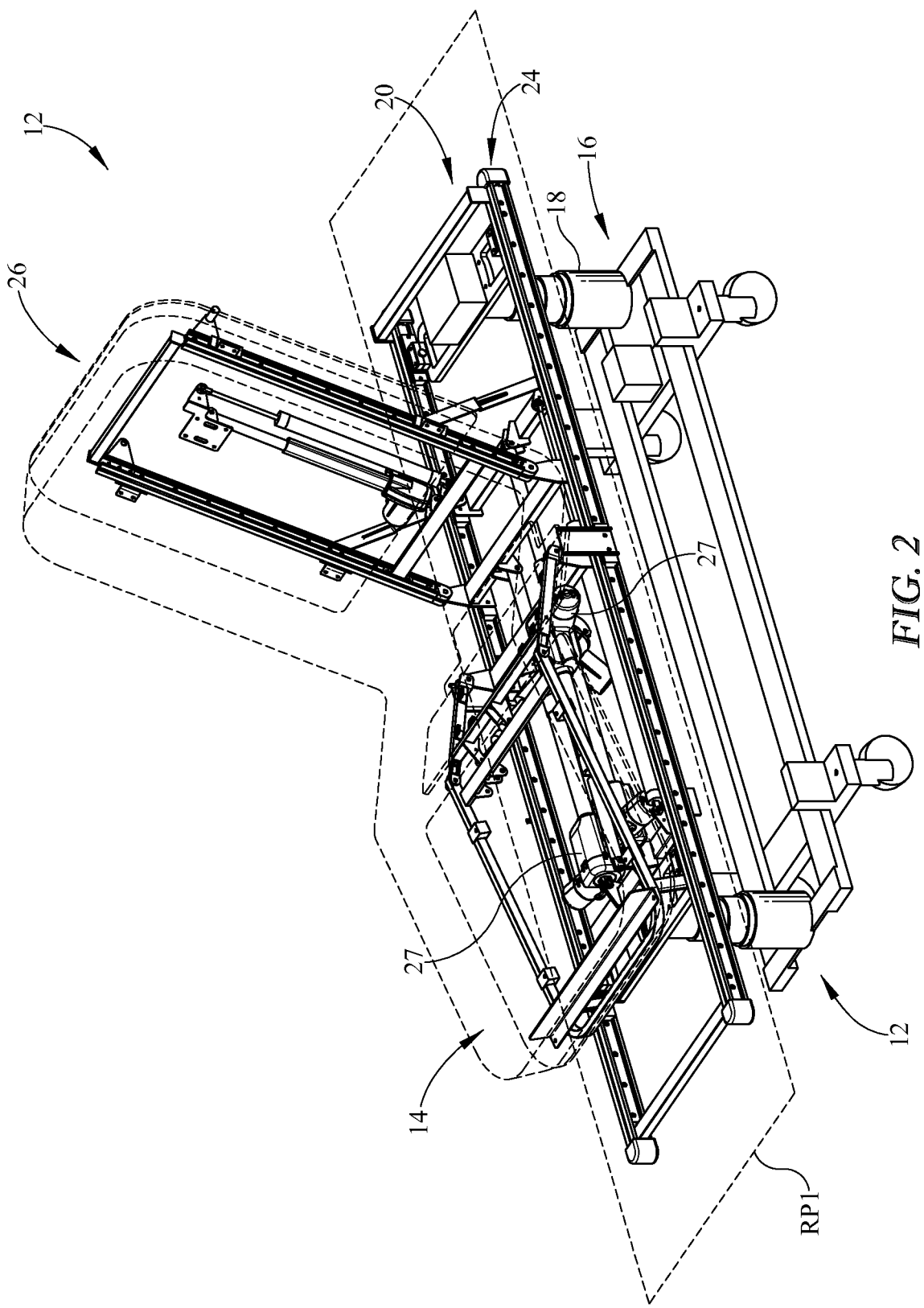
FIG. 2 is a side perspective view of a person support apparatus and person support surface of FIG. 1.

The adverse event mitigation system 10 includes a person support apparatus 12, a person support surface 14 supported on the person support apparatus 12, and a control system 16 as shown in FIG. 1. In some contemplated embodiments, the person support apparatus 12 is a hospital bed frame and the person support surface 14 is supported thereon as shown in FIG. 2. In other contemplated embodiments, the person support apparatus 12 can be a stretcher, an operating room table, or other person supporting structure. The person support apparatus 12 includes a lower frame 17, supports 18 or lift mechanisms 18 coupled to the lower frame 17, and an upper frame 20 movably supported above the lower frame 17 by the supports 18 as shown in FIG. 1. The lift mechanisms 18 are configured to raise and lower the upper frame 20 with respect to the lower frame 17 and move the upper frame 20 between various orientations, such as, Trendelenburg and reverse Trendelenburg.

The upper frame 20 includes an upper frame base 24, a deck 26 coupled to the upper frame base 24, and a plurality of actuators 27 coupled to the upper frame base 24 and the deck 26 as shown in FIG. 2. The plurality of actuators 27 are configured to move at least a portion of the deck 26 along at least one of a longitudinal axis, which extends along the length of the upper frame 20, and a lateral axis, which extends across the width of the upper frame 20, between various articulated configurations with respect to the upper frame base 24. The deck 26 includes a calf section 28, a thigh section 30, a seat section 32, and a head and torso section 34 as shown in FIG. 3. The calf section 28 and the thigh section 30 define a lower limb support section LL1. The head and torso section 34 define an upper body support section U1. The seat section 32 defines the seat section S1. The calf section 28, the thigh section 30, and the seat section 32 define a lower body support section LB1. At least the calf section 28, the thigh section 30, and the head and torso section 34 are movable with respect to one another and/or the upper frame base 24. In some contemplated embodiments, the calf section 28, the thigh section 30, the seat section 32, and the head and torso section 34 cooperate to move the person support apparatus 12 between an substantially planar or lying down configuration and a chair configuration. In some contemplated embodiments, the calf section 28, the thigh section 30, the seat section 32, and the head and torso section 34 cooperate to move the person support apparatus 12 between a substantially planar or lying down configuration and an angled or reclined configuration. In some contemplated embodiments, the head and torso section 34 is moved such that it is at an angle of at least about 30° with respect to a reference plane RP1 passing through the upper frame 20.

Figure 5:
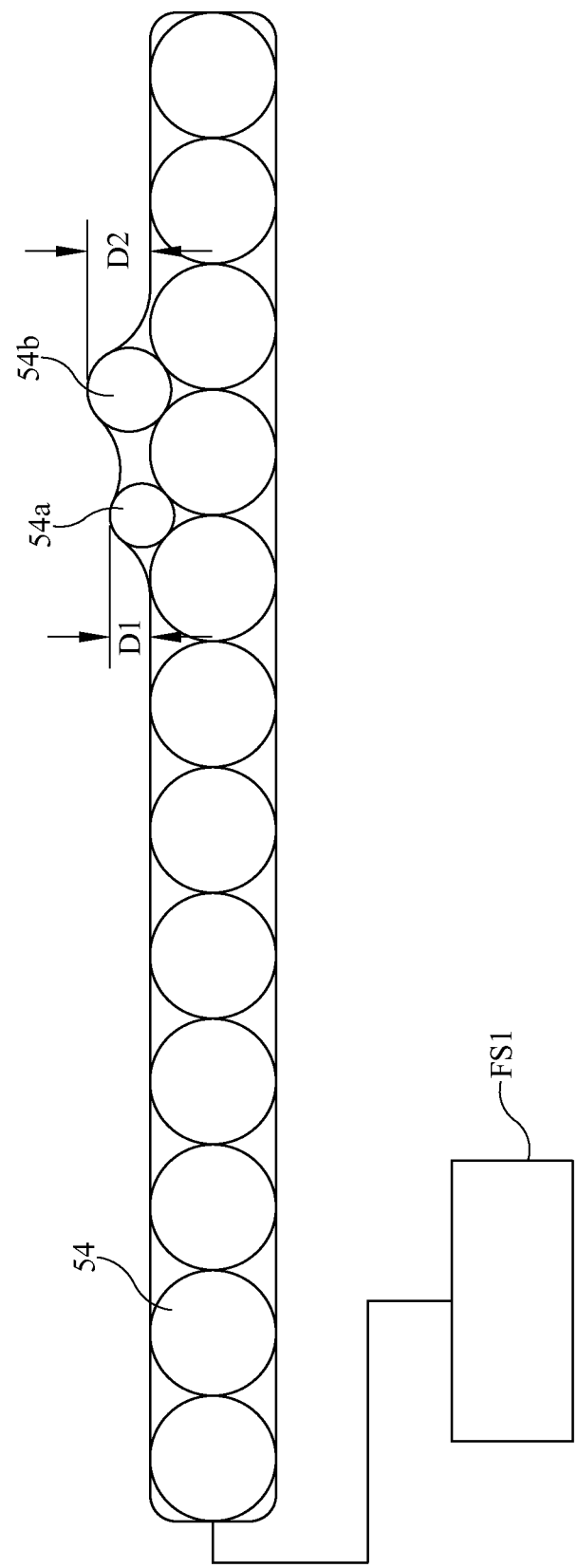
FIG. 5 is a side view of the person support surface of FIG. 2 according to another embodiment showing supports configured to support the cervical vertebrae and scapula.
Figure 6:
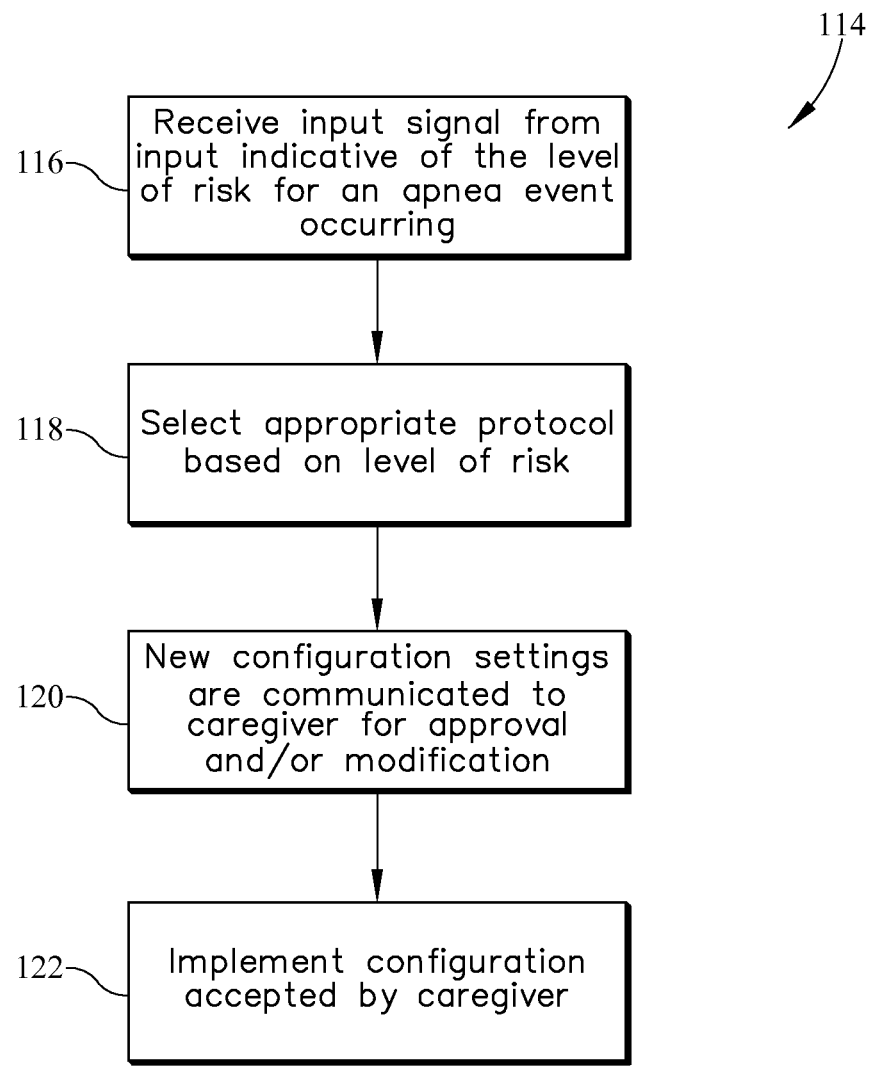
FIG. 6 is a block diagram of a proactive procedure according to one embodiment.
Figure 7:
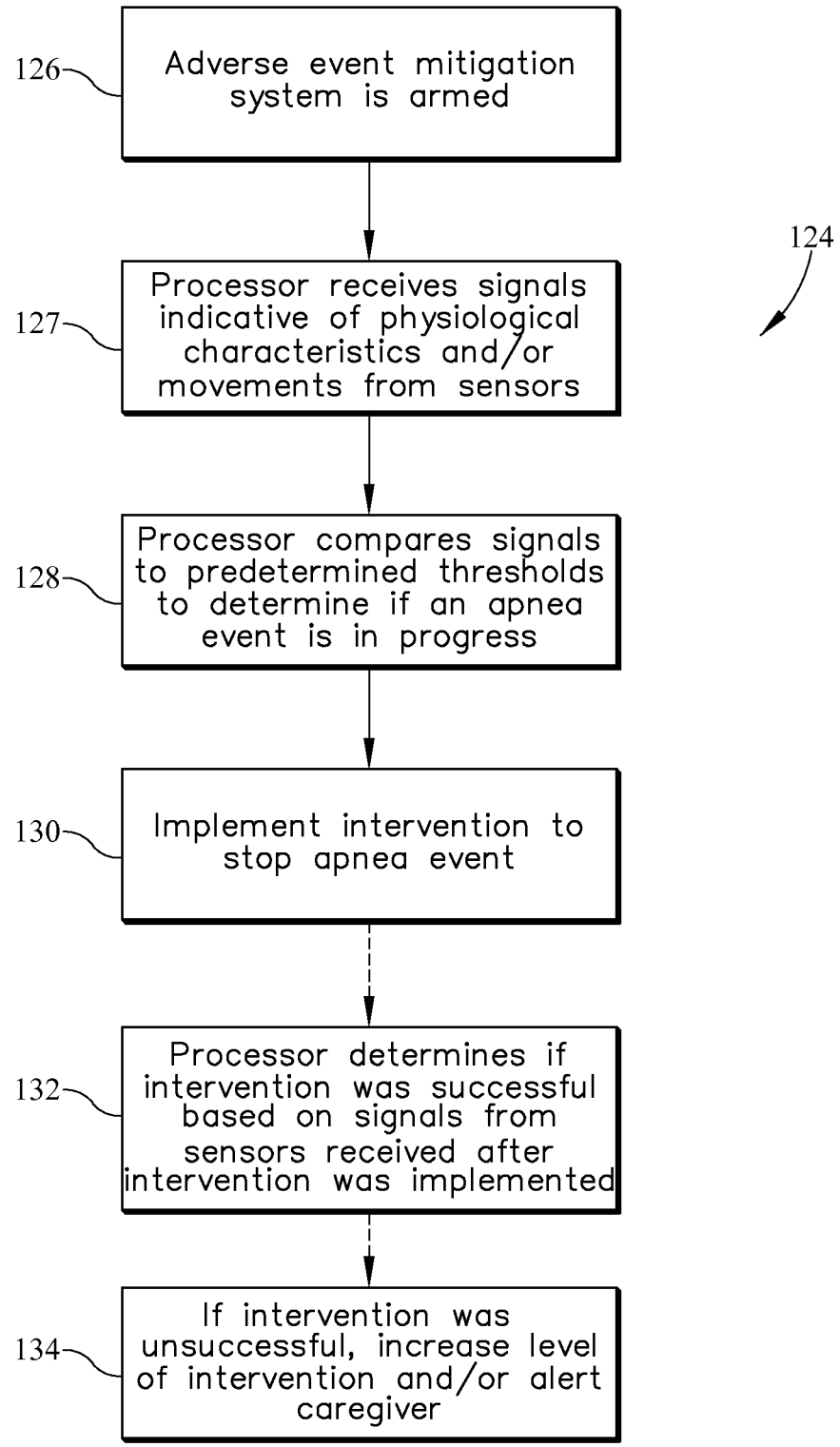
FIG. 7 is a block diagram of a reactive procedure according to one embodiment.
Figure 8:
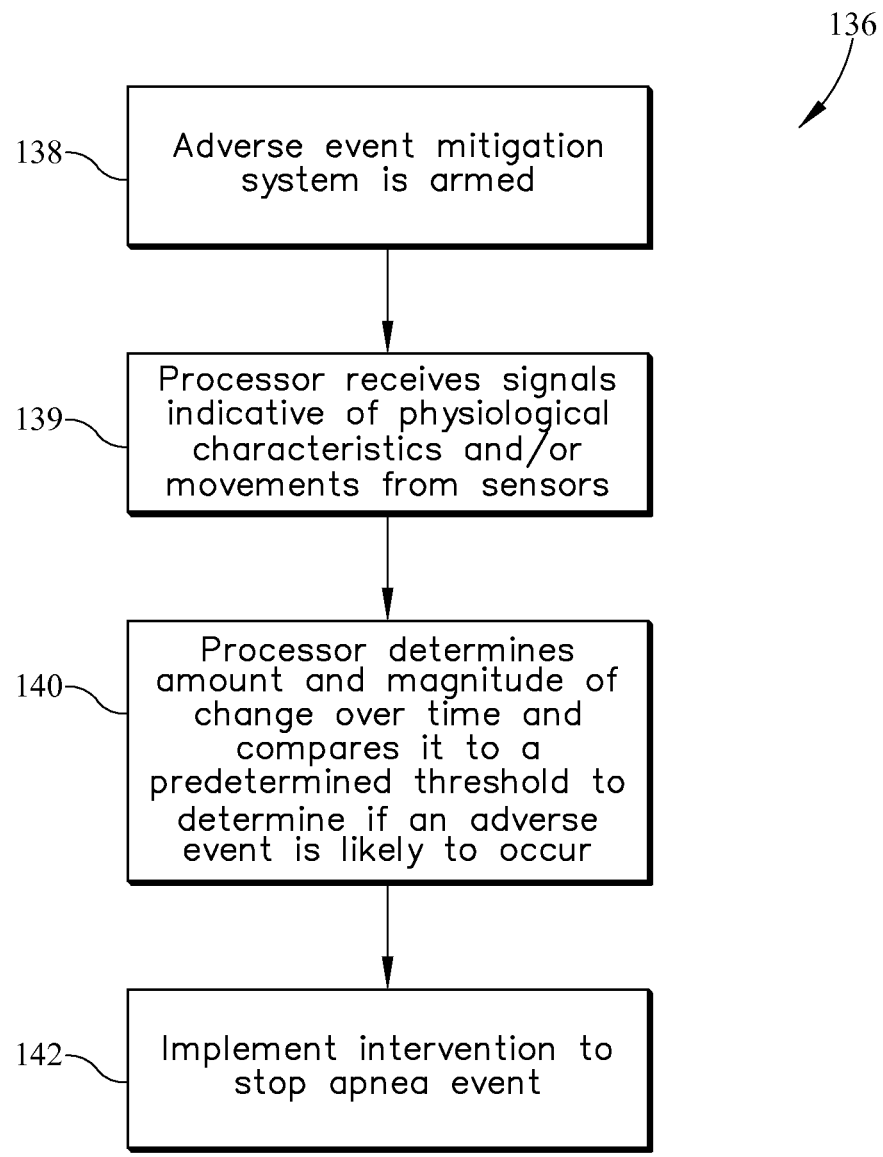
FIG. 8 is a block diagram of a predictive procedure according to one embodiment.

The person support surface 14 is configured to support a person thereon and move with the deck 20 between the various configurations. In some contemplated embodiments, the person support surface 14 is a hospital bed mattress as shown in FIG. 2-4. In some contemplated embodiments, the person support surface 14 is a consumer mattress. In some contemplated embodiments, the person support surface 14 includes a heat and moisture regulating topper positioned on the person support surface 14. In some contemplated embodiments, the person support surface 14 can include a pressure mapping topper positioned on the person support surface 14. The person support surface 14 includes a calf portion 36, a thigh portion 38, a seat portion 40, and a head and torso portion 42 as shown in FIG. 3, which is supported on corresponding sections of the deck 26. In one illustrative embodiment, the deck sections help move and/or maintain the various portions of the person support surface 14 at angles $\alpha$, $\beta$ and $\gamma$ with respect to the reference plane RP1. In some contemplated embodiments, the person support surface 14 is a non-powered (static) surface. In some contemplated embodiments, the person support surface 14 is a powered (dynamic) surface configured to receive fluid from a fluid supply FS1 as shown in FIG. 5.

The person support surface 14 includes a mattress cover 44 and a mattress core 46 as shown in FIGS. 3 and 4. In some contemplated embodiments, the person support surface 14 includes a temperature and moisture regulating topper (not shown) coupled to the mattress cover 44. The mattress cover 44 encloses the mattress core 46 and includes a fire barrier 48, a bottom ticking 50 or durable layer 50, and a top ticking 52. In some contemplated embodiments, the fire barrier 48 is the innermost layer of the cover 44, the top ticking 52 is the outermost layer, and the bottom ticking 50 is positioned between the fire barrier 48 and the top ticking 52 and is not coupled to the top ticking 52. The bottom ticking 50 and the top ticking 52 are vapor and air impermeable. In some contemplated embodiments, the top ticking 52 and the bottom ticking 50 are composed of polyurethane coated nylon and the bottom ticking 50 is configured to facilitate movement of the top ticking 52 with respect to the fire barrier 48. In other contemplated embodiments, the top ticking 52 and/or the bottom ticking 50 can be air and/or moisture permeable.

The mattress core 46 can be composed of a single type of material or a combination of materials and/or devices. In the case of a powered surface, the mattress core 46 includes at least one fluid bladder 54 therein that receives fluid from a fluid supply (not shown) to maintain the fluid pressure within the fluid bladder 54 at a predetermined level. In some contemplated embodiments, the powered surface can include non-powered components, such as, a foam frame that at least one fluid bladder 54 is positioned between. In some contemplated embodiments, a fluid bladder 54 can be positioned proximate to the thigh section and inflated or the calf portion 36, thigh portion 38, and/or seat portion 40 (including their corresponding deck sections) can be articulated to help prevent the occupant from sliding down the person support surface 14 as, for example, the inclination of the head and torso section 34 increases with respect to the reference plane RP1. In some contemplated embodiments, wedge shaped bladders are mirrored laterally about the centerline of the person support surface 14 and are configured to be inflated consecutively to laterally tilt the occupant, thereby relieving pressure on various portions of the occupant's body to help reduce the occurrences of pressure ulcers.

In some contemplated embodiments, the mattress core 46 includes inflatable fluid bladders 54a and 54b, which are configured to protrude from the patient facing surface of the person support surface 14 by at least about 70 mm (adjusted for pillow height) and about 20 mm to about 30 mm to support the cervical vertebrae and scapula, respectively. In some contemplated embodiments, the inflatable fluid bladders 54a and 54b are replaced foam bolsters or static air bladders or a combination thereof. In some contemplated embodiments, the distance the fluid bladders 54a and 54b protrude from the patient facing surface of the person support surface 14 can vary depending on any number of factors, including, but not limited to, a person's body type and the angle at which the surface is at with respect to the reference plane RP1. In some contemplated embodiments, the fluid bladders 54a and 54b can also be configured to laterally tilt the head and/or torso of the occupant. In some contemplated embodiments, wedge shaped fluid bladders (not shown) are positioned in the head and torso portion 42 and are configured to increase the angle of the occupant contacting surface of the head and torso portion 42 with respect to the seat portion 40 when inflated.

Figure 9:
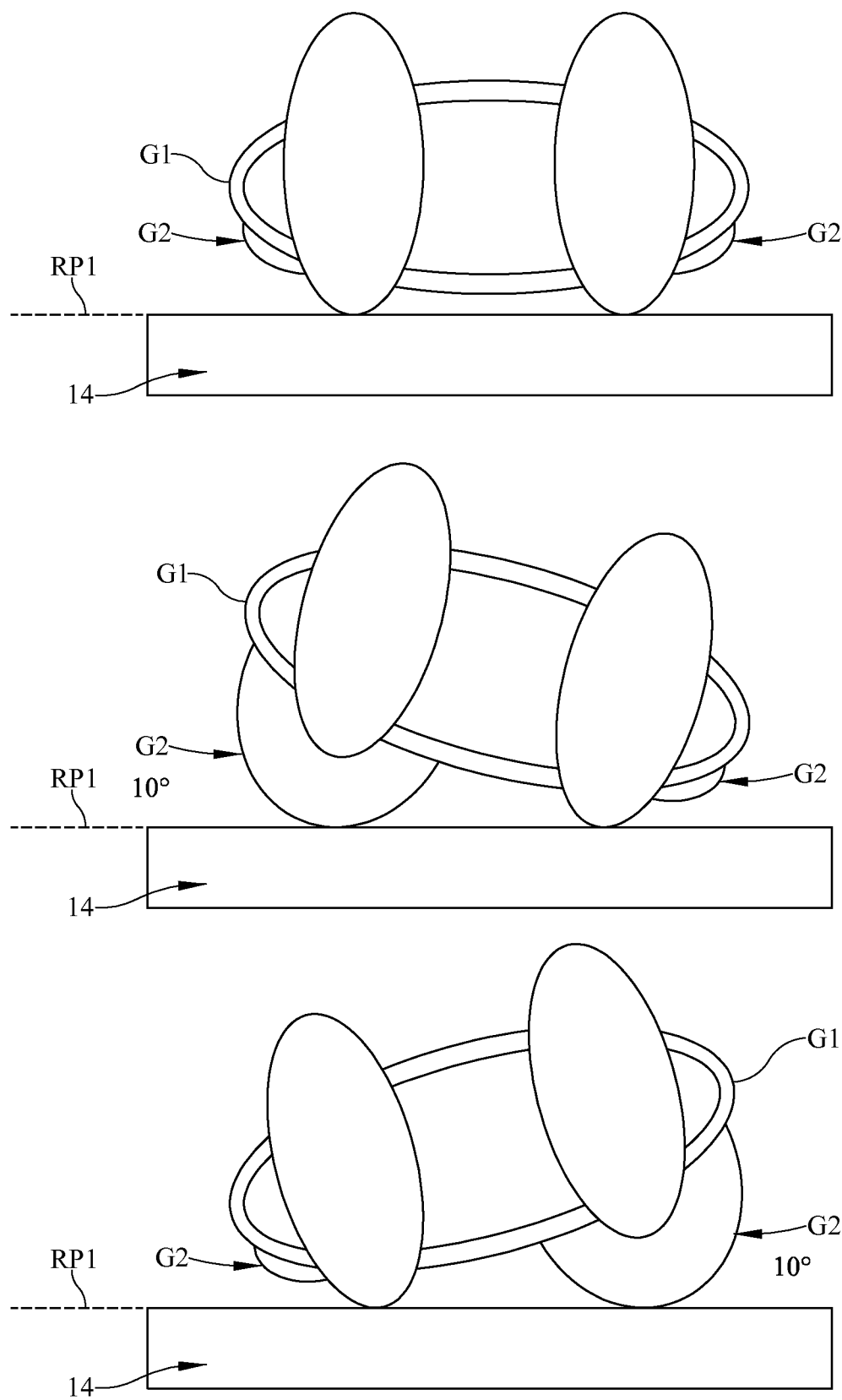
FIG. 9 is a partial diagrammatic view of a garment configured to rotate a person.
Figure 10A:
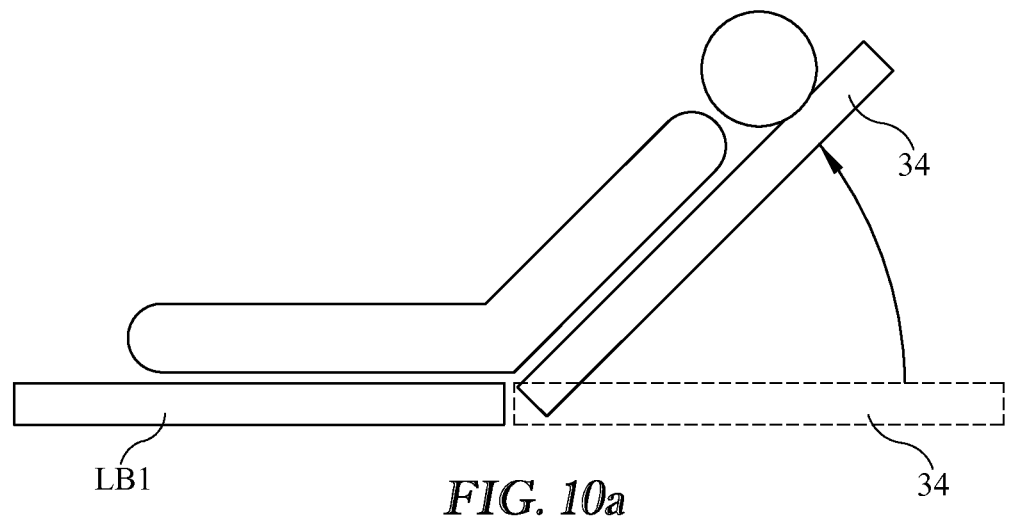
FIGS. 10A-10C are partial diagrammatic views of a person support apparatus configured to rotate a person in accordance with one or more embodiments disclosed herein.
Figure 10B:
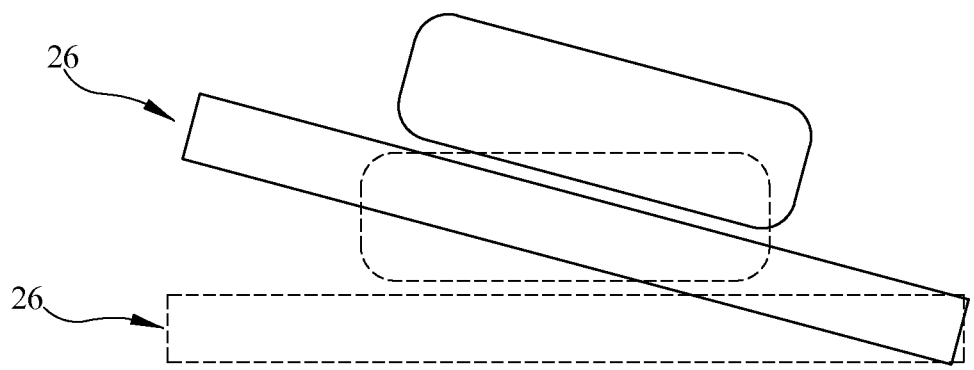
Figure 10C:
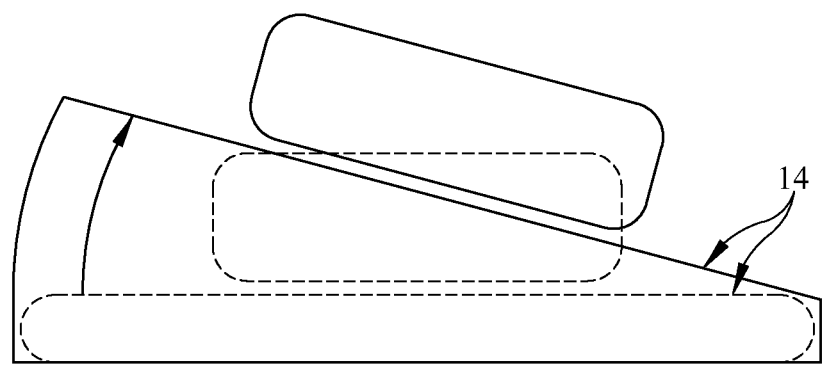

In some contemplated embodiments, the head and torso of the occupant can be tilted at different angles. For example, the person support apparatus 12 and/or the person support surface 14 can laterally rotate the occupant so that the torso is at an angle of about 10° with respect to the reference plane RP1 and the head is at an angle of about 180° with respect to the reference plane RP1. Rotation of the occupant's torso can help an occupant maintain their head at an angle of about 180° with respect to the reference plane RP1. In some contemplated embodiments, the person support surface 14 is configured to allow the occupant's body to be immersed into the surface to improve comfort with lateral positioning. In some contemplated embodiments, support blocks (not shown) can be placed on the surface 14 adjacent to the occupant to help maintain the position of the occupant. In some contemplated embodiments, the person support apparatus 12 and/or person support surface 14 can laterally rotate the occupant so that the torso is at an angle of about 10° with respect to the reference plane RP1 and fluid bladders 54a and 54b can rotate the occupant's head so that it is at an angle of at least about 180°. In some contemplated embodiments, the occupant can be wearing a garment G1 with fluid bladders G2 configured to be inflated to help laterally rotate the occupant so that the torso is at an angle of at least 10% with respect to the reference plane RP1 as shown in FIG. 9. In some contemplated embodiments, the garment G1 is configured to provide therapy, including, for example, percussion, vibration, and compression therapies. In some contemplated embodiments, the garment G1 is an airway clearance vest, such as the Vest® Airway Clearance System sold by Hill-Rom. In other contemplated embodiments, the garment G1 can be other therapy garments, including sequential compression devices (SCD). In some contemplated embodiments, fluid can be supplied to the garment G1 via the fluid supply FS1 configured to supply fluid to the fluid bladders 54a and 54b. In some contemplated embodiments, fluid is supplied to the garment G1 and/or fluid bladders G2 by a dedicated fluid supply (not shown). The angle of the occupant's head with respect to the reference plane RP1 may vary depending on the occupant's preferences, their risk of the adverse condition, or other factors.

In the case of a non-powered surface, the mattress core 46 is composed of a cellular engineered material, such as, single density foam. In some contemplated embodiments, the mattress core 46 includes at least one bladder 54, such as, a static air bladder or a static air bladder with foam contained there within, a metal spring and/or other non-powered support elements or combinations thereof. In some contemplated embodiments, the mattress core 46 includes multiple zones with different support characteristics configured to enhance pressure redistribution as a function of the proportional differences of a person's body. Also, in some embodiments, the mattress core 46 includes various layers and/or sections of foam having different impression load deflection (ILD) characteristics, such as, in the NP100 Prevention Surface, AccuMax Quantum™ VPC Therapy Surface, and NP200 Wound Surfaces sold by Hill-Rom®.

The control system 16 is configured to change at least one characteristic of the person support apparatus 12 and/or person support surface 14 to help reduce the likelihood of an adverse event occurring and/or stop an adverse event in progress. The control system 16 includes a processor 100, an input 102, and memory 104. In some contemplated embodiments, the input 102 includes a sensor 106, such as, a position sensor, a pressure sensor, a temperature sensor, an acoustic sensor, and/or a moisture sensor, configured to provide an input signal to the processor 100 indicative of a physiological characteristic of the occupant, such as, the occupant's heart rate, respiration rate, respiration amplitude, skin temperature, weight, and position. In some contemplated embodiments, the sensors 106 are incorporated into the person support surface 14 or topper positioned on the person support surface, for example, as disclosed in U.S. Pat. No. 7,515,059 to Price et al. and U.S. Patent Publication No. 2011/0068928 to Riley et al. In some contemplated embodiments, the sensors 106 include, for example, RFID tags, accelerometers, proximity sensors, level sensors, or other physical tracking sensors that may be integrated into or coupled to, for example, ear plugs, ear phones, adhesive sensors, earlobe clips, eye covers, hats, nose strips or other devices that are attached to the patient's head or worn by the patient so that the position/orientation of the patient's head can be tracked. Information captured by monitoring the lateral position of the user's upper respiratory tract has several benefits, including one or more of the following: providing more accurate measurements of the upper respiratory angle for diagnosis of positional obstructive sleep apnea (in one example, sleep labs can use the information to more accurately diagnose POSA); providing biofeedback to help the user to train to maintain a posture that prevents POSA; tracking performance of the system to determine if the system is achieving a sufficient upper respiratory angle to prevent apnea; monitoring compliance to determine if the system is being used; monitoring the upper respiratory angle and recording the angle when a sleep apnea event occurs; and controlling a surface capable of providing lateral rotation as a function of the inputs from the sensors 106, tracking whether optimal lateral position has been achieved, and controlling the system to achieve a desired head lateral position and/or upper respiratory angle. In some contemplated embodiments, the sensors 106 are tracked by reading devices (i.e., an RFID reader) in a siderail, person support surface, deck, headboard, or location on or in the person support apparatus 10 or person support surface 14, or on or in a headwall in the room or other location in the room. In some contemplated embodiments, the sensor 106 includes a camera positioned at the foot of the bed or above the bed, as disclosed in U.S. Patent Publication No. 2012/0029879 to Sing et al., for example, to track the orientation of the person's head.

In some contemplated embodiments, the input 102 includes a user interface 108 configured to receive information from a caregiver or other user. In other contemplated embodiments, the input 102 is an Electronic Medical Record (EMR) system 110 in communication with the processor 100 via a hospital network 112. In some contemplated embodiments, the processor 100 can output information, automatically or manually upon caregiver input, to the EMR for charting, which can include therapy initiation and termination, adverse event occurrence information, therapy protocol used, caregiver ID, and any other information associated with the occupant, caregiver, person support apparatus 12, person support surface 14, and adverse event.

The memory 104 stores one or more instruction sets configured to be executed by the processor 100. The instruction sets define procedures 114 that, when executed by the processor, cause the processor 100 to implement one or more protocols that modify the configuration of the person support apparatus 12 and/or the person support surface 14. In one illustrative embodiment, the instruction set defines a proactive procedure 114 that causes the processor 100 to configure the person support apparatus 12 and/or the person support surface 14 in response to an input specifying that the occupant is at risk for sleep apnea. Procedure 114 begins with step 116 in which the processor 100 receives an input signal from the input 102 indicative of the level of risk for an apnea event occurring. In some contemplated embodiments, the level of risk is input from a field in the occupant's EMR. In some contemplated embodiments, the level of risk is input by a caregiver through the user interface 108, which may arise from a doctor's order or be based on a patient scoring system. In some contemplated embodiments, the level of risk is determined based on a risk score that is calculated by the processor 100 based on a number of factors, including, but not limited to, those listed in the table below:

| | |
|---|---|
| Predisposing physical characteristics | BMI in the 95th percentile for age and gender (i.e., 35 kg/m2) |
| | 17 inch neck circumference for men (16 inches for women) |
| | craniofacial abnormalities that affect the airway |
| | anatomical nasal obstructions |
| | tonsils that nearly touch or do touch in the medline |
| History of apparent airway obstruction during sleep | loud or frequent snoring |
| | observed pauses in breathing while asleep |
| | awakening from sleep with a choking sensation |
| | frequent arousal from sleep |
| Somnolence | frequent somnolence or fatigue despite getting an adequate amount of sleep |
| | falling asleep easily in a nonstimulating place despite adequate sleep |
| Sleep study results | |
| Invasiveness of surgery and anesthesia | superficial under local or peripheral nerve block without sedation |
| | superficial with moderate sedation or general anesthesia |
| | peripheral with spinal or epidural anesthesia and no more than moderate sedation |
| | peripheral with general anesthesia |
| | airway surgery with moderate sedation |
| | major surgery with general anesthesia |
| | airway surgery with general anesthesia |
| Requirement of postoperative opioids | none |
| | low-dose oral opioids |
| | high-dose oral opioids or neuraxial or parenteral opioids |
| Estimation of perioperative risk | |
| Sex and age of occupant | Estimated sleep disordered breathing is 9% in women and 24% in men with the prevalence for obstructive sleep apnea being 2% in women and 4% in men. The percentages likely increase for older and more obese people |

In circumstances where an occupant is known to snore frequently, has a high BMI, has had major surgery, and/or requires postoperative opioids, the occupant may have an elevated risk. In circumstances where an occupant has a low BMI, is not known to snore, had superficial surgery, and/or does not require postoperative opioids, the occupant may have a reduced risk. An example of a scoring system is shown in the table below, where a score of 4 can indicate an increased risk, and a score of greater than 4 can indicate a significantly increased risk.

| | | |
|---|---|---|
| I. Severity of apnea | Based on sleep study Based on predisposing physical characteristics, history of apparent airway obstruction during sleep, and somnolence | 0-3 points |
| | None | 0 points |
| | Mild | 1 point |
| | Moderate | 2 points |
| | Severe | 3 points |
| II. Surgery and Anesthesia | Invasiveness Type | 0-3 points |
| | Superficial under local or peripheral nerve block without sedation | 0 points |
| | Superficial with moderate sedation or general anesthesia | 1 point |
| | Peripheral with spinal or epidural anesthesia and no more than moderate sedation | 1 point |
| | Peripheral with general anesthesia | 2 points |
| | Airway surgery with moderate sedation | 2 points |
| | Major surgery with general anesthesia | 3 points |
| | Airway surgery with general anesthesia | 3 points |
| III. Postoperative opioids | Requirement Dosage | 0-3 points |
| | None | 0 points |
| | Low-dose oral | 1 point |
| | High dose oral, parenteral or neuraxial | 3 points |

Risk = Score from I + Score from the greater of II and III (0-6 points)

In step 118, the processor 100 determines which protocol should be implemented based on the level of risk. One type of the protocol is a default protocol set according to the hospital's standard operating procedures/guidelines for patients with specific risk profiles. Another type of protocol is a variable protocol that modifies the default protocol based on the occupant's preferences (i.e., prefers to sleep on their left side), the caregiver's observations, and/or information about the occupant's medical condition (i.e., pressure ulcer susceptibility, BMI, type of surgery, etc.) from the occupant's EMR, sensors 106, and/or other input 102. In some contemplated embodiments, the protocol can be modified to exclude or limit a therapy or movement. For example, the protocol can be prevented from increasing the head of bed angle (the angle between the reference plane RP1 and the head and torso section 34 or head and torso portion 42) above a predetermined threshold where the occupant is recovering from abdominal surgery. In some contemplated embodiments, the protocol can caution the caregiver against implementing the configurations based on information obtained from the occupant's EMR or other sources.

In step 120, once the protocol is selected, the configuration settings are communicated to the caregiver, for example, on a graphical user interface or other display device, and the caregiver is prompted to accept/modify the settings. In some contemplated embodiments, the configuration settings can be communicated to a hand held device. In one example, the protocol may require the head of bed angle to be greater than about 35° and the lateral tilt angle to be greater than 15° with respect to the reference plane RP1 for an occupant with an elevated risk score. In another example, the protocol may require the head of bed angle to be about 10° to about 15° and the lateral tilt angle to be about 10° to about 15° with respect to the reference plane RP1 for an occupant with a reduced risk score. In some contemplated embodiments, the upper frame 20 can also be moved to a Trendelenburg or reverse Trendelenburg orientation. In some contemplated embodiments, the protocol can require additional therapies to be active, such as, continuous lateral rotation where, for example, the lateral tilt angle changes every 30-120 minutes depending on the occupant's risk of developing pressure ulcers. In some contemplated embodiments, the sleep stage of the occupant can be taken into account so that the occupant is moved only when they are in a sleep state that would allow them to be moved without waking up. In some contemplated embodiments, the person support apparatus 12 and/or the person support surface 14 are returned to the configuration they were in prior to the implementation of the protocol before the occupant wakes up. In some contemplated embodiments, a manual stop button can be included so that the caregiver, occupant, or other person can terminate the protocol in the event of an emergency. In some contemplated embodiments, the protocol can automatically be terminated when an emergency condition occurs, such as, when the CPR handle (not shown) is pulled by a caregiver or the occupant is coding. In some contemplated embodiments, the procedure 114 can be terminated remotely by a caregiver, such as, via the hospital network or over a nurse call system.

In some contemplated embodiments, the position and/or the orientation of the occupant with respect to patient facing surface of the person support surface 14 is detected and can influence how the person support surface 14 and/or the person support apparatus 12 are configured to move the occupant to the desired position. For example, if the occupant is positioned along the left edge of the patient facing surface of the person support surface 14, the protocol will not rotate them to the left. In some contemplated embodiments, the protocol is terminated because the occupant is in the correct position. In some contemplated embodiments, the protocol helps to maintain the occupant in the position. The position of the occupant on the person support surface 14 can be determined a number of ways, including sensing the force distribution on the upper frame 20 utilizing one or more load cells (not shown) coupled to the upper frame 20, calculating the occupant's center of gravity using the one or more load cells, sensing pressures within the fluid bladders 54, using a camera (not shown) or 3D sensor (not shown), or using other methods.

In step 122, if the caregiver accepts the configuration or changes the configuration and accepts the new configuration, the processor 100 implements the configuration for a predetermined time. In some contemplated embodiments, the processor 100 can implement the configuration the moment the caregiver approves it and stop or change the configuration when the caregiver deactivates it. In some contemplated embodiments, the processor 100 will wait to implement the configuration until the occupant is in a predetermined sleep stage and will return to the initial configuration when the occupant begins to wake up. In some contemplated embodiments, procedure 114 does not require the caregiver to confirm or accept the settings, and instead automatically initiates the configuration. For example, the configuration can be automatically initiated a predetermined time after the occupant departed from the surgical room, which can be determined based on the occupant's EMR. In some contemplated embodiments, the configuration will not be implemented if the bed is unoccupied.

Procedure 114 can be used for a number of other adverse conditions. In some contemplated embodiments, procedure 114 can be used to determine if a person is at risk for or has gastroesophageal reflux disease and select a protocol that assists the occupant in maintaining a left lateral decubitus position or semi-reclining position while sleeping. In some contemplated embodiments, procedure 114 can be used to determine if a person is at risk for or has chronic respiratory insufficiency and select a protocol for the caregiver to approve that assists the occupant in maintaining a left lateral decubitus position while sleeping. In some contemplated embodiments, the procedure can be used to determine if a person is at risk for of has allergies to, for example, feather or down filled pillows, cushions or covers, and can alert the caregiver so that they can remove the item. In other contemplated embodiments, procedure 114 can be used to determine if the person is at risk for or has one or more other conditions, such as, for example, asthma, pregnancy, sleep paralysis or hallucinations, snoring, stroke bruxism, coughing, hypoxaemia in geriatric inpatients, stroke, or tuberculosis, that might be affected negatively by sleeping in the supine position and select a protocol and/or alert the caregiver so that the person support apparatus 12 and/or the person support surface 14 can be configured to maintain the occupant in a desirable position. In some contemplated embodiments, the procedure 114 can be used to change the sleeping position of occupants to help stimulate blood oxygenation, which can undesirably decrease as the occupant remains stationary.

In another illustrative embodiment, the instruction set causes the processor 100 to carry out a responsive procedure 114 that configures the person support apparatus 12 and/or the person support surface 14 in response to detection of an adverse event, such as, an apnea event. Procedure 124 begins with step 126 where the adverse event mitigation system is armed manually by the caregiver or automatically based on information from the occupant's EMR, the caregiver, or calculated by the processor 100.

In step 127, the processor 100 receives signals from the sensors 106 indicative of the physiological characteristics of the occupant, including, but not limited to, the occupant's heart rate and the respiration characteristics, such as, amplitude and rate, and/or the amount of movement of the occupant.

In step 128, the processor 100 compares the signals from the sensors 106 to predetermined thresholds to determine if an apnea event is in progress. For example, if there is an interval of at least about 10 seconds between breaths then the person is likely having an apnea event. In another example, if the person is taking less than about 25% of a normal breath for at least about 10 seconds, then the person is likely having an apnea event. In another example, if there is a drop in oxygen saturation of at least about 4%, then the person is likely having an apnea event. If the person is taking between about 26% and about 69% of a normal breath, the person is likely having a hypopnea event. In some contemplated embodiments, the processor 100 determines that an adverse event is in progress and alerts the caregiver that an adverse event is occurring and that it is likely not an apnea event based on the position of the occupant and/or the configuration of the person support apparatus 12 and/or the person support surface 14, the occupant's risk score, and/or the occupant's physiological characteristics, medical information from the occupant's EMR, and/or other information. In some contemplated embodiments, the caregiver can be alerted by a visual or audible alarm on the person support apparatus 12, a visual or audible alarm located in the room where the person support apparatus 12 is located, and/or a visual or audible alarm located proximate to the room, such as, in the hall way.

In some contemplated embodiments, the caregiver can be notified remotely by a communication system (not shown). In some contemplated embodiments, the communication system is a patient/nurse call system that can include patient stations capable of generating hospital calls and a remote master station which can prioritize and store the calls. One example of such a system is disclosed in U.S. Pat. No. 5,561,412 issued on Oct. 1, 1996 to Novak et al., which is incorporated by reference herein in its entirety. Another example of such a system is disclosed in U.S. Pat. No. 4,967,195 issued on May 8, 2006 to Shipley, which is incorporated by reference herein in its entirety.

In another contemplated embodiment, the communication system is a system for transmitting voice and data in packets over a network with any suitable number of intra-room networks that can couple a number of data devices to an audio station, where the audio station couples the respective intra-room network to a packet based network. One example of such a system is disclosed in U.S. Pat. No. 7,315,535 issued on Jan. 1, 2008 to Schuman, which is incorporated by reference herein in its entirety. Another example of such a system is disclosed in U.S. Patent Publication No. 2008/0095156 issued on Apr. 24, 2008 to Schuman, which is incorporated by reference herein in its entirety.

In yet another contemplated embodiment, the communication system is includes a patient/nurse call system, a nurse call/locating badge, an electronic medical record (EMR) database, and one or more computers programmed with work-flow process software. One example of such a system is disclosed in U.S. Patent Publication No. 2008/0094207 published on Apr. 24, 2008 to Collins, Jr. et al., which is incorporated by reference herein in its entirety. Another example of such a system is disclosed in U.S. Patent Publication No. 2007/0210917 published on Sep. 13, 2007 to Collins, Jr. et al., which is incorporated by reference herein in its entirety. Yet another example of such a system is disclosed in U.S. Pat. No. 7,319,386 published on Jan. 15, 2008 to Collins, Jr. et al., which is incorporated by reference herein in its entirety. It should be appreciated that the work-flow process software can be the NaviCare® software available from Hill-Rom Company, Inc. It should also be appreciated that the work-flow process software can be the system disclosed in U.S. Pat. No. 7,443,303 issued on Oct. 28, 2008 to Spear et al., which is incorporated by reference herein in its entirety. It should further be appreciated that the badge can be of the type available as part of the ComLinx™ system from Hill-Rom Company, Inc. It should also be appreciated that the badge can also be of the type available from Vocera Communications, Inc.

In still another contemplated embodiment, the communication system is configured to organize, store, maintain and facilitate retrieval of bed status information, along with the various non-bed calls placed in a hospital wing or ward, and remotely identify and monitor the status and location of the person support apparatus, patients, and caregivers. One example of such a system is disclosed in U.S. Pat. No. 7,242,308 issued on Jul. 10, 2007 to Ulrich et al., which is incorporated by reference herein in its entirety. It should be appreciated that the remote status and location monitoring can be the system disclosed in U.S. Pat. No. 7,242,306 issued on Jul. 10, 2007 to Wildman et al., which is incorporated by reference herein in its entirety. It should also be appreciated that the remote status and location monitoring can be the system disclosed in U.S. Patent Publication No. 2007/0247316 published on Oct. 25, 2007 to Wildman et al., which is incorporated by reference herein in its entirety.

In step 130, if the processor determines an apnea event is in progress, the processor 100 configures the person support surface 14 and/or the person support apparatus 12 to intervene and help stop the apnea event. In one illustrative embodiment, the processor 100 inflates a bladder 54 in the person support surface 14 to rotate the occupant onto their side such that they are at an angle of about 10° with respect to the reference plane RP1. In some contemplated embodiments, the upper frame 20 can be rotated along the longitudinal axis to laterally tilt the occupant. In another illustrative embodiment, the processor 100 increases the head of bed angle to about 15° by moving the head and torso section 34 of the person support apparatus 12 and/or inflating a bladder 54 in the person support surface 14. In some contemplated embodiments, the processor 100 increases the head of bed angle and laterally rotates at least a portion of the occupant's body. In some contemplated embodiments, the processor 100 implements additional therapies, such as, for example, continuous lateral rotation therapy (CLRT), percussion vibration therapy, heat and moisture management therapy, rotation therapy, or other therapies depending on the occupant's risk for developing additional adverse conditions, such as, pressure ulcers.

In some contemplated embodiments, procedure 124 includes step 132 and step 134 in which the processor 100, after implementing the intervention, receives signals from the sensors 106 indicative of the occupant's physiological characteristics and/or the amount of movement of the occupant, and compares them with the predetermined thresholds to determine if the intervention was successful and the apnea event has ceased. In one illustrative embodiment, the processor 100 waits a predetermined amount of time, such as, 5 seconds, after the intervention has been implemented before it receives signals from the sensors 106. In some contemplated embodiments, the processor 100 can receive signals from the sensors 106 as the intervention is implemented and stop intervening or maintain the current level of intervention when the apnea event has ceased. For example, the processor 100 receives signals from the sensors 106 as the head of bed angle and/or the lateral tilt angle are gradually increased and stops increasing the head of bed angle and/or the lateral tilt angle once the apnea event has ceased. In some embodiments, the head of bed angle and/or the lateral tilt angle are gradually increased and an alarm is activated when the angle reaches a predetermined threshold. If the processor 100 determines that the intervention was successful, the processor 100 can cause the person support apparatus 12 and/or the person support surface 14 to maintain the current configuration or cause it to return to its initial position.

If the processor 100 determines that the apnea event is still in progress, the processor 100 can increase the level of intervention. In one illustrative embodiment, the head of bed angle and/or the lateral tilt angle can be increased an additional 5°. In other embodiments, the stimuli can include vibration, sound, temperature, smells, lights (flashing and/or constant), or other stimulus or combinations thereof that may or may not wake the person. In some instances, the goal of the intervention is to stop the apnea event without waking the occupant up, which can include moving the person while the person is in a particular sleep stage and/or causing the person to move from a deeper sleep stage to a lighter sleep stage. In some contemplated embodiments, movement of the occupant can cease if the processor 100 detects the person is waking up (based on increased heart rate, respiration rate, and/or movement) or is moving to a lighter sleep stage. If the increased levels of intervention continue to be unsuccessful then the processor 100 can initiate an alarm on or near the person support apparatus 12 to wake the occupant and/or notify a caregiver via nurse call or other means of communication that they need to intervene. In some contemplated embodiments, if the processor 100 receives information that the occupant is sedated, the processor 100 can move the occupant to a position, such as, for example, a sitting position or chair position.

In another illustrative embodiment, the instruction set causes the processor 100 to carry out a proactive procedure 136 that configures the person support apparatus 12 and/or the person support surface 14 when the processor 100 predicts the onset of an adverse event. Procedure 136 begins with step 138 where the system for mitigating adverse conditions is armed by the caregiver or the bed or EMR based on the occupant's risk profile.

In step 139, the processor 100 receives signals from the sensors 106 indicative of the physiological characteristics of the occupant and/or the amount of movement of the occupant.

In step 140, the processor 100 stores the signal values in the memory 104 and determines an amount and/or a magnitude of change in the values for a predetermined time period. The processor 100 then compares the amount and/or the magnitude of change to a predetermined threshold to determine if an adverse event is likely to occur. In some contemplated embodiments, the processor 100 considers other factors, such as, the occupant's risk score, body position or orientation, person support apparatus 12 and/or person support surface 14 configurations, medical conditions, and/or other information from the caregiver, occupant's EMR, sensors 106, and/or person support apparatus 12 and/or person support surface 14 when determining the likelihood of an adverse event occurring. For example, if an occupant is at a high risk for apnea, is in the supine position, and the occupant's respiration rate is decreasing, then an apnea event may occur. In another example, if an occupant's respiration amplitude decreases and the occupant's oxygen saturation decreases then an apnea event may occur. In another example, if an occupant's snoring is very loud and the occupant is at a high risk for apnea, an apnea event may occur. In another example, if an occupant is at high risk and the occupant is receiving 90% normal breath, an apnea event may be unlikely.

In some contemplated embodiments, prediction of an apnea event can be accomplished using a time-domain model of nonlinear time-lagged interactions between heart rate, respiration, and oxygen saturation to help determine when an apnea event is likely. In some contemplated embodiments, prediction of an apnea event can be accomplished using a Bayesian "belief network" model. In some contemplated embodiments, prediction of an apnea event can be accomplished using large memory storage and retrieval (LAMSTAR) artificial neural networks to analyze signals indicative of heart rate variability, nasal pressure, oronasal temperature, submental EMG, and electrooculography. In some contemplated embodiments, prediction of an apnea event can be accomplished by analyzing tracheal breath sounds.

In step 142, the processor configures the person support surface 14 and/or the person support apparatus 12 as previously described above with respect to procedure 114 and procedure 124 to intervene and help prevent the apnea event.

In another contemplated embodiment, referring to FIGS. 11-18, a support system includes one or more support pieces or units that form a lateral support plane to prevent or restrict the user from sleeping in a supine position, and, more specifically, reduce a time duration that the user sleeps with his/her upper respiratory tract oriented vertically or at an undesirable lateral rotational angle with respect to a vertical plane substantially perpendicular to a horizontal plane. In certain embodiments, the lateral rotational angle of the user's head with respect to the vertical plane is at least 30 degrees and, more specifically, at least 45 degrees. In an alternative embodiment, the lateral rotational angle of the user's head with respect to the vertical plane may be less than 30 degrees. In one embodiment, the support pieces provide multiple support planes for supporting the user's body.

In one embodiment as shown in FIGS. 11-18, a support system 1100 suitable for supporting a user, such as a person, for example, includes plurality of support pieces, namely a first or leg support piece 1102 forming a first support plane 1104, a second or torso support piece 1106 forming a second support plane 1108, and a third or head support piece 1110 forming a third support plane 1112 that collectively define a segmented, multi-plane, laterally angled sleep surface 1114 having progressively greater angles of rotation along a longitudinal axis 1115 of support system 1100, from a first or bottom edge 1116 of sleep surface 1114 to an opposing second or top edge 1118 of sleep surface 1114, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass). In alternative embodiments, sleep surface 1114 is formed using any suitable number of support pieces defining corresponding support planes, for example, one support piece forming a smooth contour over a length of sleep surface 1114 from first edge 1116 to opposing second edge 1118 or a plurality of support pieces, such as two support pieces, three support pieces, or more than three support pieces forming a smooth contour over the length of sleep surface 1114.

Unlike conventional positional therapies for the prevention of obstructive sleep apnea, which attempt to manipulate the user's sleep position and/or orientation using rotation of one plane, in certain embodiments the system described herein uses multiple support planes formed by one or more support pieces to laterally rotate the user. For example, in one embodiment, two support pieces provide two separate support planes, with a first support plane defined by the first support piece configured to support the torso and the legs of the user, and a second support plane defined by the second support piece configured to support the neck and the head of the user.

In an alternative embodiment, three support pieces provide three separate support planes, with a first support plane defined by the first support piece configured to support the legs of the user, a second support plane defined by the second support piece configured to support the torso of the user, and a third support plane defined by the third support piece configured to support the head of the user.

In a further alternative embodiment, more than three support pieces, for example, numerous independent support pieces having a length in a longitudinal direction of sleep surface 1114 of 2-18 inches or, more specifically, 4-12 inches, or, even more specifically, 6 inches, provide a corresponding number of separate support planes. Each support piece can be laterally rotated independently of other support pieces to collectively form sleep surface 1114. In a particular embodiment, the numerous support pieces can be combined to form separate support pieces, for example, creating a first support piece having a length of 18 inches in the longitudinal direction at the foot of the support system 1100, an adjacent second support piece having a length of 12 inches in the longitudinal direction, and a third support piece adjacent the second support piece having a length in the longitudinal direction of 6 inches. In these embodiments, the support pieces forming the support planes can be rotated as necessary or desired to achieve an optimal configuration that is clinically effective (i.e., prevents apnea) and demonstrates acceptable tolerance (i.e., allows the user to sleep comfortably). In an alternative embodiment, a continuously sloped sleep surface is formed by a plurality of support pieces without step increases in lateral rotational angle; this is illustrated as a sleep surface with an infinite number of support pieces.

In the embodiments described herein, the length in the longitudinal direction of each support piece and defined support plane (and the resulting location of transitions between support planes) is designed to achieve clinical efficacy and tolerability. Therefore, a specific length can be defined in a number of configurations, including without limitations: (a) generic plane dimensions (e.g., based on average body geometry, a length of a torso section of the user defined so that when an average user's head is supported by a head support piece, a transition between the torso support piece and the leg support piece occurs below the user's S3 vertebrae); (b) customized plane dimensions (e.g., a torso support plane has a suitable length in the longitudinal direction appropriate to the user's leg length, torso length, and/or a distance from the user's shoulder to his/her inseam); or (c) dynamic plane dimensions (e.g., transitions selected on dynamic surface appropriate to user, selection being either user-selected, care-giver defined, or automatically calculated).

In certain embodiments, each support piece defining the corresponding support planes is independently rotatable about an axis extending parallel with a longitudinal axis of the support system. The independent rotation of each support piece allows the caregiver or the user the ability to focus on progressively increasing an angle of rotation in one or more support pieces having support planes positioned to support the torso of the user, and the neck and/or the head of the user. In certain embodiments, an angle of rotation (or lateral rotational angle) at which the one or more support planes defined by the support pieces configured to support the neck and/or the head of the user is positioned is greater than a rotational angle of the one or more support planes defined by the support pieces configured to support the torso of the user, which is greater than a rotational angle at which the one or more support planes defined by the support pieces configured to support the legs of the user is positioned.

In a particular embodiment, the support plane defined by the support piece configured to support the legs and the torso of the user is positioned at a rotational angle of 10° with respect to a base surface of the support piece, while the support plane defined by the support piece configured to support the head of the user is positioned at a rotational angle of 20° with respect to a base surface of the support piece. In an alternative embodiment, a first support plane defined by the support piece configured to support the legs of the user is positioned at a rotational angle of 10° with respect to a base surface of the first support piece, a second support plane defined by a second support piece configured to support the torso of the user is positioned at a rotational angle of 15° with respect to a base surface of the second support piece, and a third support plane defined by the third support piece configured to support the head of the user is positioned at a rotational angle of 20° with respect to a base surface of the third support piece. In alternative embodiments, the support planes can be positioned at any suitable rotational angle including any suitable lateral rotational angle and/or any suitable longitudinal rotational angle.

Referring further to FIGS. 14 and 15, in a particular embodiment, first support piece 1102 defines support plane 1104 positioned at a lateral rotational angle α of 20° to 30°, or more specifically, 20° to 25°, or, even more specifically, 25° with respect to a base surface 1122 of first support piece 1102. Second support piece 1106 defines support plane 1108 positioned at a lateral rotational angle β of 10° to 20°, or more specifically, 10° to 15°, or, even more specifically, 15°, with respect to a base surface 1124 of second support piece 1106. Third support piece 1110 defines support plane 1112 positioned at a lateral rotational angle γ of 5° to 15°, or more specifically, 10°, with respect to a base surface 1126 of third support piece 1106. Other lateral rotational angles and step increases in lateral rotational angles between each support piece may also be used to achieve a progressive lateral rotational angle.

In one embodiment as shown in FIG. 15, one or more contoured transitional pieces, such as a first transitional piece 1130 and a second transitional piece 1132, are positionable between adjacent support pieces or at or near a transition line between the adjacent support pieces to provide a gradual continuous transition between support planes. As shown in FIG. 15, in one embodiment, a first transitional piece 1130 is positioned at a transitional line where first support piece 1102 meets with adjacent second support piece 1106 to provide lumbar support for the user. Similarly, a second transitional piece 1132 is positioned at a transitional line where second support piece 1106 meets with adjacent third support piece 1110 to provide lumbar support for the user. In particular embodiments, one or more additional transitional pieces can be positioned on the support planes to provide additional support at the neck region and/or the knee region of the user, for example. In other embodiments, increasing the number of contoured transitional pieces allows for more contouring and gradual changes in the angle of support along the length of the support system 1100.

As shown in FIG. 17, each of first support piece 1102, second support piece 1106, and third support piece 1110 has a respective height in a direction perpendicular to longitudinal axis 1115 of support system 1100. In one embodiment, first support piece 1102 has a maximum height from base surface 1122 to support plane 1116 in a direction perpendicular to longitudinal axis 115 of 14 to 18 inches, or more specifically, 16 to 17 inches; second support piece 1106 has a maximum height from base surface 1124 to support plane 1108 in a direction perpendicular to longitudinal axis 1115 of 8 to 12 inches, or more specifically, 9 to 10 inches; and third support piece 1110 has a maximum height from base surface 1126 to support plane 1112 in a direction perpendicular to longitudinal axis 1115 of 4 to 8 inches, or more specifically, 6 to 7 inches. As a result, the support pieces can be designed with desired heights and defining support planes positioned at desired rotational angles such that support system 1100 provides a composite longitudinal plane angle (e.g., reverse Trendelenburg angle) to facilitate the prevention and/or treatment of sleep apnea as well as to improve tolerability.

As described in greater detail below, in certain embodiments, support system 1100 includes a system control, such as a controller 1140 shown in FIG. 18, having a display configured to display information about support system 1100 including, without limitation, lateral plane angles of each support piece and/or composite plane angles of each support piece. In one embodiment, controller 1140 includes one or more processors configured to adjust the rotational angles of the support planes based on data input by the user or a caregiver and/or data signals received from one or more sensors positioned at locations on or near support system 1100.

Referring again to FIG. 15, in one embodiment, support system 1100 includes a bolster 1142 or other suitable boarder positioned along at least one lateral side of support system 1100 to limit or prevent lateral migration of the user. More specifically, bolster 1142 extends along at least a portion of the lateral side generally parallel with longitudinal axis 1115 to prevent or limit lateral movement of the user positioned on sleep surface 1114 to prevent the user from moving or sliding off sleep surface 1114. Bolster 1142 is bolstered at lower edge 1116 of sleep surface 1114 to define an envelopment zone. In one embodiment, bolster 1142 extends from lower edge 1116 partially along a length of support system 1100 to a torso region of the user, but, in this embodiment, terminates below a head portion of the user. In a particular embodiment, at least a portion of bolster 1142 includes a suitable material to provide a textured surface to facilitate retaining the user in the desired position on the support system 1100. Additionally or alternatively, bolster 1142 may include a formable material, such as a suitable foam material, having one or more different densities along a length of bolster 1142 to provide an increased envelopment throughout sleep surface 1114. A belt and/or an adjustable strap (not shown in FIG. 15) or a body may be operatively coupled to bolster 1142 to facilitate maintaining the user properly positioned on sleep surface 1114.

In one embodiment, each of support pieces 1102, 1106, 1110 are rotatable about longitudinal axis 1115 to provide sleep surface 1114 having a right side slope or, alternatively, a left side slope to allow the user to sleep on his/her right side or left side, respectively. In one embodiment, one or more cylindrical or tubular sections are positioned within at least a portion of first support piece 1102, second support piece 1106, and third support piece 1110 and coaxially aligned with longitudinal axis 1115 to allow each support piece 1102, 1106, 1110 to rotate about longitudinal axis 1115 independently of the other support pieces 1102, 1106, 1110.

Figure 20A:
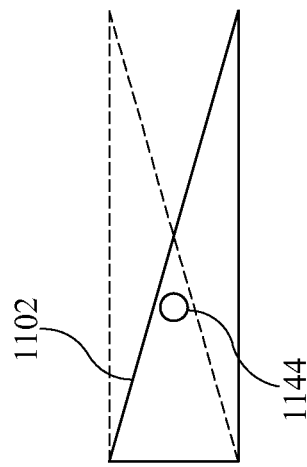
FIG. 20A is a cross-sectional view of the support system shown in FIG. 19 taken along sectional line 20A in FIG. 19.
Figure 20B:
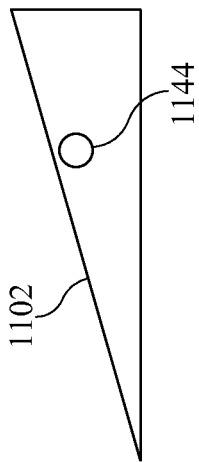
FIG. 20B is a cross-sectional view of the support system shown in FIG. 19 taken along sectional line 20A in FIG. 19 and rotated 180° about a longitudinal axis of the support system.
Figure 19:
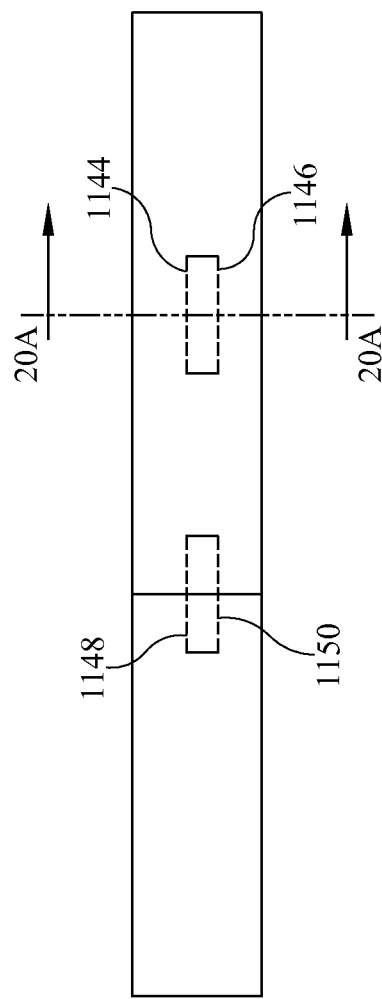
FIG. 19 is a side view of an exemplary support system including a plurality of independently rotatable support pieces.

As shown in FIG. 19, a first cylindrical section 1144 is positioned within a bore 1146 defined within a portion of first support piece 1102 and second support piece 1106 along longitudinal axis 1115 to allow first support piece 1102 and second support piece 1106 to rotate about longitudinal axis 1115 and with respect to each other. Similarly, a second cylindrical section 1148 is positioned within a bore 1150 defined within a portion of second support piece 1106 and third support piece 1110 along longitudinal axis 1115 to allow second support piece 1106 and third support piece 1110 to rotate about longitudinal axis 1115 and with respect to each other. In an alternative embodiment not shown, a single cylindrical section extends through a bore defined through second support piece 1106 and into at least a portion of first support piece 1102 and into at least a portion of third support piece 1110 to allow each of first support piece 1102, second support piece 1106, and third support piece 1110 to rotate about longitudinal axis 1115 and with respect to each other. In this embodiment, each support piece 1102, 1106, 1110 is rotatable between a first orientation having a right side slope, as shown in FIG. 20A, and a second orientation having a left side slope, as shown in FIG. 20B. Axial rotation allows each support piece 1104, 1106, 1110 to lie flat with a right side slope or a left side slope as shown in FIGS. 20A and 20B.

In certain embodiments, support pieces 1102, 1106, 1110 are formed of more than one material, for example, two or more materials, such as two foam materials, having different densities, with the less dense material covering the denser material. In this embodiment, the less dense material is laid on the denser material at the respective base surface and the respective support plane of the support piece to allow sleep surface 1114 to function properly, whether with a right side slope or a left side slope. With the denser material sandwiched between the less dense material, the user will be positioned on the less dense material in either the first or the second orientation.

In this embodiment, support system 1100 allows the user to sleep on either his/her right side or left side, based on the user's sleeping preference. This sleeping preference may not be static. For example, if the user has an injury, an ache, or a desire to change his/her sleeping preference, the orientation of sleep surface 1114 can be changed at any time to accommodate the user's sleeping preference. The orientation can be changed from day to day or during the night. Moreover, from a manufacturing standpoint, a versatile support system 1100 prevents having to manufacture and distribute a sleep surface 1114 having a right side slope and a separate sleep surface 1114 having a left side slope, which would increase production and distribution costs. Finally, a potential purchaser would not have to commit to a sleep side before purchasing the product, which might be a deterrent to purchasing the product.

Figure 21:
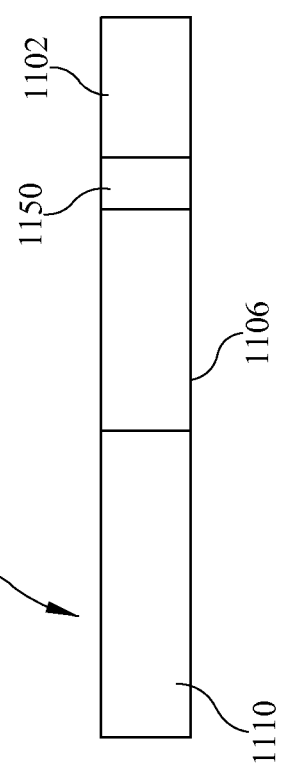
FIG. 21 is side view of an exemplary support system including a plurality of support pieces.
Figure 22:
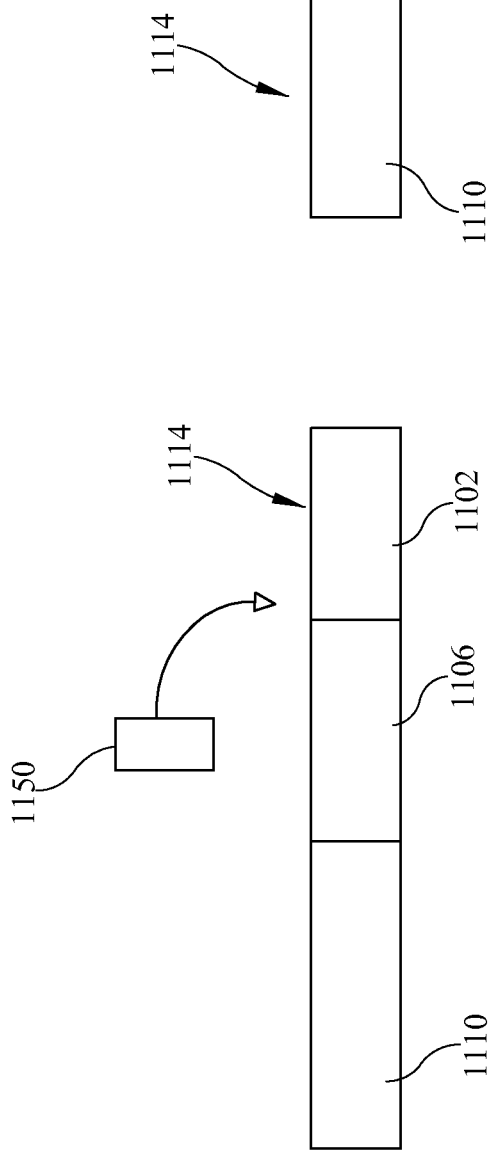
FIG. 22 is a side view of the support system shown in FIG. 21 including a spacer positioned between adjacent support pieces.
Figure 23:
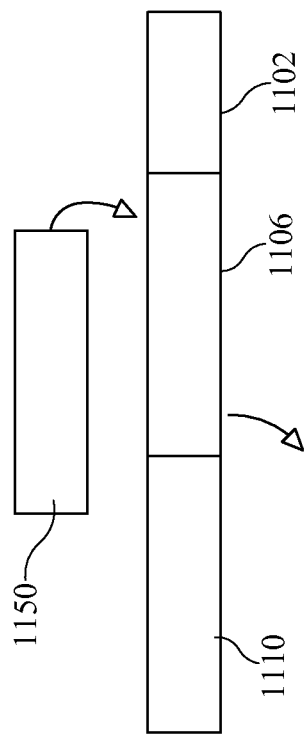
FIG. 23 is a side view of an exemplary support system including a plurality of support pieces.
Figure 24:
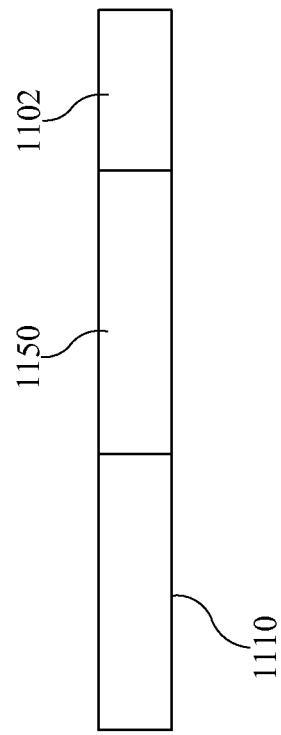
FIG. 24 is a side view of the support system shown in FIG. 23 including a spacer replacing one of the support pieces.

In one embodiment, support system 1100 includes one or more spacers 1152 that allow a length of support system 1100 to be adjusted and customized to a height of the user supported by support system 1100. For example, the length of sleep surface 1114 can be adjusted by adding one or more suitable spacers 1152 or replacing one or more support pieces 1102, 1106, 1110 with a suitable spacer 1152 of a different length, so that transitional lines between lateral angles of support planes defined by adjacent support pieces 1102, 1106, 1110 will desirably occur at a neck region and a hip region of the user. In one embodiment, spacer 1152 has a same or similar lateral rotational angle and/or a same or similar longitudinal rotational angle as the respective lateral rotational angle and the respective longitudinal rotational angle of an adjacent support piece or the support piece that spacer 1152 replaces. In an alternative embodiment, spacer 1152 has a different lateral rotational angle and/or a different longitudinal rotational angle as the respective lateral rotational angle and the respective longitudinal rotational angle of an adjacent support piece or the support piece that spacer 1152 replaces. As shown in FIGS. 21 and 22, spacer 1152 is positioned between first support piece 1102 and second support piece 1106 to adjust the length of sleep surface 1114. As shown in FIGS. 23 and 24, first support piece 1102 is replaced with spacer 1152 to adjust the length of sleep surface 1114.

Assuming the user positions his/her neck at the appropriate location on sleep surface 1114, and an overall length of sleep surface 1114 is adjustable, in one embodiment only second support piece 1106 of support system 1100 has an adjustable length. In alternative embodiments having a support system 1100 with a fixed length, both first support piece 1102 and second support piece 1106 have adjustable lengths. In this embodiment, a length of first support piece 1102 increases as a length of second support piece 1106 decreases and, conversely, the length of first support piece 1102 decreases as the length of second support piece 1106 increases.

In one embodiment, adjacent support pieces 1102, 1106, 1110 and spacers 1152 can be coupled together using a suitable coupling mechanism including, without limitation, one or more of the following: snaps, straps, buttons, and hook-and-loop fasteners. In certain embodiments, the length of sleep surface 1114 is adjustable by any combination of inserting one or more spacers 1152, replacing one or more support pieces 1102, 1106, 1100 with a longer or shorter spacer 1152, cutting or trimming one or more support pieces 1102, 1106, 1110 to a desired length, and removing one or more support pieces 1102, 1106, 1110. In alternative embodiments, the length of sleep surface 1114 is not adjustable but one or more of a leg region, a torso region, and a head region of sleep surface 1114 is adjustable by any combination of inserting one or more spacers 1152, replacing one or more support pieces 1102, 1106, 1100 with a longer or shorter spacer 1152, cutting or trimming one or more support pieces 1102, 1106, 1110 to a desired length, and removing one or more support pieces 1102, 1106, 1110 without adjusting the length of sleep surface 1114.

In a further alternative embodiment, each support piece 1102, 1106, 1110 includes one or more inflatable fluid bladders configured to contain a fluid, such as air. In this embodiment, a length of each support piece 1102, 1106, 1110 is adjustable by adding fluid or removing fluid from one or more respective fluid bladders. By adding fluid to one or more of the respective fluid bladders, the length of the respective support piece 1102, 1106, 1110 is increased and the length of the respective support plane 1104, 1108, 1112 is also increased. Conversely, removing fluid from one or more of the respective fluid bladders, the length of the respective support piece 1102, 1106, 1110 is decreased and the length of the respective support plane 1104, 1108, 1112 is also decreased. The amount of fluid within the respective fluid bladders can be monitored and controlled electronically or by the user or caregiver using a suitable device including, without limitation, a suitable pneumatic pump or nozzle. In certain embodiments, a coupler, such as one or more snaps or straps, are utilized to maintain the desired amount of fluid within the respective fluid bladders and provide additional support to the respective support plane(s), for example, when the fluid bladders are not inflated.

As described herein, sleep surface 1114 is customizable to anthropometric dimensions of the individual user to facilitate support system 1100 performance that optimizes or matches the design intent—the body position of the user will prevent or limit undesirable sleep apnea episodes and provide improved comfort.

In certain embodiments, support system 1100 includes a plurality of support pieces, such as two support pieces, three support pieces, or more than 3 support pieces, and more specifically, at least 6 support pieces, and even more specifically, 8-20 support pieces. For example, referring to FIG. 25, in one embodiment each of a leg region 1160 corresponding to first support piece 1102, a torso region 1162 corresponding to second support piece 1106, and a head region 1164 corresponding to third support piece 1110 of support system 1100 includes a plurality of independent support wedges forming a finer gradation in the longitudinal slope of sleep surface 1114 to increase user compliance and the effectiveness of support system 1100 in preventing or limiting sleep apnea episodes and providing more comfort for the user supported on sleep surface 1114. The support wedges may be formed of one or more suitable materials including, without limitation, a formable material, a semi-rigid material, a foam material or one or more fluid bladders.

Figure 25:
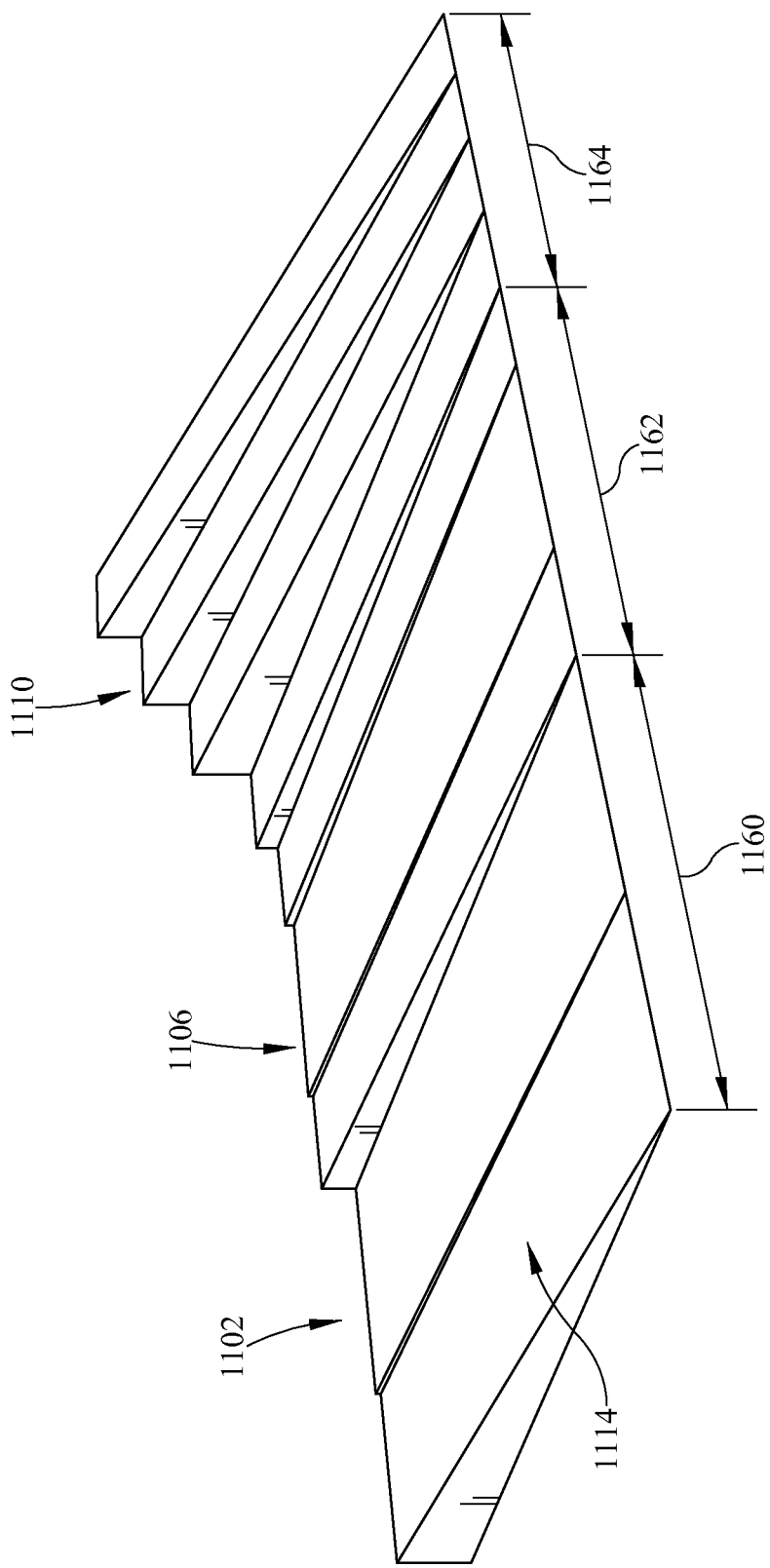
FIG. 25 is a perspective view of an exemplary support system showing a greater number of support wedges to allow more gradual changes in edge angle along a length of a sleep surface.

In the embodiment shown in FIG. 25, first support piece 1102 includes two independent support wedges defining respective support planes positioned at different lateral rotational angles, second support piece 1106 includes three independent support wedges defining respective support planes positioned at different lateral rotational angles, and third support piece 1110 includes four independent support wedges defining respective support planes positioned at different lateral rotational angles. In alternative embodiments, each support piece 1102, 1106, 1110 includes any suitable number of independent support wedges. Generally, an increasing number of independent support wedges within a selected support piece allows for more detailed and specific contouring of sleep surface 1114 and more gradual changes in rotational angles of adjacent support wedges and support pieces along the length of sleep surface 1114.

For example, a support system including a series of support wedges may twist or urge the user's body to rotate and tilt the user's head in a more gradual trend than a support system including only three larger support pieces with respective support planes of different lateral rotational angles. The additional support wedges allow for more comfortable transitions between and within the lower body, the torso, and the upper body of the patient. The increased number of support wedges allow for more specific positioning of the patient's body, and a more effective therapy.

Figure 26:
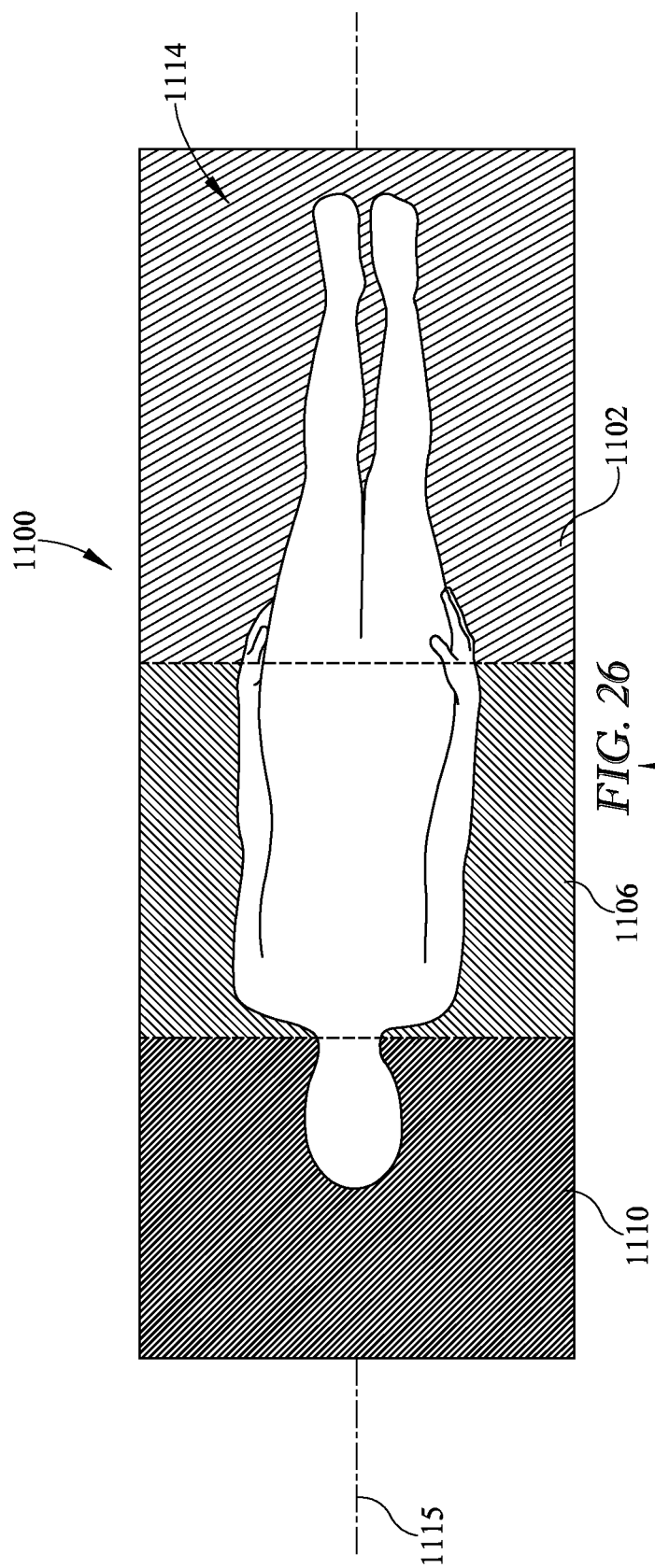
FIG. 26 is a top plan view of an exemplary support system supporting a user on a sleep surface defined by the support system.
Figure 27:
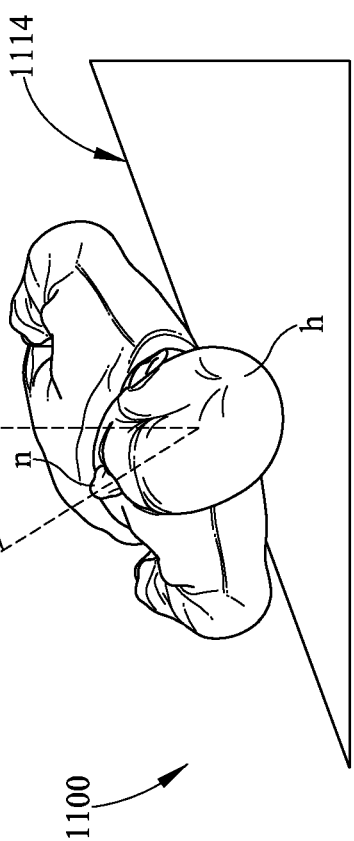
FIG. 27 is a side view of the support system shown in FIG. 26 illustrating a continuous support piece exhibiting a gradual density transition along a longitudinal length of the sleep surface.

Referring to FIGS. 26 and 27, in one embodiment, each support piece 1102, 1106, 1110 defines a support plane positioned at the same or similar lateral rotational angle; however, each support piece 1102, 1106, 1110 is made of a material having a different density than the material used to make the other support pieces. The base material of each support piece 1102, 1106, 1110 may be the same or different than the base material of the other support pieces, but with a different density. In a particular embodiment, support system 1100 utilizes varied foam density to achieve a variation in the lateral rotation of the user's body across different body segments. In one particular embodiment, support piece 1102 is composed of the least dense material, support piece 1106 is composed of the medium density material, and support piece 1110 is composed of the most dense material.

In this embodiment, sleep surface 1114 is formed of support pieces cut to form support planes at the same lateral rotational angle but with different densities. To achieve a greater relative rotation at the head portion of the user, third support piece 1110 is denser than second support piece 1106, while first support piece is less dense than second support piece 1106 and third support piece 1110 to achieve a lesser or limited relative rotation at the leg region of the user. In a particular embodiment, rather than having a plurality of discrete support pieces, sleep surface 1114 is one continuous support piece exhibiting a gradual density transition along a longitudinal length of sleep surface 1114 such that the leg portion of sleep surface 1114 is less dense than the opposite head portion of the sleep surface 1114. This feature may result in a support system that appears less intimidating to the user and more aesthetically pleasing. Moreover, sleep surface 1114 is rotatable about longitudinal axis 1115, shown in FIG. 26, so that sleep surface 1114 is oriented in one of a lateral right side slope or a lateral left side slope shown in FIG. 27.

Referring to FIGS. 28-35, in an alternative embodiment, sleep surface 1114 is formed of a closed air system 1160 that induces the user's body to rotate laterally when sleeping to facilitate preventing or limiting the incidence of sleep apnea. In certain embodiments, closed air system 1160 does not require electrical power or control, and allows the user to quietly move sleep orientations between the lateral left side slope and the lateral right side slope during sleep.

Figure 28:
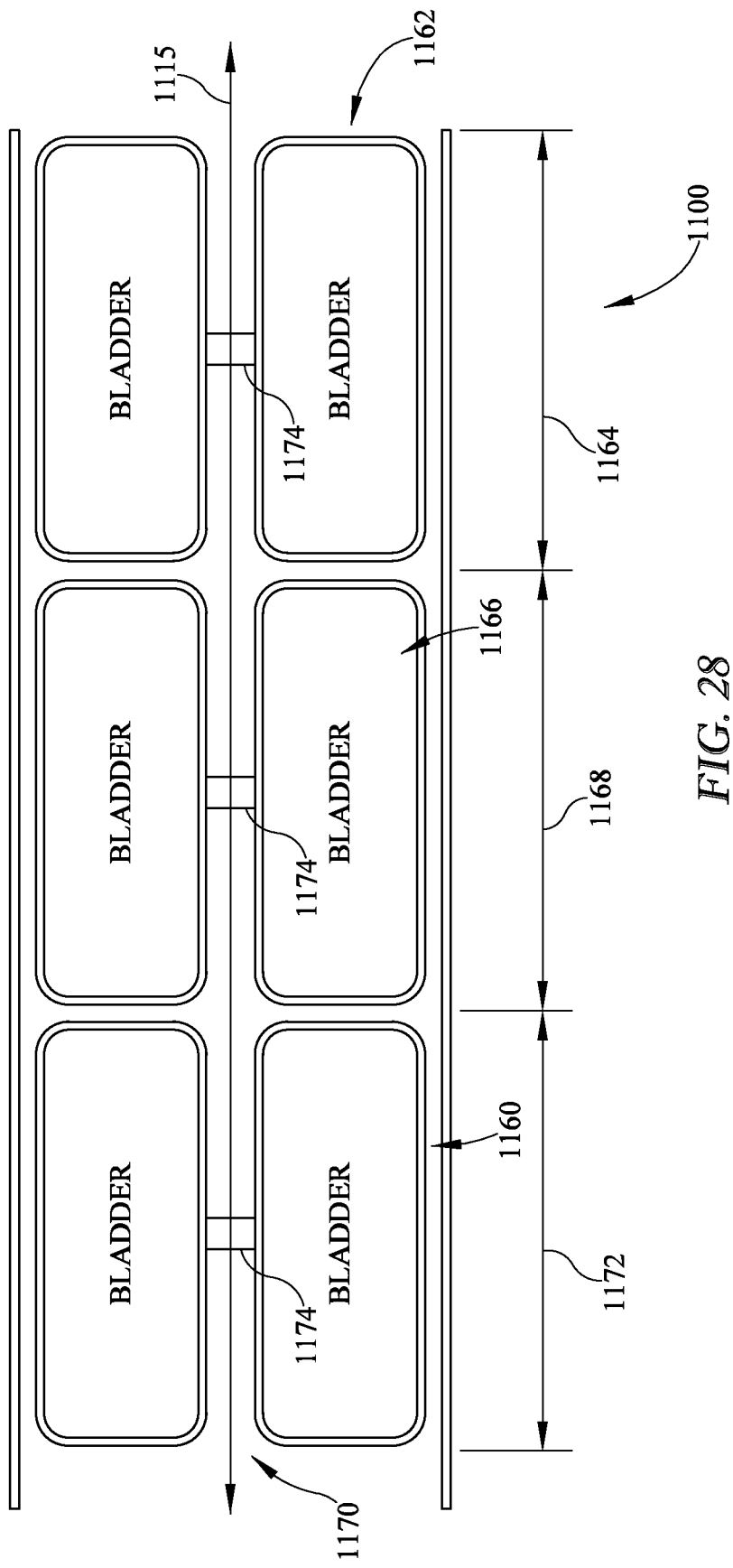
FIG. 28 is a top plan view of an exemplary dynamic support system.
Figure 30:
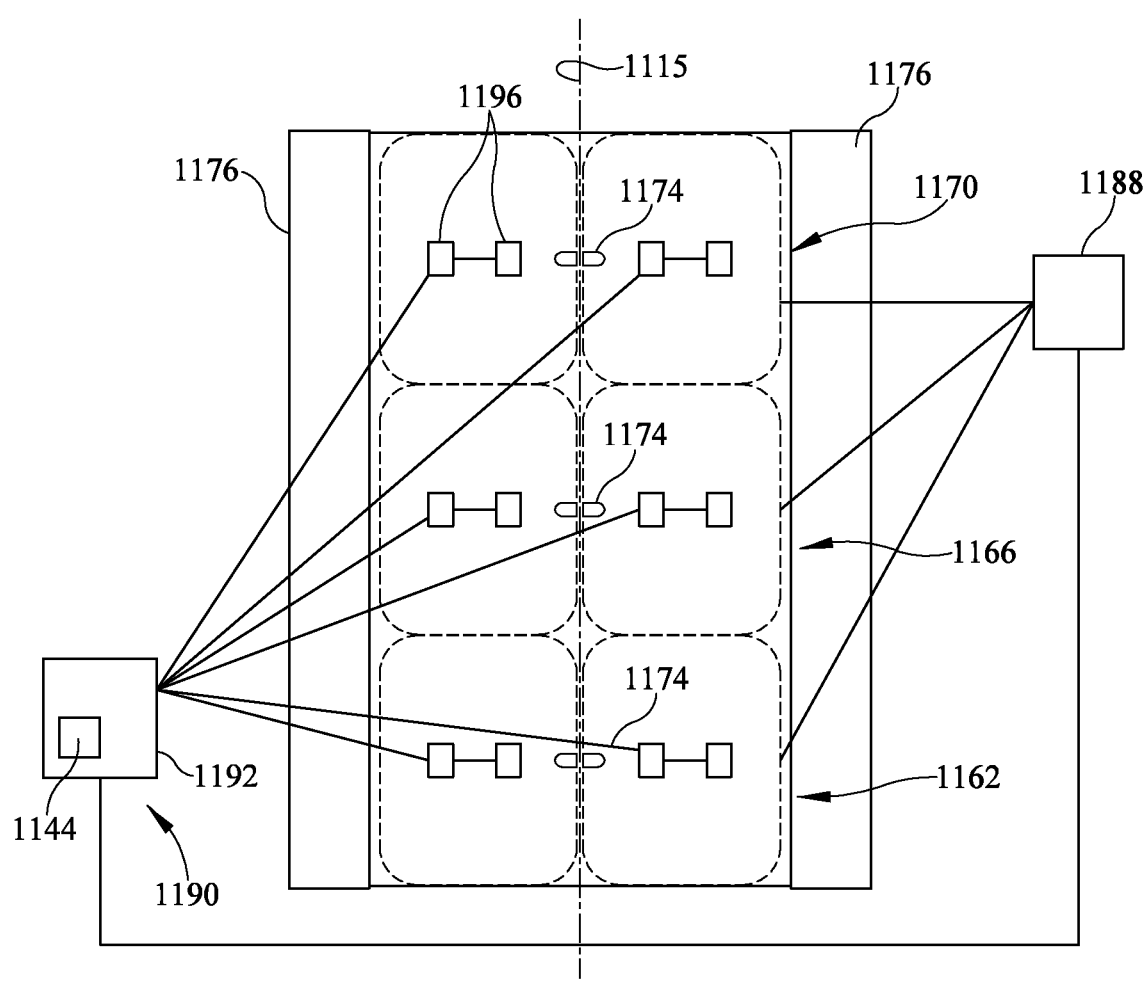
FIG. 30 is a top view of the dynamic support system shown in FIG. 29.

In one embodiment, closed air system 1160 includes one or more pairs of fluid bladders communicatively coupled to each other. For example, as shown in FIGS. 28 and 30, a first pair of fluid bladders 1162 is positioned within the leg region 1164 of closed air system 1160, a second pair of fluid bladders 1166 is positioned within a torso region 1168 of closed air system 1160, and a third pair of fluid bladders 1170 is positioned within a head region 1172 of closed air system 1160. In a particular embodiment, a sleep sensor is positioned in a pillow or on the bladder 1166. In a particular embodiment, the fluid bladders are plumbed together using a suitably sized tube or hose, shown schematically by reference number 1174 in FIGS. 28 and 30, or any suitable coupling mechanism providing communication between the interior cavities of the fluid bladders to allow fluid to move at a desired rate between the coupled bladders. Fluid, such as air, can be added manually or using a suitable pump to each pair of fluid bladders, for example, through one or more nozzles to adjust the firmness and lateral rotational angle of the respective pair of fluid bladders. In this embodiment, the user can adjust the side upon which he/she sleeps (even during sleep) and an amount of fluid contained within the fluid bladders to adjust the firmness of sleep surface 1114 and/or the lateral rotational angle of each support plane forming sleep surface 1114. In this embodiment, each pair of fluid bladders is separated along longitudinal axis 1115 of support system 1100. In a particular embodiment, fluid can be added to the bladders 1166 based on the sleep state of the person.

Figure 29:
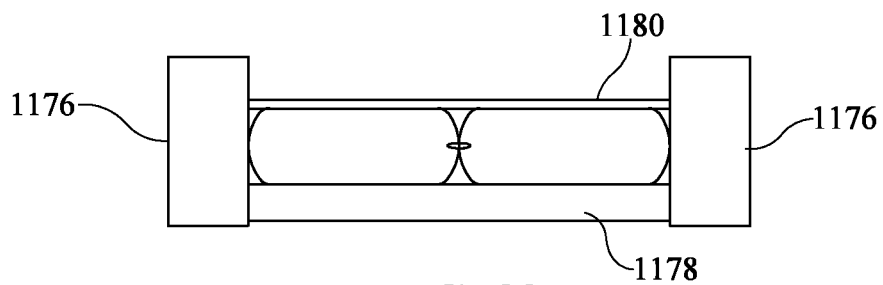
FIG. 29 is a front view of an exemplary dynamic support system.
Figure 31:
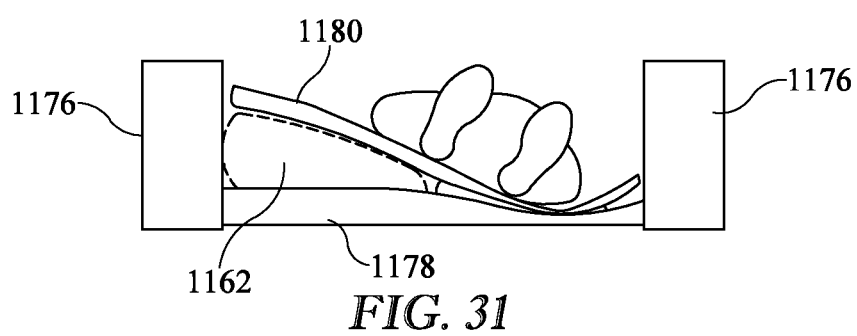
FIG. 31 is an end view of the dynamic support system shown in FIG. 29 illustrating a lateral rotation of planes.

In a particular embodiment, closed air system 1160 includes one or more bolsters 1176, as shown in FIGS. 29-31, positioned along at least a portion of the opposing lateral sides of support system 1100 to prevent or limit lateral migration of the user during sleep. In one embodiment, bolsters 1176 are the same or similar to bolster 1142 described above with reference to FIG. 15. Referring further to FIG. 29, each air bladder rests on and is supported by a suitable bottom layer, such as a foam material layer 1178 and/or a mattress, and can also be covered by another suitable top layer, such as a foam material layer 1180. Materials other than foam materials known to those having ordinary skill in the art can be utilize to form the bottom layer and/or the top layer. In a certain embodiment, material layer 1180 at least partially encloses or envelops one or more of the fluid bladders to retain the fluid bladders properly positioned within support system 1100. One or more of the fluid bladders in one or more of the pairs of fluid bladders are inflatable to rotate the user onto his/her right side or left side based at least in part on his/her sleep state.

In one embodiment, one or more pairs of fluid bladders 1162, 1166, 1170 include two wedge-shaped fluid bladders that are removably coupled to material layer 1178 and/or material layer 1180 using a suitable coupler, such as a hook and loop fastener system. For example, third pair of fluid bladders 1170 are positioned with respect to the user's upper body or head region and are removably coupled to material layer 1180 using a hook and loop fastener system such that sleep surface 1114 is adjustable based at least in part on the size and weight of the user. These fluid bladders are inflatable based on the user's sleep state to urge the upper body of the user to rotate. Additionally, first pair of fluid bladders 1162 and/or second pair of fluid bladders 1166 are also inflatable to urge the user's legs and/or the user's torso, respectively, to rotate.

Figure 32:
FIGS. 32-35 illustrate various configurations of fluid bladders forming at least a portion of the dynamic support system shown in FIG. 29.
Figure 33:
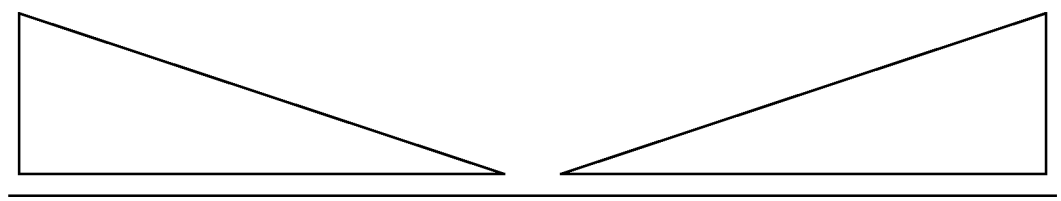
Figure 34:
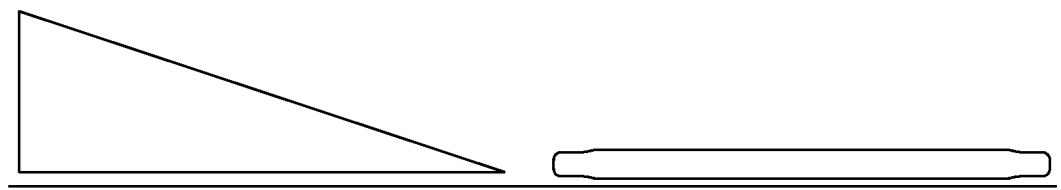
Figure 35:
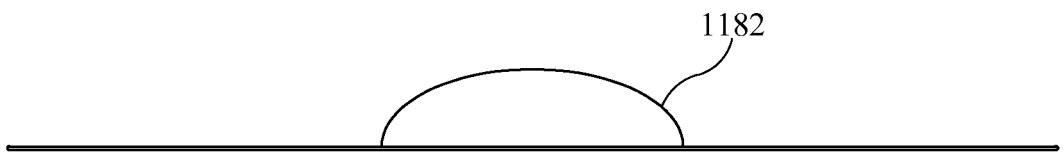

Referring further to FIGS. 32-35, each fluid bladder of each pair of fluid bladders 1162, 1166, 1170 is inflatable to form a support piece having a desired or selected shape. Select fluid bladders may remain substantially deflated, as shown in FIG. 32, or both fluid bladders or only one fluid bladder of one or more pairs of fluid bladders may be inflated to form a desired sleep surface 1114, as shown in FIGS. 33 and 34 respectively. In an alternative embodiment, as shown in FIG. 35 a single fluid bladder 1182 may be utilized in one or more of leg region 1164, torso region 1168, and head region 1172 of closed air system 1160 positioned along longitudinal axis 1115 of support system 1100 that, when inflated, urges the user to roll towards either the lateral right side or the lateral left side after the user is in a predetermined sleep state. In this embodiment, fluid bladder 1182 can be deflated occasionally to allow the user to reposition himself/herself. A pillow can be positioned on third pair of fluid bladders, for example, such that the pillow is inclined when one or more of the fluid bladders are inflated.

The fluid bladders are inflatable with air or another suitable fluid (which can be drained as desired from within the cavities of the fluid bladders into a reservoir). A fluid supply 1188, shown in FIG. 30, is positioned at or near support system 1100, such as on the floor, beneath the bed, or coupled to the bed. The fluid supply is in independent fluid communication with each pair of fluid bladders 1162, 1166, 1170 to supply a desired amount of fluid to each fluid bladder based on a signal from a control, for example.

In one embodiment as shown in FIG. 30, support system 1100 includes a suitable computer-implemented control system 1190 operatively coupled to closed air system 1160, such as in operational control communication with closed air system 1160. The computer-implemented control system includes a computer 1192 having one or more processors 1194 and one or more sleep sensors 1196, such as one or more pressure sensors, coupled in signal communication with processors 1194. Sleep sensors 1196 are configured to monitor the user's sleep patterns and transmit signals indicative of the sensed sleep patterns to processors 1194 for manipulation and evaluation of the data. Based at least in part on the one or more signals received from one or more sleep sensors 1196, control system 1190 is configured to inflate or deflate select fluid bladders to reposition the user during sleep to prevent or limit the occurrence of a sleep apnea episode, for example.

Additionally, in certain embodiments, closed air system 1160 is configured to rest on a conventional mattress or may be configured or reinforced to rest directly on a support structure, such as a bed frame or a floor. With the fluid substantially removed from each of the fluid bladders, closed air system 1160 can be folded or rolled into a compact configuration to facilitate storing and transporting closed air system 1150. In certain embodiments, closed air system is less expensive than a conventional mattress and more compact to facilitate portability of support system 1100. Additionally, closed air system 1160 as configured prevents or limits disturbance to the user's partner sleeping next to the user.

In certain embodiments as described herein, support system 1100 is a dynamic support system, rather than a static support system, that is configured to control the configuration of sleep surface 1114 based at least in part on data entered into control system 1190 using computer 1192, or another control operatively coupled to computer 1192, and/or sensed by one or more sleep sensors 1196, for example, to improve the performance of sleep surface 1114 in terms of clinical efficacy and user tolerability.

Figure 36:
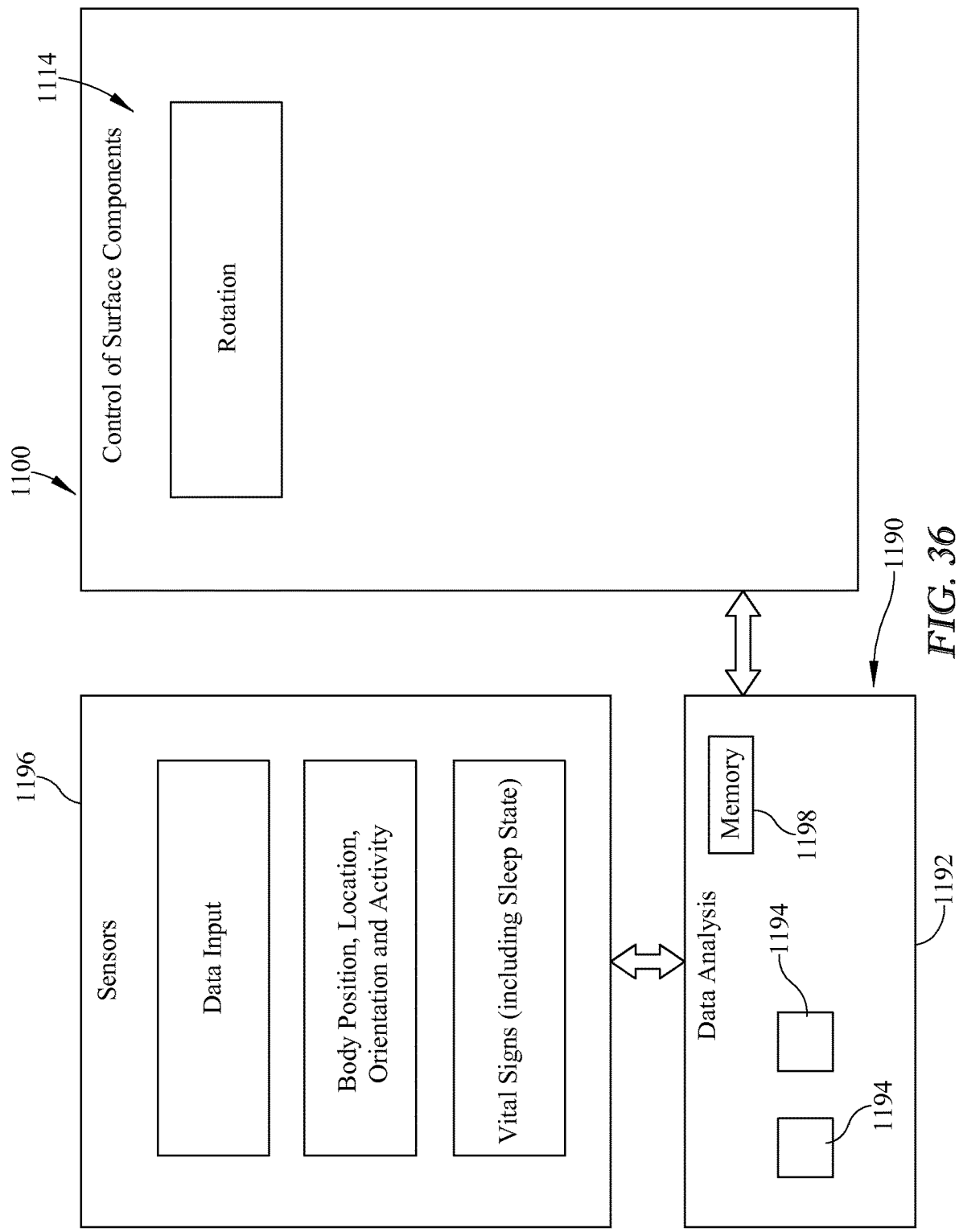
FIG. 36 is a schematic view of an exemplary dynamic support system.
Figure 37:
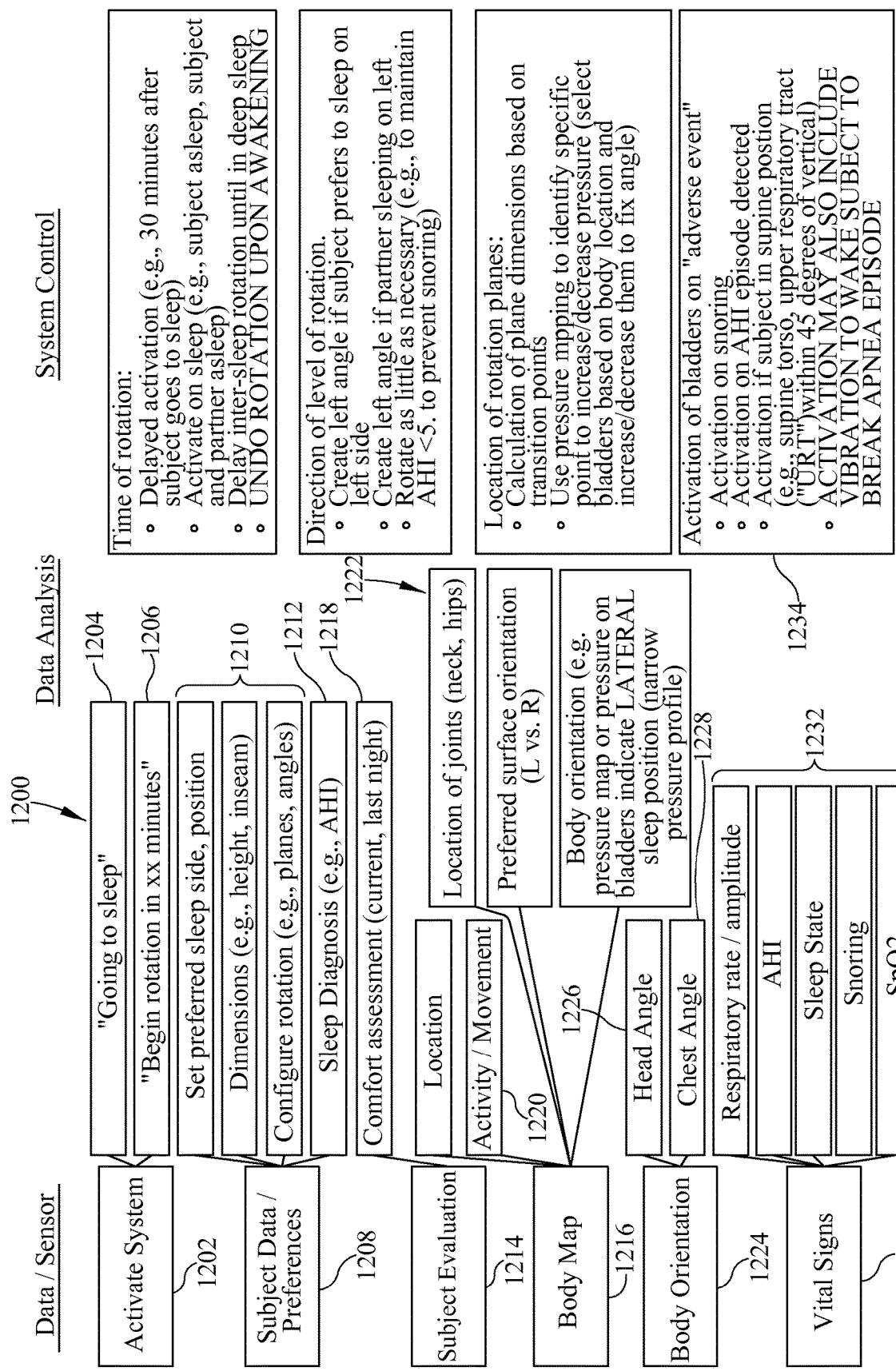
FIG. 37 illustrates an exemplary method for monitoring sleep activities of a user positioned on a dynamic support system, such as the support system shown in FIG. 36.

As described herein and shown schematically, for example, in FIGS. 36 and 37, dynamic support system 1100 includes, in addition to other components, a plurality of sleep sensors 1196 configured to sense and monitor various activities including without limitation, the user's body position, a location of the user with respect to sleep surface 1114, an orientation, for example, a left side orientation or a rights side sleep orientation, of the user, the user's vital signs including his/her sleep state, and additional relevant user activity during sleep. Each sleep sensor 1196 is in signal communication with one or more processors 1194 contained within computer 1192 and configured to gather relevant data and generate and transmit to processors 1194 signals indicative of the data gathered. Sleep sensors 1196 are also configured to receive operation control signals from processors 1194.

Within computer 1192, data received from sleep sensors 1196 is analyzed and operational control signals are transmitted to sleep sensors 1196 as well as to other components of support system 1100, such as to fluid supply 1188 to activate fluid supply 1188 to provide air to one or more fluid bladders and/or remove air from one or more fluid bladders to adjust sleep surface 1114 based on signals generated by sleep sensors 1196 and analyzed within computer 1192. In one embodiment, computer 1192 includes suitable memory 1198 to store data sensed and/or generated by control system 1190.

An exemplary method 1200 utilizing control system 1190 for monitoring the sleep activities of a user positioned on support system 1100 is illustrated in FIG. 37. As described above, control system 1190 includes one or more processors 1194 configured to perform the steps as described herein.

Control system 1190 is activated 1202 either manually or automatically to monitor the user's sleep activities and patterns as user begins to sleep. In one embodiment, control system 1190 detects when the user begins to fall asleep 1204 and activates support system 1100 (or a dynamic sleep surface) on a delay 1206 to rotate the user at a suitable time after sleep is detected, such as after the user has been asleep for 30 minutes. In an alternative embodiment, control system 1190 is programmed to activate support system 1100 at a preset time, for example, at a 30 minute delay, without relying on monitoring the user's sleep activity. In a particular embodiment, control system 1190 delays inter-sleep rotation of the user until the user is in a deep sleep. Further, when control system 1190 detects that the user is waking, control system 1190 will activate support system 1100 to move sleep surface 1114 to an initial configuration such that the user can exit from support system 1100. In a further embodiment, control system 1190 prevents activation of support system 1100 if control system 1190 detects the user is sleeping in a lateral decubitus position.

Prior to sleep, the user is able to input 1208 to control system 1190 sleep data 1210 including without limitation, preferred sleeping sides and positions, the user's measurements including, for example, the user's height, weight, and inseam and torso measurements, preferred lateral rotational angles and/or longitudinal rotational angles of one or more support planes defining sleep surface 1114. Based at least in part on the user's input data, control system 1190 is configured to activate support system 1100 to adjust a direction and/or a level of rotation of one or more support planes defining sleep surface 1114. For example, if the user prefers a left side slope to sleep surface 1144, control system 1114 activates fluid bladders within support system 1100 to form the desired lateral left side slope, or if the user's partner is sleeping on the left side of the user, a left angle may be created. In one embodiment, minimal adjustments are made to sleep surface 1114 to maintain the user's AHI under 5 and/or prevent snoring because apneas events and snoring may or may not be equivalent, depending on the user.

Additionally, control system 1190 is configured to collected and record data obtained as the user sleeps to diagnose any undesirable or abnormal sleep activities or conditions, including the user's apnea-hypopnea index (AHI), for example.

During sleep, control system 1190 assesses the user's comfort level 1214 and, in a particular embodiment, compares the current evaluation with previous evaluations. The user's body is then mapped 1216 to map body region locations 1218, and user activities and movements 1220 during sleep. The collected data is then analyzed 1222 to determine: the location of joints including, for example, the user's neck, hips, and knees; preferred surface orientation (right side vs. left side orientation); and body orientation (e.g., mapping pressures at various locations on sleep surface 1114 as a result of the user's body orientation, for example, a lateral sleep position indicated by a narrow pressure mapping profile). In one embodiment, location of one or more support planes are calculated and located based on transition points. Under the pressure mapping, specific pressure points are identified to increase or decrease pressure. For example, select fluid bladders are inflated or deflated based on body location and desired lateral rotational angles.

Control system 1190 then assesses 1224 the user's body orientation including, for example a determination of head angle 1226 and chest angle 1228. During sleep, control systems also actively monitors 1230 the user's vital signs, which includes measuring and monitoring the user's respiratory rate and amplitude, AHI, sleep state, snoring, and oxygen saturation ($SpO_2$), for example. If an adverse event is detected, control system 1190 activates 1234 one or more components of support system 1100 to respond appropriately. For example, fluid supply 1188 may be activated to inflate or deflate one or more fluid bladders. Control system 1190 may activate fluid supply 1188 based on one or more of the following events: detection of snoring, detection of an AHI episode (apnea and/or hypopnea), and detection that the user is in a supine position (e.g., supine torso, upper respiratory tract (URT) within 45° of vertical). Control system 1190 may also activate support system 1100 to vibrate to wake the user should control system 1190 detect an adverse event, such as an apnea episode.

Referring to FIGS. 38-41, in one embodiment a sleep apnea therapy system is a design based on how an average user responds to the therapy tested on a sufficiently large population. The sleep apnea therapy system will effectively and tolerably treat any user's sleep apnea. As a result, the therapy can be modified to decrease a level of therapy (specifically, an amount of rotation) and still achieve clinical efficacy while optimizing user comfort and increasing usage compliance. By learning how the user reacts to variations in therapy, the sleep apnea therapy system is adjustable to optimize the results of therapy. As shown in FIGS. 38-41, the sleep apnea therapy system is design to include, in the embodiment illustrated, an active control of surface (e.g., rotation planes, rotation angles, rotation time/duration, fluid bladder pressure); capabilities to sense and assess tolerability (e.g., sleep state/stage, vitals, movement, user assessment); and sense and assess clinical efficacy (e.g., AHI, respiratory rate, head orientation). With these assessments, tolerability and user compliance is maximized for a clinically effective treatment of obstructive sleep apnea.

Figure 38:
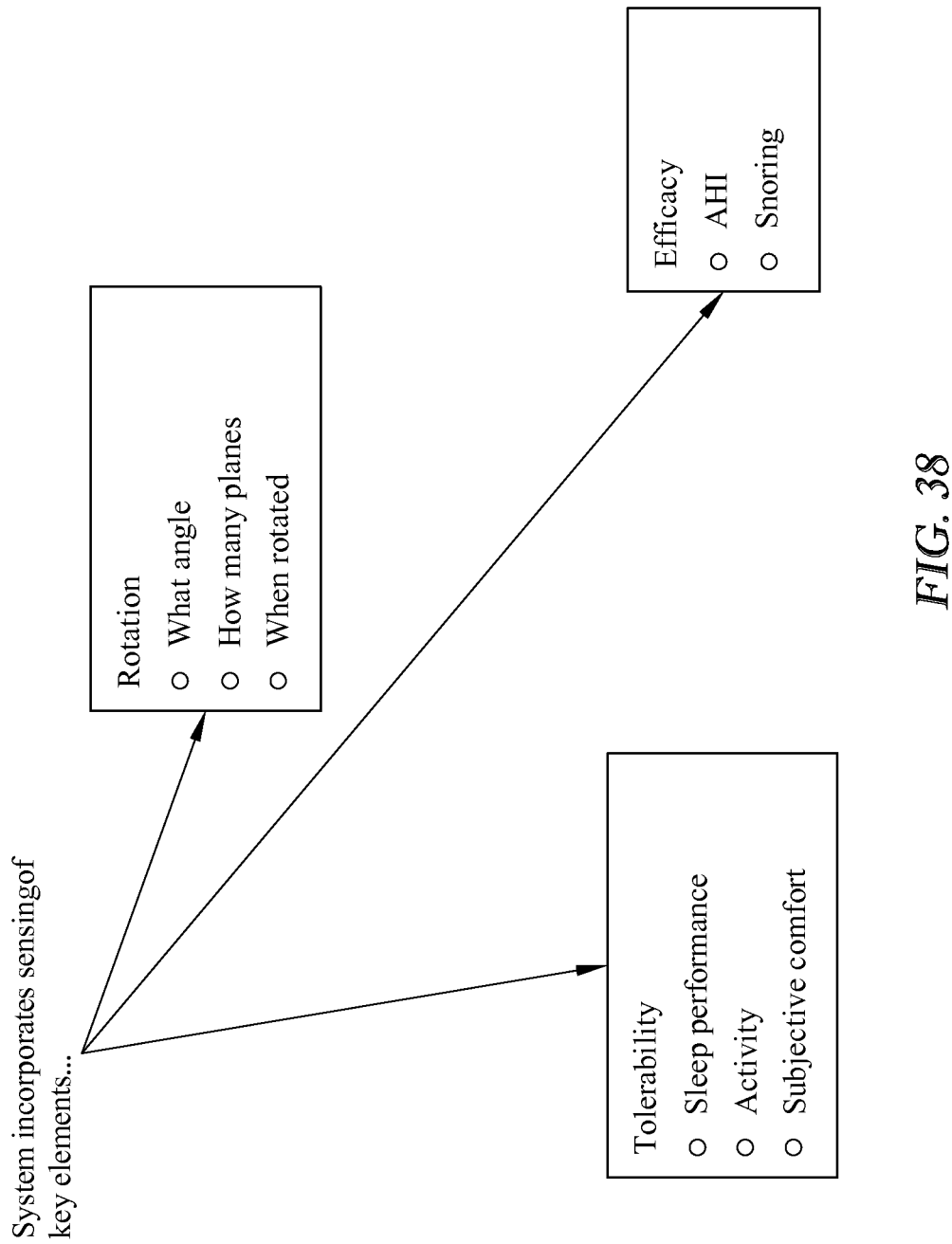
Figure 40:
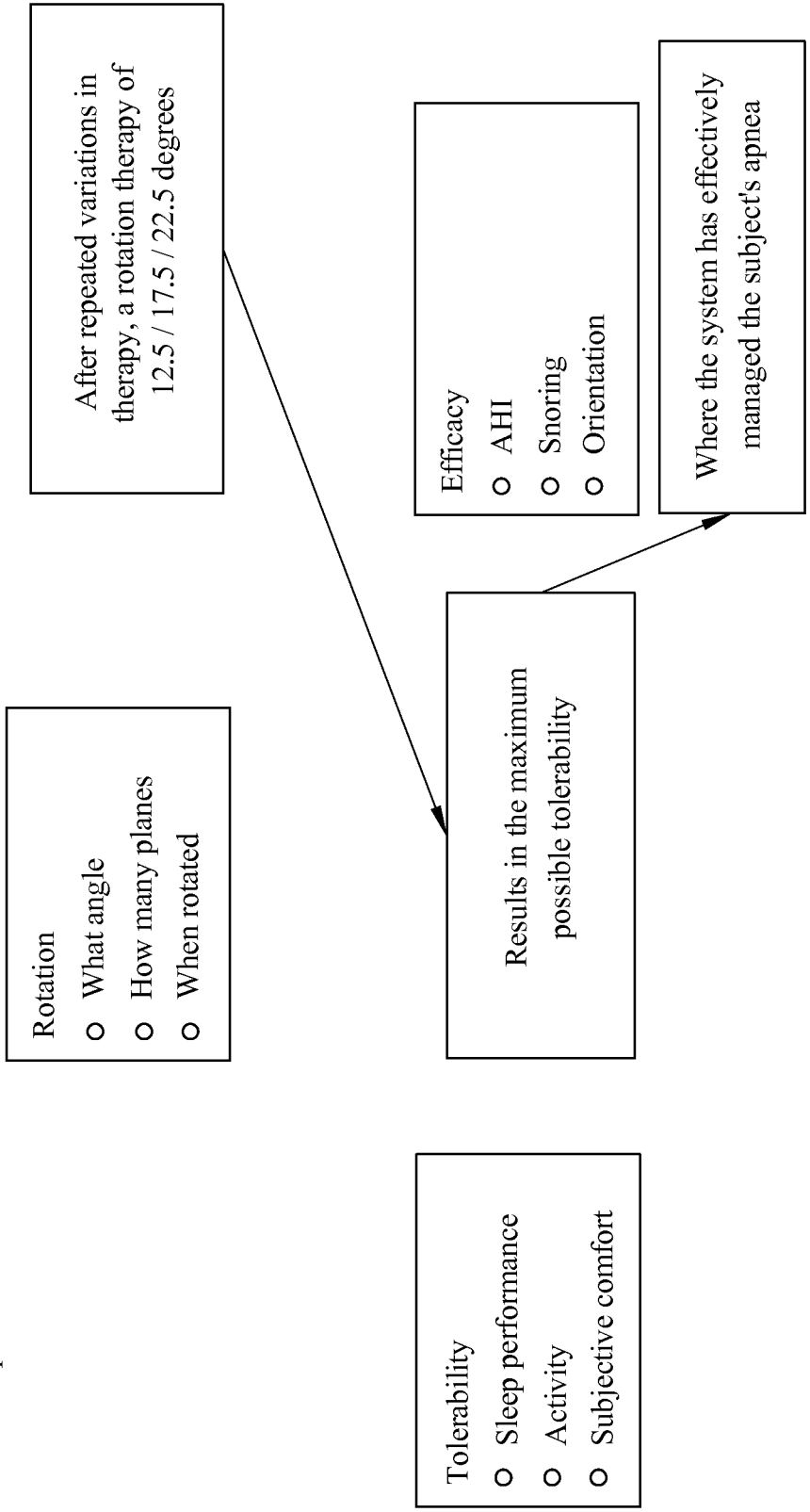
Figure 41:
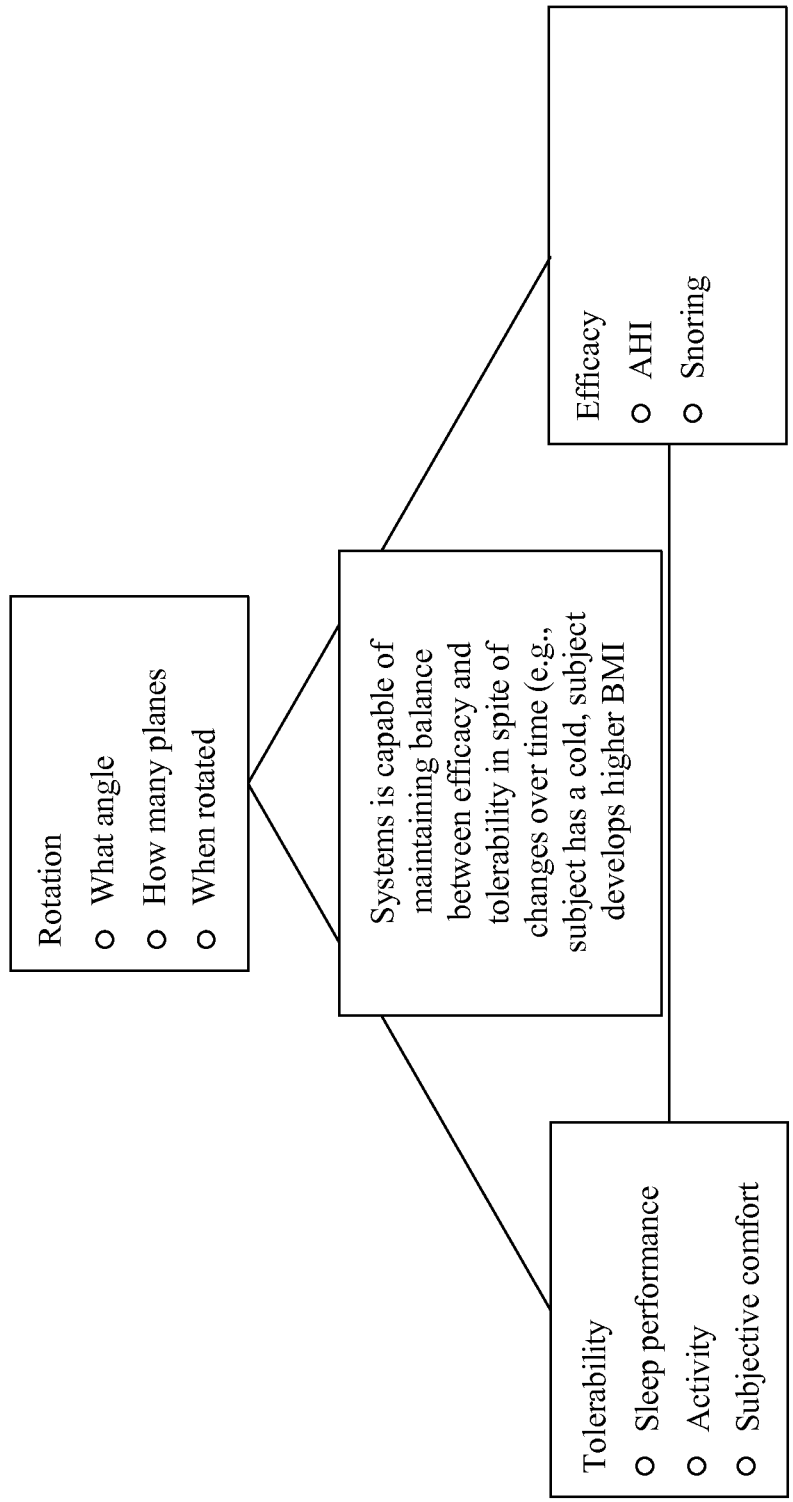

As shown in FIG. 38, the sleep apnea therapy system incorporates sensing of key elements and evaluates connections between those elements until the balance between the elements is optimized, as shown in FIGS. 39 and 40. As a result, the system is capable of maintaining balance between efficacy and tolerability in spite of changes over time (e.g., the user has a cold or develops a higher body mass index (BMI) illustrated in FIG. 41.

In one embodiment, apnea therapy can be integrated as an option in a continuous lateral rotation therapy (CLRT) system. An exemplary CLRT system is configured to deliver lateral rotation as a therapy for the prevention of pressure ulcers, as well as for use in the prevention of ventilator-associated pneumonia and muscular wasting associated with prolonged immobility. The exemplary CLRT system is suitable for use as a therapy for the prevention of sleep apnea with the addition of the following components or elements. In one embodiment, the CLRT system includes a restrained lateral rotation to create or develop progressively greater rotation by limiting rotation in a torso region and/or a head region of the user. Additionally, an augmented lateral rotation increases rotation in the torso region and/or the head region of the user.

Figure 42:
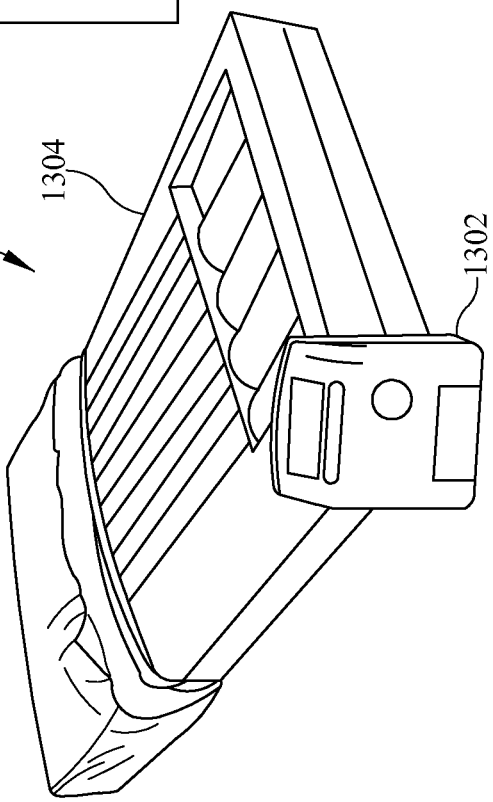
FIG. 42 is a perspective view of an exemplary continuous lateral rotation therapy (CLRT) system.

Referring to FIGS. 42-46, an exemplary CLRT system 1300 includes a control system 1302 configured with a rotation function (augmented or restrained rotation). Referring to FIG. 42, control system 1302 is operatively coupled to a support system 1304. Control system 1302 includes an apnea setting configured to select a number of support planes, dimensions of each support plane, and a desired lateral rotational angle and/or a desired longitudinal rotational angle at which one or more support planes are positioned to define the sleep surface. Further, control system 1302 includes a rotation function that allows constrained rotation at a torso region and/or a head region of the sleep surface (e.g., by pressure modification or by physical constraint), as well as supplemented rotation via a cushion.

Figure 43:
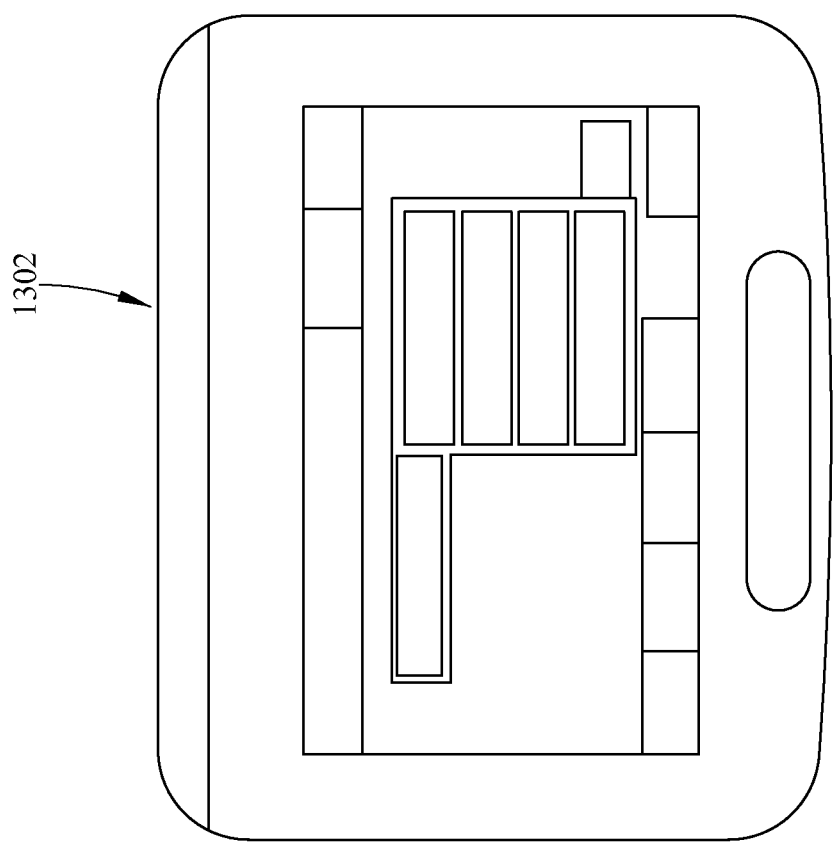
FIG. 43 is a front view of a control system configured to control the CLRT system shown in FIG. 42.

As shown in FIG. 43, control system 1302 includes an apnea mode, wherein blowers are controlled to initiate and maintain rotation of the support planes. Within the apnea mode, control system 1302 allows the user or a caregiver to select and/or define one or more therapy modes (e.g., an amount and/or a location of rotation). In one embodiment, control system 1302 is configured or programmed to suggest rotation protocol based on sensed or input data including, without limitation, one or more of the following: AHI score, BMI, sensed respiratory rate, and sensed $SpO_2$ history. Control system 1302 is also configured or programmed to select a left side slope or a right side slope based on user preference or an alternating lateral rotation, select a reverse trend or composite longitudinal angle, and manually cancel a protocol and/or return the sleep surface immediately to a flat, initial position. Alternating lateral rotation can be specified to alternate after an elapsed time period, to rotate at a certain speed to avoid waking the user, and to gradually increase lateral rotational angles from a low initial lateral rotational angle at a first rotation toward the maximum desired lateral rotational angle after a specified number of rotations.

Figure 44:
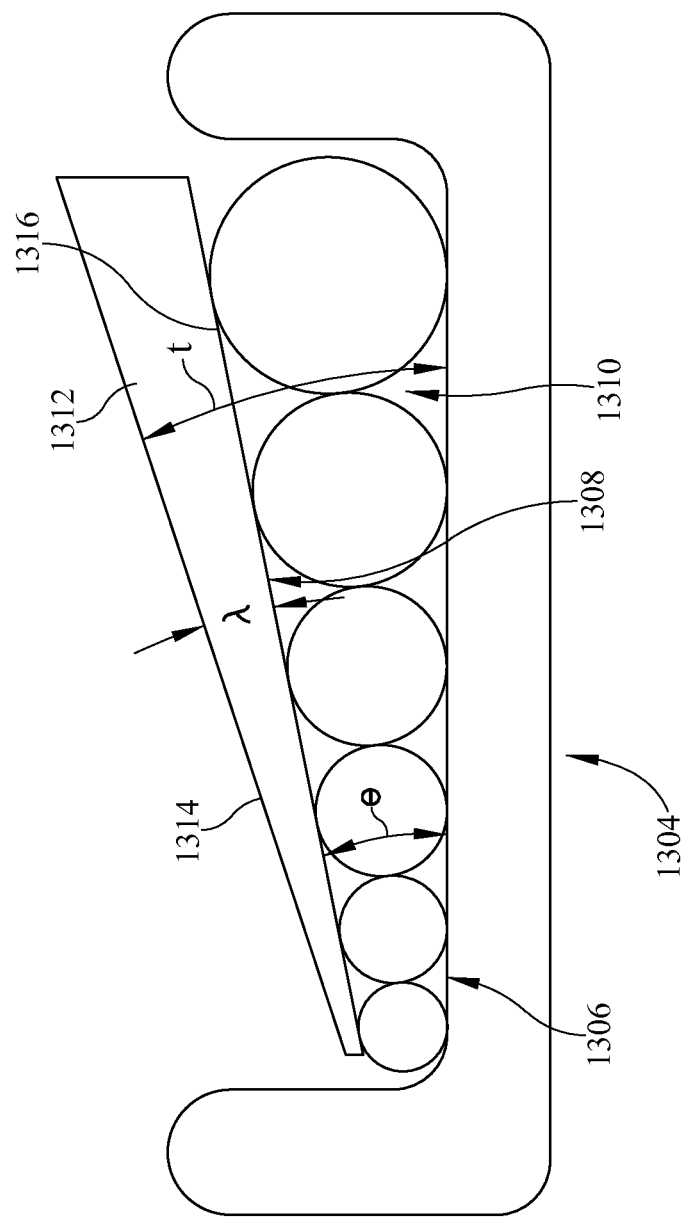
FIG. 44 is a cross-sectional view of the support system shown in FIG. 42.

In one embodiment, support system 1304 includes a base support 1306 including a plurality of inflatable fluid bladders aligned generally parallel to a longitudinal axis of support system 1304 forming a single support plane 1308 having a lateral rotation angle θ of 5° to 15°, or more specifically, 10°, with respect to a base plane 1310 of base support 1306. One or more supplemental support wedges 1312 are positioned on support plane 1308 within one or more of the leg region, the torso region, and the head region of support system 1304. In this embodiment, supplemental support wedge 1312 is a wedge-shaped inflatable fluid bladder. As shown in FIG. 44, supplemental support wedge 1312 is positioned at the head region of support system 1304 and forms a supplemental support plane 1314 having a lateral rotation angle γ of 5° to 15°, or more specifically, 10°, with respect to a base plane 1316 of supplemental support wedge 1312. As a result, in the embodiment shown in FIG. 44 a supplemental support plane 1314 is positioned at a total lateral rotational angle τ of 20° with respect to base plane 1310 of base support 1306 (the sum of angle θ and angle γ). In alternative embodiments, the total lateral rotational angle may be any suitable angle, less than 20° or greater than 20°. Further, one or more supplemental support wedges 1312 can be positioned within one or more of the leg region, the torso region, and the head region of support system 1304.

Figure 45:
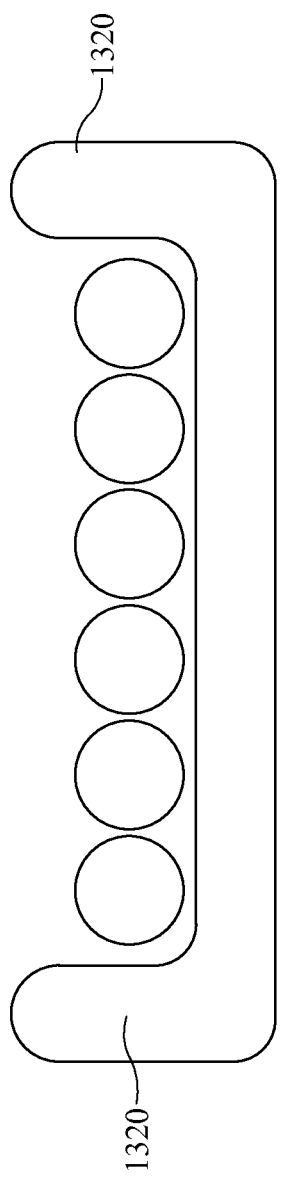
FIG. 45 is a cross-sectional view of a portion of the support system shown in FIG. 42.
Figure 46:
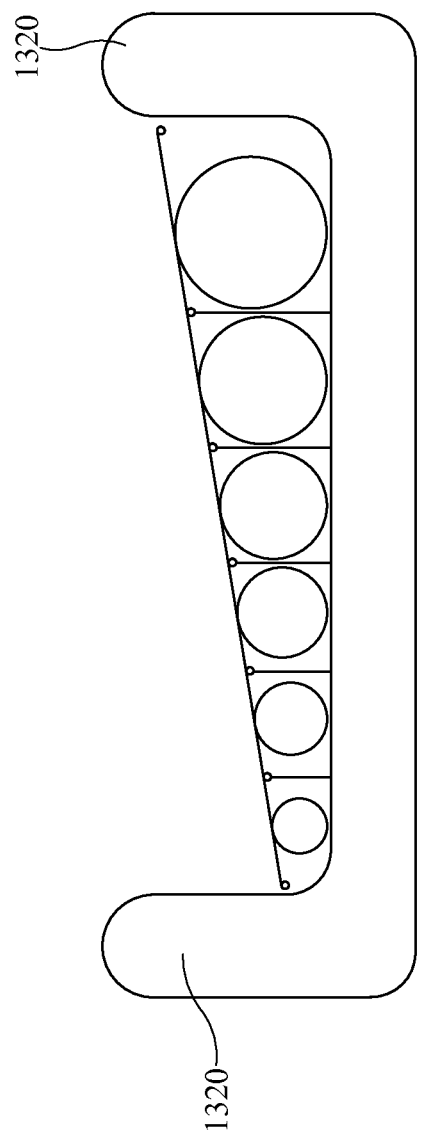
FIG. 46 is a cross-sectional view of an exemplary support system with fixed-length bands to restrict fluid bladder inflation.

Referring to FIGS. 45 and 46, in one embodiment support system 1304 includes laterally positioned side constraints 1320 to limit inflation of individual fluid bladders forming base support 1306. Support system 1304 may include, with or without laterally positioned side constraints 1320, a plurality of fixed length bands 1322 positioned with respect to individual fluid bladders, such as between adjacent fluid bladders, to limit inflation of the individual fluid bladders.

In one embodiment, a posture garment or shirt 1500 is worn by a user suffering from sleep apnea to apply an appropriate force, such as a tugging force, on the shoulders, arms, and/or head of the user to urge or cause the desired or necessary head turn to open up the user's upper respiratory tract to prevent or limit the occurrence of sleep apnea or in the event of a sleep apnea episode. Applying forces to cause the user to turn his/her entire body to the lateral decubitus position is an alternative approach to achieving this desired head angle; this may involve the use of whole-body garments or a pant garment in combination with a shirt garment.

Figure 48:
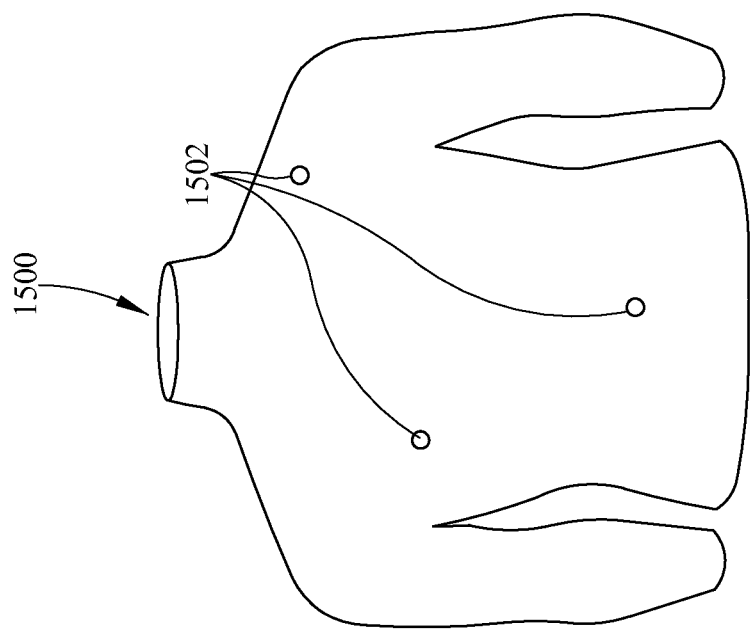
FIG. 48 is a rear view of a back portion of the posture shirt shown in FIG. 47.
Figure 47:
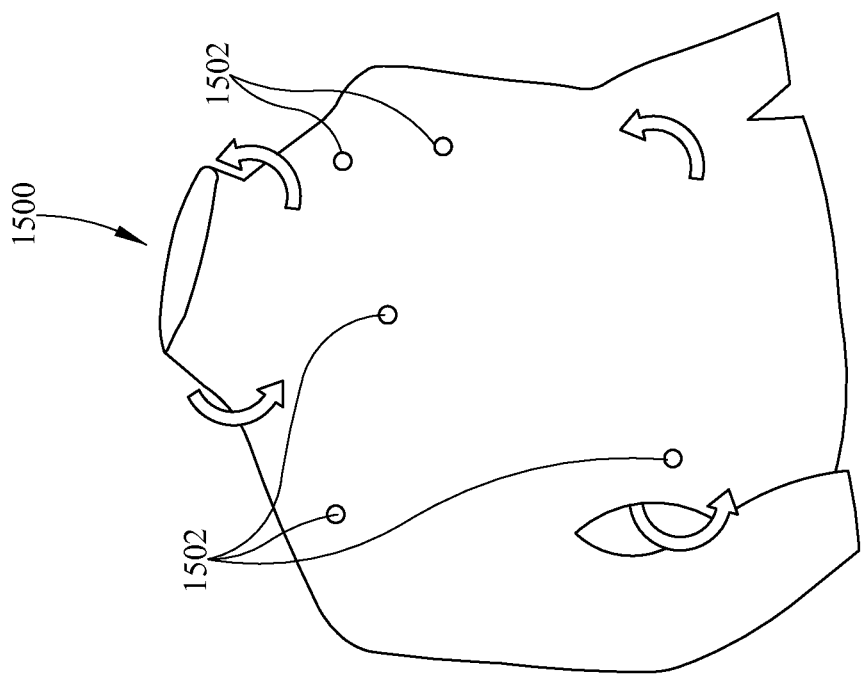
FIG. 47 is a front perspective view of a front portion of an exemplary posture shirt.

As shown in FIGS. 47 and 48, posture shirt 1500 includes one or more areas 1502 located on a front portion of posture shirt 1500, as shown in FIG. 47, and/or a back portion of posture shirt 1500, as shown in FIG. 48, including a material panel and/or material weaves having a different elasticity than other areas of posture shirt 1500. Because of the different material elasticity within areas 1502, areas 1502 tend to pull or urge select parts of the user's torso, extremities, head, and/or neck in a desired direction to open the upper respiratory airway. In a particular embodiment, sections or panels of posture shirt 1500 within areas 1502 are made of a different elastic material that work cooperatively to properly position the user's body. Posture shirt 1500 may have long sleeves, short sleeves, or may not include sleeves, and/or have a hood. Any suitable material known to those having ordinary skill in the art may be used within areas 1502 and include, without limitation, elastic materials based on composition (one or more of nylon, polyester, polyester fleece, and/or cotton) or weave (one or more of plain, basket, and twill weaves) that impart preferential deformability and recovery inducing a change in the user's posture.

In one embodiment, a compression posture shirt 1500 is worn like a typical shirt and naturally twists the torso, neck and/or head of the user. Unlike conventional posture shirts, there is no need to insert bladders or tennis ball-like inserts to urge the user to turn or rotate from a supine sleep position. Moreover, compression posture shirt 1500 for sleep apnea does not require any user training because posture shirt 1500 pulls and tugs on the user without the need of intervention from the user.

In certain embodiments, electrical circuitry, such as one or more processors and/or one or more circuit boards, is operatively coupled to, such as in electrical or electronic communication with, control system 1190 to monitor operation of one or more components of support system 1100 or control system 1302 to monitor operation of one or more components of support system 1304, collect, process, and/or store information, such as operation data and motor usage data, and transmit information, such as operation data and motor usage data, to one or more of the following computer-implemented machines or devices including, without limitation, a control and/or display device within or operatively coupled to support system 1100 or support system 1304, and/or a control and/or display device on a computer or network of computers at one or more nurse stations or administrative stations, for example.

In one embodiment, electrical circuitry, such as one or more processors and/or one or more circuit boards, is contained within control system 1190 or control system 1302 and connected in communication with support system 1100 or support system 1304, respectively. In a particular embodiment, one or more sensors or other suitable detection components are operatively coupled to support system 1100 or support system 1304 and/or control system 1190 or control system 1302 to detect operation. The one or more sensors are configured to generate and transmit electronic signals representative of the detected operation to the circuit board, which is configured to collect, process, and/or store such information, and generate and transmit information to one or more computer-implemented machines or devices in communication with the circuit board, as described above.

In certain embodiments, the one or more computer-implemented machines or devices in communication with the circuit board include a controller in signal communication, either wired or wireless signal communication, with the circuit board contained within support system 1100 or support system 1304. The controller includes a suitable display to display information received from the circuit board and/or information generated by the controller based on the information received from the circuit board. In a particular embodiment, the controller is configured to generate command signals and transmit the command signals to the circuit board contained within support system 1100 or support system 1304 to control operation of support system 1100 or support system 1304 and/or adjust parameters and/or limits, for example, programmed into the circuit board.

In one embodiment, a chest constriction device 400 assists in expiring air from the user's lungs. Referring to FIGS. 49-52, a belt 402 or strap made of a suitable material, such as nylon, is placed generally around the circumference of the user at the thorax or chest region of the user and coupled using a suitable fastener, such as a buckle 404, to retain belt 402 properly positioned about the user. Any suitable material known to those having ordinary skill in the art that is comfortable to the user and provides the required strength and flexibility may be used to make belt 402. A constrictor device 406 is operatively coupled to belt 402. Constrictor device 406 is movable between an initial or relaxed position, as shown in FIG. 39, and an activated or constricted position, as shown in FIG. 49. More specifically, referring to FIGS. 49-52, constructor device 406 is configured to selectively shorten a length of belt 402, thereby applying a compressive force on the thorax of the user.

In one embodiment, one or more physiological sensors 408 are coupled to or integrated in belt 402 and configured to detect the user's sleep state. Physiological sensor 408 may include one or more of the following sensors: a position sensor, a pressure sensor, a temperature sensor, an acoustic sensor, a moisture sensor, an RFID tag, an accelerometer, a proximity sensor, a level sensor, or another physical tracking sensor in signal communication with a processor 410 positioned within or operatively coupled to constriction device 406 and configured to provide an input signal to processor 410. Upon receiving an input signal from physiological sensor 408, processor 410 is configured to activate an actuator 412 in signal communication with processor 410 to rotate a lever 414 against a spring 416. As lever 414 rotates, a length of belt 402 shortens to apply pressure against the thorax region of the user. Lever 414 is rotatable against spring 416 in an opposite rotational direction to increase the length of belt 402 and release pressure against the thorax region of the user. Constrictor device 406 is programmed to perform a regime of constrictions and relaxations to mitigate sleep apnea.

In one embodiment, constrictor device 406 may also be used as a continuous positive airway pressure (CPAP) device and therapy may be activated by a caregiver or the user. Although not shown, the data may be communicated to an electronic medical records (EMR) system, and the caregiver and the user may be provided with a graphical user interface (GUI) to control chest constriction device 400.

Figure 53:
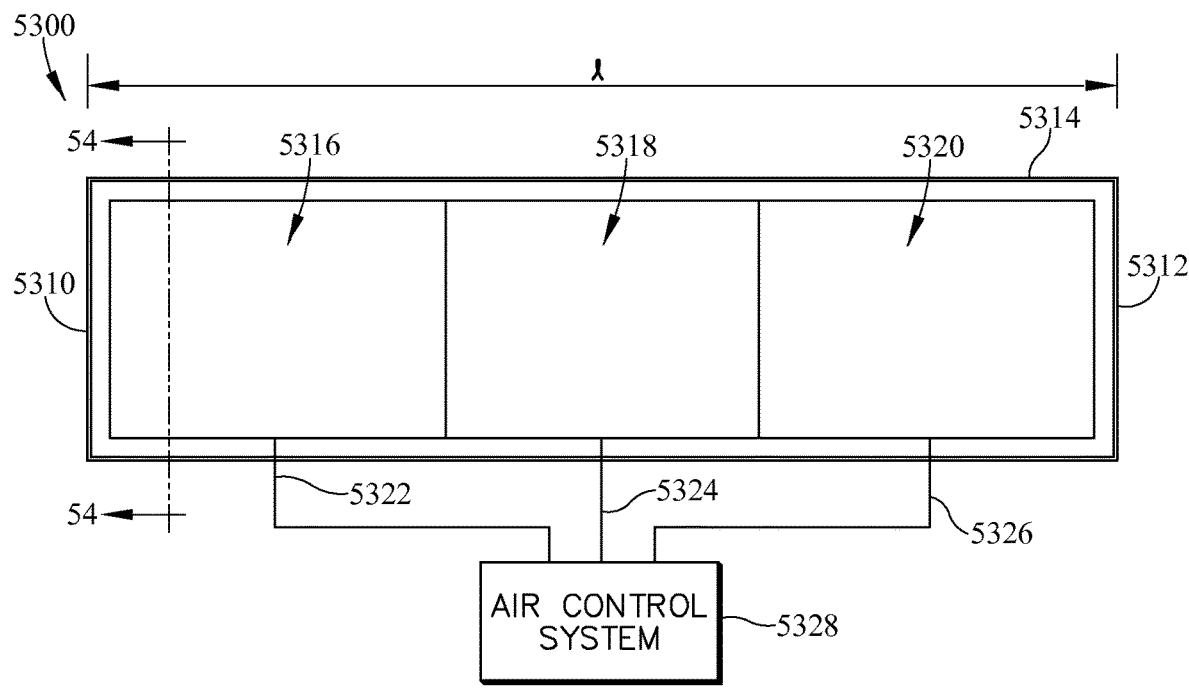
FIG. 53 is a simplified plan view of at least one embodiment of a person support apparatus including a number of support sections configured to position a support surface of the support section at a lateral tilt angle, shown with a top portion of the cover removed, and a simplified schematic view of an air control system in communication with the support sections of the person support apparatus.
Figure 54:
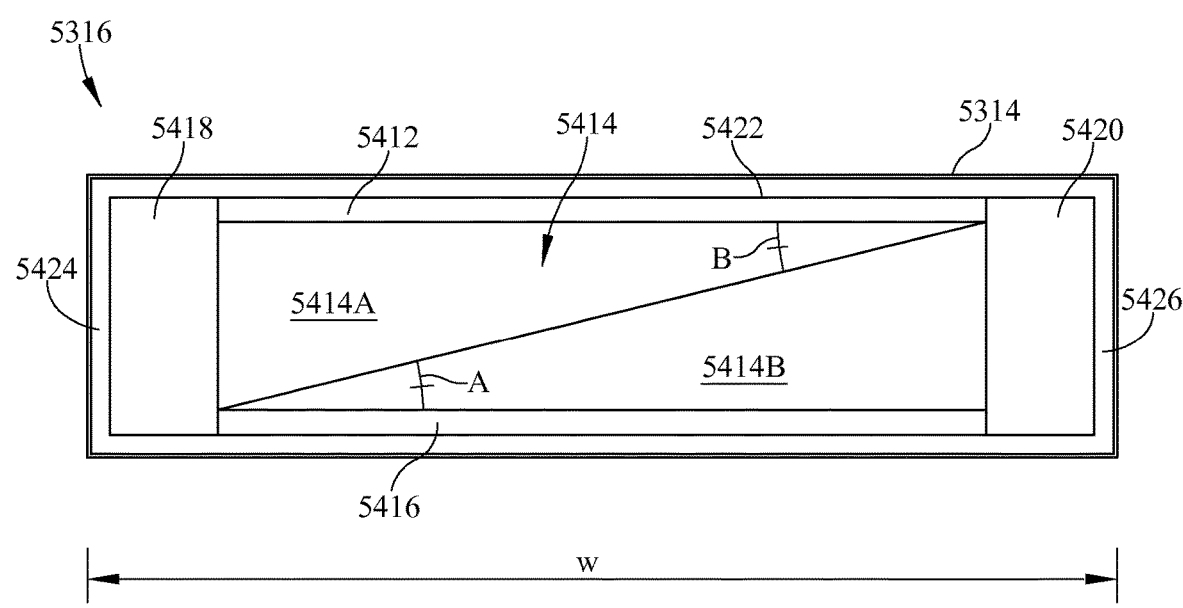
FIG. 54 is a simplified sectional view 54-54 of a support section of the person support apparatus of FIG. 53, where the support section is configured to position a support surface of the support section at a lateral tilt angle.

Referring now to FIGS. 53-94, various illustrative embodiments of a person support apparatus configurable to assume a "progressive" lateral tilt position are shown. The person support apparatus may have any of the features described in this document, or any combination of such features and/or other features. The person support apparatus or portions thereof may be embodied as a mattress, a mattress overlay or topper, a cover for a mattress, a cushion or a pad, for example. In a progressive lateral tilt position, the person support apparatus assumes a ramp-like configuration intended to tilt a person's body laterally, to one side, such that different portions of the person's body are tilted laterally in the same general direction (e.g., all tilted to the same side), but at different lateral angles. As used herein, "lateral tilt," "lateral angle," or "tilt" may be used to refer to, among other things, an angle of a surface of the person support apparatus relative to the horizontal and with reference to (e.g., defined by rotation about) a longitudinal axis of the person support apparatus. In some cases, the different lateral tilt angles are defined so that the maximum lateral tilt angle of a portion of the person support apparatus supporting the person's head is greater than the maximum lateral tilt angles of portions of the person support apparatus supporting other portions of the person's body. An example of the general construction of such an apparatus is shown in FIGS. 53-54, and exemplary embodiments are shown in FIGS. 55-94. In FIG. 53, a person support apparatus 5300 includes a number of support sections 5316, 5318, 5320 enclosed in an interior region defined by a cover 5314. Although only three support sections 5316, 5318, and 5320 are shown, it should be understood that the person support apparatus 5300 may contain any number of such sections, depending on the requirements of a particular design or for other reasons.

The support sections 5316, 5318, 5320 are positioned along a length l of the person support apparatus 5300, with the support section 5316 positioned adjacent a head end 5310 of the person support apparatus 5300, the support section 5320 positioned adjacent a foot end 5312 of the person support apparatus 5300, and the support section 5318 positioned between the support sections 5316, 5320. Each of the support sections 5316, 5318, 5320 has a support surface 5422 (FIG. 54), which is configured to bear a load, e.g., to support at least a body portion of a person on the person support apparatus 5300. Portions of the support surface 5422 may be rigid, semi-rigid, or non-rigid, depending on the requirements (e.g., patient comfort, stability, etc.) of a particular design and/or configuration of the person support apparatus 5300. Illustratively, the support section 5316 is configured to support a person's head and/or neck region, the support section 5318 is configured to support a person's torso, hip, and/or thigh region, and the support section 5320 is configured to support a person's legs and/or feet. In embodiments having a greater number of support sections, each support section may be configured to support a correspondingly smaller portion of the person's body, and vice versa.

As explained in more detail below with respect to the embodiments of FIGS. 55-94, each of the support sections 5316, 5318, 5320 includes an inflatable portion which, alone or in combination with one or more other support portions (e.g., non-inflatable support portions, such as foam pieces or three-dimensional fiber network layers), can cause the support surface 5422 to assume a progressively greater maximum lateral tilt angle along the length l from the foot end 5312 to the head end 5310, or vice versa, in order to provide a therapeutic effect to a person positioned on the person support apparatus 5300 or for other reasons. As used herein, "progressive lateral tilt angle" may refer to, among other things, a maximum lateral tilt angle that begins with a relatively small tilt angle in the foot section 5320 (e.g., in the range of about 0 to about 10 degrees), increases to a larger maximum tilt angle in the seat section 5318 (e.g., in the range of about 10 to about 20 degrees) and increases to still a larger maximum tilt angle in the head section 5316 (e.g., in the range of about 15 to about 35 degrees). As used herein, "maximum" may be used to, among other things, convey the idea that each support section 5316, 5318, 5320 may be configurable to assume smaller tilt angles or the same tilt angle from time to time, but that the largest tilt angle achievable by each of the support sections 5316, 5318, 5320 is different.

The support sections 5316, 5318, 5320 are also each configurable to assume a substantially flat position, e.g., to provide a more typical flat or horizontal rest surface during periods in which the progressive lateral tilt angle is not required or desired. As such, the person support apparatus 5300 is selectively configurable by, for example, an air control system 5328, to assume a progressive lateral tilt position and at least one other position (e.g., the flat position). The air control system 5328 can selectively inflate and deflate the inflatable portions of the support sections 5316, 5318, 5320 to achieve a desired or required (e.g., flat or tilt) configuration of the person support apparatus 5300, and can adjust such position dynamically in response to various inputs as described in this document.

In the simplified view of FIG. 53, each of the connections 5322, 5324, 5326 represents a number of different types of couplings including an air conduits (e.g., plastic tubing) and electronic signal paths (e.g., insulated wiring and/or wireless connections), in order to electronically and pneumatically couple the air control system 5326 to the each of the support sections 5316, 5318, 5320, respectively. For example, one or more sensors (e.g., pressure sensors, force sensors, and/or angle sensors) may be coupled to each of the support sections 5316, 5318, 5320, and some of the connections 5322, 5324, 5326 may electronically communicate data obtained from the sensors to the air control system 5326. The sensor data may indicate, for example, the air pressure inside the inflatable portions and/or the current lateral tilt angle of the support surface 5422. Although not specifically shown in FIG. 53, it should be understood that the air control system 5328 may be communicatively coupled to other devices, e.g., via a direct wired or wireless connection or by an electronic communication network. For example, the air control system 5328 may communicate air pressure data and/or lateral tilt angle data for the various support sections 5316, 5318, 5320 over a network to a healthcare communication system, such as a facility's nurse call system, an electronic medical records system, and/or other devices and systems. Such a network may be embodied as, for example, a healthcare facility's internal network, a "private cloud," a secure portion of the Internet, and/or others, and may enable longer range communications (e.g., via ETHERNET) and/or shorter range communications (e.g., via WIFI, BLUETOOTH, WLAN, or Near Field Communication (NFC)).

Referring to FIG. 54, an exemplary sectional view of the support section 5316 is shown. It should be understood that each of the other support sections 5318, 5320, may have the same or a similar composition as the support section 5316, although not specifically shown. Illustratively, the support section 5316 includes a number of support portions or pieces including an upper layer 5412, a middle layer 5414 (which includes illustrative support portions 5414A and 5414B), a lower layer 5416, a side member 5418, and a side member 5420. The support portions 5412, 5414, 5416, 5418, 5420 are located in the interior region defined by the cover 5314. In some embodiments, the cover 5314 may be omitted or may enclose less than all of the support sections 5316, 5318, 5320 and/or the support portions 5412, 5414, 5416, 5418, 5420. Further, some embodiments of the person support apparatus 5300 may not include all of the support sections 5316, 538, 5320 and/or the support portions 5412, 5414, 5416, 5418, 5420. For example, one or more of the support portions 5412, 5416, 5418, and/or 5420 may be omitted from the support section 5316 and/or the support sections 5318, 5320.

The support section 5316 has a width w, which in some embodiments is sized to substantially coincide with a width of an underlying mattress or other support structure (e.g., a frame or a deck section of a bed). The side members 5418, 5420 are each positioned adjacent to a side 5424, 5426 of the support section 5316, respectively. The support portions 5412, 5414, 5416 are positioned between the side members 5418. At least one of the upper layer 5412, the middle layer 5414, and the lower layer 5416 includes one or more inflatable portions as described herein. In some embodiments, the upper layer 5412 may include a non-inflatable material, such as foam and/or a three-dimensional woven or nonwoven fiber network or other material (e.g., SPACENET or TYTEX). In some embodiments, the lower layer 5416 may include a non-inflatable material, such as a molded foam base. Illustratively, the middle portions 5414A, 5414B alone or in combination with the upper layer 5412 and the lower layer 5410 are each configured to provide the desired lateral tilt angle of the support surface 5422. In some embodiments, each of other portions 5414A and 5414B include one or more inflatable bladders that can be selectively inflated and deflated to provide a desired lateral tilt position or a flat position of the support surface 5422. For example, the portion 5414B may be embodied as a wedge-shaped inflatable (e.g., one or more air bladders) or non-inflatable (e.g., foam) piece that is configurable to provide a lateral tilt angle A, to tilt the person situated on the person support apparatus 5300 in the direction of the side 5424, when the middle portion 5414A is either absent or deflated and the portion 5414B is present and/or inflated. Similarly, the portion 5414A may be embodied as a wedge-shaped inflatable or non-inflatable piece that is configurable to provide a lateral tilt angle B to tilt the person situated on the person support apparatus 5300 in the direction of the side 5426 when the middle portion 5414B is either absent or deflated and the portion 5414A is present and/or inflated.

Figure 55:
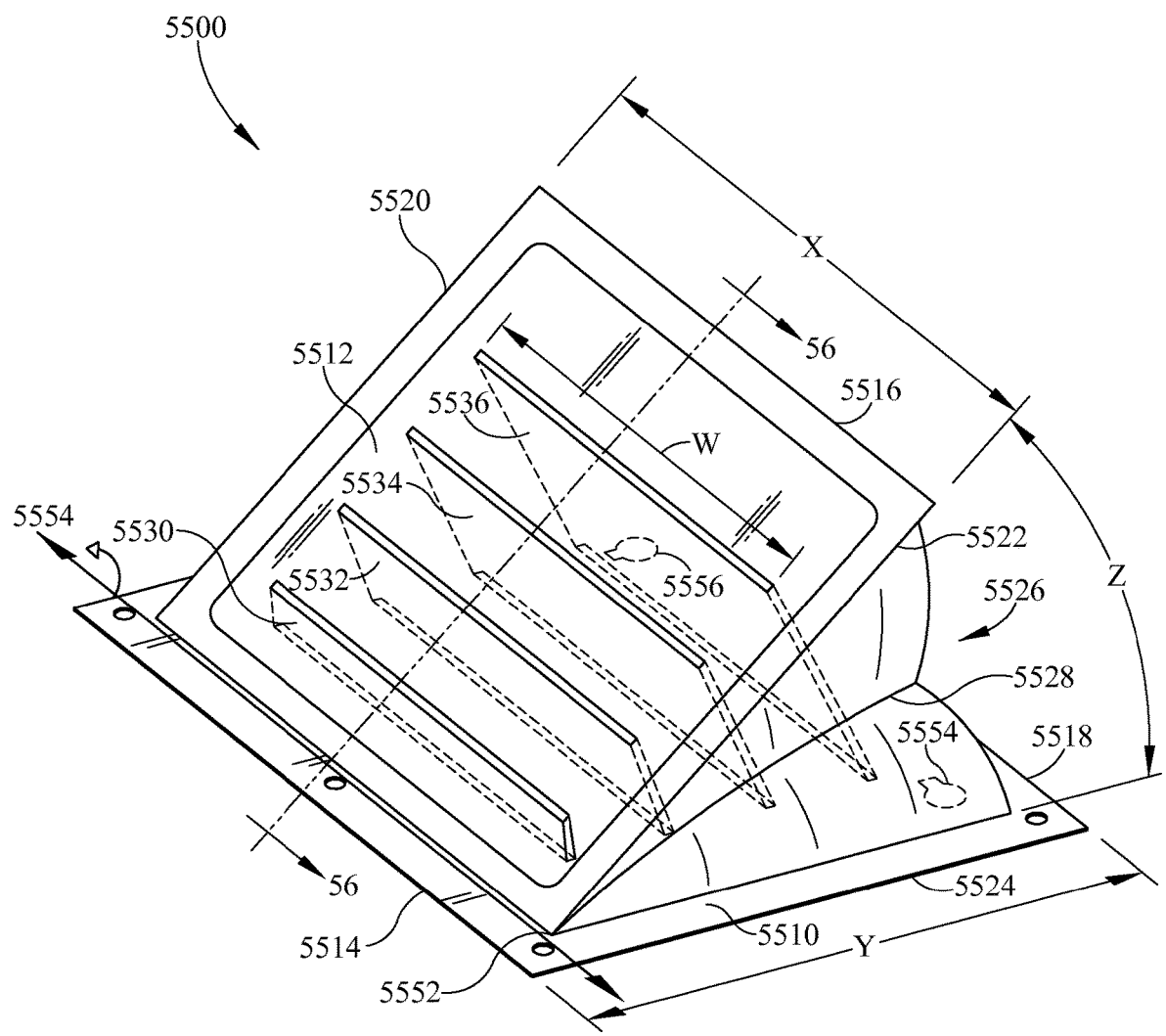
FIG. 55 is a simplified perspective view of at least one embodiment of a support section for the person support apparatus of FIGS. 53-54.
Figure 56:
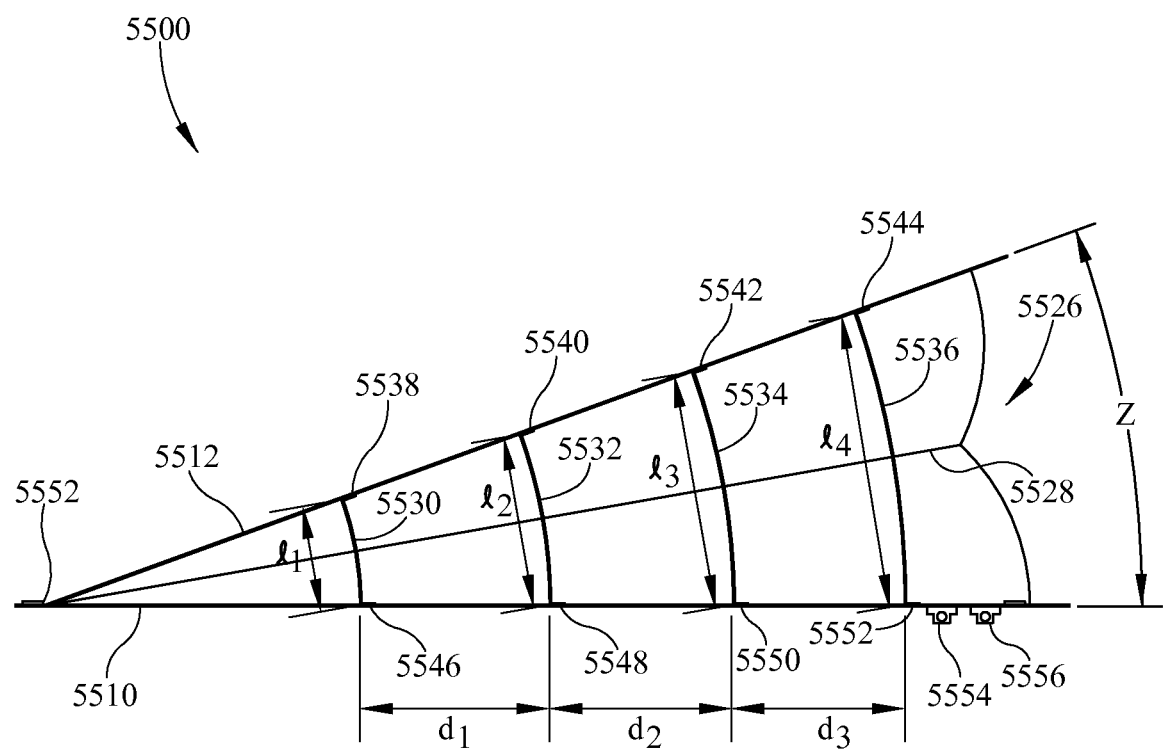
FIG. 56 is a simplified sectional view 56-56 of the support section of FIG. 55.

Referring now to FIGS. 55-56, an illustrative embodiment 5500 of a support portion, which may be used as a middle portion 5414A and/or a middle portion 5414B of a support section 5316, 5318, 5320, for example, is shown. The support portion 5500 is embodied as a bellows-style bladder having a substantially triangular cross section 56-56 when inflated (FIG. 56). The support portion 5500 includes a lower surface 5510 and an upper surface 5512, each of which are defined by a pair of laterally spaced sides (side 5514 and side 5516 of the upper surface 5512; side 5514 and side 5518 of the lower surface 5510) and longitudinally spaced ends (end 5520 and end 5522 of the upper surface 5512; end 5524 and opposite end, obscured in FIG. 55, of the lower surface 5510). The upper surface 5512 and the lower surface 5510 are joined together (e.g., by radio frequency (RF) welding, adhesive, or other suitable technique) along the side 5514 to form a hinge 5522. A bellows bladder 5526 is coupled to and extends between the upper surface 5512 and the lower surface 5510 such that when inflated, the upper surface 5512 is rotated about an axis 5554, which extends along the hinge 5552. The upper surface 5512 can thereby be tilted at a desired lateral tilt angle relative to the lower surface 5510, where the desired lateral tilt angle may differ depending on, for example, a characteristic of a person situated on the person support apparatus 5300 (e.g., the person's height, weight, and/or therapeutic needs) and/or the position of the support section 5316, 5318, 5320 in which the support portion 5500 is used relative to the person support apparatus 5300 as a whole.

The bellows bladder 5526 has a pleat 5528, which extends around the perimeter of the bladder 5526 and enables the bladder 5526 to fold in on itself when deflated. A number of baffles 5530, 5532, 5534, 5536 each having different lengths l1, l2, l3, l4 are positioned in an interior region defined by the bellows bladder 5526. Each of the baffles 5530, 5532, 5534, 5536 has a top end 5538, 5540, 5542, 5544, which is coupled to an underside of the upper surface 5512, and a bottom end 5546, 5548, 5550, 5552, which is coupled to an underside of the lower surface 5510. The illustrative baffles 5530, 5532, 5534, 5536 each have substantially the same width w1, although they may have different widths in other embodiments. The baffles 5530, 5532, 5534, 5536 are spaced from one another by distances d1, d2, d3, as shown in FIG. 56. The distances d1, d2, d3 may be the same or different, depending on the requirements of a particular design, or for other reasons. In general, the dimensions of each of the baffles 5530, 5532, 5534, 5536 are defined to retain the support portion 5500 in a position in which the upper surface 5512 is tilted at the desired maximum lateral tilt angle. For example, if the upper surface 5512 is to be tilted at a lateral tilt angle in the range of about 20 degrees when the bellows bladder 5526 is inflated, the lengths l1, l2, l3, l4 and the distances d1, d2, d3 are configured to retain the support section 5500 in the proper position to achieve such angle.

The illustrative support section 5500 is generally made of one or more cloth materials, such as nylon sheets (e.g., twill and/or taffeta). Portions of the support section 5500 that are coupled together may be coupled by any suitable fastening techniques, such as RF welding, stitching, snaps, rivets, and/or others. One or more fluid ports, e.g., a fill port 5554 and a vent port 5556, are coupled to the bellows bladder 5526 and, in use, connected to a fluid supply (e.g. a blower), which may be incorporated into or in communication with the air control system 5328.

Figure 57:
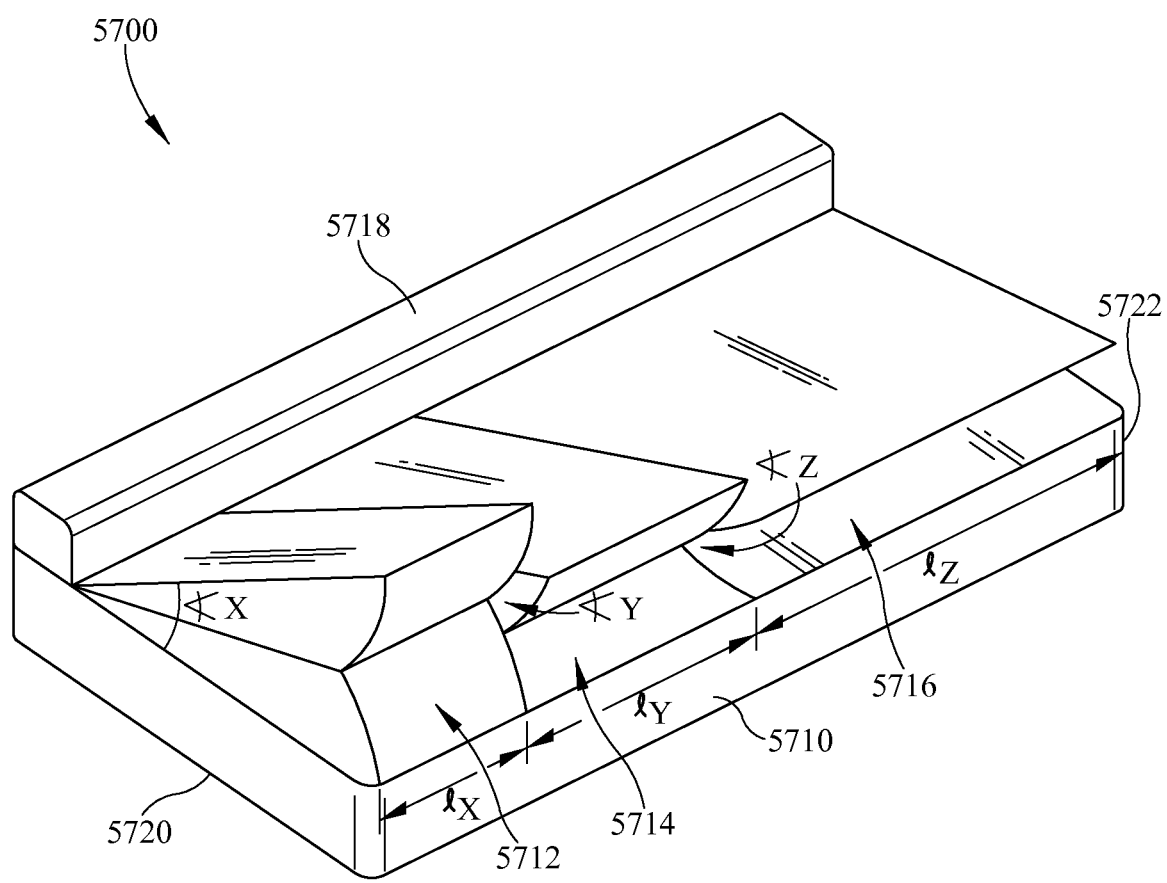
FIG. 57 is a simplified perspective view of at least one embodiment of the person support apparatus of FIG. 53, shown in a progressive lateral tilt position.
Figure 58:
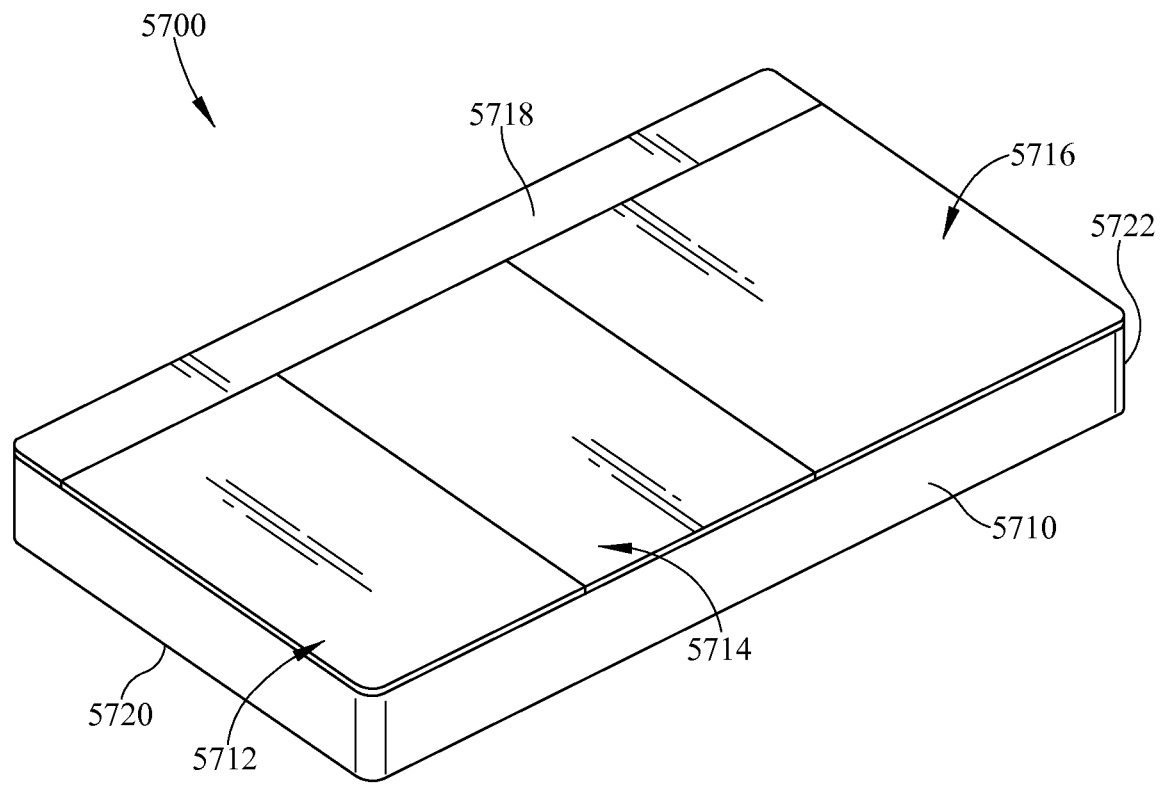
FIG. 58 is a simplified perspective view of the embodiment of FIG. 57, shown in a substantially flat position.

Referring now to FIGS. 57-58, an embodiment 5700 of a person support apparatus includes a number of support sections 5712, 5714, 5716, each of which incorporates least one of the support portions 5500, is shown. The support sections 5712, 5714, 5716 are supported by a base 5710. The base 5710 may be constructed of foam and/or one or more air bladders, for example. Each of the support sections 5712, 5714, 5716 has a bellows-type bladder that, when inflated, tilts a person situated on the person support apparatus 5700 in a direction toward a side member 5718. The side member 5718 may be constructed of foam and/or one or more air bladders, for example, and is sized to retain the person on the person support apparatus 5700 notwithstanding the lateral tilt angles provided by the support sections 5712, 5714, 5716.

The bellows bladder 5526 of each of the support sections 5712, 5714, 5714 is constructed to provide the maximum lateral tilt angle desired of the respective section 5712, 5714, 5716. To do this, the pleat 5528 or the baffles 5530, 5532, 5534, 5536 may be differently sized for each of the sections 5712, 5714, 5716 (e.g., by having different lengths). In other embodiments, the bellows bladder 5526 of each of the support sections 5712, 5714, 5716 may have the same or similar construction, and the desired maximum lateral tilt angle may be achieved by varying the amount of air pressure in the interior region of the bellows bladder 5526.

In the embodiment of FIGS. 57-58, each of the support sections 5712, 5714, 5718 has a different maximum lateral tilt angle x, y, and z. Further, the support sections 5712, 5714, 5718 have different lengths $l_x$, $l_y$, $l_z$. In other embodiments, one or more of the support sections 5712, 5714, 5718 may have the same maximum lateral tilt angle and/or the same length.

In the person support apparatus 5700, the support section 5712 is positioned adjacent a head end 5720 of the person support apparatus 5700, the support section 5716 is positioned adjacent a foot end 5722, and the support section 5714 is positioned between the head end 5720 and the foot end 5722. Further, in the illustrative person support apparatus 5700, the maximum lateral tilt angle x is greater than the maximum lateral tilt angle y, and the maximum lateral tilt angle y is greater than the maximum lateral tilt angle 5716. In FIG. 57, the bellows bladder 5526 of each of the support sections 5712, 5714, 5716 is inflated, causing the person support apparatus 5700 to assume a progressive lateral tilt position as described herein. In FIG. 58, the bellows bladders 5526 of each of the sections 5712, 5714, 5716 are deflated, causing the person support apparatus 5700 to assume a substantially flat position. In the substantially flat position, the side member 5718 is also deflated. While only the progressive lateral tilt position and the substantially flat position are shown in the drawings, it should be understood that the bellows bladders 5526 of each of the sections 5712, 5714, 5716 and the side member 5718 can be selectively inflated (e.g., to different levels or angles), so that the person support apparatus 5700 can assume a range of positions between the progressive lateral tilt position and the substantially flat position.

Referring now to FIGS. 59-60, an embodiment 5900 of a support section, which may be used as a support section 5316, 5318, 5320, for example, is shown. The support section 5900 includes a pair of complementary bellows-type bladders 5910, 5912, each of which may be embodied as the support portion 5500, described above. The bladders 5910, 5912 are supported by a lower layer 5914 and a base 5916. The lower layer 5914 may be embodied as a number of support cushions and may be similar in construction to the lower layer 5416 described above. The base 5916 may be constructed of, for example, one or more air bladders, foam, or a combination thereof. Illustratively, the base 5916 is crib or tray shaped, having side portions 5924, 5926 extending upwardly to form a substantially u-shaped cross-section. Additionally, side members 5918, 5922 are supported by or integrated with the side portions 5924, 5926. The side members 5918, 5922 may be constructed of, for example, one or more air bladders, foam, or a combination thereof. The side members 5918, 5922 are, alone or in combination with the base 5916, sized to extend upwardly above the height of the bellows bladder vertices 5930, 5932.

In FIG. 59, the bellows bladder 5910 is inflated and the bellows bladder 5912 is deflated, to tilt the upper surface 5512 at an angle having a vertex at 5930 (and thereby tilt a body portion of a person situated thereon toward the side member 5922. In FIG. 60, the bellows bladder 5910 is deflated and the bellows bladder 5912 is inflated, to tilt the upper surface 5512 at an angle having a vertex at 5932 (and thereby tilt a body portion of a person situated thereon toward the side member 5918.

Figure 61:
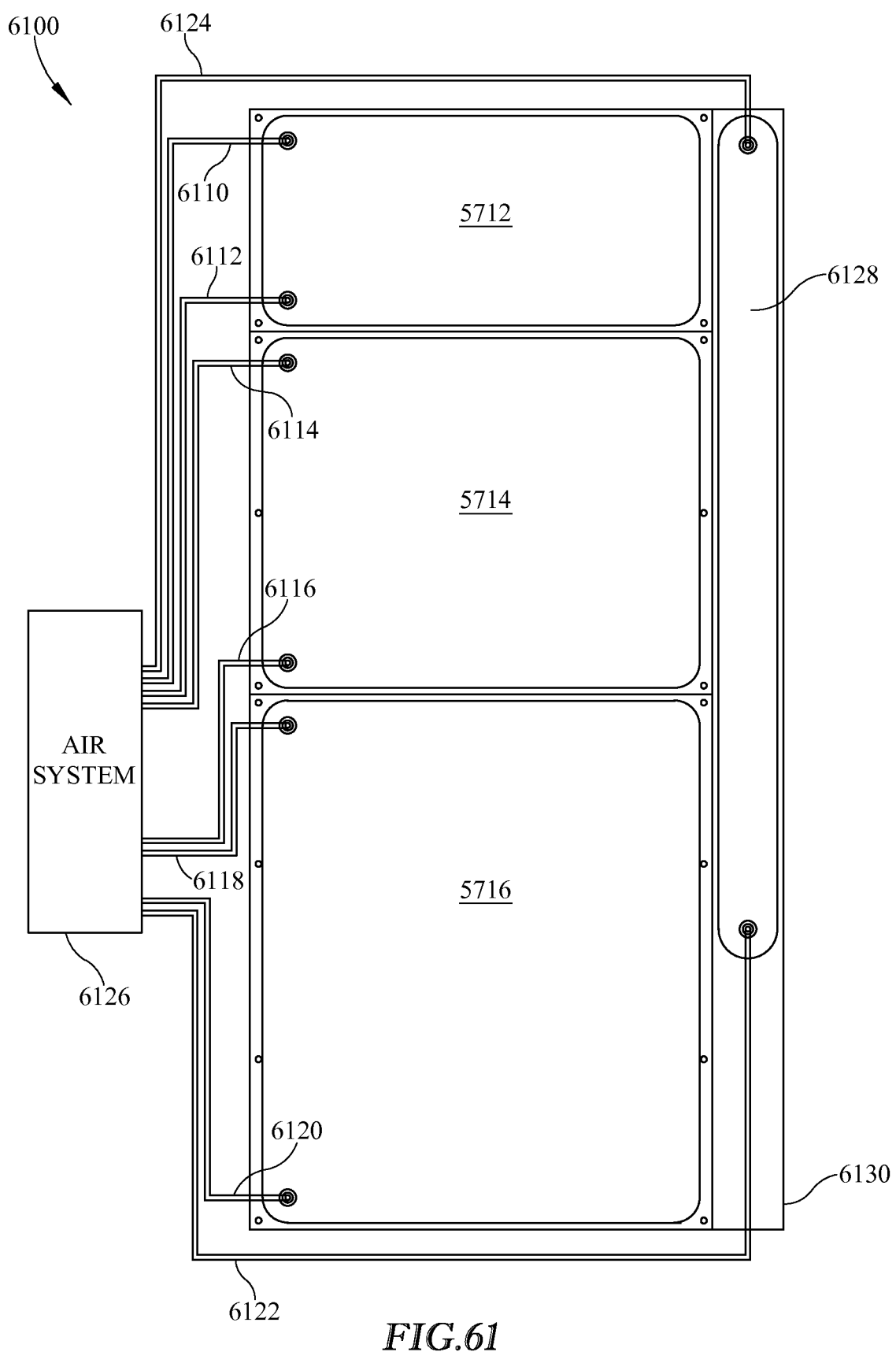
FIG. 61 is a simplified top plan view of at least one embodiment of an arrangement of support sections and fluid communication channels for the person support apparatus of FIGS. 53-54, showing the fluid communication channels coupling the support sections to the air control system.

Referring now to FIG. 61, a top view of an embodiment 6100 that is similar to the person support apparatus 5700 is shown. A difference between the embodiment 5700 and the embodiment 6100 is that the embodiment 6100 includes a side member 6128 that has a length $l_s$, which is less than the length of the person support apparatus (e.g., the length l shown in FIG. 53). The side member 6128 and each of the support sections 5712, 5714, 5716 are coupled to a base sheet by any suitable fastening technique, such as any of the techniques mentioned herein. The side member 6128 and each of the support sections 5712, 5714, 5716 are pneumatically coupled to an air system 6124 by fill lines 6110, 6114, 6118, 6122 and vent lines 6112, 6116, 6120, 6124, respectively. In general, the air system 6126 includes a processor or controller that executes control logic (which may be embodied as computer-executable instructions or routines, etc.), to operate an air supply/vacuum device (e.g., a blower, compressor, etc.) to selectively inflate and deflate the inflatable portions of the support sections 5712, 5714, 5716 and the side member 6128. The air system 6126 or portions thereof may be embodied as the air control system 5328, described above.

Figure 62:
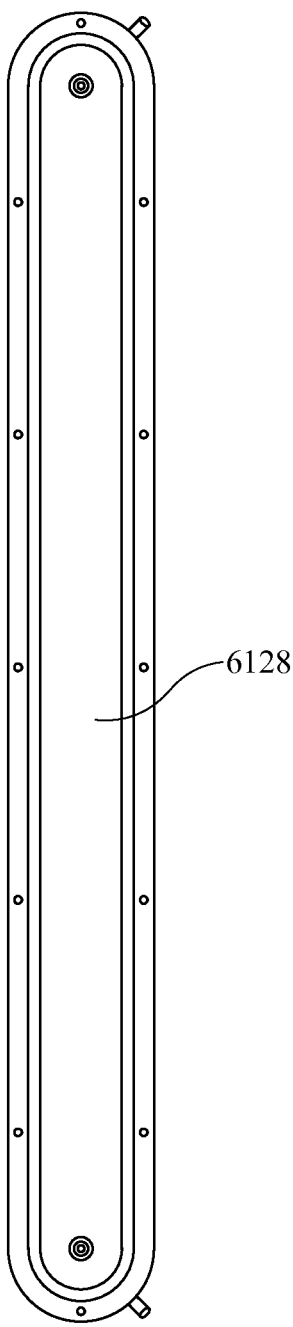
FIG. 62 is a simplified top plan view of at least one embodiment of a side support member for the person support apparatus of FIGS. 53-54.
Figure 63:
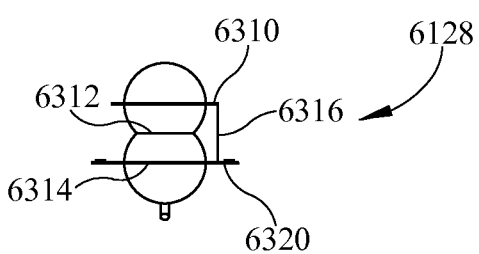
FIG. 63 is a simplified side view of the side support member of FIG. 62, taken while the side support member is inflated.

FIGS. 62-63 illustrate additional details of the side member 6128. The illustrative side member 6128 is an elongated inflatable bladder having a length that is greater than its width. As shown in FIG. 63, the side member 6128 has perimeter welds or seams (e.g., RF welds) 6310, 6312, 6314. In the illustration, the welds 6310, 6312, 6314 are spaced substantially equidistantly from one another, however this need not be the case. The welds 6310, 6312, 6314 may be configured to provide vertical stability to the side member 6128 or for other reasons. Additionally, a tether 6316 may couple the side member 6128 to the base sheet 6130.

Figure 64:
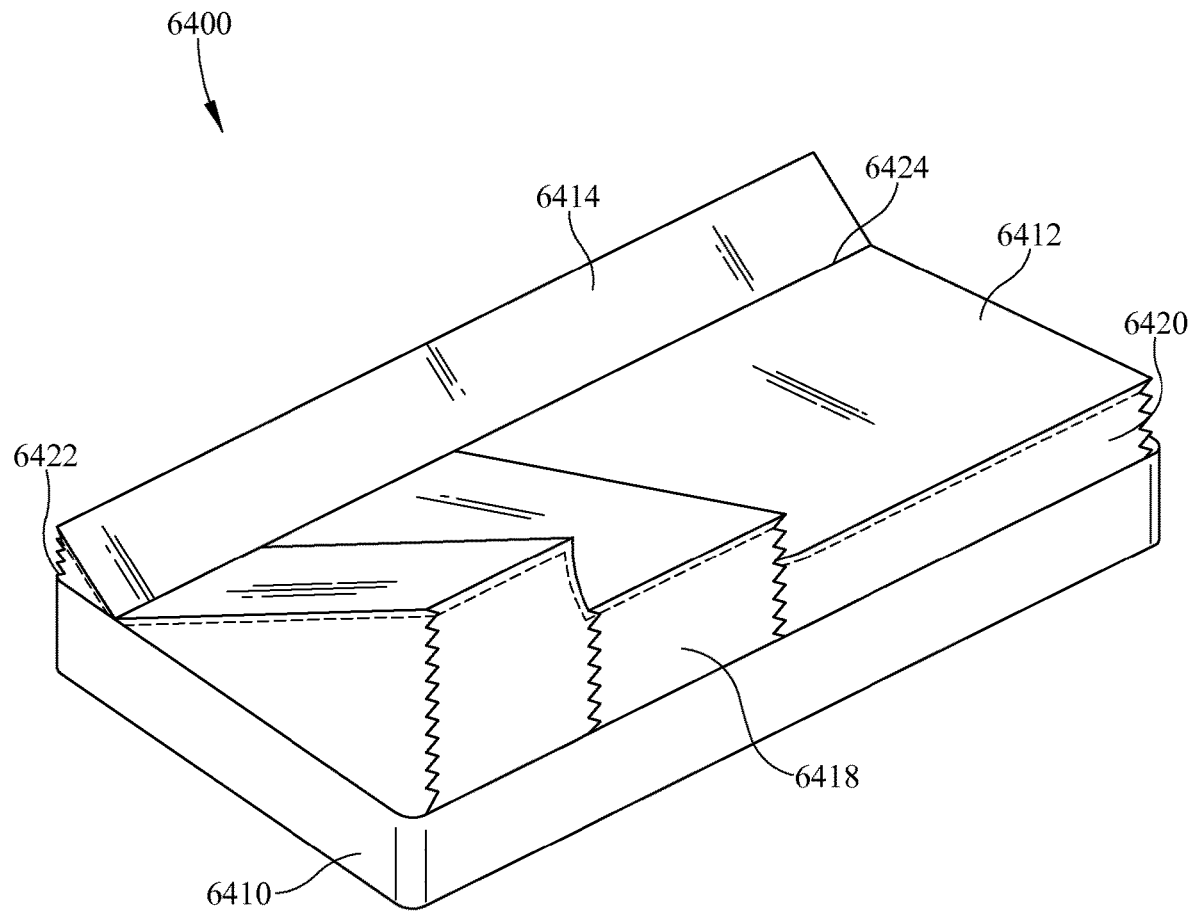
FIG. 64 is a simplified perspective view of at least one embodiment of a cover for the person support apparatus of FIG. 53.

Referring now to FIG. 64, a cover 6400 for the person support apparatus 5300, or any of the embodiments thereof disclosed herein, including the embodiment 5700, is shown. In general, the cover 6400 is configured to slide over the components of the person support apparatus 5300 such that all of the components (e.g., support portions 5712, 5714, 5716 and side member 5718) are retained or enclosed in an interior region of the cover 6400. Additionally, the cover 6400 has a number of expandable portions 6416, 6418, 6420, 6422 corresponding to the support portions 5712, 5714, 5716 and the side member 5718. The expandable portions 6416, 6418, 6420, 6422 are designed to allow the cover 6400 to accommodate the support portions 5712, 5714, 5716 in the lateral tilt positions, flat positions, and positions therebetween, as well as the side member 5718 when it is inflated. Illustratively, the portions 6416, 6418, 6420, 6422 are pleated, with each of the portions 6416, 6418, 6420 having a different number of pleats as needed to accommodate the different maximum lateral tilt angles of each of the portions 5712, 5714, 5716. The expandable portions 6416, 6418, 6420, 6422 are coupled to a perimeter skirt 6410, which may be elasticized to secure the cover 6400 around the person support apparatus 5700. The expandable portions 6416, 6418, 6420, 6422 are also coupled to top surfaces 6412, 6414. The top surface 6414 is coupled to the top surface 6412 by a seam 6424, which allows the top surface 6414 to move independently of the top surface 6412. Together, the skirt 6410, the expandable portions 6416, 6418, 6420, 6422, and the top surfaces 6412, 6414 form a hollow interior region that can receive a person support apparatus such as the person support apparatus 5700. The various portions of the cover 6400 may be constructed of a nylon material, for example.

Figure 65:
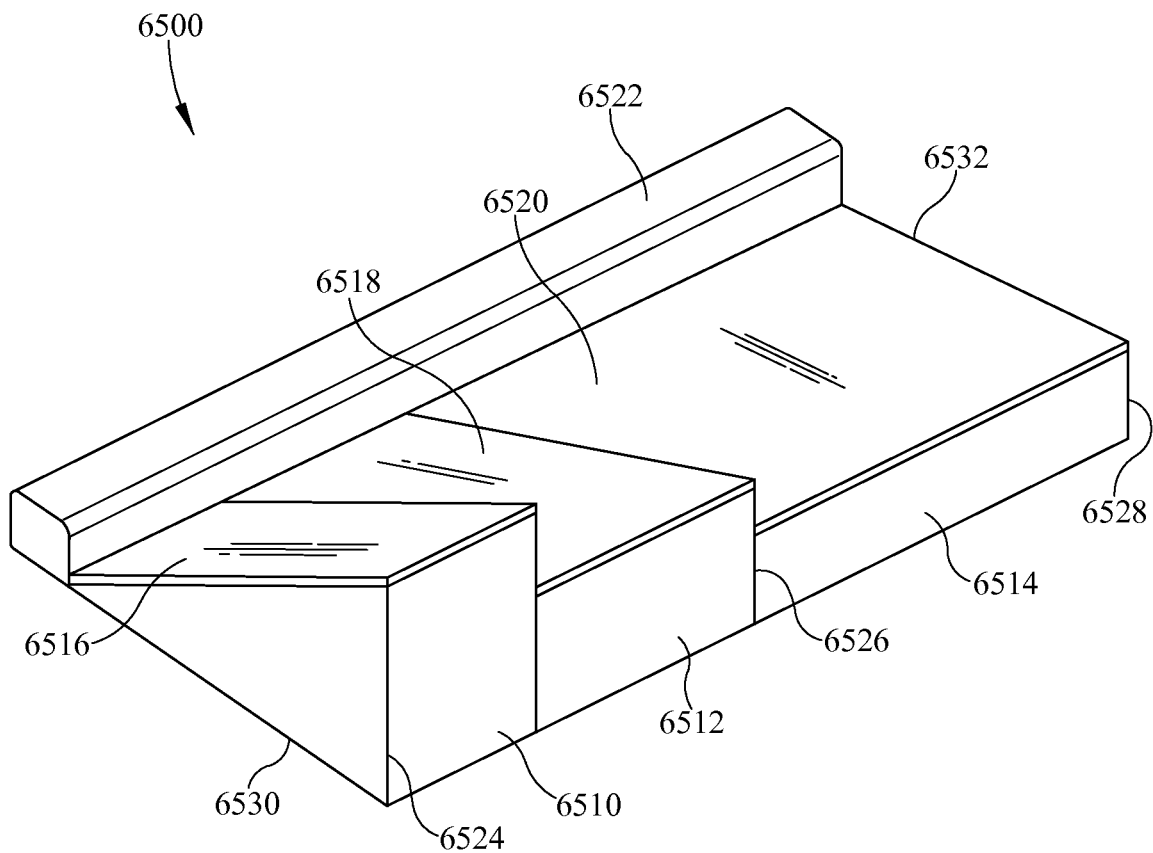
FIG. 65 is a simplified perspective view of at least one embodiment of the person support apparatus of FIG. 53, shown in a progressive lateral tilt position.
Figure 66:
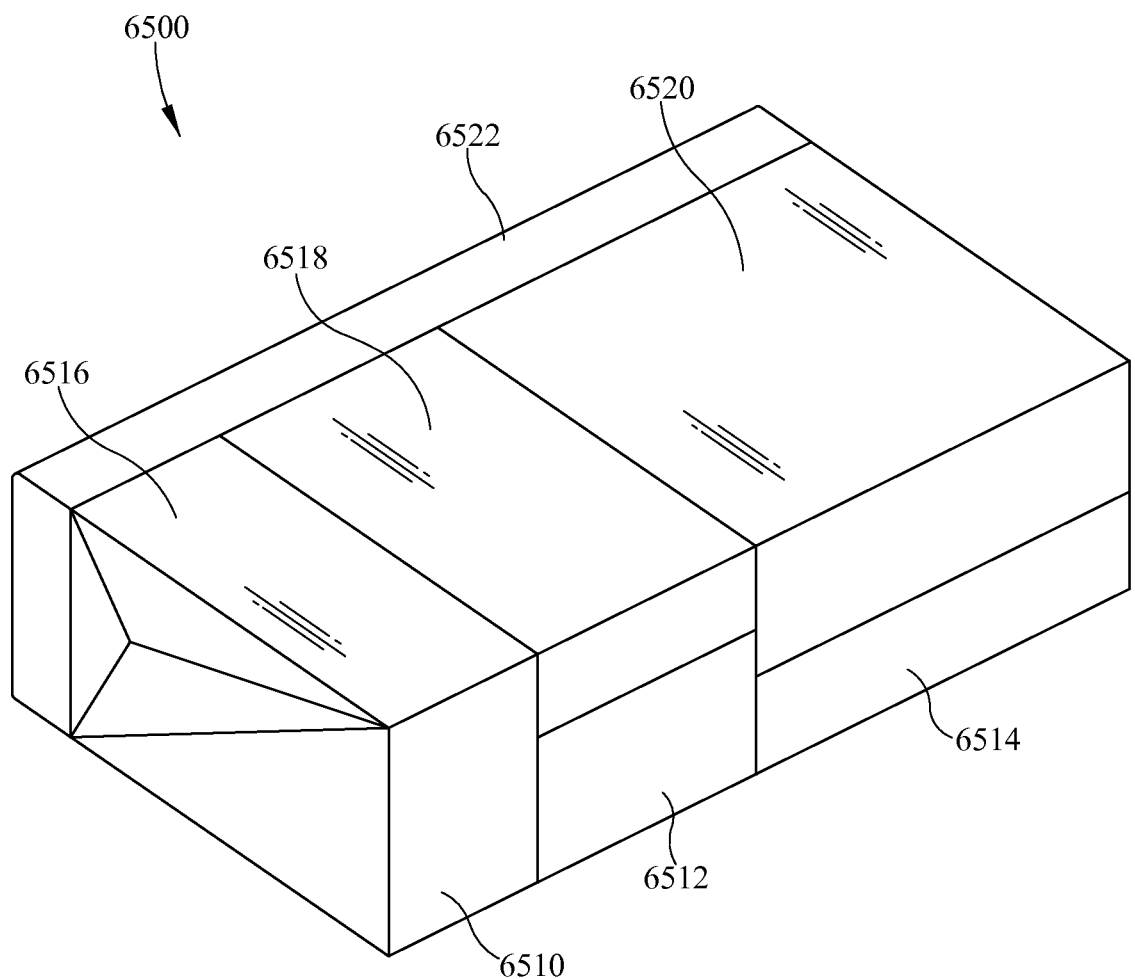
FIG. 66 is a simplified perspective view of the embodiment of FIG. 65, shown in a substantially flat position.

Referring now to FIGS. 65-66, an embodiment 6500 of a person support apparatus is shown. The person support apparatus 6500 includes a number of non-inflatable support portions 6510, 6512, 6514, a number of inflatable support portions 6516, 6518, 6520 supported by the non-inflatable support portions 6510, 6512, 6514, respectively, and a non-inflatable side member 6522. The non-inflatable support portions 6510, 6512, 6514 and the side member 6522 may be constructed of foam, for example. The inflatable support portions 6516, 6518, 6520 may include one or more air bladders, and may each be embodied as the support portion 5500, described above.

The illustrative non-inflatable support portions 6510, 6512, 6514 are each embodied as a substantially triangular or wedge-shaped support piece, each having a hypotenuse side 6524, 6526, 6528. The length of the side 6526 is greater than the length of the side 6528, and the length of the side 6524 is greater than the length of the side 6526, such that when the inflatable portions 6516, 6518, 6520 are deflated, the person support apparatus 6500 has progressively greater lateral tilt angles, with the lateral tilt angle increasing from the foot end 6532 to the head end 6530 of the person support apparatus 6500. When the inflatable portions 6516, 6518, 6520 are inflated, the person support apparatus 6500 assumes a substantially flat position as shown in FIG. 66. Intermediate positions are also provided. For example, one or more of the inflatable portions 6516, 6518, 6520 may be deflated while the other(s) are inflated, to allow a greater degree of variation in the elevation of the support sections, or for other reasons. The side member 6522 is positioned adjacent the vertex side of the non-inflatable support portions 6510, 6512, 6514 (opposite the hypotenuse sides 6510, 6512, 6514) and sized so that its vertical height substantially corresponds to the vertical height of the inflatable support portions 6516, 6518, 6520 when inflated. The side member 6522 may be constructed of, for example, foam.

Figure 67:
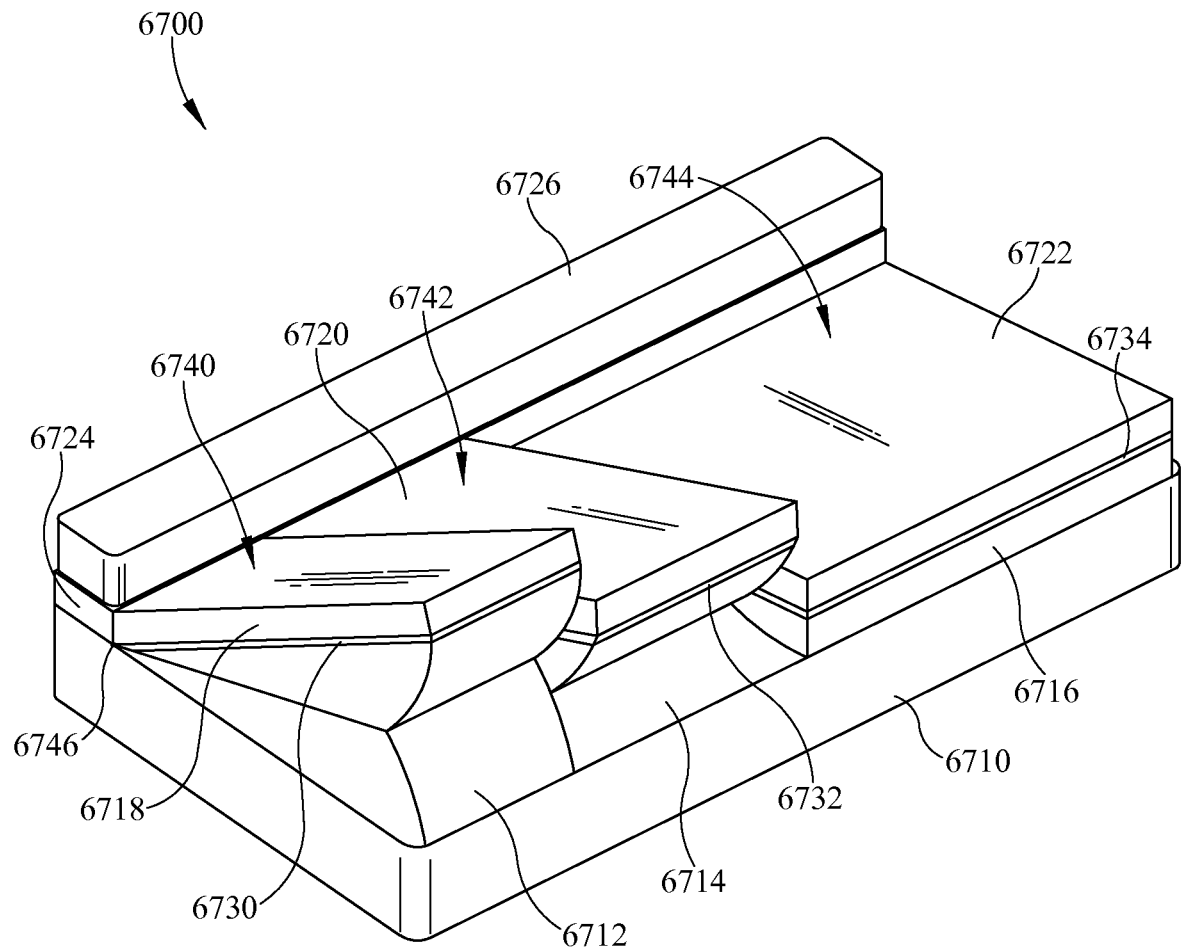
FIG. 67 is a simplified perspective view of at least one embodiment of the person support apparatus of FIG. 53, shown in a progressive lateral tilt position.
Figure 68:
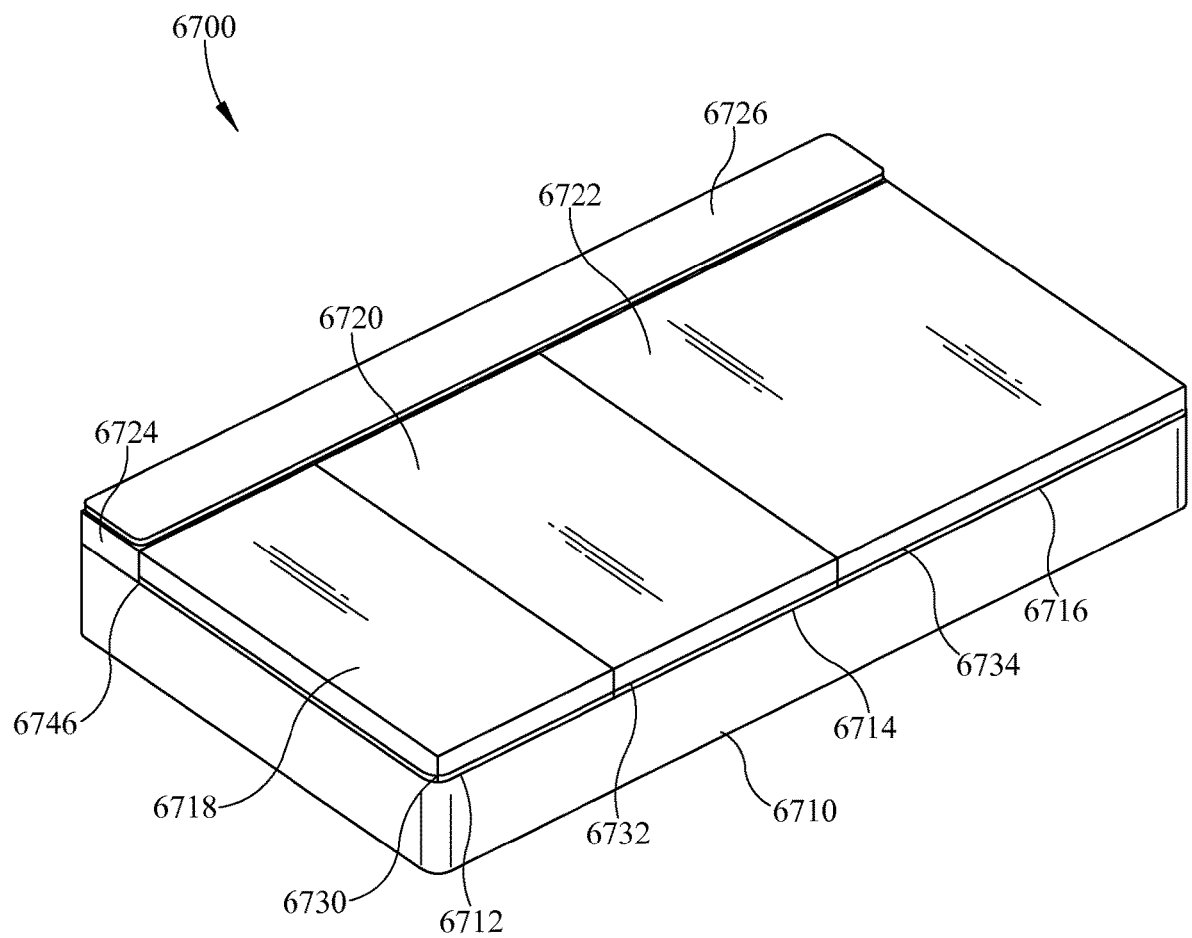
FIG. 68 is a simplified perspective view of the embodiment of FIG. 67, shown in a flat position.

Referring now to FIGS. 67-68, an embodiment 6700 of a person support apparatus includes a base 6710 and a number of support sections 6740, 6742, 6744, which generally correspond to the support sections 5316, 5318, 5320 of FIG. 53. The support sections 6740, 6742, 6744 are supported by the base 6710. Each of the support sections 6740, 6742, 6744 includes an inflatable support portion 6712, 6714, 6716, a stiffener plate 6730, 6732, 6734 supported by the inflatable support portion 6712, 6714, 6716, and a non-inflatable support portion 6718, 6720, 6722 supported by the stiffener plate 6730, 6732, 6734.

The base 6710 is substantially rectangular in shape and has a width that is wider than the width of the support sections 6740, 6742, 6744. A non-inflatable support member 6724 is supported by the base 6710 and positioned along an edge of the base 6710, adjacent a hinge 6746, which extends along the length of the person support apparatus 6700. An inflatable support member 6726 is supported by the non-inflatable support member 6724. The inflatable support member 6726 is sized to have a vertical height that extends upwardly above a portion of the top surface of the support sections 6740, 6742, 6744 that is adjacent to the support member 6726.

When inflated, the inflatable support portions 6712, 6714, 6716 cause the top surfaces of the non-inflatable support portions 6718, 6720, 6722 to assume the desired progressive lateral tilt angle as described above. When the inflatable support portions 6712, 6714, 6716 are deflated, the top surface of the non-inflatable support portions 6718, 6720, 6722 is substantially flat as shown in FIG. 68. Intermediate positions of the person support apparatus 6700, in which less than all of the inflatable support portions 6712, 6714, 6716 are inflated, are also provided, as mentioned above.

The stiffener plates 6730, 6732, 6734 may be constructed of, for example, a rigid or semi-rigid plastic, stainless steel, or other suitable material. The stiffener plates 6730, 6732, 6734 provide additional support for the non-inflatable portions 6718, 6720, 6722 and may thereby facilitate pivoting of the non-inflatable portions 6718, 6720, 6722 to the desired lateral tilt angle. Additionally or alternatively, the stiffener plates 6730, 6732, 6734 may provide a substrate to which one or more sensors may be mounted for the purpose of detecting and monitoring the lateral tilt angle of each of the support sections 6740, 6742, 6744. For example, an angle sensor (e.g., an inclinometer or accelerometer) may be mounted to each stiffener plate 6730, 6732, 6734 to measure the lateral tilt angle of its respective support section 6740, 6742, 6744. The angle data obtained by such sensors may be transmitted to and analyzed by a control system (e.g., by a feedback loop of the control system 5238), in order for the control system to make adjustments to the air pressure supplied to the inflatable portions 6712, 6714, 6716, as may be needed to maintain the desired lateral tilt angles for each of the sections 6740, 6742, 6744.

Figure 69:
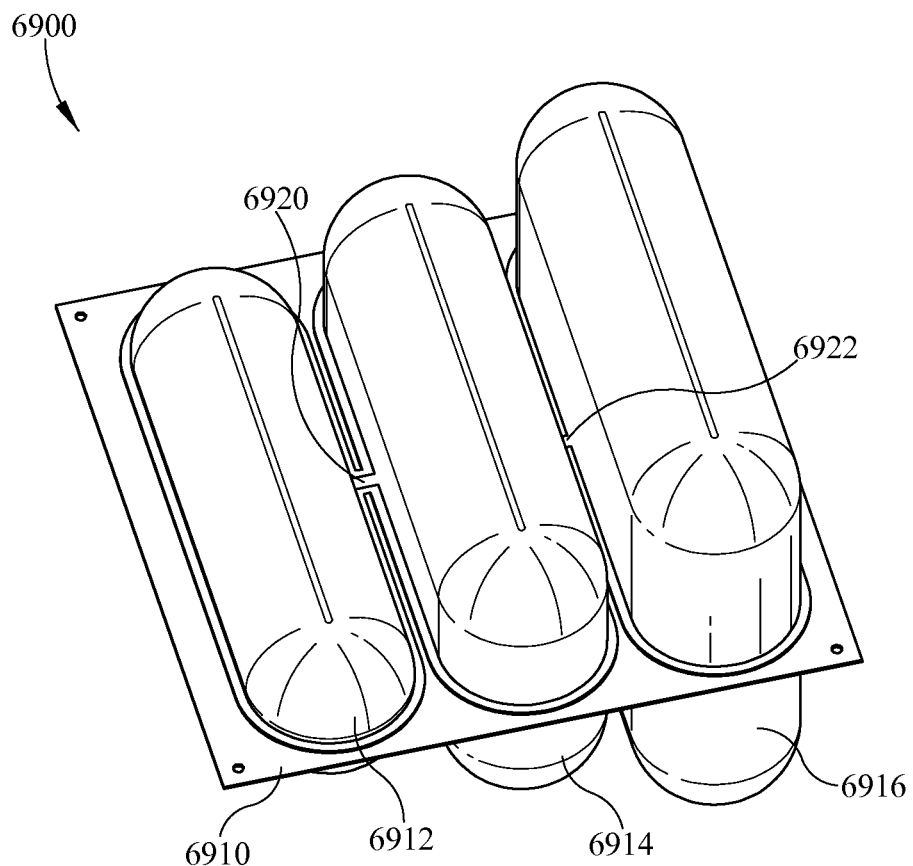
FIG. 69 is a simplified perspective view of at least one embodiment of a support section for the person support apparatus of FIG. 53.
Figure 70:
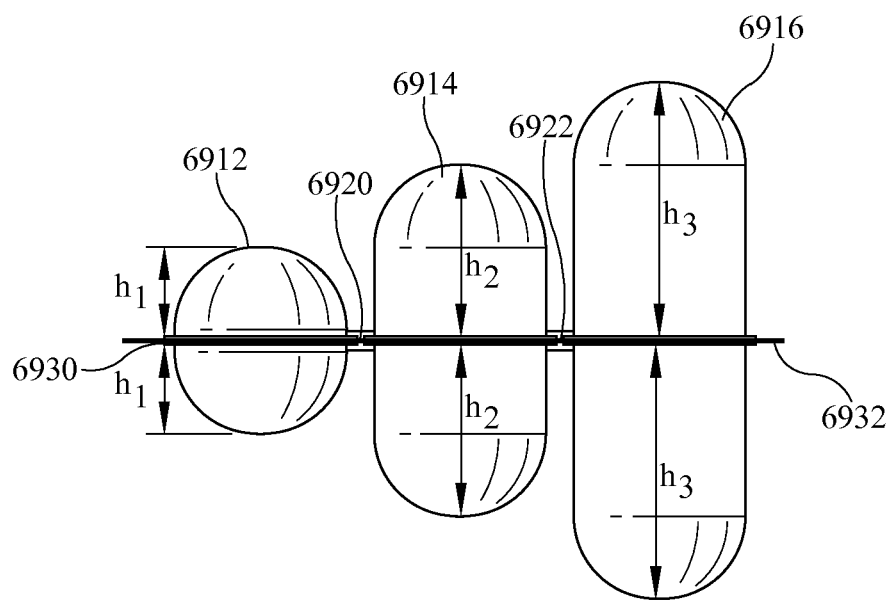
FIG. 70 is a simplified side view of the support section of FIG. 69.

Referring now to FIGS. 69-70, an embodiment 6900 of an inflatable support section, which may be used as a middle section 5414A and/or 5414B, for example, is shown. A number of fluidly connected bladders 6912, 6914, 6916 are formed from a base sheet 6910. Each of the bladders 6912, 6914, 6916 has a vertical height $h_1$, $h_2$, $h_3$, respectively, which extends vertically upwardly from the base sheet 6910 and also equally vertically downwardly below the base sheet 6910. The vertical heights $h_1$, $h_2$, $h_3$ progressively increase, such that the height $h_1$ is smaller than the height $h_2$ and the height $h_2$ is smaller than the height $h_3$. As such, when inflated, the bladders 6912, 6914, 6916 can provide the desired lateral tilt angle.

Channels 6920, 6922 fluidly couple the bladders 6912, 6914, 6916 to one another. The length of the channels 6920, 6922 generally defines the amount of space between the bladders 6912, 6914, 6916. The amount of space between the bladders 6912, 6914, 6916 may be the same or different, in accordance with the requirements of a particular design. Fluid ports 6930, 6932 couple the bladders 6912, 6914, 6916 to an air supply (e.g., via plastic tubing). The ports 6930, 6932 may each include a valve, which may be selectively opened and closed (e.g., by the control system 5328) to retain air in or vent air from the bladders 6912, 6914, 6916 as needed. While the support section 6900 is illustrated with three inflatable bladders 6912, 6914, 6916, it should be understood that any number of bladders may be used. For example, two bladders may be used in some embodiments, and more than three bladders may be used in other embodiments.

Referring now to FIGS. 71-74, a number of embodiments of a support section (e.g., support section 5316, 5318, 5320) including a bellows-type bladder construction (as in the support section 5500, for example) are shown. In FIG. 71, an embodiment 7100 includes a bellows-type inflatable bladder 7110. The bladder 7110 may be embodied as shown in FIGS. 55-56 and described above, for example. A rigid or semi-rigid panel 7118 is supported by the bladder 7110. A non-inflatable support portion 7114 is supported by the panel 7118. When the bladder 7110 inflates, the panel 7118 pivots about a hinge point 7112 to position a top surface 7116 of the non-inflatable portion 7114 at the desired lateral tilt angle as described above.

A sensor 7120 is mounted to the panel 7118 and configured to measure the lateral tilt angle 7122 as the inflatable bladder 7110 inflates and/or after the bladder 7110 is inflated. The sensor 7120 may be embodied as, for example, an accelerometer, inclinometer, ball switch, or other suitable type of angle sensor. The sensor 7120 communicates the angle data to a control system (e.g., the control system 5328) as described above. The sensor 7120 may be embedded in the non-inflatable portion 7114, in some embodiments.

In FIG. 72, an embodiment 7200 similar to the embodiment 7100 is shown. However, rather than an angle sensor mounted to the panel 7118, the embodiment 7200 includes a string potentiometer 7210, which is mounted to a base portion 7216 of the bellows bladder 7110. A distal end 7214 of the string 7212 is attached to the panel 7118. As the bladder 7110 inflates, the string potentiometer 7210 measures the distance traveled by the panel 7118 based on the change in length of the string 7212. The data generated by the string potentiometer 7210 is processed (e.g., by the control system 5328) to determine the angle 7122.

In FIG. 73, an embodiment 7300 utilizes a pair of sensors 7310, 7312, which are embedded in the interior region of the bellows bladder 7110, to monitor the lateral tilt angle. While the panel 7118 and support portion 7114 are omitted from FIG. 73, it should be understood that one or both of the panel 7118 and the support portion 7114 may be included in some versions of the embodiment 7300.

The sensors 7310, 7312 are each mounted to the internal side of the base portion 7216 of the bellows bladder 7110. The sensors 7310, 7312 are ultrasonic or laser sensors that transmit a signal through the interior region of the bellows bladder 7110 and vertically upwardly toward an internal side of the top portion 7314. As a result of the signal propagation, the output of the sensors 7310, 7312 is used to determine the vertical height from the base surface 7216 to the top surface 7316 at the locations of the sensors. The difference in the vertical heights measured by the two sensors 7310, 7312 is analyzed (e.g., by the control system 5328) to determine the angle 7122. While two sensors are shown in the embodiment 7300, it should be understood that any number of sensors may be used. Further, the spacing between the sensors 7310, 7312 may be varied according to the requirements of a particular design.

In FIG. 74, another version of an internal angle sensor 7410 is shown. The sensor 7410 is constructed as a vertical column of alternating portions of crushable/deformable foam 7412, 7416, 7420, 7424 and electrical switches 7414, 7418, 7422. The sensor 7410 extends vertically upwardly from the base portion 7216 to the top surface 7314, within the interior region of the bladder 7110. When the bladder 7110 is fully inflated, all of the switches 7414, 7418, 7422 are open. When the bladder 7110 is deflated, all of the switches 7414, 7418, 7422 are closed. In other words, as the angle 7122 increases, the electrical signals generated by the sensor 7410 decrease, and vice versa. The data generated by the sensor 7410 can thus be processed (e.g., by the control system 5328) to determine the angle 7122.

Figure 75:
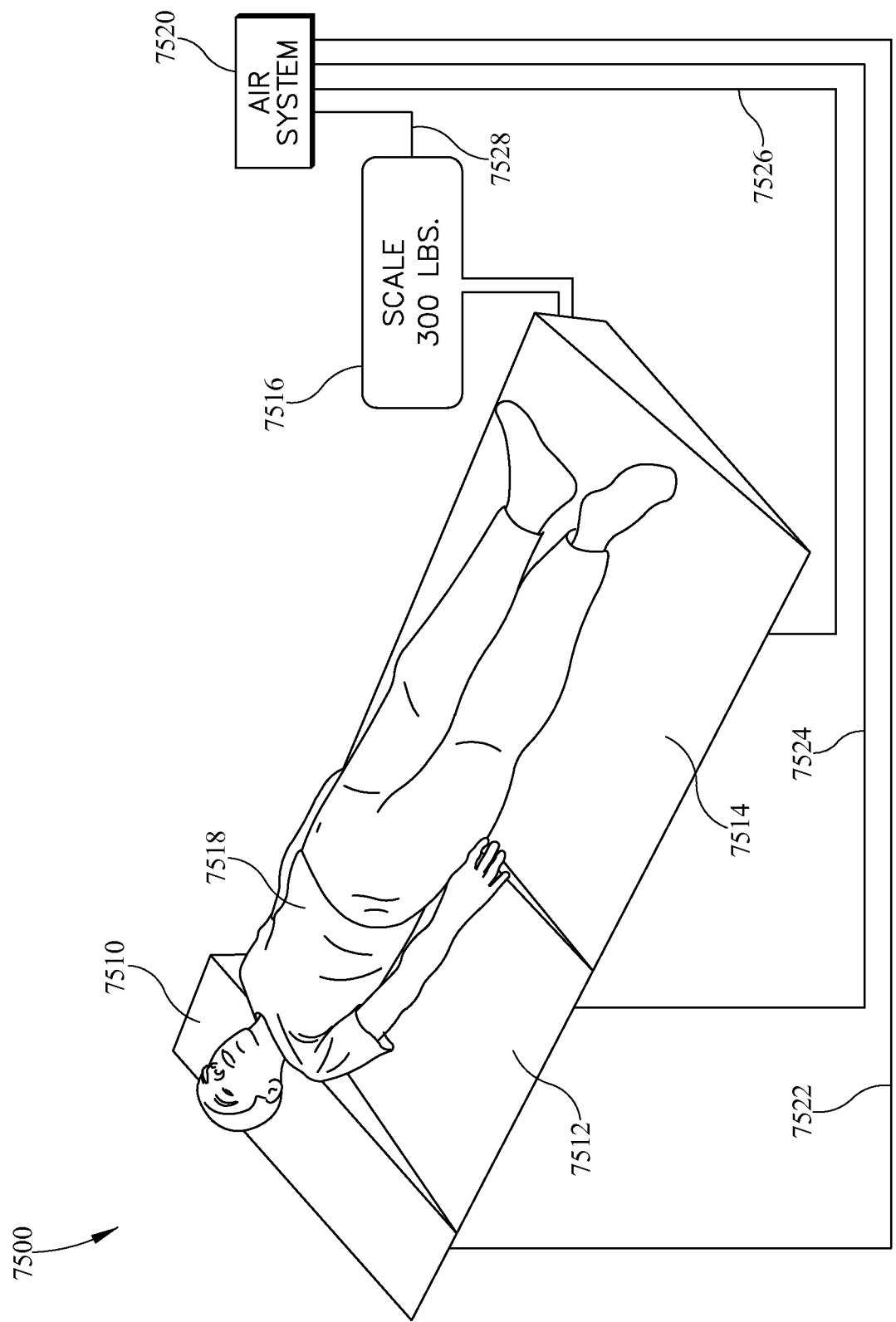
FIG. 75 is a simplified perspective view of at least one embodiment of the person support apparatus of FIG. 53, shown in communication with a weighing system.

Referring now to FIG. 75, an embodiment 7500 of a person support apparatus includes a number of support sections 7510, 7512, 7514, which are inflatable to provide the progressive lateral tilt angle as described above. The person support apparatus 7500 is in communication with a weighing system 7516. In general, the weighing system 7516 includes sensors, a processor, and computer instructions executable by the process to determine the weight of a person 7518 positioned on the person support apparatus 7500. For example, the sensors of the weighing system 7516 may be embodied as load cells mounted to a support frame supporting the person support apparatus 7500. Some examples of beds with integrated weighing systems are disclosed in, for example, U.S. Pat. No. 4,934,468.

An air system 7520 supplies and controls the amount of air pressure delivered to each of the support sections 7510, 7512, 7514 by conduits 7522, 7524, 7526, respectively. The air system 7520 receives person weight information from the weighing system 7516 via a data communication link 7528. Instructions executable by the air system 7520 (e.g., by a processor thereof) determine the appropriate amount of air pressure to deliver to each of the support sections 7510, 7512, and 7514 based on the person's weight as detected by the weighing system 7516 and the desired lateral tilt angle of each of the sections 7510, 7512, 7514. To do this, the air system may, for example, consult a look-up table or database that maps person weights, tilt angles, and air pressures. Such mappings may be determined in advance, e.g., through experimentation or through mathematical calculations. In one example, the weighing system 7516 detects the person 7518's weight as 300 pounds. In response, the air system 7520 supplies air pressure at 9 inches of water to the sections 7510 and 7512, and supplies air pressure at 5 inches of water to the section 7514. In another example, the weighing system 7516 detects the person 7518's weight as 151 pounds. In response, the air system 7520 supplies air pressure at 6 inches of water to the sections 7510 and 7512, and supplies air pressure at 5 inches of water to the section 7514.

Referring now to FIGS. 76-77, an embodiment 7600 of a support section for a person support apparatus, which may be used as a middle portion 5414A, 5414B, for example, is shown. The support section 7600 includes a substantially triangularly shaped non-rigid material 7610 and a pair of differently-sized air bladders 7612, 7614 coupled to the material 7610. The material 7610 may be constructed of, for example, a type of nylon. The air bladders 7612, 7614 may be coupled to the material 7610 by RF welding or other suitable fastening technique. The bladder 7614 is larger than the bladder 7612 (e.g., the bladder 7614 has a larger diameter than the bladder 7612). The bladders 7612, 7614 are spaced from one another so that the bladder 7612 is positioned nearer to the vertex of the lateral tilt angle 7616. The spacing of the bladders 7612, 7614 relative to the material 7610 and the size difference between the bladder 7612 and the bladder 7614 allow the support section 7600 to assume a substantially triangular shape when the bladders 7612, 7614 are inflated (FIG. 76) and a substantially flat shape when the bladders 7612, 7614 are deflated (FIG. 77).

Referring now to FIGS. 78-80 and FIG. 81, an embodiment 7800 of a person support apparatus is shown. The person support apparatus 7800 includes a base 7810, a number of support sections 7812, 7814, 7816 supported by the base 7810, and a side member 7818 supported by the base 7810. Each of the support sections 7812, 7814, 7816 includes, supported between the base 7810 and a top surface 7822, 78243, 7826, 7828, a three-dimensional matrix of longitudinal or log-shaped bladders 7820. The bladders 7820 are arranged in columns of vertically stacked bladders, where the columns are positioned adjacent one another across the lateral width of the support section 7812, 7814, 7816. The top surface 7822, 7824, 7826, 7828 may be constructed of foam or fabric, for example. A seam 7830 allows the top surface 7828 to move independently of the top surfaces 7822, 7824, 7826.

Figure 78:
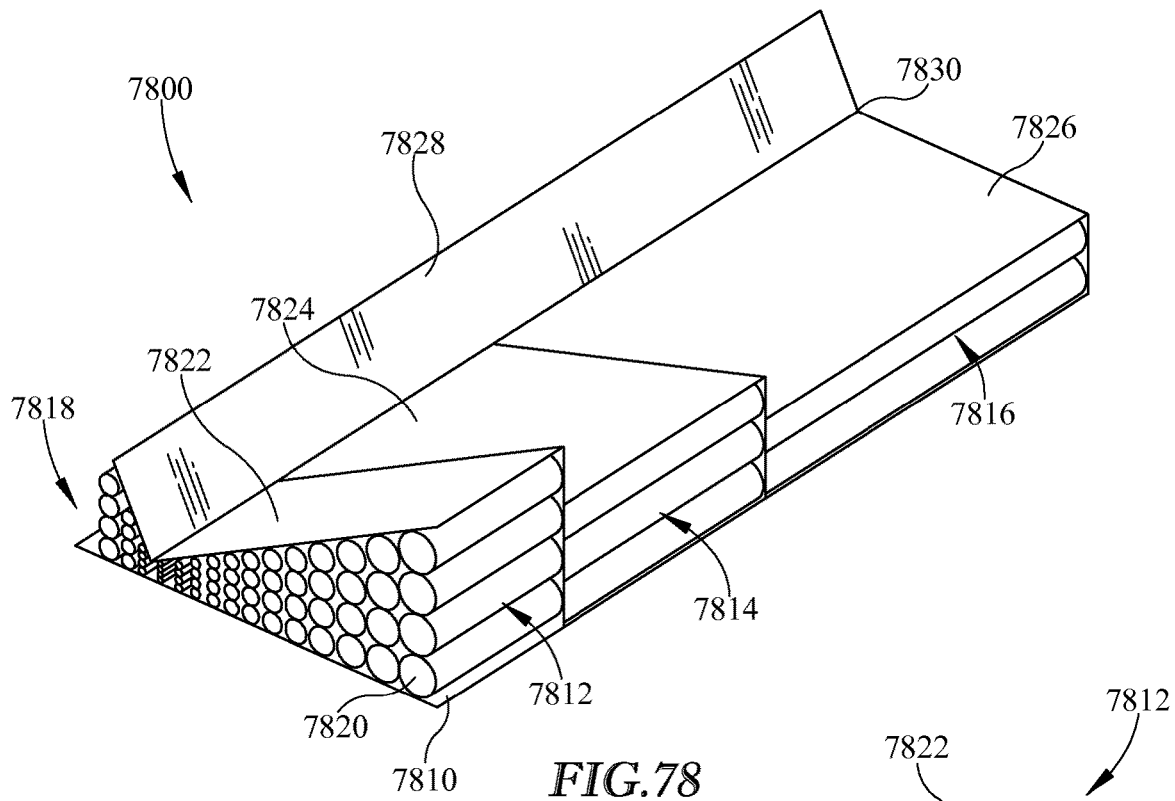
FIG. 78 is a simplified perspective view of at least one embodiment of the person support apparatus of FIG. 53, shown in a progressive lateral tilt position.
Figure 79:
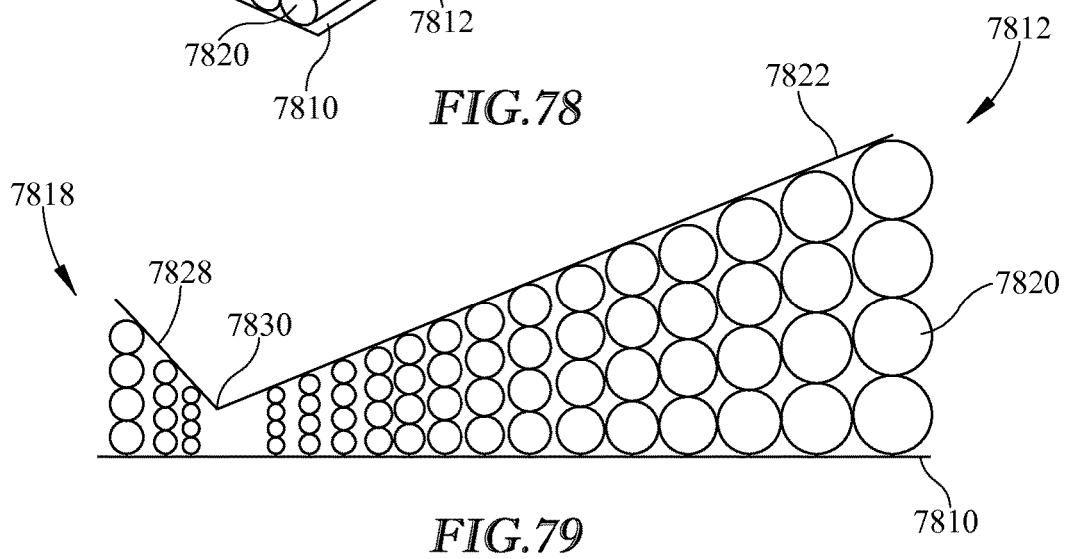
FIGS. 79-80 are simplified end views of the support section of FIG. 78, showing a lateral tilt position and a substantially flat position, respectively.
Figure 80:
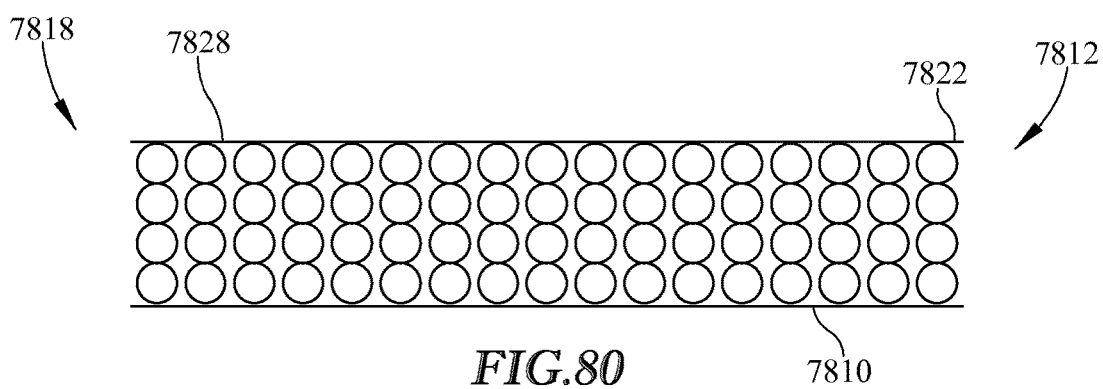

The air pressure within each of the bladders 7820 can be independently adjusted to create the desired progressive lateral tilt angle as described above. That is, a control system may control the inflation and deflation of each individual bladder 7820 independently of the other bladders. For example, as shown in FIG. 79, bladders that are nearer to the seam 7830 and thus nearer to the vertex of the lateral tilt angle may be inflated to a lesser degree than the bladders 7820 that are further away from the seam 7830. When all of the bladders 7820 are inflated by the same amount, the support section 7800 assumes a substantially flat position as shown in FIG. 80. As shown in FIG. 78, the bladders of the different sections 7812, 7814, 7816 may have different lengths. For example, the bladders 7814 may be longer in length than the bladders 7812, and the bladders 7816 may be longer in length than the bladders 7814. Illustratively, the bladders of each of the sections 7812, 7814, 7816 have the same or similar diameter. However, it should be understood that the bladder diameters may differ in other embodiments. For example, the diameter of the bladders in one of the sections 7812, 7814, 7816 may be different than the diameter of the bladders in one or more of the other sections 7812, 7814, 7816.

Figure 81:
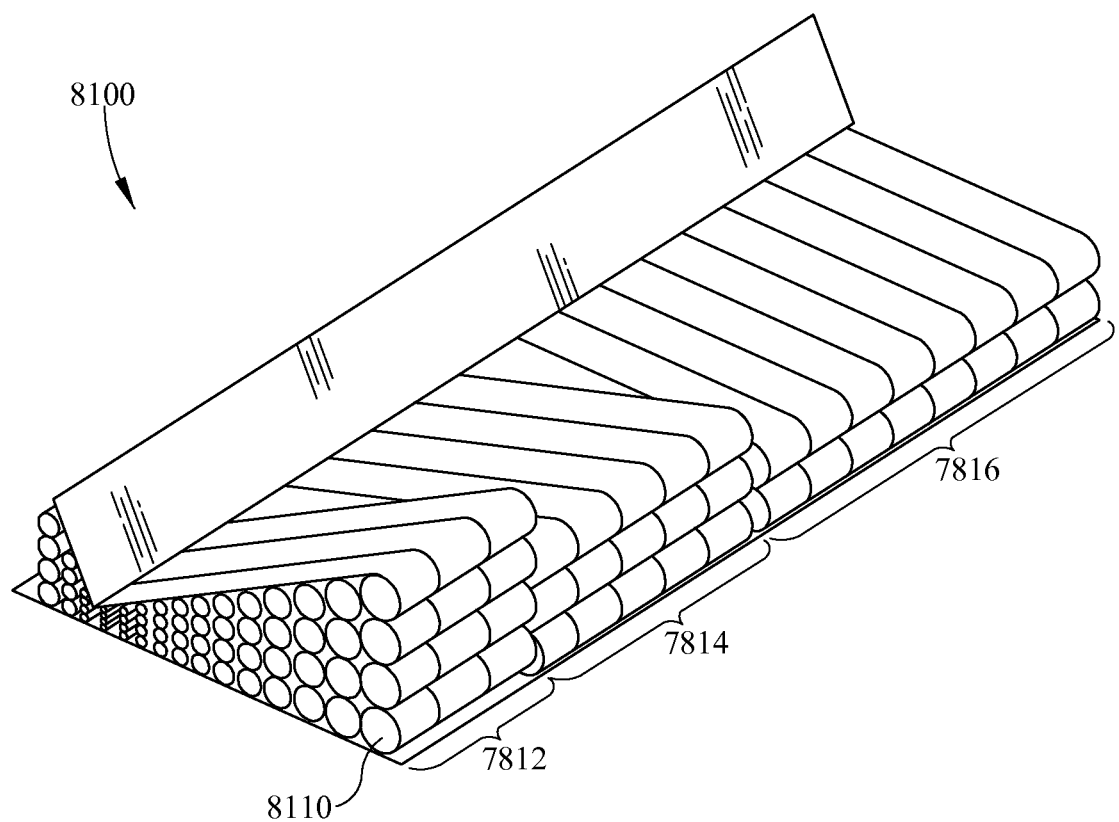
FIG. 81 is a simplified perspective view of at least one embodiment of the person support apparatus of FIG. 53, shown in a progressive lateral tilt position.
Figure 82:
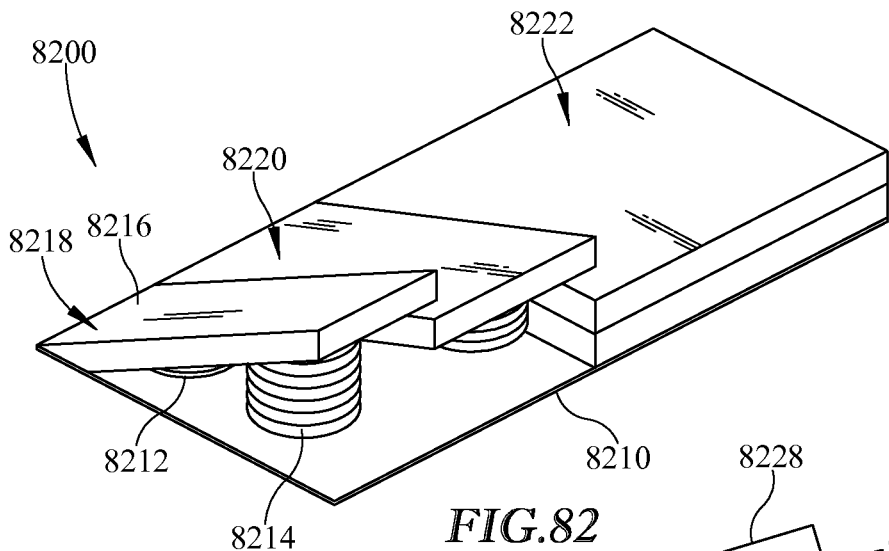
FIG. 82 is a simplified perspective view of at least one embodiment of the person support apparatus of FIG. 53, shown in a progressive lateral tilt position.

FIG. 81 illustrates a person support apparatus 8100 that is similar to the support section 7800, except that the support section 8100 has a number of bladder matrix subsections 7818. The bladder matrix subsections 7818 can be grouped together (e.g., by hook and loop fasteners or other fastening techniques) to form the bladder sections 7812, 7814, 7816. As such, the progression of the lateral tilt angle described herein can be controlled with a finer degree of granularity. Additionally, the size of the bladder sections 7812, 7814, 7816 can be dynamically adjusted (e.g., to accommodate differently-sized persons, for different therapeutic purposes, or other reasons).

Figure 83:
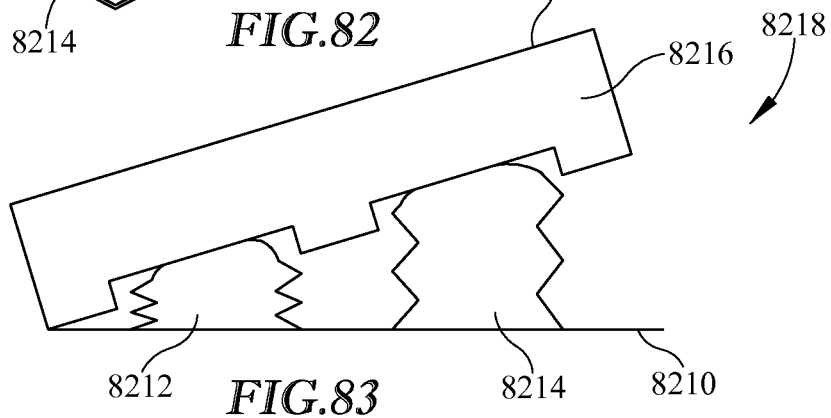
FIGS. 83-85 are simplified side views of the support section of FIG. 82, showing a lateral tilt position, another lateral tilt position, and a substantially flat position, respectively.
Figure 84:
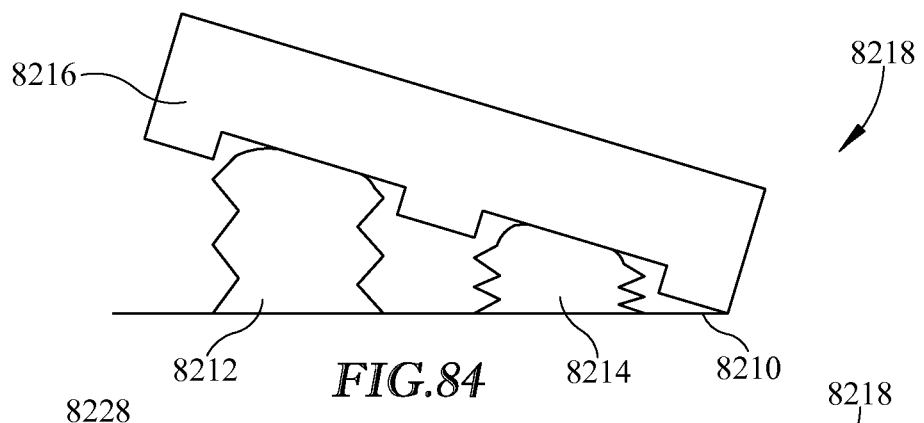
Figure 85:
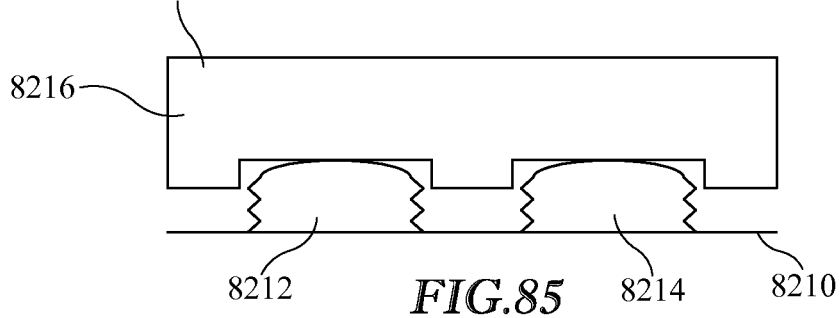

Referring now to FIGS. 82-85, an embodiment 8200 of a person support apparatus includes a base 8210 and a number of support sections 8218, 8220, 8222 supported by the base 8210. The support section 8218 includes a pair of side by side cylindrically-shaped pleated bladders 8212, 8214 and a non-inflatable panel 8216 supported by the bladders 8212, 8214. Each of the support sections 8220, 8222 is similarly configured. The air pressure in the bladders 8212, 8214 is selectively adjustable to alter the respective vertical heights of the bladders 8212, 8214 to achieve different angular orientations of the top surface 8228 of the non-inflatable structure 8216. The structure 8216 has a pair of recesses 8224, 8226 in its lower surface, which are sized to receive and retain a top portion of the bladders 8212, 8214, respectively. As shown in FIG. 83, the internal air pressure in the bladder 8214 is higher than the pressure in the bladder 8212, resulting in a lateral tilt toward the left side of the page. In FIG. 84, the pressure in the bladder 8212 is higher than the pressure in the bladder 8214, resulting in a lateral tilt toward the right side of the page. In FIG. 85, both of the bladders 8212, 8214 are at a medium pressure, resulting in a substantially flat surface 8228. To control the pressures in the bladders 8212, 8214, the bladders 8212, 8214 are fluidly coupled to a control system as described above.

Figure 86:
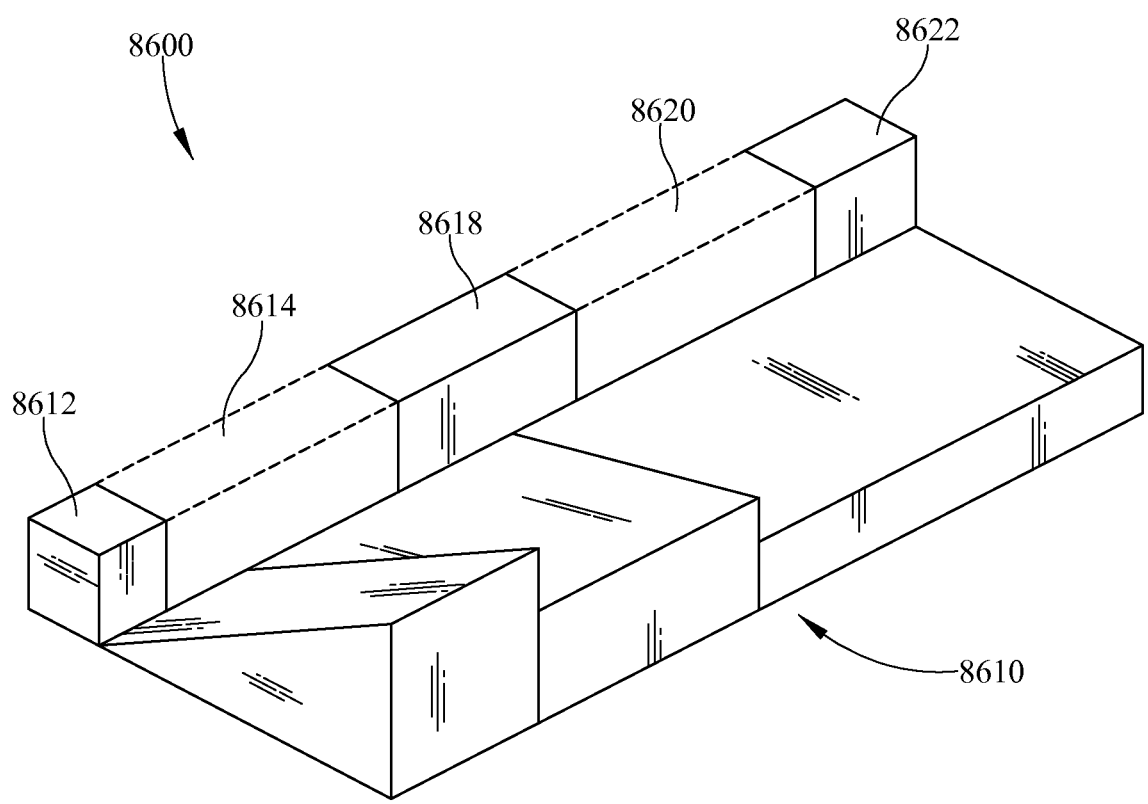
FIG. 86 is a simplified perspective view of at least one embodiment of the person support apparatus of FIG. 53, shown in a progressive lateral tilt position, and including at least one side member.

Referring now to FIG. 86, a person support apparatus 8600 includes a support structure 8610, which is configured to provide a progressive lateral tilt angle or "ramp" shape as described herein. In the embodiment 8600, side members 8612, 8618, 8622 are positioned along the vertex side of the structure 8610 so as to prevent a person rotated by the structure 8610 from exiting the structure unintentionally. The side members each have length that is substantially less than the length of the support structure 8610, leaving gaps therebetween through which the person may exit the support structure 8610 if desired. As shown by the dashed lines in FIG. 86, such gaps may be filled by additional side members 8614, 8620 to form a continuous support member if desired. The support members 8612, 8618, 8622, 8614, 8620 may be constructed of inflatable bladders, such that the support members 8612, 8618, 8622, 8614, 8620 only need to be inflated when they are needed (e.g., when the support structure 8610 is in a lateral tilt position). Accordingly, the side members 8614, 8620 may be deflated, e.g., to allow egress, and inflated, as needed.

Figure 87:
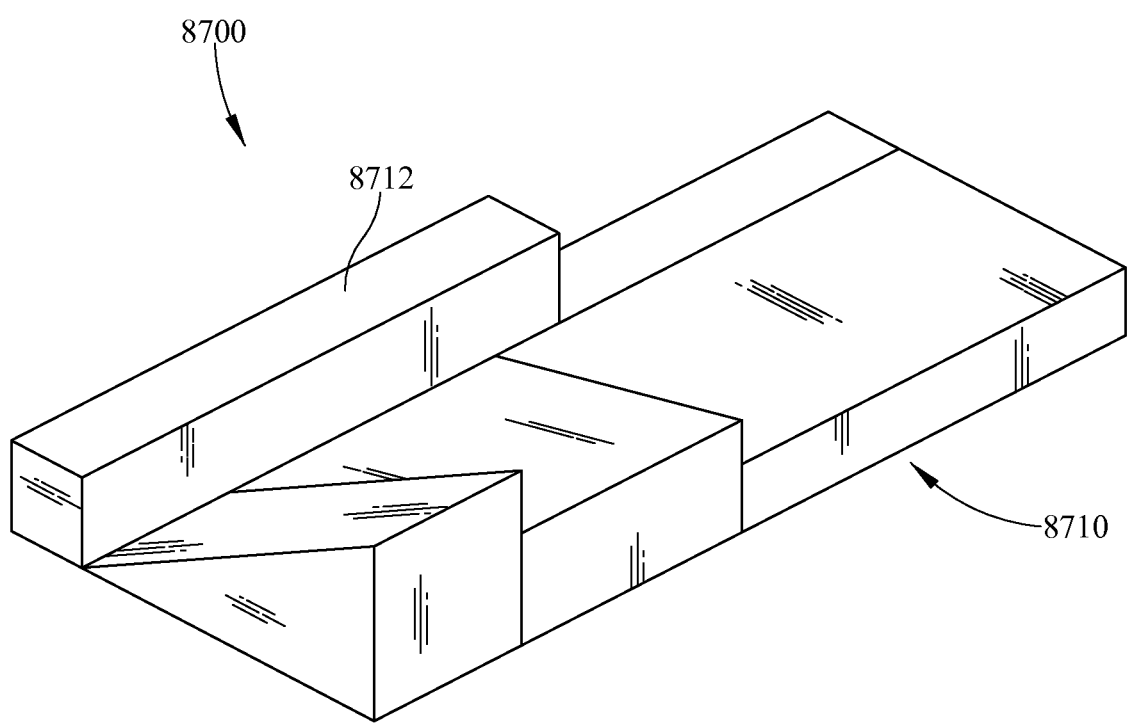
FIG. 87 is a simplified perspective view of at least one embodiment of the person support apparatus of FIG. 53, shown in a progressive lateral tilt position, and including a side member.

Referring now to FIG. 87, a person support apparatus 8700 includes a support structure 8710, which is configured to provide the progressive lateral tilt or "ramp" shape as described above, and a side member 8712. The side member 8712 has a length that is less than the entire length of the support structure 8710. As such, ingress and egress are permitted through the area in which the side member 8712 is not present.

Figure 88:
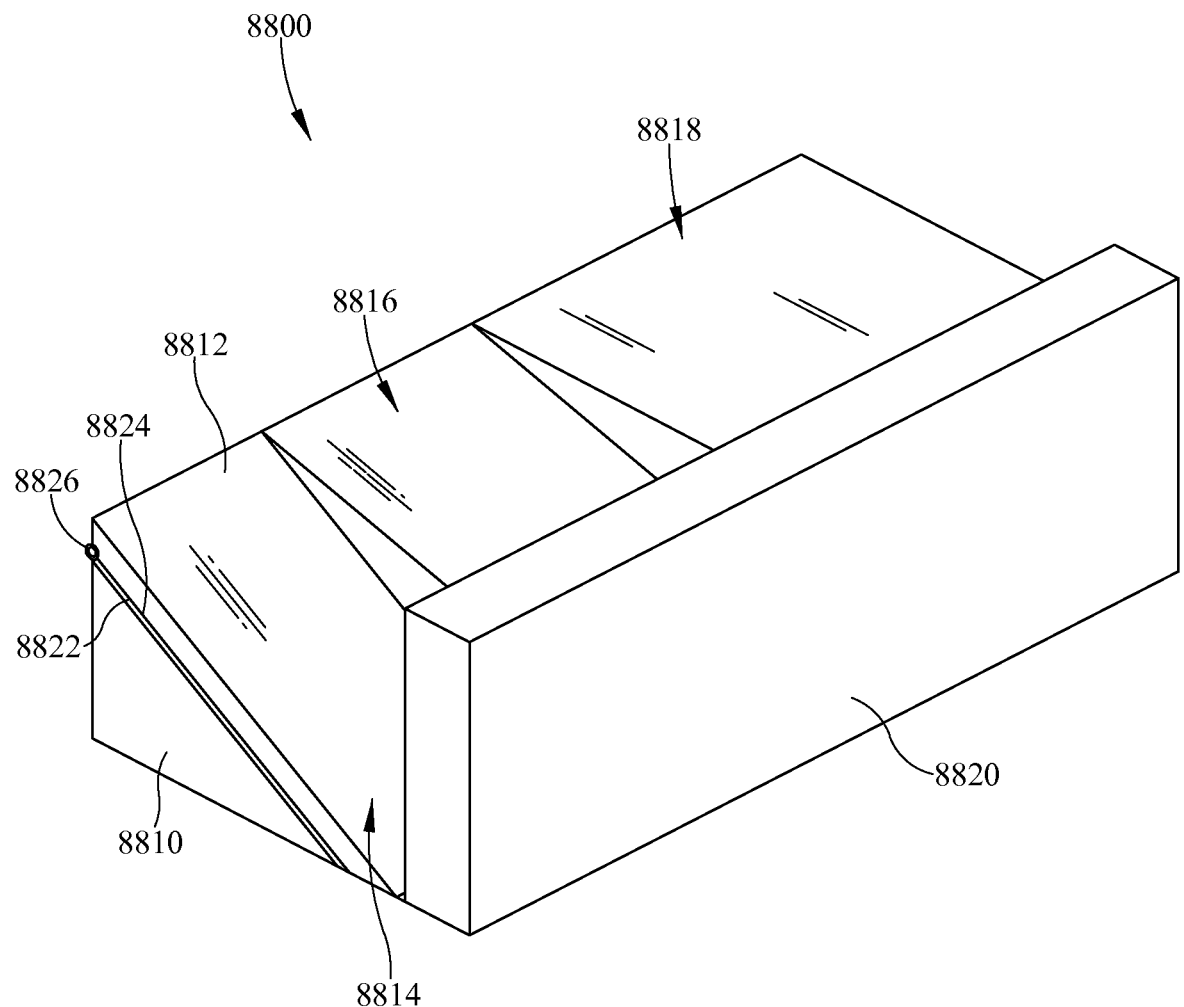
FIG. 88 is a simplified perspective view of at least one embodiment of the person support apparatus of FIG. 53, shown in a progressive lateral tilt position, and including at least one side member.
Figure 89:
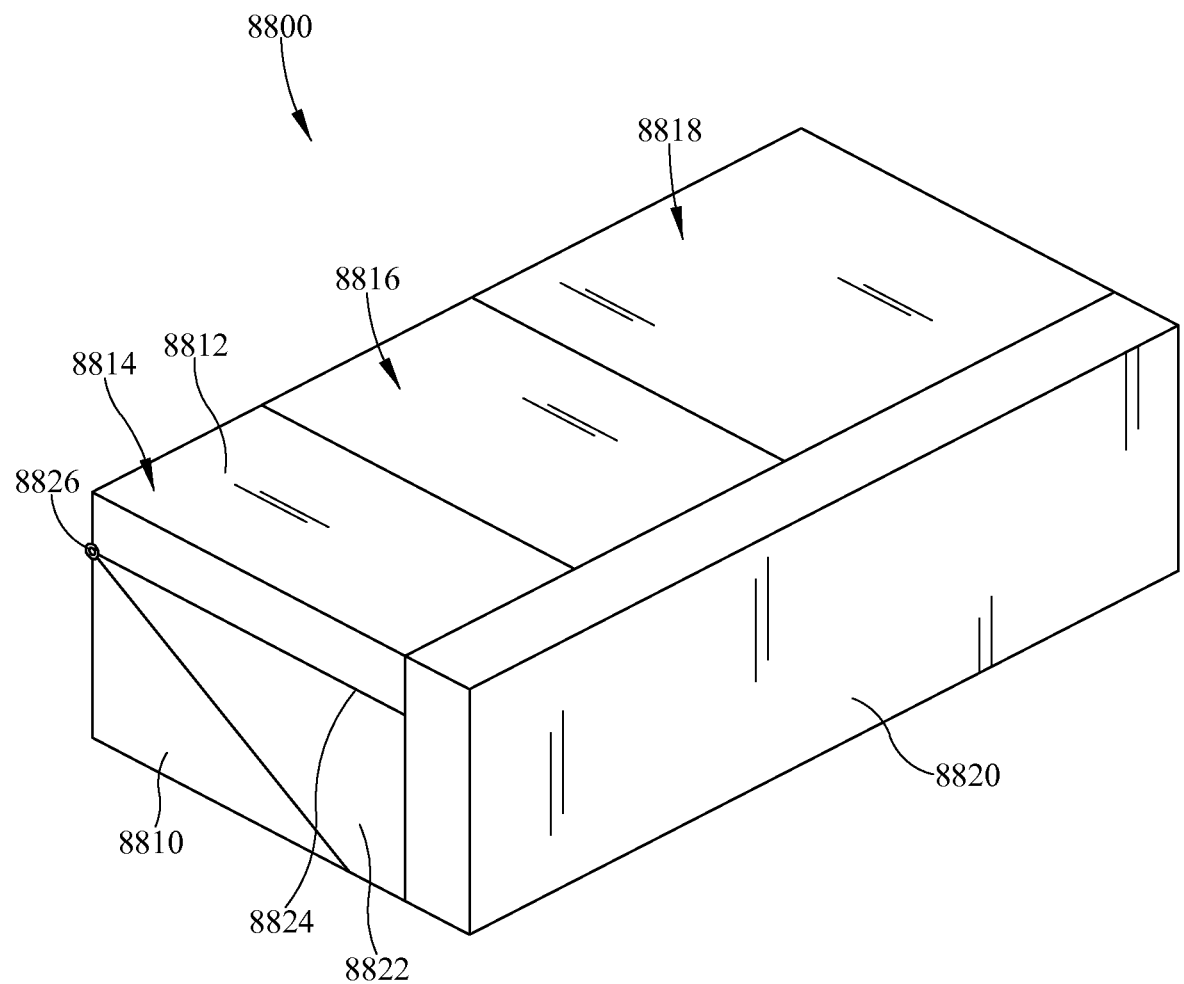
FIG. 89 is a simplified perspective view of the person support apparatus of FIG. 88, shown in a substantially flat position.

Referring now to FIGS. 88-89, a person support apparatus 8800 includes a number of support sections 8812, 8816, 8818 and a side member 8820. Each of the support sections 8812, 8816, 8818 includes a wedge-shaped non-inflatable support portion 8810, an inflatable portion 8822 supported by the portion 8810, a stiffener plate 8824 supported by the inflatable portion 8822, and a top portion 8812. In the embodiment 8800, the inflatable portion 8822 of each of the support sections 8812, 8816, 8818 is deflated to drop a person down into the progressive lateral tilt position (rather than raising the person up into the lateral tilt position). To accomplish the progressive lateral tilt position, the size of the wedge 8810 is different for each of the sections 8812, 8816, 8818 (to provide the different lateral tilt angles as described herein). FIG. 88 shows the person support apparatus 8800 with the inflatable portion 8822 deflated, while FIG. 89 shows the inflatable portion 8822 inflated.

Figure 90:
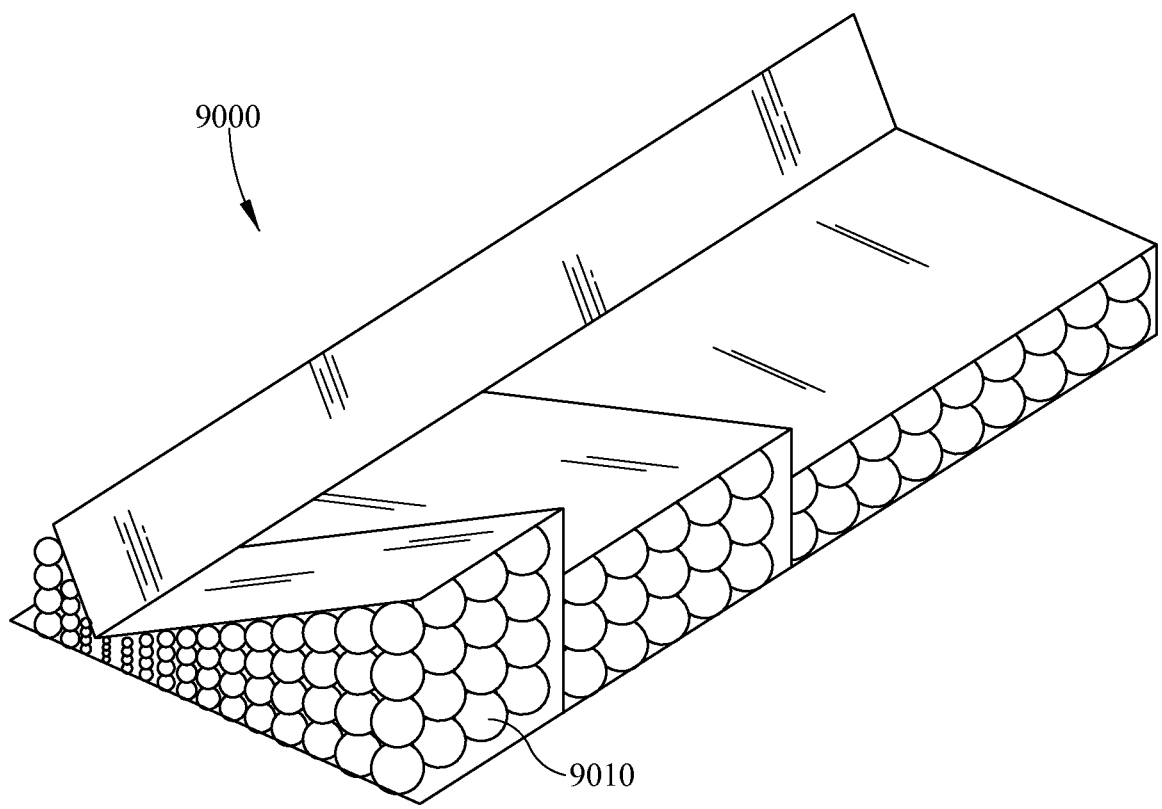
FIG. 90 is a simplified perspective view of at least one embodiment of the person support apparatus of FIG. 53, shown in a progressive lateral tilt position.

Referring now to FIG. 90, a person support apparatus 9000 has the same or similar construction as the person support apparatus 7800, except that the three dimensional bladder matrix includes spherical bladders 9010 rather than longitudinal or log-shaped bladders. The spherical bladders 9010 are vertically stacked and selectively inflatable to achieve the desired lateral tilt position.

Figure 91:
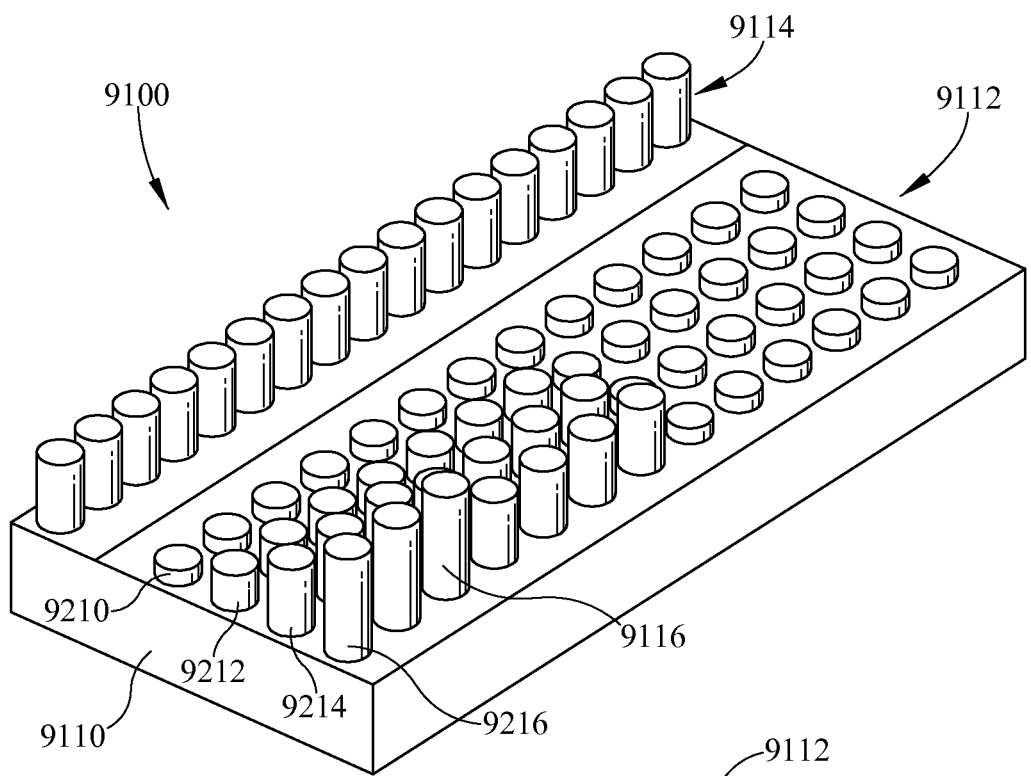
FIG. 91 is a simplified perspective view of at least one embodiment of the person support apparatus of FIG. 53, shown in a progressive lateral tilt position.
Figure 92:
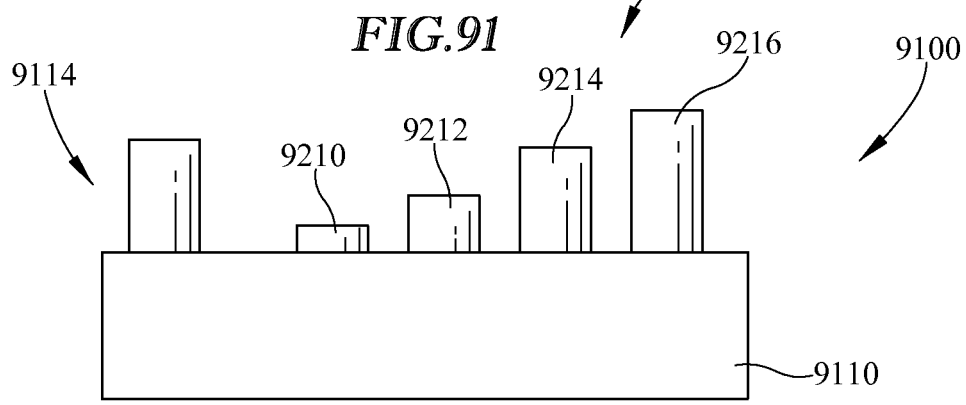
FIGS. 92-93 are simplified side views of the support section of FIG. 91, showing a lateral tilt position and a substantially flat position, respectively.
Figure 93:
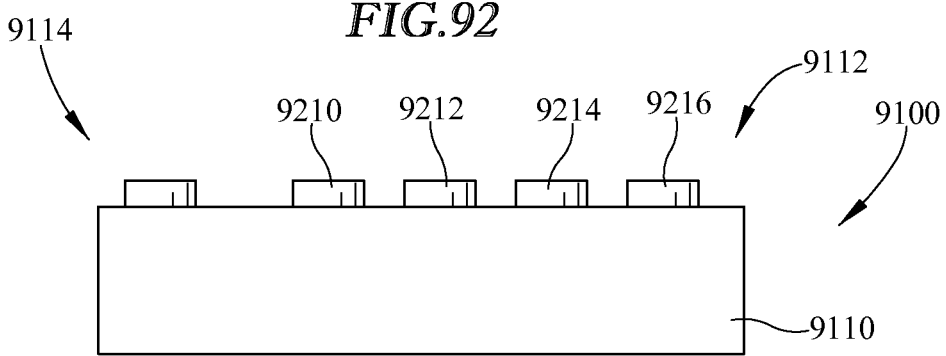

Referring now to FIGS. 91-93, an embodiment 9100 of a person support apparatus includes a base 9110 and two-dimensional matrix of can-shaped or upright vertical bladders 9416. A row of bladders 9114 is selectively inflatable to form a side bolster or side member. The arrangement of bladders 9116 allows a high degree of customization of the progressive lateral tilt position. In the illustrative embodiment, all of the bladders 9112, 9114 are manufactured to have at least the same maximum vertical height but the height of the individual bladders is varied by a control system as described herein, to achieve the desired lateral tilt angles. For example, as shown in FIG. 92, the progressively taller height of the bladders 9210, 9212, 9214, 9216 is due to the degree to which each of these bladders is inflated.

Figure 94:
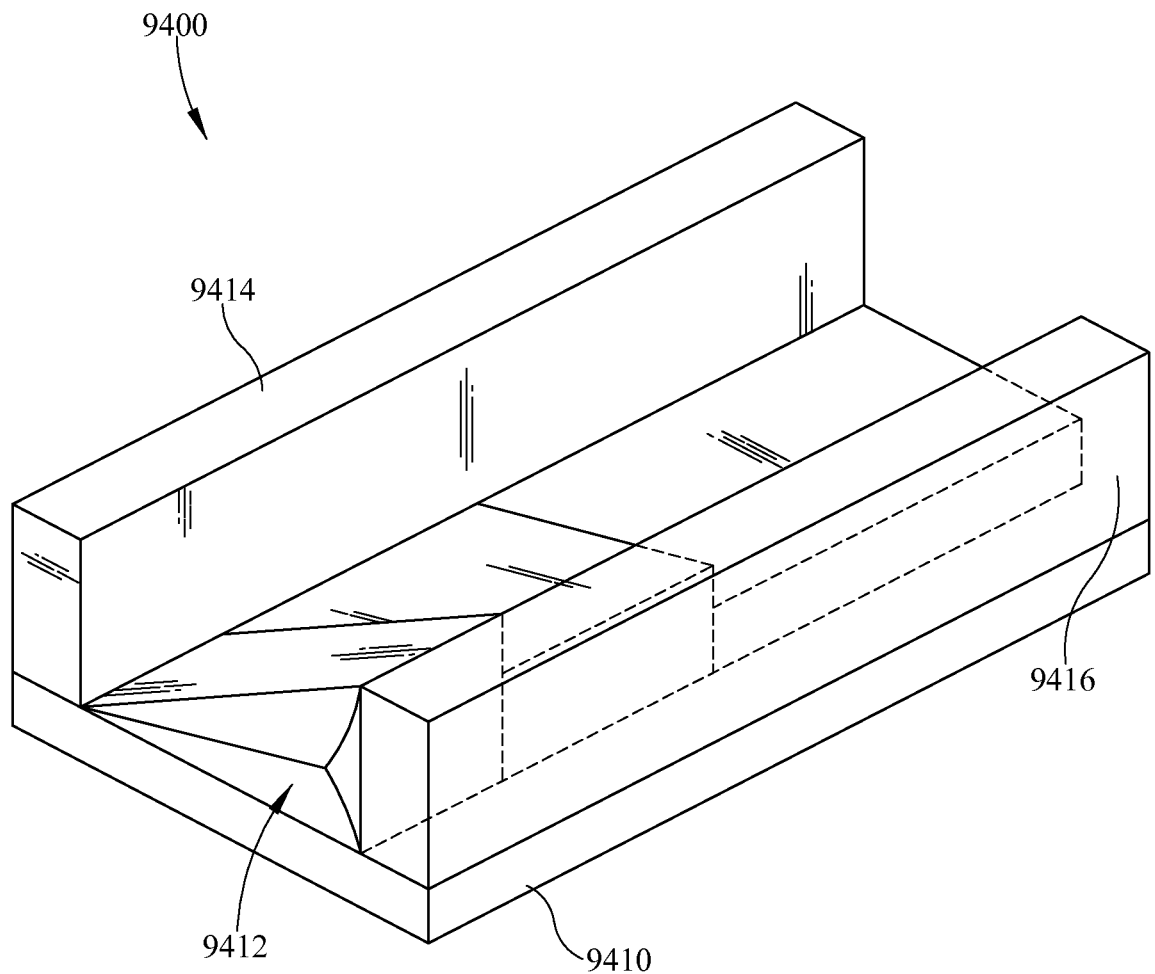
FIG. 94 is a simplified perspective view of at least one embodiment of the person support apparatus of FIG. 53, shown in a progressive lateral tilt position, and including at least two side members.

Referring now to FIG. 94, an embodiment 9400 of a person support apparatus includes a support structure 9412 and a pair of side members 9414, 9416. Each of the side members 9414, 9416 has substantially the same length as the length of the base 9410 and thereby can prevent the person from unintentionally exiting the structure 9412.

Figure 95:
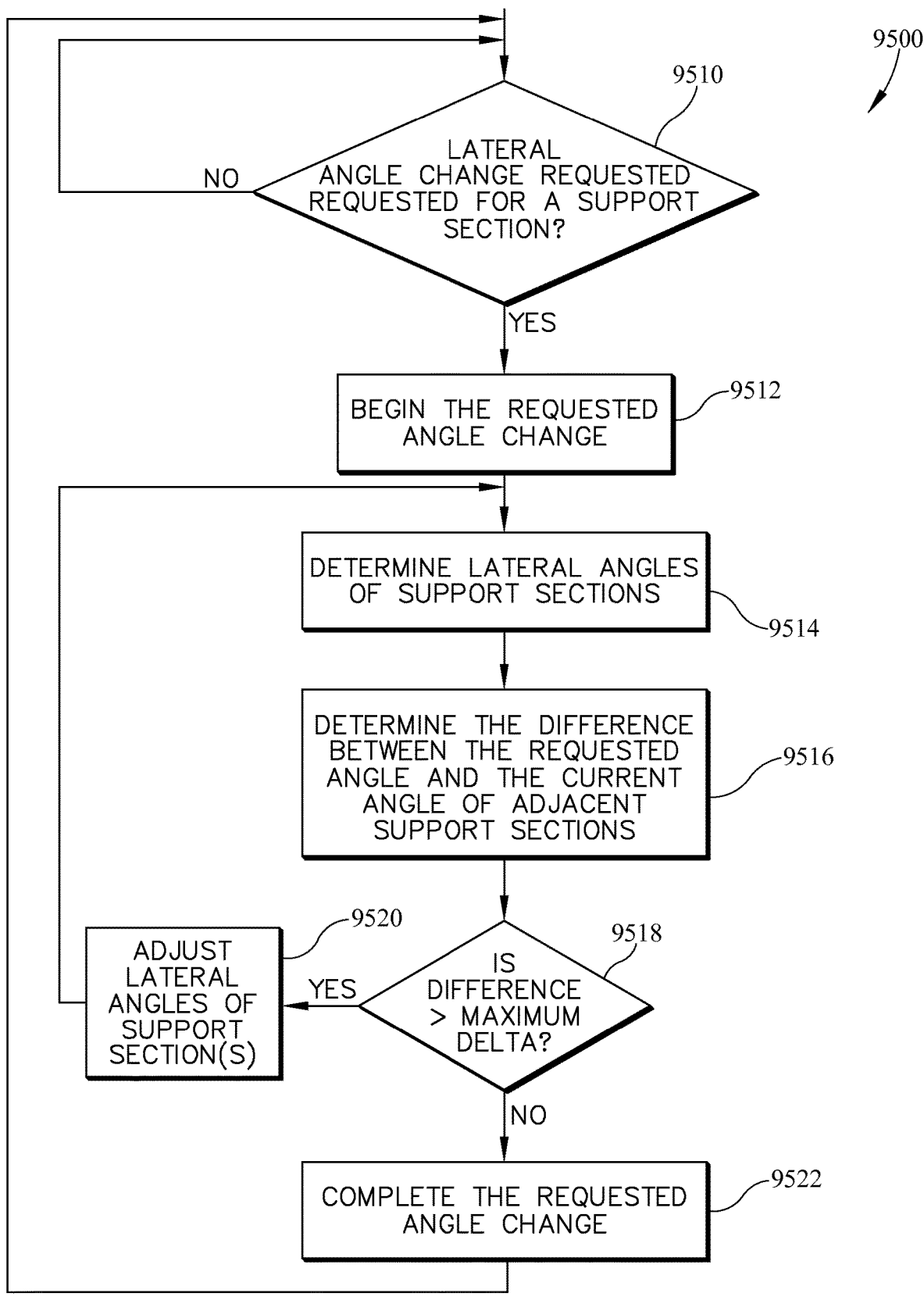
FIG. 95 is a simplified flow diagram of a method for controlling lateral angles of a person support apparatus.

Referring now to FIG. 95, a method 9500 for controlling the lateral tilt angle of a support section (e.g., the support sections 5316, 6318, 5320 of FIG. 53) is shown. The method 5300 may be embodied as computerized instructions, modules, or routines, which may be executed by a processor (by the air control system 5328, for example). Laterally angled support apparatuses can have multiple sections that provide different lateral angles above the horizontal, as described herein. To provide some forms of therapy, or for other reasons, the lateral angle may be smallest toward the foot end of the support apparatus and progressively increase toward the head end of the support apparatus. This progression of increasingly greater lateral angles can allow a person's head to rotate laterally a desired amount while still providing a comfortable and stable rest surface for the person.

Some embodiments include a static implementation, in which the progressive lateral tilt angles are established at a point in time (e.g., at manufacture) and then maintained throughout the use of the person support apparatus. Other embodiments include a dynamic implementation, in which control algorithms are used to move the person support apparatus in and out of the progressive lateral tilt position from time to time as needed or desired. For example, control algorithms may wait until after the person using the support apparatus has fallen asleep to implement the progressive lateral tilt position, and then return the support apparatus to the flat position before the person wakes up. In either case, controlling the difference in the lateral tilt angles of adjacent sections of the person support apparatus can, among other things, reduce the risk of discomfort. In static implementations, the person support apparatus can be designed and/or customized so that the difference in the lateral tilt angles of adjacent support sections (which may be referred to herein as the "delta") is minimized or at least does not exceed a defined threshold value (which may be referred to herein as the "maximum delta." In dynamic implementations, the control algorithms can monitor lateral tilt angle change requests and either minimize the delta or enforce the maximum delta while the person support apparatus is transitioning from one position to another (e.g., from a flat position to a progressive lateral tilt position or vice versa).

In FIG. 95, the person support apparatus control system (e.g., control system 5328) monitors for and detects requests to change the lateral angle of one or more support sections (e.g., section(s) 5316, 5318, 5320) of the person support apparatus, at block 9510. Such requests may come from a user (e.g., by activation of a touchscreen control to initiate the progressive lateral tilt position) or an automated process (e.g., in response to expiration of a timer). If a lateral angle change request is received, the system begins to execute the requested angle change at block 9512 (e.g., by inflating/deflating bladders as needed). While executing the angle change request, the system determines and monitors the current lateral angles of the support sections (e.g., the support section that is the subject of the request and the current lateral angles of each of the adjacent support sections), at block 9514. To do this, the system receives and analyzes sensor inputs that indicate the current lateral angles. Such inputs may be provided to the system by one or more angle sensors (e.g., accelerometers, inclinometers, ball switches, etc.) that are mounted to the respective support sections in, for example, any of the manners described herein. At block 9516, the system determines the difference (e.g., by mathematical subtraction) between the requested lateral angle and the current lateral angle of the support section being adjusted and each of its adjacent support sections. At block 9518, the system compares the difference between the requested angle and the current angles to the aforementioned maximum delta. In some cases, the maximum delta may be defined differently for different support sections, while in other cases, the maximum delta may be the same for all of the support sections. For instance, the maximum delta for a head support section with respect to its adjacent (e.g., seat) section may be larger than the maximum delta for the seat section with respect to the adjacent foot section. If the system determines that the lateral angle difference exceeds the maximum delta, the system adjusts the lateral angles of the support sections as needed at block 9520, and returns to block 9514. At block 9520, the system adjusts the lateral angle of one or more of the support sections (e.g., the support section for which the angle change is requested at block 9510 and/or the lateral angle(s) of one or more of the adjacent support sections). For example, if the request is to increase the lateral angle of the head support section, and the lateral angle difference between the requested angle and the current lateral angle of the adjacent (e.g., seat) section is greater than the maximum delta, the system may increase the lateral angle of the adjacent section. If the angle difference does not exceed the maximum delta, the system continues executing the requested angle change, at block 9522, and then ends the method 950 or returns to block 9510 as shown.

FIGS. 96a-96d are views of a mattress 900 according to another illustrative embodiment of the present disclosure. In this embodiment, the mattress 900 comprises a base 902 which supports a head section 904, a torso section 906, a leg section 908, and a bolster 909. The mattress 900 has a longitudinal length l and a lateral width w. A central longitudinal axis, or centerline, a1 runs through the middle of the mattress 900 longitudinally from end to end and a central lateral axis a2 runs through the mattress laterally from side to side. In this embodiment, the mattress 900 is made of polyurethane foam, although the mattress could be made from many other foam (including memory foam or closed cell foam), cloth, and/or fabric materials, and/or structural elements such as springs and air bladders. For example, a viscoelastic foam with an ILD (indention load deflection) rating of about 50 could be used when the angle Ø1 (described below) is from about 25 to about 30 degrees. Depending on the stiffness (ILD) of the material, the angles disclosed herein can be adjusted somewhat. Smaller angles maybe used when a higher ILD (stiffer) material is utilized, and vice versa. In some embodiments, the material comprises foam having an ILD of from about 25 to about 275.

The mattress 900 in this embodiment is coated with three coats of F-874 Muraculon vinyl based coating, and one coat of F-894 Muraculon vinyl based coating. Other coverings can be utilized, including those which preserve the density or durability of the foam, or increase its infection control or antimicrobial properties. In some embodiments, no coatings or coverings could be utilized.

FIG. 96b is a top view of the illustrative embodiment of FIG. 96a looking in the direction labeled 96b in FIG. 96a. As seen in this view, the head section 904 includes a flat top surface 903 and an angled top surface 905 which slants in the lateral direction at an angle relative to the lateral axis a2. The bolster 909 includes a flat top surface 907 and an angled top surface 911 which slants in the longitudinal direction at an angle relative to the longitudinal axis a1. As seen in FIG. 96b, in this embodiment, the bolster 909 extends along the leg section 908 and a portion of the torso section 906, but not along the head section 904. As shown in FIGS. 96a and 96b, a ramping or tapering down of the bolster 909 occurs about midway along the torso section 906 (below the location where the elbow would typically be supported). Accordingly, when this embodiment is used as intended, the head of the patient will typically not migrate adjacent the bolster 909 and will turn sideways at an angle, with a cheek supported by the angled top surface 903, thereby supporting the head at an angle relative to the lateral axis a2.

FIG. 96c is a longitudinal side view (viewed along the longer side) of the illustrative embodiment of FIG. 96a, looking in the direction labeled 96c in FIG. 96b. FIG. 96d is a lateral side view (viewed along the shorter side, or end) of the illustrative embodiment of FIG. 96a, looking in the direction labeled 96d in FIG. 96c. As best seen in FIGS. 96a and 96d, each of the head section 904, torso section 906, and leg section 908 includes an angled top support surface in this embodiment. In particular, the head section 904 includes the angled top surface 905 which slants in the lateral direction, the torso section 906 includes an angled top surface 915 which slants in the lateral direction, and the leg section includes an angled top surface 917 which slants in the lateral direction. The top surface 905 of the head section 904 is intended to support at least a portion of a person's head, and is generally tilted in the lateral direction at a first angle relative the lateral axis a2. The top surface 915 of the torso section 906 is intended to support at least a portion of a person's torso, and is generally tilted in the lateral direction at a second angle relative to the lateral axis a2. The top surface 917 of the leg section 908 is intended to support at least a portion of a person's leg, and is generally tilted in the lateral direction at a third angle relative to the lateral axis a2. In this embodiment, the top surface 905 of the head section 904 is at an angle Ø1 of about 25 degrees, the top surface 915 of the torso section is at an angle Ø2 of about 17.5 degrees, and the top surface 917 of the leg section is at an angle Ø3 of about 10 degrees. In some embodiments, the angle Ø1 is from about 10 to about 30 degrees, and the angle Ø2 is from about 0 to about 25 degrees (such as from about 1 to about 20 degrees). In some embodiments, angle Ø1 is at least about 10 degrees, and in some embodiments is at least about 15 degrees. In some embodiments angle Ø1 is at least 20 degrees, such as from about 20 to about 25 degrees, and the angle Ø2 is at least about 10 degrees, such as from about 10 to about 25 degrees.

In some embodiments, the angle Ø2 is from about 5 to about 15 degrees less than the angle Ø1. In some embodiments, the angle Ø2 is from about 5 to about 10 degrees less than the angle Ø1, and in some embodiments the angle Ø2 is about 7.5 degrees less than the angle Ø1. In some embodiments, the angle Ø2 is from about 15 to about 17.5 degrees. In some embodiments where the head section angle Ø1 is at about 30 degrees, the angle Ø2 is at about 15 to about 22.5 degrees. In some embodiments, such gradual turning by having angle Ø2 be somewhat less than angle Ø1, and somewhat more horizontal, has been found to increase comfort while still promoting a good sleeping position and urging the head turn significantly away from the vertical up direction (e.g., 35 degrees or more in both directions, clockwise and counterclockwise from vertical up, regardless of sleeping position.)

In some embodiments, the angle Ø3 is from about 0 degrees to about 15 degrees. In some embodiments, the angle Ø3 is from about 0 degrees to about 12.5 degrees, and in some embodiments is about 10 degrees. In some embodiments, the angle Ø3 is from about 0 to about 15 degrees less than the angle Ø2. In some embodiments, the angle Ø3 is from about 5 to about 10 degrees less than the angle Ø2, and in some embodiments the angle Ø3 is about 7.5 degrees less than the angle Ø2.

Because the base 902 is flat in this embodiment, on both its top and bottom, these angles Ø1, Ø2, and Ø3 are likewise relative to the base and to the underside of the mattress in this embodiment. In some embodiments, the top surfaces 905, 915, and 917 can be curved or non-linear or otherwise follow a non-straight or smooth path in the longitudinal and/or lateral directions. In such cases, where these angles are nonlinear in the lateral direction, the angle Ø1 of general lateral sloping of the top surface 905 of the head section can be defined by the angle of a line connecting a point defining the lateral start of the head support surface to a point defining its lateral end (laterally directly across, left to right), or a point at the approximate middle of the support surface (or by averaging the angles of all, or a plurality, of such lines, taken along the section). Likewise, the angle Ø2 of general sloping of the top surface 915 of the torso section can be defined by the line connecting the point defining the lateral start of the torso support surface to the point defining its lateral end, or a point at the approximate middle of the support surface (or by averaging the angles of all or a plurality of such lines taken along the section). Furthermore, the angle Ø3 of general sloping of the top surface 917 of the leg section can be defined by the line connecting the point defining the lateral start of the leg support surface to the point defining its lateral end, or a point at the approximate middle of the support surface (or by averaging the angles of all or a plurality of such lines taken along the section).

In this embodiment of FIG. 96, the head support surface 905 is sized to support a person's head, the torso support surface 915 is sized to support a person's torso, and the leg support surface 917 is sized to support a person's legs. In some embodiments, the head section 904 is from about 5 inches to about 30 inches in length (such as from about 15 to about 25 inches, or at about 20 inches for example), the torso section 906 is from about 15 inches to about 50 inches in length (such as from about 20 to about 35 inches, or at about 24 inches for example), and the leg section is from about 25 inches to about 50 inches in length (such as from about 30 to about 40 inches, or about 35 inches for example).

FIG. 97a is a perspective view of the base 902 (having the side bolster 909 on top of it) of the illustrative embodiment of FIG. 96. FIG. 97b is a top view of the base 902 and bolster 909 of FIG. 97a, looking in the direction labeled 97b in FIG. 97a. FIG. 97c is a side view of the base 902 and bolster 909 of FIG. 97a, looking in the direction labeled 97c in FIG. 97b. FIG. 97d is a side view of the base 902 and bolster 909 of FIG. 97a, looking in the direction labeled 97d in FIG. 97c.

FIG. 98a is a perspective view of the head section 904 of the illustrative embodiment of FIG. 96. FIG. 98b is a top view of the head section 904 of FIG. 98a, looking in the direction labeled 98b in FIG. 98a. FIG. 98c is a head end view of the head section 904 of FIG. 98a, looking in the direction labeled 98c in FIG. 98b. FIG. 98d is a right side view of the head section 904 of FIG. 97a, looking in the direction labeled 98d in FIG. 98c.

FIG. 99a is a perspective view of the torso section 906 of the illustrative embodiment of FIG. 96. FIG. 99b is a top view of the torso section 906 of FIG. 99a, looking in the direction labeled 99b in FIG. 99a. FIG. 99c is a head end view of the torso section 906 of FIG. 99a, looking in the direction labeled 99c in FIG. 99b. FIG. 99d is a right side view of the torso section 906 of FIG. 99a, looking in the direction labeled 99d in FIG. 99c.

Figure 100A:
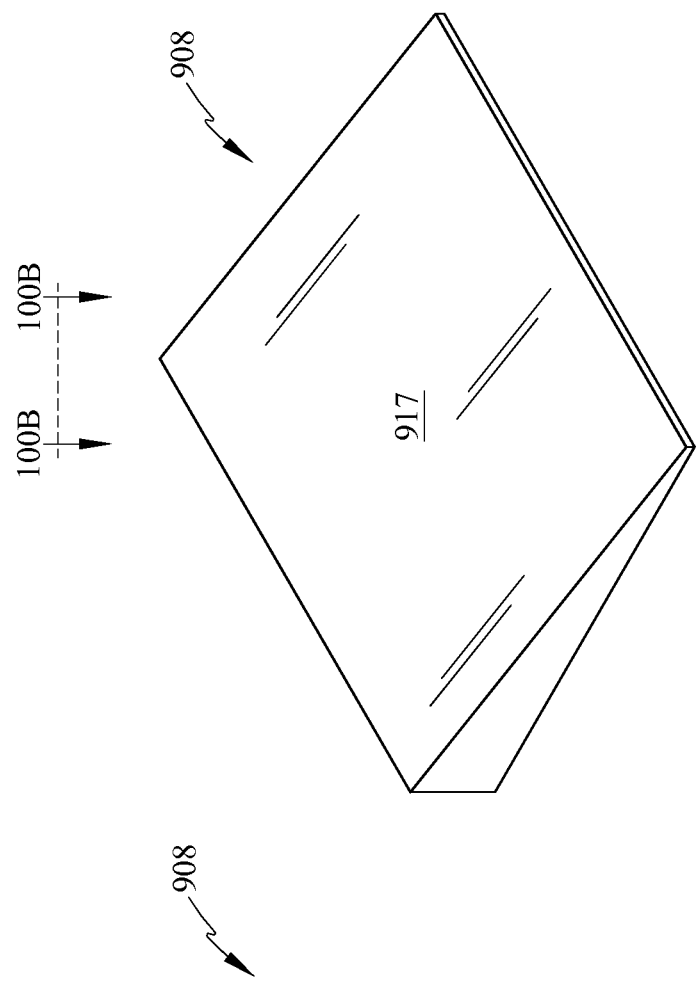
FIG. 100a is a perspective view of the leg section of the illustrative embodiment of FIG. 96.
Figure 100B:
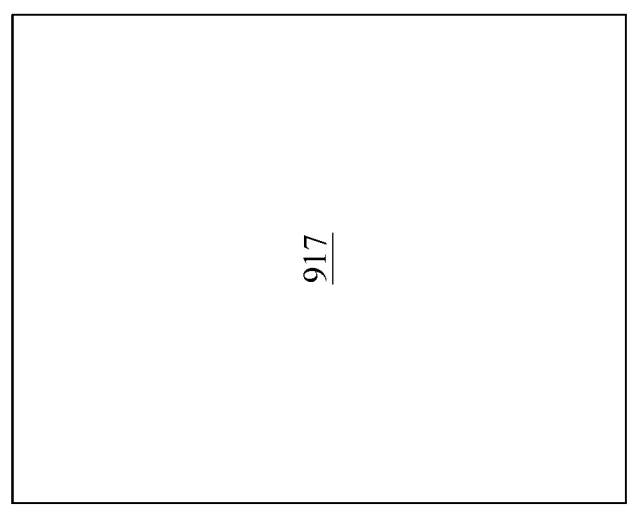
Figure 100D:
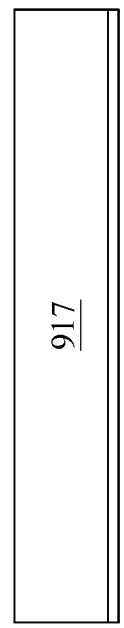
FIG. 100d is a side view of the leg section of FIG. 100a, looking in the direction labeled 100d in FIG. 100c.
Figure 100C:
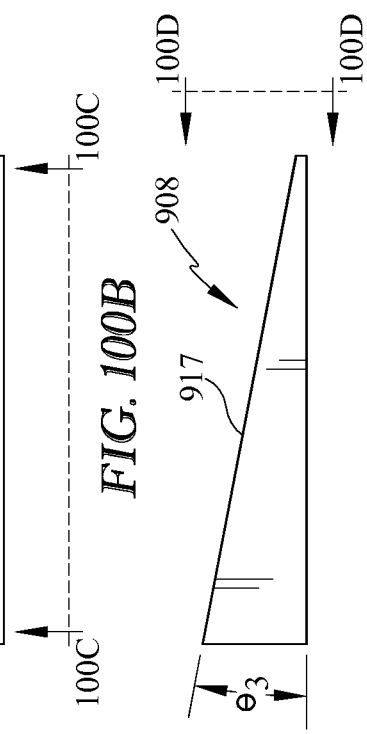
FIG. 100c is an end view of the leg section of FIG. 100a, looking in the direction labeled 100c in FIG. 100b.

FIG. 100a is a perspective view of the leg section 908 of the illustrative embodiment of FIG. 96. FIG. 100b is a top view of the leg section 908 of FIG. 100a, looking in the direction labeled 100b in FIG. 100a. FIG. 100c is a head end view of the leg section 908 of FIG. 100a, looking in the direction labeled 100c in FIG. 100b. FIG. 100d is a right side view of the leg section 908 of FIG. 100a, looking in the direction labeled 100d in FIG. 100c.

In use, the mattress 902 can be placed on a bed frame. The user lies on the top surfaces 905, 915, and 917, with the head section surface 905 generally supporting the user's head, the torso section surface 915 generally supporting the user's torso, and the leg section surface 917 generally supporting the user's legs. Due to the angle Ø1 of the top surface 905, the side of the user's head is urged to lie at a significant angle (e.g., plus or minus about 35 degrees or more relative to vertical). In this embodiment, it has been found that, in use, a straight line along the approximate surface of the user's face from the ear toward the eye will often lie at an angle (or the plane defined generally by the centerline of the nose), will be at an angle or offset from the vertical up direction and vertical plane. It has been found that, in some embodiments, regardless if the patient is being supported on the patient's back, front, or side, and regardless of whether the patient is sleeping with the face pointed "uphill" relative to the surface 905 or pointed "downhill" relative to the surface 905, the face will be urged to a left or right angle and away from looking straight up to the ceiling, when the mattress 907 is in the generally horizontal position. In some embodiments, this urging is to an angle that is 35 degrees or more left or right of the plane that the nose centerline would point if the patient had the nose/face/eyes square with the ceiling, pointing straight ahead. The face can be urged to an angle similar to the lateral plane angle of the top surface 905 (or at least to an angle perpendicular thereto), and it has been found that the effects of certain sleep disorders, such as sleep apnea, can be reduced. In some embodiments, the patient is urged by the surfaces to sleep in a position wherein the soft tissues (e.g., the soft pallet, tongue, uvula, tonsils, pharynx, and/or adenoids) in the upper respiratory tract are at a significant angle relative to vertical down and/or are less restrictive of the breathing passages so as to minimize apnea events. In this embodiment of FIG. 100, because the mattress has an angled top surface where the angle gradually reduces angle from head end to foot end, it has been found that tolerability/comfort of the mattress 902 for sleeping can be improved. Because the mattress 900 is made of a flexible material (which is a foam material in this embodiment) when placed on a support deck or frame with a pivoting or raisable leg and/or thigh portion, the leg section 908 can be pivoted relative to the torso section 906, to thereby create a raised knee and/or thigh, and/or a knee gatch or knee bed in the patient. It has been found that this configuration can help resist the migration of the patient toward the foot end and maintain the head in an angled position similar. Furthermore, in this embodiment, the height of the head support surface 905 is generally greater than the longitudinally corresponding height of the torso support surface 915, which is generally greater than the longitudinally corresponding height of the leg support surface 917, so as to create a longitudinal slope on the mattress as well, and causing the body to slop slightly longitudinally downwardly during sleep as well.

Many other embodiments are also possible. For example, instead of foam, the angled surfaces could be created by air bladders, and moved between angles as desired, or moved from flat to angled and back as desired, such as described above. Additionally, fewer, none or more bolsters could be utilized. Furthermore, instead of defined sections, the sections could gradually transition to one another. The other figures herein illustrate some such embodiments, although many others are possible, by adding, subtracting or combining features or aspects.

Figure 101:
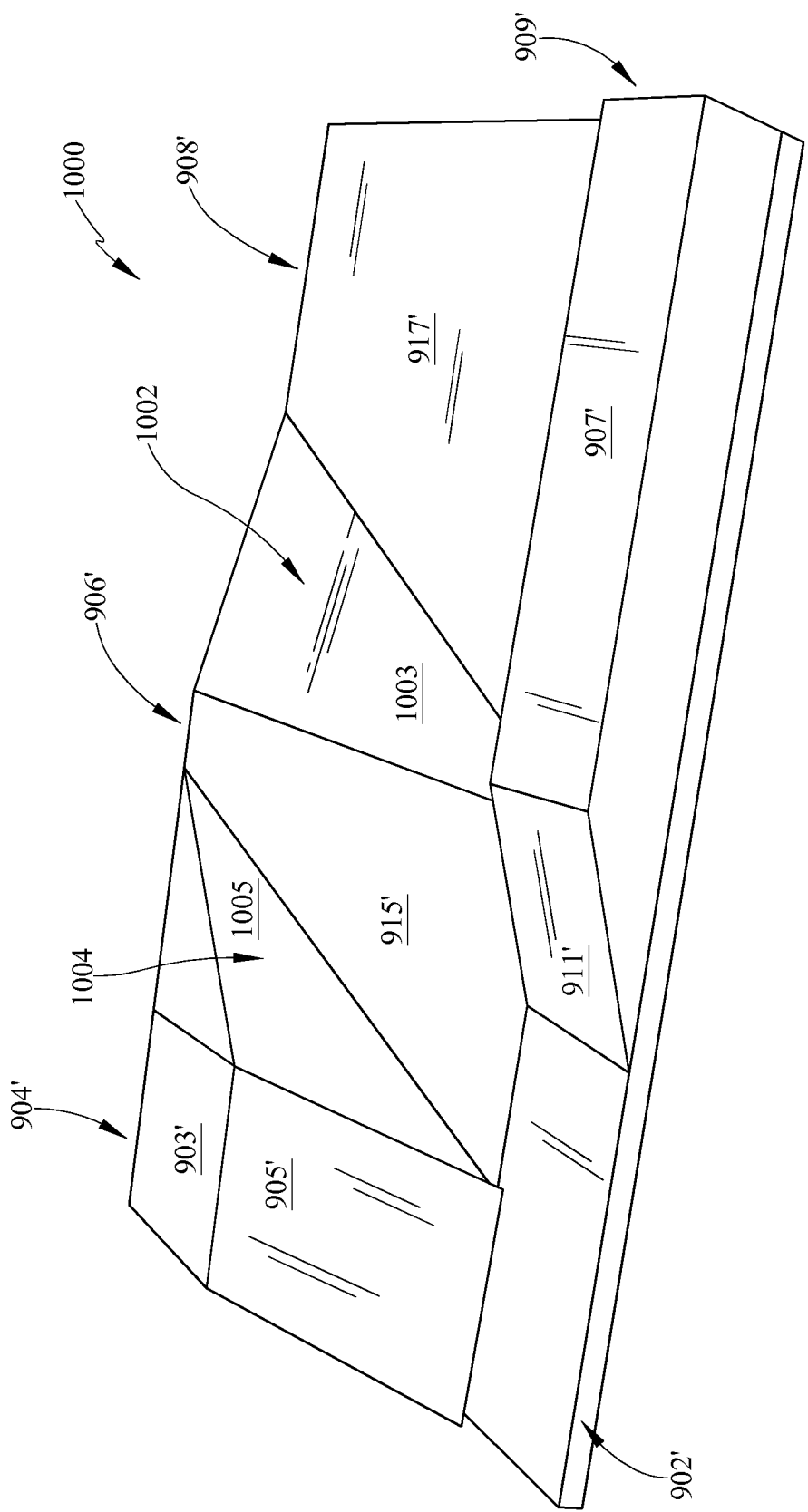
FIG. 101 is a perspective view of mattress according to another illustrative embodiment of the present disclosure, where the mattress includes transitions sections between the head section and torso section and between the torso section and leg section.

FIG. 101 is a perspective view of a sleep apparatus in the form of a mattress 1000 according to another illustrative embodiment of the present disclosure, where the mattress includes transitions 1002 and 1004 sections between the head section 904' and torso section 906' and between the torso section 906' and leg section 908'. The sections 904', 906' and 908', and the bolster 909' are configured substantially the same as in the embodiment of FIG. 96 and operate similarly. However, in this embodiment, instead of discrete or stepped transitions between the sections, there are gradual or sloped transitions, via the transition sections 1002, which are each angled in both the lateral direction and the longitudinal direction.

FIG. 102*a* is a perspective view of the first transition section 1002 of the illustrative embodiment of FIG. 101. FIG. 102*b* is a top view of the first transition section 1002 of FIG. 101, looking in the direction labeled 102*b* in FIG. 102*a*. FIG. 102*c* is a side view of the first transition section 1002 of FIG. 101, looking in the direction labeled 102*c* in FIG. 102*b*. FIG. 102*d* is a side view of the first transition section 1002 of FIG. 101, looking in the direction labeled 102*d* in FIG. 102*c*. As shown in this FIG, the transition section 1002 has a top surface 1003 that slants or angles in both the longitudinal and the lateral directions. Thus, top surface 1003 has an angle α1 relative to the longitudinal axis of the mattress and an angle α2 relative to the lateral axis of the mattress. Accordingly, a gradual transition is achieved between the head section 904' and the torso section 906'.

FIG. 103*a* is a perspective view of the second transition section 1004 of the illustrative embodiment of FIG. 101. FIG. 103*b* is a top view of the second transition section 1004 of FIG. 101, looking in the direction labeled 103*b* in FIG. 103*a*. FIG. 103*c* is a side view of the second transition section 1004 of FIG. 101, looking in the direction labeled 103*c* in FIG. 103*b*. FIG. 103*d* is a side view of the second transition section 1004 of FIG. 101, looking in the direction labeled 103*d* in FIG. 103*b*. As shown in these FIGS., the transition section 1004 has a top surface 1005 that slants or angles in both the longitudinal and the lateral directions. Thus, top surface 1005 has an angle relative to the longitudinal axis of the mattress and an angle relative to the lateral axis of the mattress. Accordingly, a gradual transition is achieved between the torso section 906' and the leg section 908'. These transition sections 1002 and 1004 can thereby help support the user's back, rear, and/or side during use. The mattress 1000 of this embodiment is made of a foam material.

Figure 104:
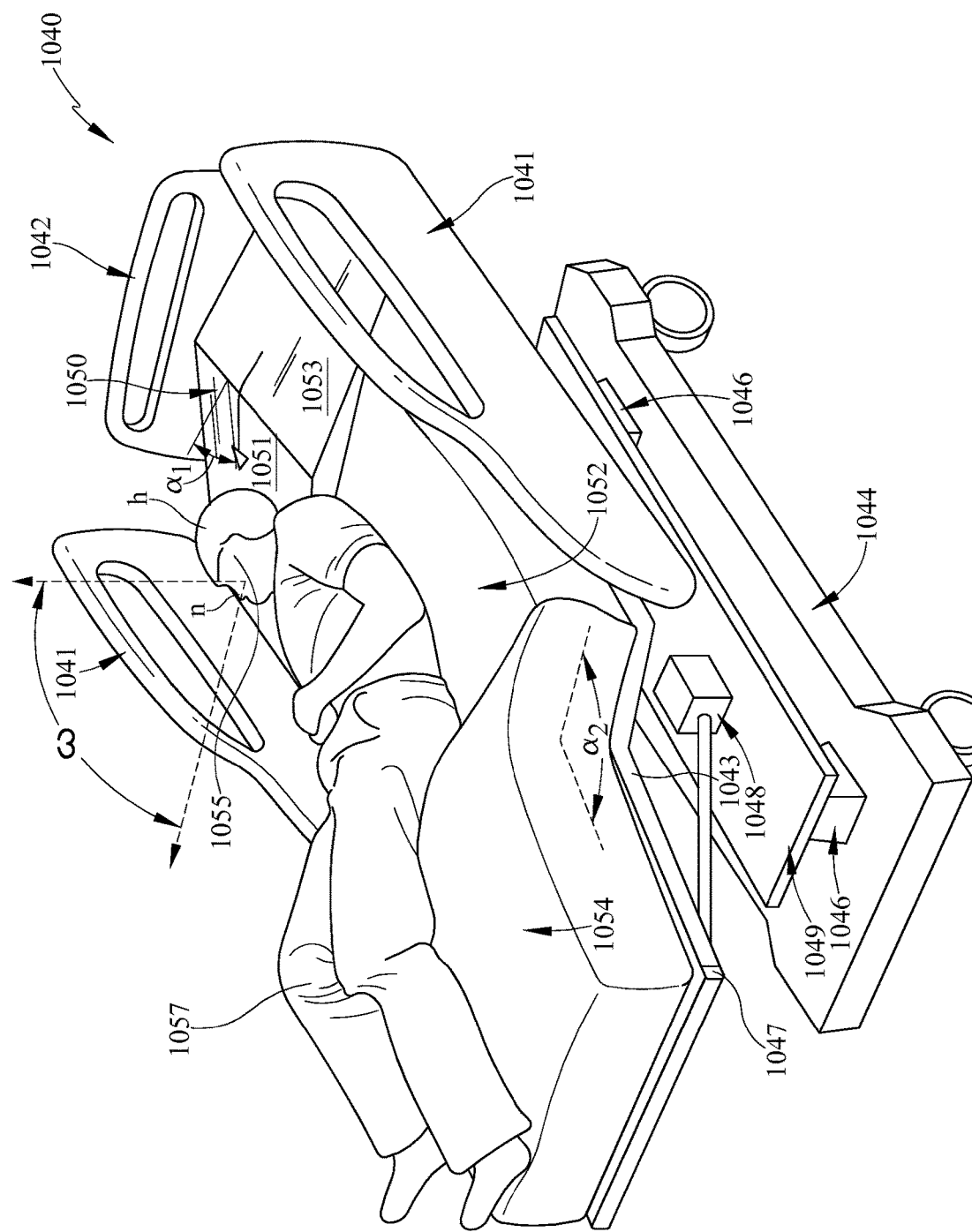
FIG. 104 is a perspective view of a person support apparatus according to another illustrative embodiment of the present disclosure, that includes a leg section that articulates near the knee of the person supported.

FIG. 104 is a perspective view of a sleep apparatus in the form of a person support apparatus 1040, according to another illustrative embodiment of the present disclosure, that includes a leg section that articulates near the knee of the person supported. In this embodiment, the person support apparatus 1040 includes a castered base 1044, and an frame 1049 movable in the vertical direction relative the base 1044 via actuators 1046. The frame 1049 supports a deck 1047 on which sits mattress 1050. The deck 1047 is movable via actuator 1048 to raise or tilt one or more deck sections. Siderails 1041 can move upwardly and downwardly at the lateral sides of the person support apparatus 1040, and headboard 1042 is positioned at the longitudinal head end of the person support apparatus 1040.

The mattress 1050 has an angled head support surface 1051 and a horizontal head section 1053, as well as a torso section 1052, and a leg section 1054. The angled head support surface 1051 slants laterally toward the side of the person support apparatus 1040, toward the siderail 1041. The torso section 1052 supports the torso of the patient, and the leg section 1054 supports the legs of the patient. The angled head support surface 1051 slopes laterally at an angle α1 relative to horizontal, while the flat head section 1053 is relatively flat to horizontal. Due to the articulation of the deck 1047 in the leg section 1054 and the flexibility of the foam material from which mattress 1050 is made, a pivot or bend is formed in the leg section 1054 near the knee 1057 of the patient. The angle α2 defined by the bend in the mattress 1050 near the knee 1057 causes the leg section 1054 to slope upwardly then downwardly (or to flat) in the longitudinal direction from head toward foot. Preferably, this angle α2 is from about 90 to about 175 degrees (i.e., the angle between the lower leg support surface and the upper leg support surface is from about 185 degrees to about 270 degrees, such as from about 210 to about 240 degrees for example.) The angled head surface 1051 can cause the head 1055 of the patient to slope away from vertical during sleep, at angle ω, while the bent leg section 1054 can cause the knees 1057 of the patient to be bent during sleep such that the legs and thighs form an angle corresponding to approximately α2 while the patient sleeps in a semi-supine position where the patient is supported on the backside of their legs and torso, and the side of their face tilts generally at an angle to vertical. The angle ω can be defined by the straight ahead line of site of the eyes, and can be greater than 35 degrees, such as greater than about 40 degrees, or greater than about 45 degrees. In some embodiments, this angle ω to goes up to the limit permitted by the angle α1 of the head support surface 1051, such as up to about 130 degrees for example. It is also possible in the embodiments of this disclosure that the patient sleeps in a semi-prone position where the patient is supported on the front side of their legs and torso, and/or stomach, but generally on the side of their face as the face tilts generally downwardly toward the floor at approximately angle α1.

FIG. 105*a* is a perspective view of a mattress 1060 according to another illustrative embodiment of the present disclosure. FIG. 105*b* is a top view of the illustrative embodiment of FIG. 105*a* looking in the direction labeled 105*b* in FIG. 105*a*. FIG. 105*c* is a longitudinal side view (viewed along the longer side) of the illustrative embodiment of FIG. 105*a*, looking in the direction labeled 105*c* in FIG. 105*b*. FIG. 105*d* is a lateral side view (viewed along the shorter side, or head end) of the illustrative embodiment of FIG. 105*a*, looking in the direction labeled 105*d* in FIG. 105*c*. In this embodiment, the mattress 1060 has a laterally sloped head section 1062, a laterally sloped torso section 1064 and a laterally sloped leg section 1066. In addition, a side bolster 1068 is provided along a portion of the longitudinal side, rising above bottom part of the slopes of the leg section 1066 and torso section 1064. Moreover, a foot bolster 1070 runs laterally along the foot end of the mattress 1060 and has a top surface 1071 that rises least a portion of the foot section 1066. The foot bolster 1070 can help minimize patient migration toward the foot end, and can help keep the patient's head on the angled head support surface of the head section 1062 and tilted laterally downwardly as some or all of the rest of the patient's body is in a generally more prone or more supine sleeping position (depending on if the patient is sleeping on the stomach or on the back).

As can best be seen in FIGS. 105A, 105B, and 105D, the mattress 1060 has four corners C1, C2, C3, and C4 around its body supporting surfaces. The height of the mattress 1060 at corner C1 (near the head end left side) is greater than the height of the mattress at corner C2 (near the foot end left side), which in turn is greater than the height of the mattress's patient support at corner C3 (near the foot end right side). Accordingly, the mattress 1060 of this embodiment generally slopes downwardly in the longitudinal direction, but also downwardly in the lateral direction In one embodiment, the height at C1 is about 12 inches, and in another embodiment is about 9 inches. In one embodiment, the height at C2 is about 7.5 inches, and in another embodiment is about 6 inches. In one embodiment, the height at C3 is about 2.5 inches and in another embodiment is about 1.5 inches. In some embodiments, the height at C1 is from about 3-7 times the height at C4. In some embodiments the height at C2 is from about 2-4 times the height at C3, but is less than the height at C1. Therefore, in some embodiments H(C1) is greater than H(C2) which is greater than H(C3).

As also can be seen in FIGS. 105A, 105B, and 105D, the sloped surface of the head support section 1062 has an upper midpoint $h_u$ at one lateral side and a lower midpoint $h_l$ at its opposite lateral side. Likewise, the sloped surface of the torso support section 1064 has an upper midpoint $T_u$ (which is longitudinally inline with the midpoint $h_u$), and a lower midpoint $T_l$ at its opposite lateral side. Finally, the sloped surface of the leg support section 1066 has an upper midpoint $L_u$ (which is longitudinally in line with midpoints $h_u$ and $T_u$), and a lower midpoint $L_l$ at its opposite lateral side. In this embodiment, the height of the mattress 1060 at point $h_u$ (which in FIG. 105A is referred to as H($h_u$)) is greater than the height of the mattress 1060 at point $T_u$ (which in FIG. 105A is referred to as H($T_u$)). Likewise, the height of the mattress 1060 at point $T_u$ (which in FIG. 105A is referred to as H($T_u$)) is greater than the height of the mattress at point $L_u$ (which in FIG. 105A is referred to as H($L_u$)). The heights at the lower midpoints (H($h_l$), H($T_l$), and H($L_l$)) can be substantially equal in some embodiments. In some embodiments, the height H($h_u$) is from about 8 to about 14 inches, the height H($T_u$) is from about 6 to about 12 inches, the height H($L_u$) is from about 2 to about 8 inches, such as 4.5 or 6 inches for example, and the height at the lower points (H($L_l$)), H($T_l$), and H($h_l$)) is from about 1 to about 3 inches. In one embodiment, the height H($h_u$) is about 12 inches, the height H($T_u$) is about 10 inches, the height H($L_u$) is about 6 inches, and the heights at the lower points is about 2.5 inches. In another embodiment, the height H($h_u$) is about 9 inches, the height H($T_u$) is about 7 inches, the height H($L_u$) is about 4.5 inches, and the heights at the lower points is about 1.5 inches.

Figure 106A:
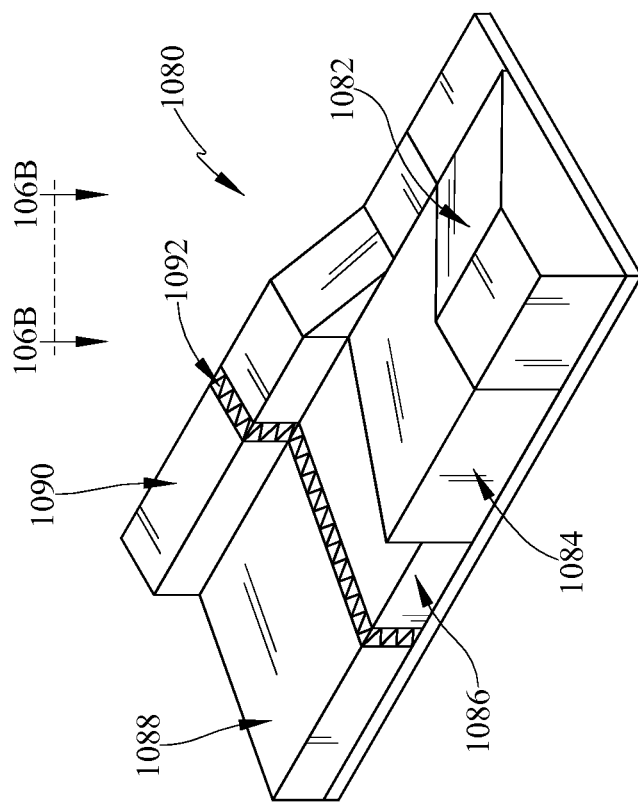
FIG. 106a is a perspective view of a mattress according to another illustrative embodiment of the present disclosure, where the mattress includes an articulating leg section.
Figure 106B:
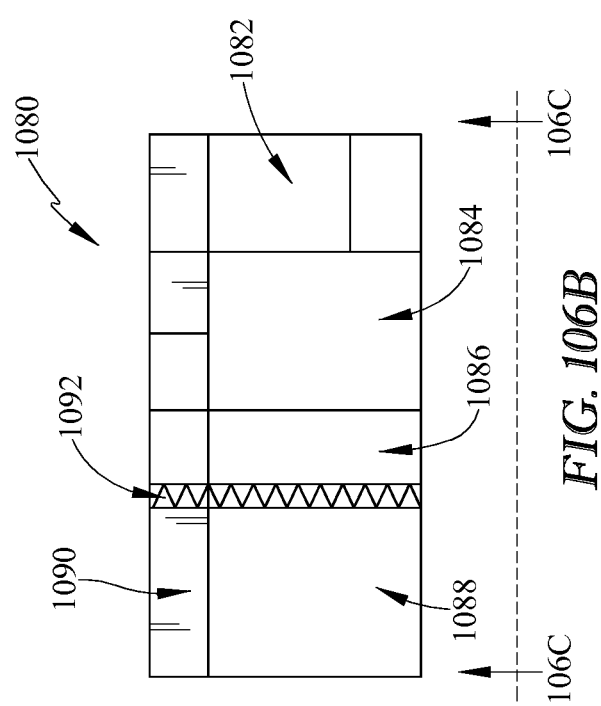
Figure 106C:
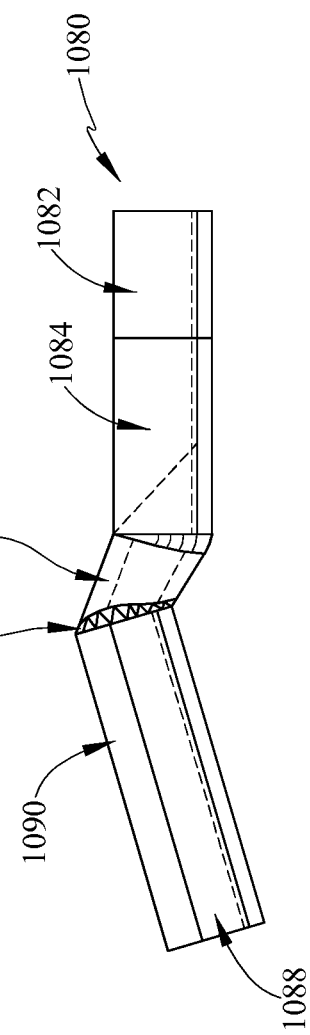
FIG. 106c is a longitudinal side view (viewed along the longer side) of the illustrative embodiment of FIG. 106a, looking in the direction labeled 106c in FIG. 106b, but showing the leg section articulated.
Figure 107:
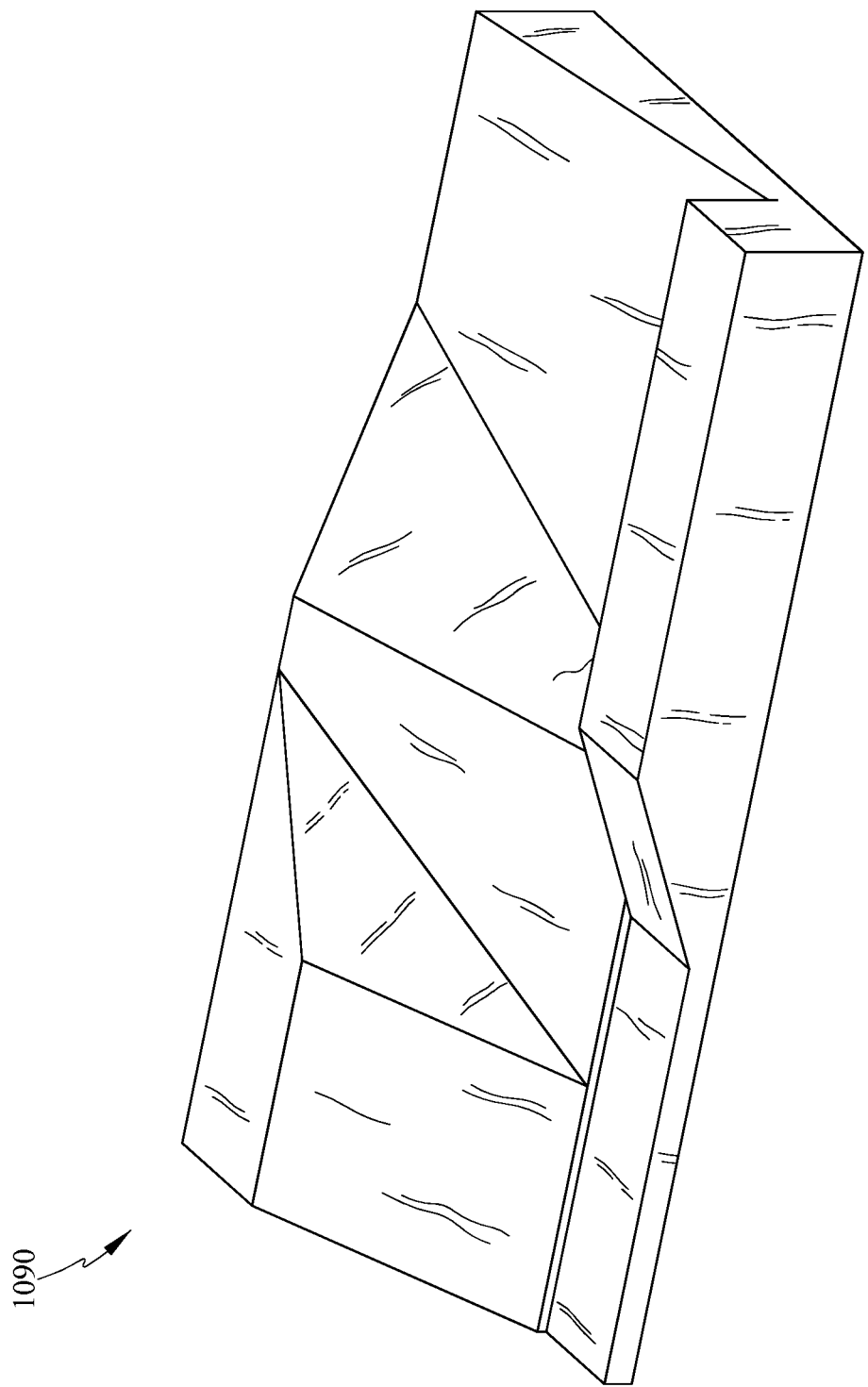
FIG. 107 is a top, foot end, perspective view of a mattress design according to another embodiment.
Figure 108:
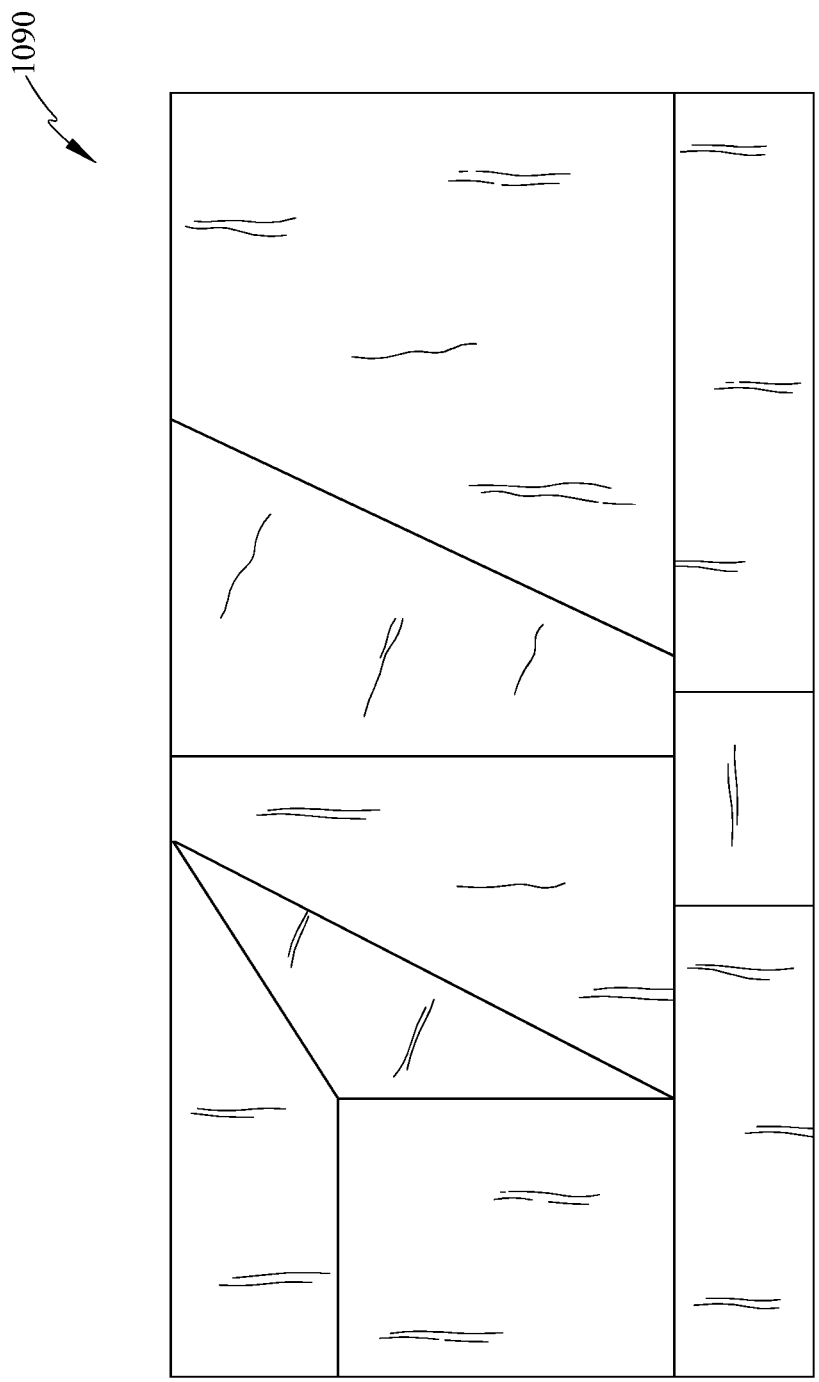
Figure 109:
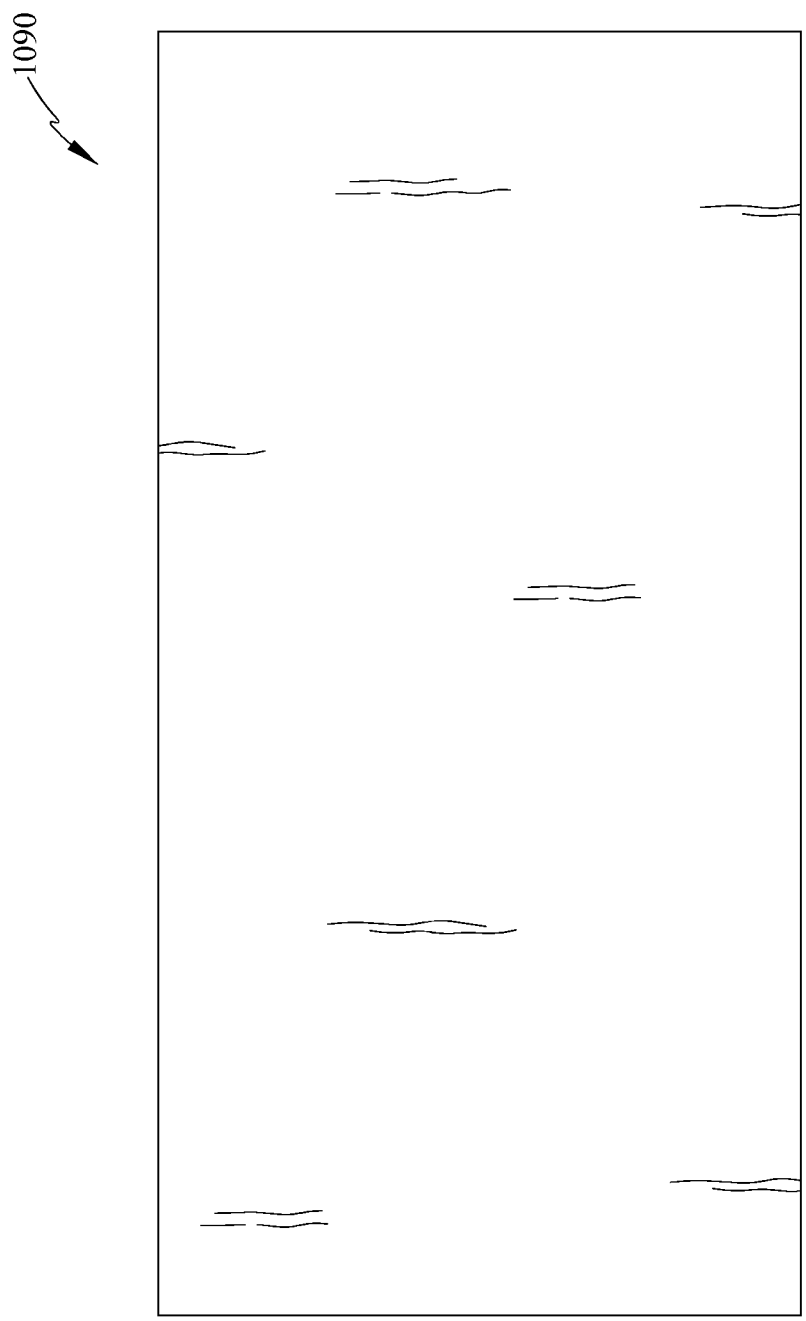
Figure 110:
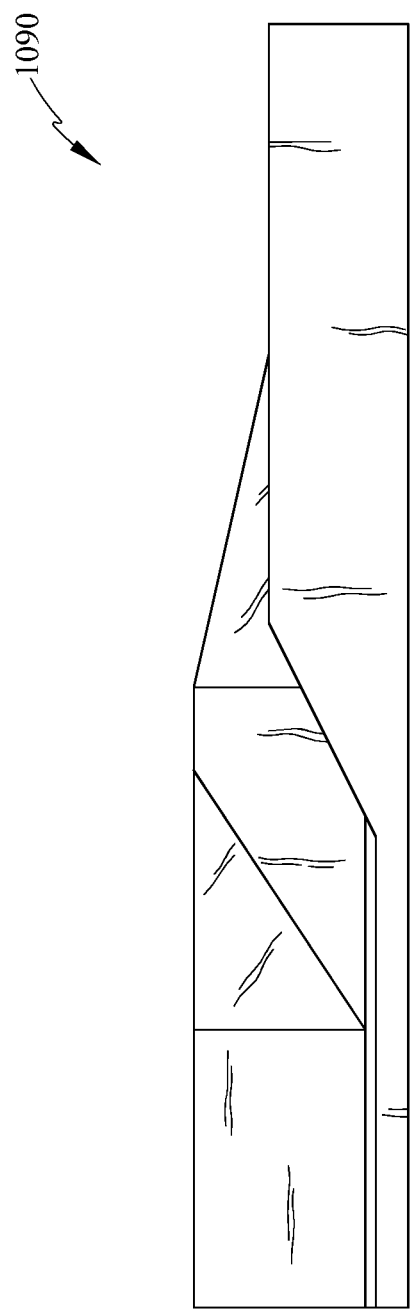
Figure 111:
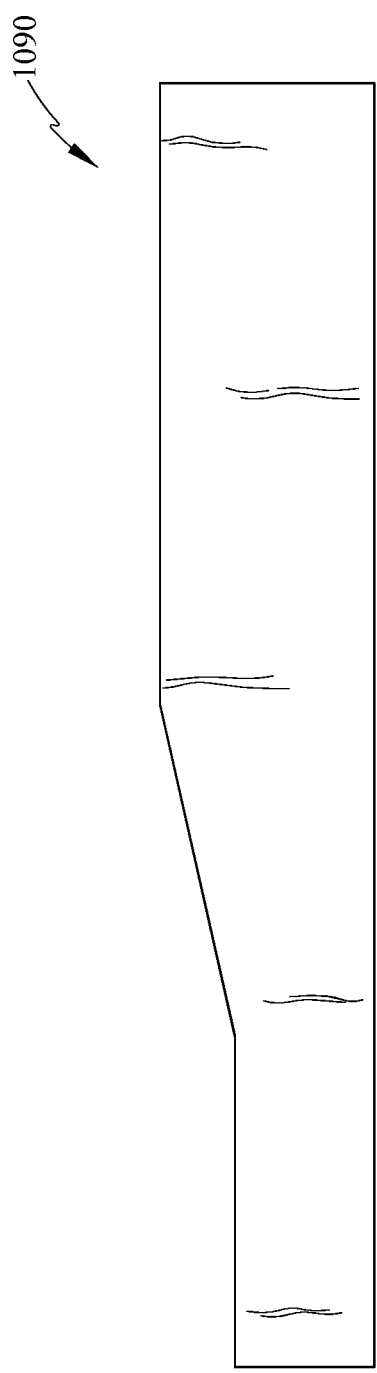

FIG. 106a is a perspective view of a mattress 1080 according to another illustrative embodiment of the present disclosure, where the mattress includes an articulating leg section. FIG. 106b is a top view of the illustrative embodiment of FIG. 106a looking in the direction labeled 106b in FIG. 106a. FIG. 106c is a left longitudinal side view of the illustrative embodiment of FIG. 106a, looking in the direction labeled 106c in FIG. 106b, but showing the leg section articulated. In this embodiment, the mattress 1080 includes a laterally angled head section 1082, a laterally angled torso section 1084, and a leg section comprising a thigh section 1086 and a lower leg section 1088. The bolster 1090 is provided along the longitudinal side. Flexible material 1092 separates the lower leg section 1088 and the thigh section 1086. The flexible material can comprise fabric, plastic, flexible foam, or corrugated foam, or foam or other material that is scored or includes voids to induce articulation along that point of the mattress 1080. Accordingly, the mattress 1080 can more easily flex at the approximate knee position of the patient, to facilitate bending near the knee when the bed on which the mattress sits is placed into a knee gatch or bent knee position, such as one where the angle between the lower leg support surface and the upper leg/thigh support surface is from about 185 degrees to about 270 degrees.

FIGS. 107-113 are views of a mattress 1090 according to another embodiment and having other various design elements.

FIGS. 114-120 are views of a mattress 1091 according to another embodiment, while having nonlinear surfaces. In this embodiment, the mattress 1091 includes a head section 1094, a torso section 1096 and a leg section 1098, each of which slope laterally downwardly, when moving in the direction w1 from the first long 1093 of the mattress to the second long side 1095 of the mattress. As shown in this embodiment, the head section 1094 can include a flat section. Additionally, the torso section 1096 includes a curved portion 1097 that curves downwardly when moving in the direction w1 and when moving in the direction $l_1$. This curved portion slopes generally laterally downwardly at an angle Ø2. Likewise, the leg section 1098 includes a curved portion 1099 that curves downwardly when moving in the direction w1 and when moving the direction $l_1$. Furthermore, the mattress 1091 also includes a bolster 1095 that extends upwardly adjacent the leg section 1098 and a portion of the torso section 1096 but does not extend upwardly adjacent the head section 1094.

As can best be seen by FIG. 119, when a person is in a resting position on the mattress 1091, with their head resting on the head support surface of the head section 1094, the head h is urged to tilt to the side such that the center plane of the face, generally running along the middle of the nose n, forms an angle ω with the vertically upward plane v. This embodiment, and one or more of the other embodiments described herein can urge the head h to tilt during sleep such that the angle ω is at least about +/−35 degrees from vertical, such as about +/−45 degrees or more, and could be up to about +130 degrees in some embodiments. This urged tilting can be accomplished by a head section that slopes generally downward laterally across the longitudinal centerline of the mattress, and/or a torso section that does the same, with an angle sufficient to cause the urged tilting. The embodiments shown by FIG. 27 and FIG. 104 can also can urge the head to tilt at an angle ω of at least about 35 degrees during sleep, while not restraining the head substantially, so as to still allow the head to turn sideways at least in one direction during sleep. Other embodiments may also achieve a similar result, but not all embodiments need achieve this result. Such a result may be achievable too by a mattress having a head support section and/or a torso support section that is generally laterally sloped by about 15 or more degrees, such as about 20 or more degrees, 25 or more degrees, or 30 or more degrees.

FIGS. 121-127 depict yet another illustrative embodiment of the present disclosure. In this embodiment, the sleep apparatus is in the form of a mattress 3000 having a head support section 3002, a torso support section 3004, and a leg support section 3006. Additionally, the mattress 3000 of this embodiment includes a bolster 3010. The mattress 3000 includes a head end 3001, a foot end 3003, a right side 3005, a left side 3007, a longitudinal central axis and a lateral (or latitudinal) central axis. In this embodiment, the vertical support sections of the mattress 3000 generally slope downwardly in both the lateral direction and in the longitudinal direction. In this example, the sloping occurs in a curved manner in both directions, rather than in a linear or stepped manner (although other embodiments may include other sloping, such as linear, curved, and/or stepped sloping for example).

Each of the sloped lying (vertical person support) sections 3002, 3004, and 3006 include a maximum height. In this example, the head section has a maximum height $h_h$, the torso section has a maximum height $h_t$, and the leg section has a maximum height $h_l$, and $h_h$ is greater than $h_t$ which is greater than $h_l$. In some embodiments, there may be irregularly shaped portions of these sections 3002, 3004, and 3006, but the average heights of these sections (taken for example by averaging the maximum heights of all lateral cross sections of each section) are generally different from one another. For example, in one embodiment, the average height of the head section is at least about 20% larger than the average height of the torso section, and the average height of the torso section is at least about 20% larger than the average height of the leg section. Accordingly, the vertical support sections of the mattress 3000 slope generally downwardly in the longitudinal direction from the head end 3001 to the foot end 3003.

Additionally, in this embodiment, the vertical support sections of the mattress 3000 slope generally downwardly in the lateral direction from the left side 3007 toward the right side 3005. Accordingly, the maximum slope of each of the sections (defined by the tangents to the curves at the highest points $h_t$, $h_h$, and $h_l$) relative to horizontal, is indicated by the angles $\theta_h$, $\theta_t$, and $\theta_l$. In this embodiment $\theta_h$ is greater than $\theta_t$ which in turn is greater than $\theta_l$. In other words, the lateral slope of the head section 3002 is generally greater than the lateral slope of the torso section 3004, and the lateral slope of the torso section 3004 is generally greater than the lateral slope of the leg section 3006. These angles $\theta_h$, $\theta_t$, and $\theta_l$ of slope could, alternatively, be determined by determining the average slope of lateral cross sections of each section 3002, 3004, and 3006.

In this embodiment, angle $\theta_h$, is about 25 degrees, $\theta_t$, is about 17.5 degrees, and $\theta_l$ is about 10 degrees. In some embodiments, the angle $\theta_h$ is from about 10 to about 30 degrees, and the angle $\theta_t$ is from about 0 to about 25 degrees (such as from about 1 to about 20 degrees). In some embodiments, angle $\theta_h$ is at least about 20 degrees, such as from about 20 to about 25 degrees, and the angle $\theta_t$ is at least about 10 degrees, such as from about 10 to about 25 degrees.

In some embodiments, the angle $\theta_t$ is from about 5 to about 15 degrees less than the angle $\theta_h$. In some embodiments, the angle $\theta_t$ is from about 5 to about 10 degrees less than the angle $\theta_h$, and in some embodiments the angle $\theta_t$ is about 7.5 degrees less than the angle $\theta_h$. In some embodiments, the angle $\theta_t$ is from about 15 to about 17.5 degrees.

In some embodiments, the angle $\theta_l$ is from about 0 degrees to about 15 degrees. In some embodiments, the angle $\theta_l$ is from about 0 degrees to about 12.5 degrees, and in some embodiments is about 10 degrees. In some embodiments, the angle $\theta_l$ is from about 0 to about 15 degrees less than the angle $\theta_t$. In some embodiments, the angle $\theta_l$ is from about 5 to about 10 degrees less than the angle $\theta_t$, and in some embodiments the angle $\theta_l$ is about 7.5 degrees less than the angle $\theta_t$.

FIG. 128 is a top, foot end perspective view of a sleep apparatus according to another embodiment, comprising a bed frame having a siderail 2004, a mattress 2000 which is bendable along at least one flexible portion 2001, and a curved tilting device 2002 which supports the mattress 2000. FIGS. 129-133 show the tilting device 2002 in more detail. The flexible portion 2001 of the mattress 2000 allows the mattress to pivot at the need along with flexing of the deck of the bed, such as described above. In this embodiment, the tilting device 2002 comprises an inflatable bellows having creases or folds 2006 allowing its size to increase when inflated. The tilting device 2002 may be inflated using a pump and the valve 2008. At its four corners, the tilting device takes on four different heights ($h_1$, $h_2$, $h_3$, and $h_4$). The heights at the head end ($h_3$, and $h_1$) are larger than those at the foot end ($h_4$, $h_2$). The heights on the left side ($h_1$, $h_2$) are larger than the heights directly laterally across from them ($h_3$, and $h_4$ respectively). Accordingly, the bellows creates a slope in both the lateral direction ($w_1$) and the longitudinal direction ($l_1$). When placed under the flexible or twistable mattress 2000 near the head end, a corresponding slope is created in the mattress in both the longitudinal direction of the mattress and the lateral direction of the mattress. Accordingly, an angle can be created $\theta_1$ near the head support section of the mattress 2000 (and smaller angle created in the torso support section of the mattress). Preferably, this angle, $\theta_1$, relative to horizontal, is at least about 20 degrees, and near the torso section is at least about 10 degrees. However, air can be provided or removed, via valve 2008, to increase or decrease these angles. The device 2002 can be made of materials other than air bladders, such as foam, plastic, fabric, textile, and/or rigid materials, for example, sufficient to support a flexible or semi-flexible or twistable mattress. In some embodiments, the device 2002 can be made from foam, and/or can be longer than shown so as to extend about half or more of the length of the mattress. In some embodiments, the device 2002 can be used on top of the mattress as an overlay to create a gradual lateral and longitudinal tilting effect.

While certain features have been described in the context of certain illustrative embodiments, it should be understood that such features may be adopted or applied to any of the disclosed embodiments or to other embodiments.

At least some of the above embodiments may be described in terms of functional block components and various processing steps. Such functional blocks may be realized by any number of hardware and/or software components configured to perform the specified functions. For example, embodiments may employ various integrated circuit components, e.g., memory elements, processing elements, logic elements, look-up tables, and the like, which may carry out a variety of functions under the control of one or more processors, microprocessors or other control devices. Similarly, where the elements of the above embodiments are implemented using software programming or software elements the embodiments may be implemented with any programming or scripting language such as C, C++, Java, assembler, or the like, with the various algorithms being implemented with any combination of data structures, objects, processes, routines or other programming elements. Furthermore, such embodiments could employ any number of techniques for electronics configuration, signal processing and/or control, data processing and the like.

The particular implementations shown and described herein are illustrative examples of a some of many possible embodiments, and are not intended to otherwise limit the scope of the claims in any way. For the sake of brevity, conventional electronics, control systems, software development and other functional aspects of the systems (and components of the individual operating components of the systems) may not be described in detail. Furthermore, connecting lines, or connectors shown in various figures are intended to represent exemplary functional relationships and/or physical or logical couplings between the various elements. It should be noted that many alternative or additional functional relationships, physical connections or logical connections may be present in a practical device.

No item or component is essential or required to the practice of the invention unless the element is specifically described as "essential" or "critical." Numerous modifications and adaptations will be readily apparent to those skilled in this art without departing from the spirit and scope of the embodiments.

The order of execution or performance of the operations in embodiments illustrated and described herein is not essential, unless otherwise specified. That is, the operations may be performed in any order, unless otherwise specified, and embodiments as described may include additional or fewer operations than those disclosed herein. For example, it is contemplated that executing or performing a particular operation before, contemporaneously with, or after another operation is within the scope of aspects of the invention.

Some embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and/or described herein. Other embodiments may include different computer-executable instructions or components having more or less functionality than illustrated and described herein.

Many other embodiments of the present disclosure are also envisioned. For example, a method comprises determining a person's level of risk for developing an adverse condition; selecting a care protocol based on the level of risk; displaying a proposed configuration of a person support structure corresponding to the care protocol for a caregiver to approve; and upon approval by the caregiver, implementing the configuration. In another contemplated embodiment, the configuration causes the person support structure to raise a first section of the person support structure such that the first section forms an angle of greater than 0° with respect to the reference plane. In another contemplated embodiment, the configuration causes the person support structure to laterally tilt an occupant supported on the person support structure to a side such that the occupant is are at an angle of greater than 0° with respect to the reference plane. In another contemplated embodiment, the configuration causes the person support structure to move to at least one of a Trendelenburg and reverse Trendelenburg position. In another contemplated embodiment, the configuration causes a therapy to be initiated. In another contemplated embodiment, the therapy includes heat and moisture regulating therapy. In another contemplated embodiment, the therapy includes continuous lateral rotation therapy. In another contemplated embodiment, the therapy includes at least one of percussion therapy and vibration therapy. In another contemplated embodiment, the proposed configuration is modified as a function of a second input indicative of the orientation of a person supported on the person support structure. In another contemplated embodiment, the proposed configuration is modified as a function of a second input indicative of the position of a person supported on the person support structure. In another contemplated embodiment, the method further comprises the steps of: receiving an input indicative of the sleep state of the person supported on the person support structure; and if the person is waking up, restoring the person support structure to a previous configuration. In another contemplated embodiment, the person support structure is configured upon an occupant reaching a predetermined sleep stage. In another contemplated embodiment, the method further comprises the steps of: receiving a configuration override command; and restoring the person support structure to a previous configuration. In one contemplated embodiment, the configuration override command is communicated from a remote location. In another contemplated embodiment, the configuration override command is communicated when a CPR function is activated. In another contemplated embodiment, the configuration override command is communicated from a GUI coupled to the person support structure. In another contemplated embodiment, the method further comprises the step of notifying a caregiver if the presence of a material would aggravate an adverse condition. In another contemplated embodiment, the method further comprises the steps of: receiving an input indicative of a material proximate to the person supported on the person support structure determining if the material increases the person's risk for developing an adverse condition.

In another example, a method comprises receiving a signal indicative of a physiological characteristic; comparing the signal to a threshold to determine if an adverse event is in progress; and upon detecting that an adverse event is in progress, initiating an intervention to stop the adverse event. In one contemplated embodiment, the second intervention includes increasing the magnitude of the first intervention. In another contemplated embodiment, the second intervention includes alerting a caregiver.

In another example, a person support surface comprises a mattress ticking and a mattress core. The mattress core is enclosed by the mattress ticking and includes at least one fluid bladder configured to selectively protrude from the person contacting surface and support a portion of at least one of the neck and the upper back of an occupant supported on the person support surface. In one contemplated embodiment, the at least one fluid bladder is configured to support the cervical vertebrae of an occupant. In another contemplated embodiment, the at least one fluid bladder is configured to protrude a distance of at least about 70 mm from the occupant facing surface. In another contemplated embodiment, the at least one fluid bladder is configured to support the scapula of an occupant. In another contemplated embodiment, the at least one fluid bladder is configured to protrude a distance of at least about 20 mm from the occupant facing surface. In another contemplated embodiment, the at least one fluid bladder is configured to protrude a distance of about 20 mm to about 30 mm from the occupant facing surface. In another contemplated embodiment, the at least one fluid bladder is configured to protrude a distance of less than about 30 mm from the occupant facing surface. In another contemplated embodiment, the at least one fluid bladder is configured to laterally tilt an occupant's head when inflated. In another contemplated embodiment, the at least one fluid bladder is inflated upon detecting the onset of an adverse condition.

In another example, a method comprises determining a person's level of risk for developing an adverse condition; selecting a care protocol based on the level of risk; sensing a first physiological characteristic of a person supported on a person support structure; sensing a second physiological characteristic of the person; comparing the first physiological characteristic to the second physiological characteristic; if the difference between the first physiological characteristic and second physiological characteristic is outside a predefined range, configuring the person support structure as a function of the care protocol.

In another example, a method comprises determining a person's level of risk for developing an adverse condition; selecting a care protocol based on the level of risk; sensing a first physiological characteristic of a person supported on a person support structure; sensing a second physiological characteristic of the person; comparing the first physiological characteristic to the second physiological characteristic; if the difference between the first physiological characteristic and second physiological characteristic is outside a predefined range, alerting a caregiver that an adverse condition is going to occur.

In another example, a person support apparatus to support a person in at least a horizontal position includes a plurality of support sections arranged along a length of the person support apparatus, where each of the support sections has a support surface to support a body portion of the person and an inflatable portion supporting the support surface, where the inflatable portion of the support section is selectively inflatable and deflatable to position the support surface of the support section in a tilt position in which the support surface is angled at a maximum lateral tilt angle and position the support surface in a flat position in which the support surface is angled at a substantially flat angle, wherein the support surfaces of at least two of the support sections have different maximum lateral tilt angles.

In some embodiments, the plurality of support sections may include a head section to support the person's head, a seat section to support the person's torso, and a foot section to support the person's feet, where the maximum lateral tilt angle of the support surface of the head section is greater than the maximum lateral tilt angle of the support surface of the seat section and the maximum lateral tilt angle of the seat section is greater than the maximum lateral tilt angle of the foot section. The inflatable portion of each of the support sections may be inflated to position the support surface in the tilt position and deflated to position the support surface in the flat position. The inflatable portion of each of the support sections may be deflated to position the support surface in the tilt position and inflated to position the support surface in the flat position. Each of the support sections may include a non-inflatable support member in cooperation with the inflatable portion to selectively position the support surface of the support section in the tilt position and the flat position. The inflatable portion may be supported by the non-inflatable support member. The inflatable portion may support the non-inflatable support member. The inflatable portion may include a bellows-shaped bladder. The bellows-shaped bladder may be inflatable to position the support surface of the support section at the maximum lateral tilt angle by rotating the support surface about a longitudinal axis of the person support apparatus located adjacent a first side of the person support apparatus.

In some embodiments, the person support apparatus may include a second bellows-shaped bladder supported by the first bellows shaped bladder and inflatable to position the support surface of the support section at the maximum lateral tilt angle by rotating the support surface about a second longitudinal axis of the person support apparatus located adjacent a second side of the person support apparatus, wherein the second side of the person support apparatus is laterally spaced from the first side.

In some embodiments, the person support apparatus may include a plurality of baffles in an interior region of the bellows-shaped bladder, wherein each of the baffles has a different length. The support section may include a side member positioned adjacent a vertex of the maximum lateral tilt angle of the support surface. The side member may extend along the length of the person support apparatus and the side member may have a length that is less than the length of the person support apparatus.

In some embodiments, the person support apparatus may include a cover sized to enclose the support sections in an interior region, where the cover includes expandable sections corresponding to the support sections to accommodate the support sections when the support surface of each of the support sections is in the tilt position and when the support surface of each of the support sections is in the flat position. The inflatable portion of each of the support sections may include a multiple-chamber bladder assembly, and each of the bladders in the multiple-chamber bladder assembly may be inflatable to a different height. Each of the bladders of the multiple-chamber bladder assembly may be substantially log shaped and the bladders may be in fluid communication with each other. Each support section may include a sensor to measure the lateral tilt angle of the support surface of the support section, where the sensor is coupled to the support section. The sensor may be enclosed within an interior region of the support section. The person support apparatus may be in communication with an air control system and a person weighing system to determine the weight of a person positioned on the person support apparatus, where the air control system adjusts the amount of air pressure supplied to the inflatable portion of each of the support sections to achieve the maximum tilt angle of the support surface of the support section in response to a weight detected by the person weighing system. The inflatable portion of each of the support sections may include a three-dimensional matrix defined by a plurality of horizontally aligned columns of vertically stacked inflatable bladders.

In some embodiments, each of the inflatable bladders may be configured to assume a log-like shape when inflated. Each of the inflatable bladders may be configured to assume a sphere-like shape when inflated. The inflatable portion of each of the support sections may include a two-dimensional matrix including a plurality of rows and columns of horizontally aligned inflatable bladders, where the maximum height of the bladders is adjustable to achieve the maximum tilt angle of the support section. The inflatable portion may include a pair of laterally-spaced inflatable bladders and a non-inflatable member supported by the pair of laterally-spaced inflatable bladders, where the non-inflatable member supports the support surface and the support surface assumes the tilt position when both of the inflatable bladders are at least partially inflated and one of the inflatable bladders is inflated to a different height than the other inflatable bladder. Each of the support sections may include a wedge-shaped non-inflatable base and the inflatable portion may be supported by the wedge-shaped non-inflatable base.

According to one embodiment, a mattress is provided having a longitudinal length defined by a longitudinal axis of the mattress when the mattress is in its most horizontal position and a lateral width defined by a lateral axis of the mattress when the mattress is in its most horizontal position. The mattress comprises a head section having a head support surface to support at least a portion of a person's head. At least a portion of the head support surface is generally sloped in the lateral direction at a first angle relative the lateral axis. The first angle is from about 10 to about 30 degrees. The mattress further comprises a torso section having a torso support surface to support at least a portion of a person's torso. At least a portion of the torso support surface is generally sloped in the lateral direction at a second angle relative to the lateral axis. The second angle is from about 1 to about 25 degrees less than the first angle, such as from about 5 to about 15 degrees less than the first angle for example. In some embodiments, the first angle can be from about 15 to about 30 degrees, and the second angle can be from about 0 to about 20 degrees, for example. In some embodiments, the first angle can be from about 20 to about 30 degrees and the second angle can be from about 5 to about 15 degrees less than the first angle. Some embodiments of the mattress can include a leg section having a leg support surface to support at least a portion of a person's legs, the leg support surface being generally sloped in the lateral direction at a third angle relative to the underside surface. The third angle can be from about 0 degrees to about 15 degrees. In some embodiments, a bolster is positioned adjacent at a bottom side of the sloped torso support surface and rising above at least a portion of the torso support surface. In some embodiments, the head section is from about 5 inches to about 30 inches in length, the torso section is from about 15 inches to about 50 inches in length, and the leg section is from about 25 inches to about 50 inches in length. Some embodiments may include a lower leg support surface and thigh surface which are pivotable in the longitudinal direction relative one another, so as to form an angle between the surfaces of from about 100 to about 170 degrees. In some embodiments, the mattress is made at least partially of a flexible material to allow for the pivoting of the lower leg support surface and the thigh surface. According to some embodiments, at least one of the head section and torso section of the mattress comprises an air bladder configured to inflate to create at least one of the first and second angles.

In accordance with one embodiment, a person support apparatus is provided having a longitudinal length from its head end to its foot end, and a lateral width from side to side. The person support apparatus comprises a head section having a head support surface to support at least a portion of a person's head. At least a portion of the head support surface is generally sloped downward in a lateral direction. The person support apparatus further comprises a torso section having a torso support surface to support a least a portion of the person's torso. At least a portion of the torso support surface is generally sloped downward in the lateral direction, and the slope of the torso support surface is different from the slope of the head support surface. The apparatus further comprises a bolster extending along a side of person support apparatus and extending above the side. In some embodiments, the bolster does not extend along at least a portion of a side of the head section. The person support apparatus in some embodiments further comprises a leg section having a leg support surface to support at least a portion of a person's leg, and the leg support surface is flat or has a slope in the lateral direction which is about equal to or less than the slope of the torso support surface. In some embodiments, the bolster extends along at least a portion of the leg section. According to some embodiments, the side comprises a foot end of the person support apparatus. The head support surface in some embodiments is sloped at an angle of from about 10 to about 30 degrees, and the torso support surface is sloped at an angle of from about 1 to about 20 degrees. In some embodiments, at least one of the head section and torso section comprises an air bladder configured to inflate to create at least a portion of the slope of the section. The person support apparatus of some embodiments comprises a leg section having a leg support surface to support at least a portion of a person's leg, and the leg support surface is flat or is generally downwardly sloped in the lateral direction at an angle that is less than the angle of the head support surface, and the leg section is pivotable between a thigh section and a lower leg section. In some embodiments, the person support apparatus further comprises a transition surface sloping between the head section and the torso section.

Furthermore, a sleeping apparatus is provided in one embodiment having a longitudinal centerline. The apparatus comprises at least one bottom surface that is generally horizontal when the person support apparatus is in a generally horizontal position for sleeping. The apparatus comprises a head support section sized to support a person's head. The support section has a top surface extending from a first side of the longitudinal centerline to a second side of the longitudinal centerline. The top surface slopes generally laterally downwardly relative to horizontal, at an angle of at least approximately 15 degrees, when the person support apparatus is in a horizontal position, and, at the same time, has a maximum height greater than the torso support section, such that the apparatus slopes downwardly from the head toward the foot.

In one embodiment, a sleep support apparatus is provided having a longitudinal axis when in a horizontal position. The sleep support apparatus comprises a body part support section. The body support section comprises at least one surface configured to support at least a portion of a person's body during sleep. The body support section allows the person's head to turn sideways substantially in at least one direction. The body support section urges the longitudinal center plane of the person's face to rest at a first angle during sleep relative to a vertical plane extending upwardly against the direction of gravity and along the longitudinal axis of the sleep support apparatus. The first angle is equal to or greater than about 35 degrees from the upwardly extending vertical plane.

In one embodiment, a sleep apparatus is provided having a longitudinal dimension moving from a head end to a foot end, and a lateral dimension moving from a first side to a second side when in a generally horizontal position for sleeping. The apparatus comprises a head support section sized to support a person's head. The head support section is generally laterally sloped moving from the first side toward the second side, and the head support section has a height when the sleeping apparatus is in the generally horizontal position. The apparatus further comprises a torso support section sized to support a person's torso. The torso support section is generally laterally sloped moving from the first side toward the second side, and the torso support section has a height when the sleeping apparatus is in the generally horizontal position. The height of the head support section is greater than the height of the torso support section. In some embodiments, the height of the head section is the average of the maximum heights of lateral cross sections of the head section, and the height of the torso section is the average of the maximum heights of lateral cross sections of the torso section. In some embodiments, the head support section slopes generally laterally downwardly relative to horizontal at an angle of at least about 20 degrees, and the torso support section slopes generally laterally downwardly relative to horizontal an angle of at least about 10 degrees. In some embodiments, the angle of the head support section is the average angle of slope of tangents to horizontal cross sections of the head support section, and the angle of the torso support section is the average angle of slope of tangents to horizontal cross sections of the torso support section. In some embodiments, the apparatus comprises a leg support section sized to support a person's legs, the leg support section is generally laterally sloped moving from the first side toward the second side, the leg support section has a height when the sleeping apparatus is in the generally horizontal position, and the height of the torso support section is greater than the height of the leg support section.

In one embodiment, a sleep apparatus is provided having a longitudinal axis when in a horizontal position. The apparatus comprises a body part support section, the support section having at least one surface configured to support at least a portion of a person's body during sleep, and the body support section allows the person's head to turn substantially in at least one direction. The body support section urges the longitudinal center plane of the person's face to rest at a first angle during sleep relative to a vertical plane extending upwardly against the direction of gravity and along the longitudinal axis of the sleep support apparatus. The first angle is equal to or greater than about 35 degrees from the upwardly extending vertical plane. In some embodiments, the support section comprises a head support section or torso support section sloping generally laterally downwardly. In some embodiments, the support section further comprises a head support section sloping generally laterally downwardly at a first angle, and a torso support section sloping generally laterally downwardly at a second angle that is different from the first angle. In some embodiments, the sleep apparatus comprises a bed or mattress.

In one embodiment, a sleep apparatus is provided having a longitudinal dimension moving from a head end to a foot end, and a lateral dimension moving from a first side to a second side when in a generally horizontal position for sleeping. The apparatus includes a head support section sized to support a person's head, and the head support section is generally laterally sloped moving from the first side toward the second side. The apparatus further includes a torso support section sized to support a person's torso, and the torso support section is generally laterally sloped moving from the first side toward the second side. The sleeping apparatus is generally longitudinally sloped moving from the head end to the foot end. In some embodiments, the slopes are achieved by linear surfaces, non-linear surfaces, or stepped surfaces. In some embodiments, the apparatus further comprises a leg support section sized to support a person's legs, and the leg support section is generally laterally sloped moving from the first side toward the second side.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

What is claimed is:

1. A mattress having a longitudinal central axis when the mattress is in its most horizontal position and a lateral central axis when the mattress is in its most horizontal position, comprising:

a head section having a head support surface to support at least a portion of a person's head and a head support bladder that is inflatable to support the head support surface for sloped arrangement, wherein at least a portion of the head support surface is generally sloped in a first lateral direction at a first angle relative to the lateral axis, wherein the first angle is from about 10 to about 30 degrees; and a torso section having a torso support surface to support at least a portion of a person's torso and a torso support bladder that is inflatable to support the torso support surface for sloped arrangement, wherein at least a portion of the torso support surface is generally sloped in the first lateral direction at a second angle relative to the lateral axis, wherein the second angle is from about 1 to about 25 degrees less than the first angle, wherein the portion of the head support surface becomes sloped at the first angle and the portion of the torso support surface becomes sloped at the second angle as a result of inflating the head support bladder of the head section and inflating the torso support bladder of the torso section automatically with an air system in response to detection of the person's upper respiratory tract (URT) being below a threshold URT angle as detected by a sensor attached to the person's head, wherein the head support bladder defines a first space that is distinct and separate from a second space defined by the torso support bladder so that the head support bladder and the torso support bladder are individually inflatable to separately control the first and second angles independently, wherein the head support bladder and the torso support bladder are generally aligned along a longitudinal dimension of the mattress, wherein the head support bladder and the torso support bladder are situated closely adjacent to each other defining a transition with no intervening bladder being situated therebetween, wherein the head support bladder has a first dimension that is parallel with the longitudinal central axis, and the torso support bladder has a second dimension that is parallel with the longitudinal central axis and that is greater than the first dimension such that the head support bladder and the torso support bladder have different sizes along the longitudinal central axis.

2. The mattress as recited in claim 1, wherein the second angle is from about 5 to about 15 degrees less than the first angle.

3. The mattress as recited in claim 1, wherein the first angle is from about 15 to about 30 degrees, and the second angle is from about 1 to about 20 degrees.

4. The mattress as recited in claim 3, wherein the first angle is from about 20 to about 30 degrees and the second angle is from about 5 to about 15 degrees less than the first angle.

5. The mattress as recited in claim 1, further comprising: a leg section having a leg support surface to support at least a portion of a person's legs, wherein the leg support surface is generally sloped in the first lateral direction at a third angle relative to the lateral axis.

6. The mattress as recited in claim 5, wherein the third angle is from about 1 degree to about 15 degrees.

7. The mattress as recited in claim 5, wherein the head section is from about 5 inches to about 30 inches in length, the torso section is from about 15 inches to about 50 inches in length, and the leg section is from about 25 inches to about 50 inches in length.

8. The mattress as recited in claim 1, further comprising: a bolster positioned adjacent a bottom side of the sloped torso support surface and rising above at least a portion of the torso support surface.

9. The mattress of claim 8, wherein the bolster extends longitudinally along the mattress and forms an upper surface for at least a portion of its longitudinal extension.

10. The mattress of claim 9, wherein the upper surface includes at least one portion having a first height and at least one portion having reduced height along its longitudinal extension.

11. The mattress as recited in claim 1, further comprising a lower leg support surface and thigh support surface which are pivotable in the longitudinal direction relative one another, so as to form an angle between the two surfaces of from about 185 to about 270 degrees.

12. The mattress as recited in claim 11, wherein the mattress is made at least partially of a flexible material to allow for the pivoting of the lower leg support surface and the thigh surface.

13. The mattress of claim 1, wherein the head support bladder is inflatable to support at least one portion of the head support surface in the first lateral direction.

14. The mattress of claim 13, wherein the head support surface includes at least one portion having near zero slope in the first lateral direction.

15. A person support apparatus having a longitudinal length from its head end to its foot end, and having a lateral width from side to side, the person support apparatus comprising:
a head section having a head support surface and a head support bladder operable to support at least a portion of the head support surface for supporting at least a portion of a person's head at a first slope, wherein at least a portion of the head support surface is generally sloped downward in a first lateral direction;
a torso section having a torso support surface and a torso support bladder operable to support at least a portion of the torso support surface for supporting a least a portion of the person's torso at a second slope, wherein at least a portion of the torso support surface is generally sloped downward in the first lateral direction, wherein the second slope of the torso support surface is different from the first slope of the head support surface; and
a bolster extending along a side of person support apparatus and extending above at least one of a side and an end of the person support apparatus, wherein the portion of the head support surface becomes sloped downward in the lateral direction and the portion of the torso support surface becomes sloped downward in the lateral direction as a result of inflating the head support bladder of the head section and inflating the torso support bladder of the torso section automatically with an air system in response to detection of the person's upper respiratory tract (URT) being below a threshold URT angle as detected by a sensor attached to the person's head,
wherein the head support bladder defines a first space that is distinct and separate from a second space defined by the torso support bladder so that the head support bladder and the torso support bladder are individually inflatable to separately control the first and second slopes independently, wherein the head support bladder and the torso support bladder are generally aligned along a longitudinal dimension of the mattress, wherein the head support bladder and torso support bladder are situated closely adjacent to each other defining a transition with no intervening bladder being situated therebetween, wherein the head support bladder has a first dimension that is parallel with the longitudinal length, and the torso support bladder has a second dimension that is parallel with the longitudinal length and that is greater than the first dimension such that the head support bladder and the torso support bladder have different sizes along the longitudinal length.

16. The person support apparatus as recited in claim 15, wherein the bolster does not extend along at least a portion of a side of the head section.

17. The person support apparatus as recited in claim 15, further comprising a leg section having a leg support surface to support at least a portion of a person's leg, wherein the leg support surface is flat or has a third slope in the first lateral direction which is about equal to or less than the second slope of the torso support surface.

18. The person support apparatus as recited in claim 15, wherein the bolster extends along at least a portion of the leg section.

19. The person support apparatus as recited in claim 15, wherein the bolster extends above the foot end of the person support apparatus.

20. The person support apparatus as recited in claim 15, wherein the head support surface is sloped at an angle of from about 10 to about 30 degrees, and the torso support surface is sloped at an angle of from about 1 to about 20 degrees.

21. The person support apparatus as recited in claim 20, further comprising a leg section having a leg support surface to support at least a portion of a person's leg, wherein the leg support surface is flat or is generally downwardly sloped in the first lateral direction at an angle relative to the plane that is less than the angle of the head support surface, wherein the leg section is pivotable between a thigh section and a lower leg section.

22. The person support apparatus as recited in claim 15, wherein at least one of the head section and torso section comprises a wedge-shaped air bladder configured to inflate to create at least a portion of the slope of the section.

23. The person support apparatus as recited in claim 15, further comprising a transition surface sloping between the head section and the torso section.

24. The person support apparatus of claim 15, wherein the bolster extends longitudinally along the mattress and forms an upper surface for at least a portion of its longitudinal extension.

25. The person support apparatus of claim 24, wherein the upper surface includes at least one portion having a first height and at least one portion having reduced height along its longitudinal extension.

26. A sleep apparatus having a longitudinal dimension moving from a head end to a foot end, and a lateral dimension moving from a first side to a second side when in a generally horizontal position for sleeping, comprising:
   a head support section sized to support a person's head and comprising a head support bladder inflatable to support the head support section, wherein the head support section is generally laterally sloped at a first slope moving from the first side toward the second side, wherein the head support section has a height when the sleeping apparatus is in the generally horizontal position; and
   a torso support section sized to support a person's torso and comprising a torso support bladder inflatable to support the torso support section, wherein the torso support section is generally laterally sloped at a second slope moving from the first side toward the second side, wherein the torso support section has a height when the sleeping apparatus is in the generally horizontal position;
   wherein the height of the head support section is greater than the height of the torso support section, wherein the portion of the head support section becomes generally laterally sloped and the torso support section becomes generally laterally sloped as a result of inflating the head support bladder of the head support section and inflating the torso support bladder of the torso support section automatically with an air system in response to detection of the person's upper respiratory tract (URT) being below a threshold URT angle as detected by a sensor attached to the person's head,
   wherein the head support bladder defines a first space that is distinct and separate from a second space defined by the torso support bladder so that the head support bladder and the torso support bladder are individually inflatable to separately control the first and second slopes independently, wherein the head support bladder and the torso support bladder are generally aligned along a longitudinal dimension of the mattress, wherein the head support bladder and torso support bladder are situated closely adjacent to each other defining an intersection with no intervening bladder being situated therebetween, wherein the head support bladder has a first dimension that is parallel with the longitudinal dimension, and the torso support bladder has a second dimension that is parallel with the longitudinal dimension and that is greater than the first dimension such that the head support bladder and the torso support bladder have different sizes along the longitudinal dimension.

27. The sleep apparatus as recited in claim 26, wherein the height of the head section is the average of the maximum heights of lateral cross sections of the head section, and the height of the torso section is the average of the maximum heights of lateral cross sections of the torso section.

28. The sleep apparatus as recited in claim 26, wherein the head support section slopes generally laterally downwardly relative to horizontal at an angle of at least about 20 degrees, and wherein the torso support section slopes generally laterally downwardly relative to horizontal an angle of at least about 10 degrees.

29. The sleep apparatus as recited in claim 28, wherein the angle of the head support section is the average angle of slope of tangents to horizontal cross sections of the head support section, and the angle of the torso support section is the average angle of slope of tangents to horizontal cross sections of the torso support section.

30. The sleep apparatus as recited in claim 26, further comprising: a leg support section sized to support a person's legs, wherein the leg support section is generally laterally sloped moving from the first side toward the second side, wherein the leg support section has a height when the sleeping apparatus is in the generally horizontal position; wherein the height of the torso support section is greater than the height of the leg support section.

31. The sleep apparatus of claim 26, wherein the head support surface includes at least one portion having near zero slope in the first lateral direction.

32. The sleep apparatus of claim 26, further comprising a bolster positioned adjacent a bottom side of the sloped torso section and rising above at least a portion of the torso support surface, wherein the bolster extends longitudinally along the mattress and forms an upper surface for at least a portion of its longitudinal extension.

33. The sleep apparatus of claim 26, wherein the upper surface includes at least one portion having a first height and at least one portion having reduced height along its longitudinal extension.

34. A person support apparatus having a longitudinal length defined between a head end and a foot end, and having a lateral width from side to side, the person support apparatus comprising:
   a head section having a head support surface and a head support operable to support at least a portion of the head support surface for supporting at least a portion of a person's head at a first slope, wherein at least a portion of the head support surface is generally sloped downward in a first lateral direction;
   a torso section having a torso support surface and a torso support operable to support at least a portion of the torso support surface for supporting a least a portion of the person's torso at a second slope, wherein at least a portion of the torso support surface is generally sloped downward in the first lateral direction, wherein the second slope of the torso support surface is different from the first slope of the head support surface; and
   a bolster extending along a side of person support apparatus and extending above at least one of a side and an end of the person support apparatus, wherein the portion of the head support surface becomes sloped downward in the lateral direction and the portion of the torso support surface becomes sloped downward in the lateral direction as a result of inflating the head support of the head section and inflating the torso support of the torso section automatically with an air system in response to detection of the person's upper respiratory tract (URT) being below a threshold URT angle as detected by a sensor attached to the person's head, wherein the head support bladder defines a first space that is distinct and separate from a second space defined by the torso support bladder so that the head support bladder and the torso support bladder are inflatable individually to separately control the first and second slopes, wherein the head support bladder and the torso support bladder are generally aligned along a longitudinal dimension of the mattress, wherein the head support bladder and torso support bladder are situated closely adjacent to each other defining a transition with no intervening bladder being situated therebetween, wherein the head support bladder has a first dimension that is parallel with the longitudinal length, and the torso support bladder has a second dimension that is parallel with the longitudinal length and that is greater than the first dimension such that the head support bladder and the torso support bladder have different sizes along the longitudinal length.

\* \* \* \* \*

UNITED STATES PATENT AND TRADEMARK OFFICE
CERTIFICATE OF CORRECTION

PATENT NO.       : 10,660,807 B2
APPLICATION NO.  : 14/454961
DATED            : May 26, 2020
INVENTOR(S)      : David Ribble et al.

It is certified that error appears in the above-identified patent and that said Letters Patent is hereby corrected as shown below:

On the Title Page

Page 3, Item [56], delete the word "Hournal" in the ninth other publication listed and replace it with --Journal--.

Page 5, Item [56], delete the word "Revisted" in the eighth other publication listed and replace it with --Revisited--.

Signed and Sealed this
Fourteenth Day of July, 2020

Andrei Iancu
*Director of the United States Patent and Trademark Office*